United States Patent
Seidel, III et al.

(10) Patent No.: US 11,692,018 B2
(45) Date of Patent: Jul. 4, 2023

(54) TGF-β POLYPEPTIDES

(71) Applicant: Cue Biopharma, Inc., Cambridge, MA (US)

(72) Inventors: Ronald D. Seidel, III, Natick, MA (US); Rodolfo J. Chaparro, Cambridge, MA (US); John F. Ross, Cambridge, MA (US); Chee Meng Low, Cambridge, MA (US)

(73) Assignee: Cue Biopharma, Inc., Boston, MA (US)

( * ) Notice: Subject to any disclaimer, the term of this patent is extended or adjusted under 35 U.S.C. 154(b) by 0 days.

(21) Appl. No.: 17/722,328

(22) Filed: Apr. 16, 2022

(65) Prior Publication Data

US 2022/0372093 A1    Nov. 24, 2022

Related U.S. Application Data

(63) Continuation of application No. PCT/US2020/056937, filed on Oct. 22, 2020.

(60) Provisional application No. 62/925,227, filed on Oct. 23, 2019.

(51) Int. Cl.
| | |
|---|---|
| *C07K 14/495* | (2006.01) |
| *A61P 37/06* | (2006.01) |
| *C07K 14/54* | (2006.01) |
| *C07K 14/545* | (2006.01) |
| *C07K 14/55* | (2006.01) |
| *C07K 14/705* | (2006.01) |
| *C12N 5/00* | (2006.01) |
| *C12N 15/62* | (2006.01) |
| *A61K 38/00* | (2006.01) |

(52) U.S. Cl.
CPC ............ *C07K 14/495* (2013.01); *A61P 37/06* (2018.01); *C07K 14/54* (2013.01); *C07K 14/545* (2013.01); *C07K 14/5406* (2013.01); *C07K 14/5412* (2013.01); *C07K 14/5418* (2013.01); *C07K 14/5428* (2013.01); *C07K 14/5443* (2013.01); *C07K 14/55* (2013.01); *C07K 14/70532* (2013.01); *C07K 14/70575* (2013.01); *C12N 5/00* (2013.01); *C12N 15/62* (2013.01); *A61K 38/00* (2013.01); *C07K 2318/10* (2013.01); *C07K 2319/74* (2013.01)

(58) Field of Classification Search
CPC ............................ C07K 14/495; A61K 38/1841
See application file for complete search history.

(56) References Cited

U.S. PATENT DOCUMENTS

| | | |
|---|---|---|
| 9,090,685 B2 | 7/2015 | Ledbetter et al. |
| 2010/0221777 A1 | 9/2010 | Choe et al. |
| 2011/0165623 A1 | 7/2011 | Sun et al. |
| 2018/0221508 A1 | 8/2018 | Kadiyala et al. |
| 2018/0327477 A1 | 11/2018 | Kumar et al. |
| 2019/0062400 A1 | 2/2019 | Seidel, III et al. |
| 2020/0308243 A1 | 10/2020 | Stagliano et al. |
| 2020/0325212 A1 | 10/2020 | Williams et al. |
| 2020/0377571 A1 | 12/2020 | Loew et al. |

FOREIGN PATENT DOCUMENTS

| | | |
|---|---|---|
| EP | 3 093 295 A1 | 11/2016 |
| WO | WO 2008/016356 A2 | 2/2008 |
| WO | WO 2011/109789 A2 | 9/2011 |
| WO | WO 2015/027082 A1 | 2/2015 |
| WO | WO 2019/113464 A1 | 6/2019 |
| WO | WO 2020/069398 A1 | 4/2020 |
| WO | WO 2021/081258 A1 | 4/2021 |

OTHER PUBLICATIONS

International Search Report and Written Opinion, International Application No. PCT/US2022/025479 (published under WO/2022/226024), 10 pages (dated Aug. 2, 2022).
International Search Report and Written Opinion, International Application No. PCT/US2022/025499 (published under WO/2022/226037), 18 pages (dated Sep. 21, 2022).
International Search Report and Written Opinion, International Application No. PCT/US2022/025532 (published under WO/2022/226058), 11 pages (dated Jul. 19, 2022).
International Search Report and Written Opinion, International Application No. PCT/US2022/025526 (published under WO/2022/226054), 15 pages (dated Oct. 18, 2022).
International Search Report and Written Opinion, International Application No. PCT/US2022/025547 (published under WO/2022/226069), 20 pages (dated Sep. 2, 2022).
International Search Report and Written Opinion, International Application No. PCT/US2022/025552 (published under WO/2022/226073), 17 pages (dated Sep. 2, 2022).
Invitation to Pay Additional Fees, International Application No. PCT/US2021/060357 (published under WO/2022/109399), 3 pages (Feb. 1, 2022).
Invitation to Correct Defects in the International Application, International Application No. PCT/US2021/060357 (published under WO/2022/109399), 5 pages (Dec. 14, 2021).

(Continued)

*Primary Examiner* — Prema M Mertz
(74) *Attorney, Agent, or Firm* — Hoffmann & Baron, LLP

(57) ABSTRACT

The present disclosure provides T-cell modulatory multimeric polypeptides (T-Cell-MMP) and their epitope conjugates comprising at least one immunomodulatory polypeptide ("MOD") that may be selected to exhibit reduced binding affinity to a cognate co-immunomodulatory polypeptide ("Co-MOD"). The epitope may be, for example, a cancer-associated epitope, an infectious disease-associated epitope, or a self-epitope. The T-Cell-MMP-epitope conjugates are useful for modulating the activity of a T-cell by delivering immunomodulatory peptides, such as IL-2 or IL-2 variants that exhibit reduced binding affinity for the IL-2R, to T-cells in an epitope selective/specific manner, and accordingly, for treating individuals with a cancer, infectious disease or autoimmune disorder.

23 Claims, 37 Drawing Sheets

Specification includes a Sequence Listing.

(56) References Cited

OTHER PUBLICATIONS

Preliminary International Preliminary Report on Patentability, International Application No. PCT/US2020/056937 (published under WO 202>12), 20 pages (dated Nov. 15, 2021).

Bettini et al., Development of Thymically-Derived Natural Regulatory T Cells; Ann N Y Acad Sci. Jan. 2010; 1183:1-2. Doi:10.1111/j.1749-6632.2009.05129.x.

Chen, et al., Cotransfection with IL-10 and TGF-_1 into immature dendritic cells enhances immune tolerance in a rat liver transplantation model; Am J Physiol Gastrointest Liver Physiol 306: G575-G581, 2014. First published Feb. 6, 2014; doi:10.1152/ajpgi.00283.2013.

Ch'ng, et al., Celiac Disease and Autoimmune Thyroid Disease; Clinical Medicine & Research vol. 5, No. 3: 184-19; © 2007 Marshfield Clinic.

De Crescenzo, et al., Three Key Residues Underlie the Differential Affinity of the TGFb Isoforms for the TGFb Type II Receptor; J. Mol. Biol. (2006) 355, 47-62.

Docagne, et al., A Soluble Transforming Growth Factor-b (TGF-b) Type I Receptor Mimics TGF-_ Responses; The Journal of Biological Chemistry; vol. 276, No. 49, Issue of Dec. 7, pp. 46243-46250, 2001.

Elyaman et al., Notch Receptors and Smad3 Signaling Cooperate in the Induction of Interleukin-9-Producing T Cells, Immunity. Apr. 20, 2012; 36(4): 623-634. doi:10.1016/j.immuni.2012.01.020.

Faghih, et al., The role of Th1 and Th17 in the pathogenesis of celiac disease; Gastroenterology & Hepatology: Open Access; Nov. 8, 2017;Published: Apr. 13, 2018; vol. 9, Issue Feb. 2018.

Francisco, et al., PD-L1 regulates the development, maintenance, and function of induced regulatory T cells; Published Online: Dec. 14, 2009 | Supp Info: http://doi.org/10.1084/jem.20090847.

Genestier,et al., Transforming Growth Factor b1 Inhibits Fas Ligand Expression and Subsequent Activation-induced Cell Death in T Cells via Downregulation of c-Myc; the Journal of Experimental Medicine; 189 (1999), 2. -S. 231-239.

Groppe, et al., Cooperative Assembly of TGF-b Superfamily Signaling Complexes Is Mediated by Two Disparate Mechanisms and Distinct Modes of Receptor Binding; Molecular Cell 29, 157-168, Feb. 1, 2008.

Ha, et al., Immunoglobulin Fc Heterodimer Platform Technology From Design to Applications in Therapeutic Antibodies and Proteins; Frontiers in Immunolog; Oct. 2016, vol. 7, pp. 1-10, Article 394.

Herbertz, et al., Clinical development of galunisertib (LY2157299 monohydrate), a small molecule inhibitor of transforming growth factor-beta signaling pathway; Drug Design, Development and Therapy 2015:9, pp. 4479-4499.

Hezareh, et al., Effector Function Activities of a Panel of Mutants of a Broadly Neutralizing Antibody against Human Immunodeficiency Virus Type 1; Journal of Virology, Dec. 2001, p. 12161-12168, vol. 75, No. 24.

Jacobsen, et al.; Engineering an IgG Scaffold Lacking Effector Function with Optimized Developability; JBC Papers in Press. Published on Dec. 19, 2016.

Jiang, et al., NADPH oxidase-dependent redox signaling in TGF-β-mediated fibrotic responses; Redox Biology 2, 2014, pp. 267-272.

Josephson, et al., Design and Analysis of an Engineered Human Interleukin-10 Monomer; The Journal of Biological Chemistry; vol. 275, No. 18, Issue of May 5, 2000, pp. 13552-13557.

Kaur, et al., Interplay between Type 1 Diabetes Mellitus and Celiac Disease: Implications in Treatment; Dig Dis 2018;36:399-408.

Komai, et al., Transforming growth Factor-β and interleukin-10 synergistically regulate humoral immunity via Modulating Metabolic Signals; Frontiers in Immunology | www.frontiersin.org Jun. 2018 | vol. 9 | Article 1364, pp. 1-15.

Kubiczkova, et al., TGF-β—an excellent servant but a bad master; Journal of Translational Medicine 2012, 10:183, pp. 1-24.

Lord, et al., Structure-based engineering to restore high affinity binding of an isoform-selective anti-TGFβ1 antibody, mAbs, 10:3, 444-452, DOI:10.1080/19420862.2018.1426421; ISSN: 1942-0862.

Mazzarella, Effector and suppressor T cells in celiac disease; World J Gastroenterol Jun. 28, 2015; 21(24): 7349-7356; ISSN 1007-9327 (print).

McNally, et al., CD4+CD25+ regulatory T cells control CD8+ T-cell effector differentiation by modulating IL-2 homeostasis; PNAS, May 3, 2011, vol. 108, No. 18, 7529.

Osgasawara, et al., IL-10, TGF-β and glucocorticoid prevent the production of type 2 cytokines in human group 2 innate lymphoid cells; J Allergy Clin Immunol, vol. 141, # 3, pp. 1147-1152.

Pakyari, et al., Critical Role of Transforming Growth Factor Beta in Different Phases of Wound Healing; Advance in Wound Care, vol. 2, No. 5, pp. 215-225.

Parra-Medina, et al., Prevalence of Celiac Disease in Latin America: A Systematic Review and Meta-Regression; PLOS ONE | DOI:10.1371/journal.pone.0124040 May 5, 2015 pp. 1-19.

Perry, et al., Fragment-based screening of programmed death ligand 1 (PD-L1); Bioorganic & Medicinal Chemistry Letters 29 (2019) 786-790.

Gerald J. Prud'homme, Pathobiology of transforming growth factor b in cancer, fibrosis and immunologic disease, and therapeutic considerations; Laboratory Investigation (2007) 87, 1077-1091; doi:10.1038/labinvest.3700669; published online Aug. 27, 2007.

Read, et al., IL-2, IL-7, and IL-15: Multistage regulators of CD4þ T helper cell Differentiation; Experimental Hematology 2016;44:799-808.

Rigas et al., Type 2 innate lymphoid cell suppression by regulatory T cells attenuates airway hyperreactivity and requires inducible T-cell costimulator—inducible T-cell costimulator ligand interaction; J Allergy Clin Immunol. vol. 139, No. 5, pp. 1468-1477.

Rubio-Tapia, et al., Liver Involvement in Celiac Disease; Minerva Med. Dec. 2008: 99(6): 595-604.

Sanjabi, et al., Anti- and Pro-inflammatory Roles of TGF-β, IL-10, and IL-22 in Immunity and Autoimmunity; Curr Opin Pharmacol. Aug. 2009 ; 9(4): 447-453. doi:10.1016/j.coph.2009.04.008.

Sanjabi, et al., Regulation of the Immune Response by TGF-b: From Conception to Autoimmunity and Infection; Cold Spring Harb Perspect Biol 2017;9:a022236, pp. 1-33.

Stathopoulou, et al., Programmed death-1 receptor signaling downregulates asparaginyl endopeptidase to maintain Foxp3 stability in induced Regulatory T cells; Immunity. Aug. 21, 2018; 49(2): 247-263.e7. doi:10.1016/j.immuni.2018.05.006.

Tovoli, et al., Autoimmune Hepatitis and Celiac Disease: Case Report, Showing an Entero-Hepatic Link Case Rep Gastroenterol 2010;4:469-475;DOI: 10.1159/000321992; Published online: Oct. 26, 2010.

Villarreal, et al., Binding Properties of the Transforming Growth Factor-β Coreceptor Betaglycan: Proposed Mechanism for Potentiation of Receptor Complex Assembly and Signaling; Biochemistry 2016, 55, 6880-6896.

Ward, et al., IL-2/CD25: A Long-Fusion Protein That Promotes Immune Tolerance by Selectively Targeting the IL-2 Receptor on Regulatory T Cells; J Immunol 2018; 201:2579-2592; Prepublished online Oct. 3, 2018; doi: 10.4049/jimmunol.1800907.

Wu, et al., Developmental and Functional Control of Natural Killer Cells by Cytokines; Frontiers in Immunology, Aug. 2017, vol. 8, Article 930.

Xu, et al., Transforming growth factor-β2 in stem cells and tissue homeostasis; Bone Research (2018) 6:2 https://doi.org/10.1038/s41413-017-0005-4.

Yen, et al., IL-23 is essential for T cell-mediated colitis and promotes inflammation via IL-17 and IL-6; J Clin Invest. 2006;116(5):1310-1316. https://doi.org/10.1172/JCI21404.

Zak, et al., Structure of the Complex of Human Programmed Death 1, PD-1, and Its Ligand PD-L1; Structure 23, 2341-2348, Dec. 1, 2015; http://dx.doi.org/10.1016/j.str.2015.09.010.

Ying E Zhang, Non-Smad pathways in TGF-β2 signaling; Cell Res. Jan. 2009; 19(1): 128-139 doi:10.1038/cr.2008.328.

Zwaagstra et al., Engineering and Therapeutic Application of Single-Chain Bivalent TGF-b Family Traps; Mol Cancer Ther 2012;11(7), 1477-1487. Published Online First May 4, 2012.

FIG. 2A

*Homo sapiens* IgA Fc  GenBank P01876 (amino acids 120-353) (SEQ ID NO:68) 234 aa
```
1    ASPTSPKVFP LSLCSTQPDG NVVIACLVQG FFPQEPLSVT WSESGQGVTA RNFPPSQDAS
61   GDLYTTSSQL TLPATQCLAG KSVTCHVKHY TNPSQDVTVP CPVPSTPPTP SPSTPPTPSP
121  SCCHPRLSLH RPALEDLLLG SEANLTCTLT GLRDASGVTF TWTPSSGKSA VQGPPERDLC
181  GCYSVSSVLP GCAEPWNHGK TFTCTAAYPE SKTPLTATLS KSGNTFRPEV HLLPPPSEEL
241  ALNELVTLTC LARGFSPKDV LVRWLQGSQE LPREKYLTWA SRQEPSQGTT TFAVTSILRV
301  AAEDWKKGDT FSCMVGHEAL PLAFTQKTID RLAGKPTHVN VSVVMAEVDG TCY
```

FIG. 2B

*Homo sapiens* IgD Fc GenBank AAA52770  (amino acids 162-383) (SEQ ID NO:69) 222 aa
```
1    PTKAPDVFPI ISGCRHPKDN SPVVLACLIT GYHPTSVTVT WYMGTQSQPQ RTFPEIQRRD
61   SYYMTSSQLS TPLQQWRQGE YKCVVQHTAS KSKKEIFRWP ESPKAQASSV PTAQPQAEGS
121  LAKATTAPAT TRNTGRGGEE KKKEKEKEEQ EERETKTPEC PSHTQPLGVY LLTPAVQDLW
181  LRDKATFTCF VVGSDLKDAH LTWEVAGKVP TGGVEEGLLE RHSNGSQSQH SRLTLPRSLW
241  NAGTSVTCTL NHPSLPPQRL MALREPAAQA PVKLSLNLLA SSDPPEAASW LLCEVSGFSP
301  PNILLMWLED QREVNTSGFA PARPPPQPRS TTFWAWSVLR VPAPPSPQPA TYTCVVSHED
361  SRTLLNASRS LEVSYVTDHG PMK
```

FIG. 2C

*Homo sapiens* IgE Fc GenBank 1F6A_B (amino acids 6-222) (SEQ ID NO:70) 212 aa
```
1    ADPCDSNPRG VSAYLSRPSP FDLFIRKSPT ITCLVVDLAP SKGTVNLTWS RASGKPVNHS
61   TRKEEKQRNG TLTVTSTLPV GTRDWIEGET YQCRVTHPHL PRALMRSTTK TSGPRAAPEV
121  YAFATPEWPG SRDKRTLACL IQNFMPEDIS VQWLHNEVQL PDARHSTTQP RKTKGSGFFV
181  FSRLEVTRAE WEQKDEFICR AVHEAASPSQ TVQRAVSVNP GK
```

FIG. 2D

**WT *Homo sapiens* IgG1 Fc Sequence (SEQ ID NO:71) 227 aa**
```
1    DKTHTCPPCP APELLGGPSV FLFPPKPKDT LMISRTPEVT CVVVDVSHED PEVKFNWYVD
61   GVEVHNAKTK PREEQYNSTY RVVSVLTVLH QDWLNGKEYK CKVSNKALPA PIEKTISKAK
121  GQPREPQVYT LPPSREEMTK NQVSLTCLVK GFYPSDIAVE WESNGQPENN YKTTPPVLDS
181  DGSFFLYSKL TVDKSRWQQG NVFSCSVMHE ALHNHYTQKS LSLSPGK
```

*Homo sapiens* IgG1 Fc GenBank 3S7G_A  (SEQ ID NO:72) 227 aa
```
1    DKTHTCPPCP APELLGGPSV FLFPPKPKDT LMISRTPEVT CVVVDVSHED PEVKFNWYVD
61   GVEVHNAKTK PREEQYNSTY RVVSVLTVLH QDWLNGKEYK CKVSNKALPA PIEKTISKAK
121  GQPREPQVYT LPPSRDELTK NQVSLTCLVK GFYPSDIAVE WESNGQPENN YKTTPPVLDS
181  DGSFFLYSKL TVDKSRWQQG NVFSCSVMHE ALHNHYTQKS LSLSPGK
```

*Homo sapiens* IgG1 Fc Mutant: L234F/L235E/P331S (Triple Mutant "TM") (SEQ ID NO:73)
```
DKTHTCPPCP APE FE GGPSV FLFPPKPKDT LMISRTPEVT CVVVDVSHED PEVKFNWYVD
GVEVHNAKTK PREEQYNSTY RVVSVLTVLH QDWLNGKEYK CKVSNKALPA SIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGK
```

*Homo sapiens* IgG1 Fc Mutant: N297A (SEQ ID NO:74)
```
DKTHTCPPCP APELLGGPSV FLFPPKPKDT LMISRTPEVT CVVVDVSHED PEVKFNWYVD
GVEVHNAKTK PREEQY A STY RVVSVLTVLH QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGK
```

FIG. 2D (continued)

*Homo sapiens* IgG1 Fc Mutant: L234A/L235A ("LALA") (SEQ ID NO:75)
```
DKTHTCPPCP APEAAGGPSV FLFPPKPKDT LMISRTPEVT CVVVDVSHED PEVKFNWYVD
GVEVHNAKTK PREEQYNSTY RVVSVLTVLH QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGK
```

*Homo sapiens* IgG1 Fc Mutant: (N-terminal Δ10) L234A/L235A ("LALA") L351K, T366S, P395V, F405R, Y407A, and K409Y (SEQ ID NO:76)

```
APEAAGGPS VFLFPPKPK DTLMISRTP EVTCVVVDV SHEDPEVKF NWYVDGVEV HNAKTKPRE
EQYNSTYRV VSVLTVLHQ DWLNGKEYK CKVSNKALP APIEKTISK AKGQPREPQ VYTKPPSRE
EMTKNQVSL SCLVKGFYP SDIAVEWES NGQPENNYK TTVPVLDSD GSFRLASYL TVDKSRWQQ
GNVFSCSVM HEALHNHYT QKSLSLSP
```

*Homo sapiens* IgG1 Fc Mutant: L234A/L235A ("LALA") and T366W Knob-in-Hole "Knob"(SEQ ID NO:77)

```
DKTHTCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPSREEMTK
NQVSLWCLVKGFYPSDIAVEWESNGQPENNYKTTPPVLDSDGSFFLYSKLTVDKSRWQQGNVFSCSVMHE
ALHNHYTQKSLSLSP
```

*Homo sapiens* IgG1 Fc Mutant: L234A/L235A ("LALA") and T366S and L368A Knob-in-Hole "Hole" (SEQ ID NO:78)

```
DKTHTCPPCPAPEAAGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQ
VYTLPPSREEMTKNQVSLSCAVKGFYPSDIAVEWESNGQPENNYKTTPPVLDSDGSFFLVSKLTV
DKSRWQQGNVFSCSVMHEALHNHYTQKSLSLSP
```

Residue numbered according to EU index (Kabat Numbering)

FIG. 2E

*Homo sapiens* IgG2 Fc GenBank AAN76044 (amino acids 99-325) (SEQ ID NO:79) 227 aa
```
1   STKGPSVFPL APCSRSTSES TAALGCLVKD YFPEPVTVSW NSGALTSGVH TFPAVLQSSG
61  LYSLSSVVTV PSSNFGTQTY TCNVDHKPSN TKVDKTVERK CCVECPPCPA PPVAGPSVFL
121 FPPKPKDTLM ISRTPEVTCV VVDVSHEDPE VQFNWYVDGV EVHNAKTKPR EEQFNSTFRV
181 VSVLTVVHQD WLNGKEYKCK VSNKGLPAPI EKTISKTKGQ PREPQVYTLP PSREEMTKNQ
241 VSLTCLVKGF YPSDIAVEWE SNGQPENNYK TTPPMLDSDG SFFLYSKLTV DKSRWQQGNV
301 FSCSVMHEAL HNHYTQKSLS LSPGK
```

FIG. 2F

*Homo sapiens* IgG3 Fc GenBank AAW65947(amino acids 19-246) (SEQ ID NO:80) 238 aa
```
1   HKPSNTKVDK RVELKTPLGD TTHTCPPCPA PELLGGPSVF LFPPKPKDTL MISRTPEVTC
61  VVVDVSHEDP EVKFNWYVDG VEVHNAKTKP REEQYNSTYR VVSVLTVLHQ DWLNGKEYKC
121 KVSNKALPAP IEKTISKAKG QPREPQVYTL PPSRDELTKN QVSLTCLVKG FYPSDIAVEW
181 ESNGQPENNY KTTPPVLDSD GSFFLYSKLT VDKSRWQQGN VFSCSVMHEA LHNHYTQKSL
241 SLSPGK
```

FIG. 2G

Homo sapiens IgG4 Fc GenBank P01861 (amino acids 100-327) (SEQ ID NO:81) 228 aa

```
1    ASTKGPSVFP LAPCSRSTSE STAALGCLVK DYFPEPVTVS WNSGALTSGV HTFPAVLQSS
61   GLYSLSSVVT VPSSSLGTKT YTCNVDHKPS NTKVDKRVES KYGPPCPSCP APEFLGGPSV
121  FLFPPKPKDT LMISRTPEVT CVVVDVSQED PEVQFNWYVD GVEVHNAKTK PREEQFNSTY
181  RVVSVLTVLH QDWLNGKEYK CKVSNKGLPS SIEKTISKAK GQPREPQVYT LPPSQEEMTK
241  NQVSLTCLVK GFYPSDIAVE WESNGQPENN YKTTPPVLDS DGSFFLYSRL TVDKSRWQEG
301  NVFSCSVMHE ALHNHYTQKS LSLSLGK
```

Homo sapiens IgG4 Fc Segment (SEQ ID NO:82) 223 aa

```
1    PPCPSCPAPE FLGGPSVFLF PPKPKDTLMI SRTPEVTCVV VDVSQEDPEV QFNWYVDGVE
61   VHNAKTKPRE EQFNSTYRVV SVLTVLHQDW LNGKEYKCKV SNKGLPSSIE KTISKAKGQP
121  REPQVYTLPP SQEEMTKNQV SLTCLVKGFY PSDIAVEWES NGQPENNYKT TPPVLDSDGS
181  FFLYSRLTVD KSRWQEGNVF SCSVMHEALH NHYTQKSLSL SPG
```

FIG. 2H

Homo sapiens IgM Fc GenBank 0308221A (SEQ ID NO:83) 276 aa

```
1    VTSTLTIKZS DWLGESMFTC RVDHRGLTFQ QNASSMCVPD QDTAIRVFAI PPSFASIFLT
61   KSTKLTCLVT DLTTYBSVTI SWTREENGAV KTHTNISESH PNATFSAVGE ASICEDBDWS
121  GERFTCTVTH TDLPSPLKQT ISRPKGVALH RPBVYLLPPA RZZLNLRESA TITCLVTGFS
181  PADVFVEWMQ RGEPLSPQKY VTSAPMPEPQ APGRYFAHSI LTVSEEEWNT GGTYTCVVAH
241  EALPNRVTER TVDKSTGKPT LYNVSLVMSD TAGTCY
```

FIG. 2I

Homo sapiens J-Chain NCBI Reference Sequence: NP_653247.1 SEQ ID NO:84)

<u>MKNHLLFWGV LAVFIKAVHV</u> KAQEDERIVL VDNKCKCARI TSRIIRSSED PNEDIVERNI
RIIVPLNNRE NISDPTSPLR TRFVYHLSDL CKKCDPTEVE LDNQIVTATQ SNICDEDSAT
ETCYTYDRNK CYTAVVPLVY GGETKMVETA LTPDACYPD

Amino acids 1-22 (underlined) are the signal peptide.

FIG. 2J

Homo sapiens Ig CH1 domain (SEQ ID NO:85)

```
1   FTVRETASTK GPSVFPLAPS SKSTSGGTAA LGCLVKDYFP EPVTVSWNSG ALTSGVHTFP
61  AVLQSSGLYS LSSVVTVPSS SLGTQTYICN VNHKPSNTKV DKKVEPKSCD KT
```

FIG. 2K

Homo sapiens Ig κ chain constant region (SEQ ID NO:86)

```
1   TVAAPSVFIF PPSDEQLKSG TASVVCLLNN FYPREAKVQW KVDNALQSGN SQESVTEQDS
61  KDSTYSLSST LTLSKADYEK HKVYACEVTH QGLSSPVTKS FNRGEC
```

Homo sapiens Ig λ chain constant region(SEQ ID NO:87)

```
1 GQPKANPTVT LFPPSSEELQ ANKATLVCLI SDFYPGAVTV AWKADGSPVK AGVETTKPSK
61 QSNNKYAASS YLSLTPEQWK SHRSYSCQVT HEGSTVEKTV APTECS
```

FIG. 3

*Homo sapiens* TGF-β-1 preproprotein NCBI Ref. Seq. NP_000651.3 (SEQ ID NO:106)

```
1   MPPSGLRLLP LLLPLLWLLV LTPGRPAAGL STCKTIDMEL VKRKRIEAIR GQILSKLRLA
61  SPPSQGEVPP GPLPEAVLAL YNSTRDRVAG ESAEPEPEPE ADYYAKEVTR VLMVETHNEI
121 YDKFKQSTHS IYMFFNTSEL REAVPEPVLL SRAELRLLRL KLKVEQHVEL YQKYSNNSWR
181 YLSNRLLAPS DSPEWLSFDV TGVVRQWLSR GGEIEGFRLS AHCSCDSRDN TLQVDINGFT
241 TGRRGDLATI HGMNRPFLLL MATPLERAQH LQSSRHRRAL DTNYCFSSTE KNCCVRQLYI
301 DFRKDLGWKW IHEPKGYHAN FCLGPCPYIW SLDTQYSKVL ALYNQHNPGA SAAPCCVPQA
361 LEPLPIVYYV GRKPKVEQLS NMIVRSCKCS
```

| | |
|---|---|
| 1..29 | Signal Peptide |
| 29..261 | TGF-β propeptide |
| 244..246 | Cell attachment site |
| 279..390 | mature peptide |
| See also | UniProtKB - P01137 having a P10L substitution in the signal sequence (SEQ ID NO:190) |

*Homo sapiens* TGF-β-2 preproprotein GenBank: AAA50405.1 (SEQ ID NO:109)

```
1   MHYCVLSAFL ILHLVTVALS LSTCSTLDMD QFMRKRIEAI RGQILSKLKL TSPPEDYPEP
61  EEVPPEVISI YNSTRDLLQE KASRRAAACE RERSDEEYYA KEVYKIDMPP FFPSEAIPPT
121 FYRPYFRIVR FDVSAMEKNA SNLVKAEFRV FRLQNPKARV PEQRIELYQI LKSKDLTSPT
181 QRYIDSKVVK TRAEGEWLSF DVTDAVHEWL HHKDRNLGFK ISLHCPCCTF VPSNNYIIPN
241 KSEELEARFA GIDGTSTYTS GDQKTIKSTR KKNSGKTPHL LLMLLPSYRL ESQQTNRRKK
301 RALDAAYCFR NVQDNCCLRP LYIDFKRDLG WKWIHEPKGY NANFCAGACP YLWSSDTQHS
361 RVLSLYNTIN PEASASPCCV SQDLEPLTIL YYIGKTPKIE QLSNMIVKSC KCS
```

| | |
|---|---|
| 1..20 | Signal Peptide |
| 21..227 | TGF-β propeptide |
| 302..413 | mature peptide |

Lys 25, Ile 92, and Lys 94 of the mature peptide are emphasized by bolding, italicization, and underline

*Homo sapiens* TGF-β-3 preproprotein isoform 1 NCBI Ref. Seq. NP_001316868.1 UniProt Ref.: P10600.1 (SEQ ID NO:112)

```
1   MKMHLQRALV VLALLNFATV SLSLSTCTTL DFGHIKKKRV EAIRGQILSK LRLTSPPEPT
61  VMTHVPYQVL ALYNSTRELL EEMHGEREEG CTQENTESEY YAKEIHKFDM IQGLAEHNEL
121 AVCPKGITSK VFRFNVSSVE KNRTNLFRAE FRVLRVPNPS SKRNEQRIEL FQILRPDEHI
181 AKQRYIGGKN LPTRGTAEWL SFDVTDTVRE WLLRRESNLG LEISIHCPCH TFQPNGDILE
241 NIHEVMEIKF KGVDNEDDHG RGDLGRLKKQ KDHHNPHLIL MMIPPHRLDN PGQGGQRKKR
301 ALDTNYCFRN LEENCCVRPL YIDFRQDLGW KWVHEPKGYY ANFCSGPCPY LRSADTTHST
361 VLGLYNTLNP EASASPCCVP QDLEPLTILY YVGRTPKVEQ LSNMVVKSCK CS
```

| | |
|---|---|
| 1..23 | Signal Peptide |
| 24..300 | mature latency associated peptide |
| 24..230 | TGF-β propeptide` |
| 261..263 | Cell attachment site |
| 301..412 | mature peptide |

FIG. 3 (continued)

*Homo sapiens* Mature TGF-β-3 isoform 1 NCBI Ref. Seq. NP_001316868.1 UniProt Ref.: P10600.1, SEQ ID NO:111 (aas 301-412 of SEQ ID NO:112)

```
1  ALDTNYCFRN LEENCCVRPL YIDFRQDLGW KWVHEPKGYY ANFCSGPCPY LRSADTTHST
61 VLGLYNTLNP EASASPCCVP QDLEPLTILY YVGRTPKVEQ LSNMVVKSCK CS
```

*Homo sapiens* Mature TGF-β-3 isoform 1 Mutant: C77S NCBI Ref. Seq. NP_001316868.1 UniProt Ref.: P10600.1, SEQ ID NO:113 (aas 301-412 of SEQ ID NO:112 with a C77S substitution)

```
1  ALDTNYCFRN LEENCCVRPL YIDFRQDLGW KWVHEPKGYY ANFCSGPCPY LRSADTTHST
61 VLGLYNTLNP EASASP*S*CVP QDLEPLTILY YVGRTPKVEQ LSNMVVKSCK CS
```

C77S substitution bolded, underlined, and italicized.

FIG. 4

**Alignment of *Homo sapiens* TGF-β sequences**

```
NP_000651.3      MPPSGLRLLPLLLPLLWLLVLTPGRPAAGLSTCKTIDMELVKRKRIEAIRGQILSKLRLA 60
P01137           MPPSGLRLLLLLLPLLWLLVLTPGRPAAGLSTCKTIDMELVKRKRIEAIRGQILSKLRLA 60
AAA50405.1       --------MHY-CVLSAFLILHLVTVALSLSTCSTLDMDQFMRKRIEAIRGQILSKLKLT 51
NP_001316868.1   ------MKMHLQRALVVLALLNFATVSLSLSTCTTLDFGHIKKKRVEAIRGQILSKLRLT 54
                         :   *   : :*    : .****.*:*:  . :**:***********:*:

NP_000651.3      SPPSQGEVPPGPLPEAVLALYNSTRDRVAGESAE-----PEPEPEADYYAKEVTRVLMVE 115
P01137           SPPSQGEVPPGPLPEAVLALYNSTRDRVAGESAE-----PEPEPEADYYAKEVTRVLMVE 115
AAA50405.1       SPPEDY-PEPEEVPPEVISIYNSTRDLLQEKASRRAAACERERSDEEYYAKEVYKIDMPP 110
NP_001316868.1   SPPEPT-V-MTHVPYQVLALYNSTRELLEEMHGEREEGCTQENTESEYYAKEIHKFDMIQ 112
                 ***.      :*   *:::*****:  :   ..    . . : :*****:  :. *

NP_000651.3      TH---NEIYDKFKQSTHSIYMFFNTSELREAVPEPVLLSRAELRLLRLKL----KVEQHV 168
P01137           TH---NEIYDKFKQSTHSIYMFFNTSELREAVPEPVLLSRAELRLLRLKL----KVEQHV 168
AAA50405.1       FFPSEAI-PPTFYRPYFRIVR-FDVSAME---KNASNLVKAEFRVFRLQNPKARVPEQRI 165
NP_001316868.1   GLAEHNELAVCPKGITSKVFR-FNVSSVE---KNRTNLFRAEFRVLRVPNPSSKRNEQRI 168
                     :    *:.* :.     :   *  :**:*:*:   **::

NP_000651.3      ELYQKYSN-----NSWRYLSNRLLAPSDSPEWLSFDVTGVVRQWLSRGGEIEGFRLSAHC 223
P01137           ELYQKYSN-----NSWRYLSNRLLAPSDSPEWLSFDVTGVVRQWLSRGGEIEGFRLSAHC 223
AAA50405.1       ELYQILKSKDLTSPTQRYIDSKVVKTRAEGEWLSFDVTDAVHEWLHHKDRNLGFKISLHC 225
NP_001316868.1   ELFQILRPDEH-IAKQRYIGGKNLPTRGTAEWLSFDVTDTVREWLLRRESNLGLEISIHC 227
                 **:*         . **...: :        ********..*::**  :    *:..:* **

NP_000651.3      SCDSRDNTLQ-----------V---DINGFTTGRRGDLATIH------GMNRPFLLLMAT 263
P01137           SCDSRDNTLQ-----------V---DINGFTTGRRGDLATIH------GMNRPFLLLMAT 263
AAA50405.1       PCCTFVPSNNYIIPNKSEELEARFAGIDGTSTYTSGDQKTIKSTRKKNSGKTPHLLLMLL 285
NP_001316868.1   PCHTFQPNGD-ILENIHEVMEIKFKGVDNEDDHGRGDLGRLK---KQKDHHNPHLILMMI 283
                  *   :   . :         .::.   **   ::      . : *.*:**

NP_000651.3      PLERAQH--LQSSRHRR**ALDTNYCFSSTEKNCCVRQLYIDFR̲KDLGWKWIHEPKGYHANF** 321
P01137           PLERAQH--LQSSRHRR**ALDTNYCFSSTEKNCCVRQLYIDFR̲KDLGWKWIHEPKGYHANF** 321
AAA50405.1       PSYRLESQ-QTNRRKKR**ALDAAYCFRNVQDNCCLRPLYIDFR̲KDLGWKWIHEPKGYNANF** 344
NP_001316868.1   PPHRLDNPGQGGQRKKR**ALDTNYCFRNLEENCCVRPLYIDFR̲QDLGWKWVHEPKGYYANF** 343
                  *  *  :      .  *::****: ***  . :.**:*  *****::******:****** ***
```

FIG. 4 (continued)

```
NP_000651.3      CLGPCPYIWSLDTQYSKVLALYNQHNPGASAAPCCVPQALEPLPIVYYVGRKPKVEQLSN  381
P01137           CLGPCPYIWSLDTQYSKVLALYNQHNPGASAAPCCVPQALEPLPIVYYVGRKPKVEQLSN  381
AAA50405.1       CAGACPYLWSSDTQHSRVLSLYNTINPEASASPCCVSQDLEPLTILYYIGKTPKIEQLSN  404
NP_001316868.1   CSGPCPYLRSADTTHSTVLGLYNTLNPEASASPCCVPQDLEPLTILYYVGRTPKVEQLSN  403
                 *  * ***:  *  ** :*  **.***   ** ***:****  *  **** *:**:*:.**:*****

NP_000651.3      MIVRSCKCS  390
P01137           MIVRSCKCS  390
AAA50405.1       MIVKSCKCS  413
NP_001316868.1   MVVKSCKCS  412
                 *:*:*****
```

Amino acid positions 25, 77, 92 and 94 of the mature TGF-β sequences are underlinded, and italicized, but not bolded.

FIG. 5A

*Homo sapiens* TGF-β receptor type-1 isoform 1 precursor, NCBI Ref. Seq. NP_004603.1 and UniProtKB/Swiss-Prot: P36897.1 (SEQ ID NO:114)

```
  1   MEAAVAAPRP RLLLLVLAAA AAAAAALLPG ATALQCFCHL CTKDNFTCVT DGLCFVSVTE
 61   TTDKVIHNSM CIAEIDLIPR DRPFVCAPSS KTGSVTTTYC CNQDHCNKIE LPTTVKSSPG
121   LGPVELAAVI AGPVCFVCIS LMLMVYICHN RTVIHHRVPN EEDPSLDRPF ISEGTTLKDL
181   IYDMTTSGSG SGLPLLVQRT IARTIVLQES IGKGRFGEVW RGKWRGEEVA VKIFSSREER
241   SWFREAEIYQ TVMLRHENIL GFIAADNKDN GTWTQLWLVS DYHEHGSLFD YLNRYTVTVE
301   GMIKLALSTA SGLAHLHMEI VGTQGKPAIA HRDLKSKNIL VKKNGTCCIA DLGLAVRHDS
361   ATDTIDIAPN HRVGTKRYMA PEVLDDSINM KHFESFKRAD IYAMGLVFWE IARRCSIGGI
421   HEDYQLPYYD LVPSDPSVEE MRKVVCEQKL RPNIPNRWQS CEALRVMAKI MRECWYANGA
481   ARLTALRIKK TLSQLSQQEG IKM
```

| | |
|---|---|
| 1..33 | signal peptide |
| 34-126 | extracellular region (ectodomain) |
| 127-147 | transmembrane region |
| 176..203 | Transforming growth factor beta type I GS-motif |
| 205..492 | Protein tyrosine kinase |
| 209..496 | Catalytic domain of the Serine/Threonine Kinases, |

*Homo sapiens* TGF-β receptor type-1 isoform 1 ectodomain (SEQ ID NO:115)

```
 34   LQCFCHL CTKDNFTCVT DGLCFVSVTE TTDKVIHNSM CIAEIDLIPR DRPFVCAPSS

91   KTGSVTTTYC CNQDHCNKIE LPTTVKSSPG LGPVEL
```

FIG. 5B

*Homo sapiens* TGF-β receptor type-2 (TβRII) isoform A precursor NCBI Ref. Seq. NP_001020018.1 (SEQ ID NO:116)

```
1    MGRGLLRGLW PLHIVLWTRI ASTIPPHVQK SDVEMEAQKD EIICPSCNRT AHPLRHINND
61   MIVTDNNGAV KFPQLCKFCD VRFSTCDNQK SCMSNCSITS ICEKPQEVCV AVWRKNDENI
121  TLETVCHDPK LPYHDFILED AASPKCIMKE KKKPGETFFM CSCSSDECND NIIFSEEYNT
181  SNPDLLLVIF QVTGISLLPP LGVAISVIII FYCYRVNRQQ KLSSTWETGK TRKLMEFSEH
241  CAIILEDDRS DISSTCANNI NHNTELLPIE LDTLVGKGRF AEVYKAKLKQ NTSEQFETVA
301  VKIFPYEEYA SWKTEKDIFS DINLKHENIL QFLTAEERKT ELGKQYWLIT AFHAKGNLQE
361  YLTRHVISWE DLRKLGSSLA RGIAHLSDH  TPCGRPKMPI VHRDLKSSNI LVKNDLTCCL
421  CDFGLSLRLD PTLSVDDLAN SGQVGTARYM APEVLESRMN LENVESFKQT DVYSMALVLW
481  EMTSRCNAVG EVKDYEPPFG SKVREHPCVE SMKDNVLRDR GRPEIPSFWL NHQGIQMVCE
541  TLTECWDHDP EARLTAQCVA ERFSELEHLD RLSGRSCSEE KIPEDGSLNT TK
```

| | |
|---|---|
| 1..23 | signal peptide |
| 24..592 | mature peptide |
| 24..177 | extracellular region (ectodomain) |

*Homo sapiens* TGF-β receptor type-2 (TβRII) isoform A ectodomain(SEQ ID NO:117)

```
24   IPPHVQK    SDVEMEAQKD EIICPSCNRT AHPLRHINND MIVTDNNGAV KFPQLCKFCD
80              VRFSTCDNQK SCMSNCSITS ICEKPQEVCV AVWRKNDENI TLETVCHDPK
130             LPYHDFILED AASPKCIMKE KKKPGETFFM CSCSSDECND NIIFSEE
```

*Homo sapiens* TGF-β receptor type-2 (TβRII) isoform B precursor, UniProtKB Ref. P37173, NCBI Ref. Seq. NP_003233.4 (SEQ ID NO:118)

```
1    MGRGLLRGLW PLHIVLWTRI ASTIPPHVQK SVNNDMIVTD NNGAVKFPQL CKFCDVRFST
61   CDNQKSCMSN CSITSICEKP QEVCVAVWRK NDENITLETV CHDPKLPYHD FILEDAASPK
121  CIMKEKKKPG ETFFMCSCSS DECNDNIIFS EEYNTSNPDL LLVIFQVTGI SLLPPLGVAI
181  SVIIIFYCYR VNRQQKLSST WETGKTRKLM EFSEHCAIIL EDDRSDISST CANNINHNTE
241  LLPIELDTLV GKGRFAEVYK AKLKQNTSEQ FETVAVKIFP YEEYASWKTE KDIFSDINLK
301  HENILQFLTA EERKTELGKQ YWLITAFHAK GNLQEYLTRH VISWEDLRKL GSSLARGIAH
361  LHSDHTPCGR PKMPIVHRDL KSSNILVKND LTCCLCDFGL SLRLDPTLSV DDLANSGQVG
421  TARYMAPEVL ESRMNLENVE SFKQTDVYSM ALVLWEMTSR CNAVGEVKDY EPPFGSKVRE
481  HPCVESMKDN VLRDRGRPEI PSFWLNHQGI QMVCETLTEC WDHDPEARLT AQCVAERFSE
541  LEHLDRLSGR SCSEEKIPED GSLNTTK
```

| | |
|---|---|
| 1..23 | Signal peptide (As noted below, NCBI records report the signal sequence to be aas 1-22.) |
| 24..567 | Mature peptide |
| 24..166 | Transforming growth factor beta receptor 2 ectodomain |

*Homo sapiens* TGF-β receptor type-2 (TβRII) isoform B, ectodomain sequence (SEQ ID NO:119)

```
                                      30 32                    52 55
                                      |  |                     |  |
1    IPPHVQKSVN NDMIVTDNNG AVKFPQLCKF CDVRFSTCDN QKSCMSNCSI TSICEKPQEV

118
                                                                  |
61   CVAVWRKNDE NITLETVCHD PKLPYHDFIL EDAASPKCIM KEKKKPGETF FMCSCSSDEC

121  NDNIIFSEEY NTSNPDLLLV IFQ
```

FIG. 5B (Continued)

***Homo sapiens* TGF-β receptor type-2 (TβRII) isoform B, ectodomain fragment sequence (SEQ ID NO:120)**

```
                          30 32                       52 55
                          |  |                        |  |
1    IPPHVQKSVN NDMIVTDNNG AVKFPQLCKF CDVRFSTCDN QKSCMSNCSI TSICEKPQEV
                                                  118
                                                   |
61   CVAVWRKNDE NITLETVCHD PKLPYHDFIL EDAASPKCIM KEKKKPGETF FMCSCSSDEC

121  NDNIIFSEE
```

***Homo sapiens* TGF-β receptor type-2 isoform B, ectodomain fragment Δ14 (N-terminus) D118A (SEQ ID NO:121)**

```
                30 32                        52 55
                |  |                         |  |
15   TDNNG AVKFPQLCKF CDVRFSTCDN QKSCMSNCSI TSICEKPQEV CVAVWRKNDE
NITLETVCHD
                                    118
                                     |
80   PKLPYHDFIL EDAASPKCIM KEKKKPGETF FMCSCSSAEC NDNIIFSEE
```

***Homo sapiens* TGF-β receptor type-2 (TβRII) isoform B, ectodomain fragment Δ25 (N-terminus) D118A (SEQ ID NO:122)**

```
         30 32                       52 55
         |  |                        |  |
26   QLCKF CDVRFSTCDN QKSCMSNCSI TSICEKPQEV CVAVWRKNDE NITLETVCHD
                                             118
                                              |
80         PKLPYHDFIL EDAASPKCIM KEKKKPGETF FMCSCSSAEC NDNIIFSEE
```

***Homo sapiens* TGF-β receptor type-2 (TβRII) isoform B, ectodomain fragment Δ25 (N-terminus), D118A ectodomain sequence (SEQ ID NO:123)**

```
26   QLCKF CDVRFSTCDN QKSCMSNCSI TSICEKPQEV CVAVWRKNDE NITLETVCH

80         DPKLPYHDFI LEDAASPKCI MKEKKKPGET FFMCSCSSAE CNDNIIFSE EYNTSNPD
```

Based upon NCBI Ref. Seq. NP_003233.4, and UniProtKB Ref. P37173; with the sequence corresponding to aas 49 to 159 of those sequences. The substitution at aspartic acid "D119" of the mature protein with an alanine "*A*" (bolded, italicized, and underlined) is marked as a "D118A" substitution for consistency with the literature describing that substitution. Note that aa D119 numbering is based on the mature protein, and accordingly it is D 141 of the precursor protein when the 22 aa signal sequence is included. The location of D32, sometimes substituted with asparagine (D32N), is also shown bolded, italicized, and underlined. D32 in corresponds to D55 in the precursor protein.

FIG. 5C

*Homo sapiens* TGF-β receptor type 3 isoform A precursor, (BETA Glycan), NCBI Ref. Seq. NP_003234.2 and UniProtKB/Swiss-Prot: Q03167.3 (SEQ ID NO:124)

```
1    MTSHYVIAIF ALMSSCLATA GPEPGALCEL SPVSASHPVQ ALMESFTVLS GCASRGTTGL
61   PQEVHVLNLR TAGQGPGQLQ REVTLHLNPI SSVHIHHKSV VFLLNSPHPL VWHLKTERLA
121  TGVSRLFLVS EGSVVQFSSA NFSLTAETEE RNFPHGNEHL LNWARKEYGA VTSFTELKIA
181  RNIYIKVGED QVFPPKCNIG KNFLSLNYLA EYLQPKAAEG CVMSSQPQNE EVHIIELITP
241  NSNPYSAFQV DITIDIRPSQ EDLEVVKNLI LILKCKKSVN WVIKSFDVKG SLKIIAPNSI
301  GFGKESERSM TMTKSIRDDI PSTQGNLVKW ALDNGYSPIT SYTMAPVANR FHLRLENNAE
361  EMGDEEVHTI PPELRILLDP GALPALQNPP IRGGEGQNGG LPFPFPDISR RVWNEEGEDG
421  LPRPKDPVIP SIQLFPGLRE PEEVQGSVDI ALSVKCDNEK MIVAVEKDSF QASGYSGMDV
481  TLLDPTCKAK MNGTHFVLES PLNGCTRPR  WSALDGVVYY NSIVIQVPAL GDSSGWPDGY
541  EDLESGDNGF PGDMDEGDAS LFTRPEIVVF NCSLQQVRNP SSFQEQPHGN ITFNMELYNT
601  DLFLVPSQGV FSVPENGHVY VEVSVTKAEQ ELGFAIQTCF ISPYSNPDRM SHYTIIENIC
661  PKDESVKFYS PKRVHFPIPQ ADMDKKRFSF VFKPVFNTSL LFLQCELTLC TKMEKHPQKL
721  PKCVPPDEAC TSLDASIIWA MMQNKKTFTK PLAVIHHEAE SKEKGPSMKE PNPISPPIFH
781  GLDTLTVMGI AFAAFVIGAL LTGALWYIYS HTGETAGRQQ VPTSPPASEN SSAAHSIGST
841  QSTPCSSSST A
```

| | |
|---|---|
| 1..18 | Signal peptide |
| 27..787 | Extracellular domain (ectodomain) |
| 788-809 | Transmembrane domain |
| 567..724 | Zona pellucida-like domain |
| 737..751 | Interaction with TGF-beta ligand |
| 788..809 | site_type="transmembrane region" |

*Homo sapiens* TGF-β receptor type 3 isoform B precursor, (BETA Glycan) NCBI Ref. Seq. NP_001182612.1 and (SEQ ID NO:125)

```
1    MTSHYVIAIF ALMSSCLATA GPEPGALCEL SPVSASHPVQ ALMESFTVLS GCASRGTTGL
61   PQEVHVLNLR TAGQGPGQLQ REVTLHLNPI SSVHIHHKSV VFLLNSPHPL VWHLKTERLA
121  TGVSRLFLVS EGSVVQFSSA NFSLTAETEE RNFPHGNEHL LNWARKEYGA VTSFTELKIA
181  RNIYIKVGED QVFPPKCNIG KNFLSLNYLA EYLQPKAAEG CVMSSQPQNE EVHIIELITP
241  NSNPYSAFQV DITIDIRPSQ EDLEVVKNLI LILKCKKSVN WVIKSFDVKG SLKIIAPNSI
301  GFGKESERSM TMTKSIRDDI PSTQGNLVKW ALDNGYSPIT SYTMAPVANR FHLRLENNEE
361  MGDEEVHTIP PELRILLDPG ALPALQNPPI RGGEGQNGGL PFPFPDISRR VWNEEGEDGL
421  PRPKDPVIPS IQLFPGLREP EEVQGSVDIA LSVKCDNEKM IVAVEKDSFQ ASGYSGMDVT
481  LLDPTCKAKM NGTHFVLESP LNGCTRPRW  SALDGVVYYN SIVIQVPALG DSSGWPDGYE
541  DLESGDNGFP GDMDEGDASL FTRPEIVVFN CSLQQVRNPS SFQEQPHGNI TFNMELYNTD
601  LFLVPSQGVF SVPENGHVYV EVSVTKAEQE LGFAIQTCFI SPYSNPDRMS HYTIIENICP
661  KDESVKFYSP KRVHFPIPQA DMDKKRFSFV FKPVFNTSLL FLQCELTLCT KMEKHPQKLP
721  KCVPPDEACT SLDASIIWAM MQNKKTFTKP LAVIHHEAES KEKGPSMKEP NPISPPIFHG
781  LDTLTVMGIA FAAFVIGALL TGALWYIYSH TGETAGRQQV PTSPPASENS SAAHSIGSTQ
841  STPCSSSSTA
```

| | |
|---|---|
| 1..18 | Signal peptide |
| 27..786 | Extracellular domain (ectodomain) |
| 566..723 | Zona pellucida-like domain |
| 736..750 | Interaction with TGF-beta ligand |
| 787..808 | site_type="transmembrane region" |

FIG. 6A
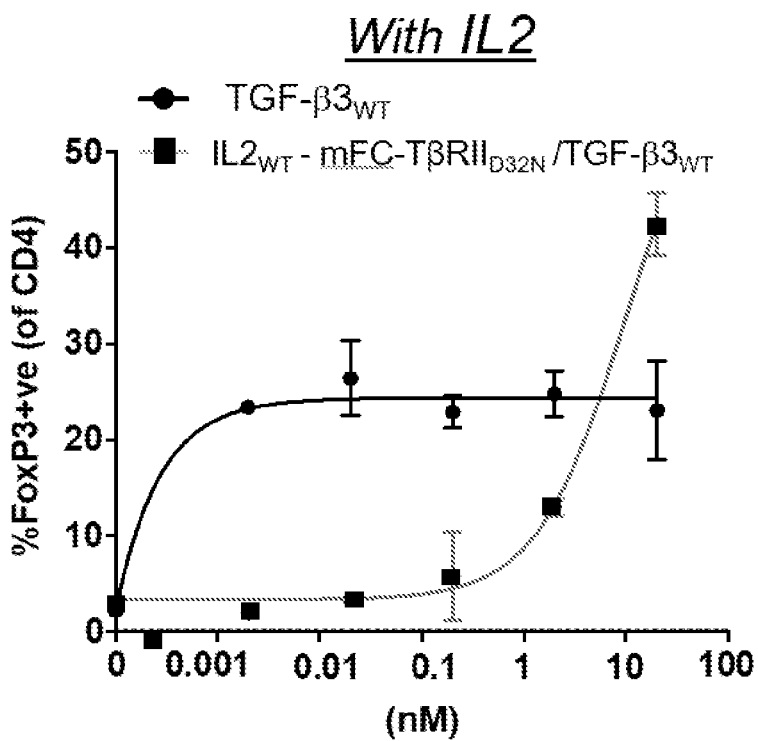
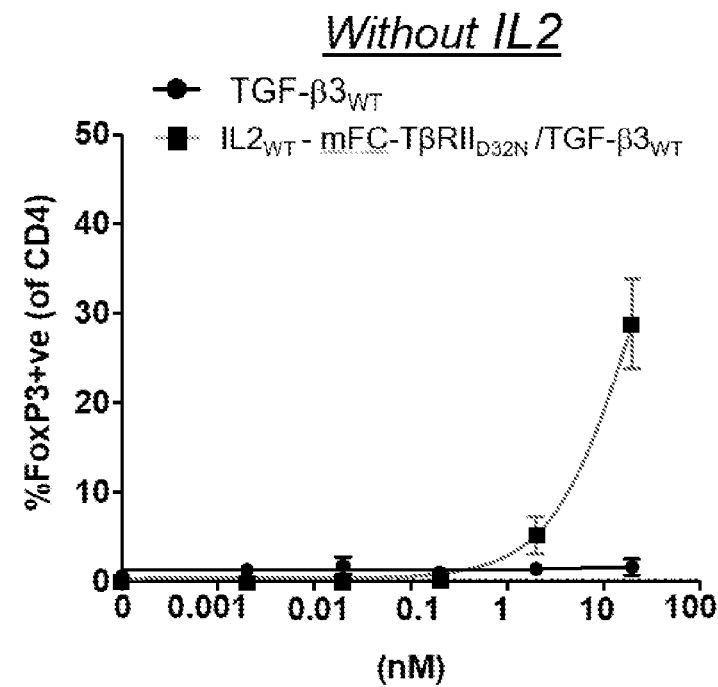

FIG. 7D

APTSSSTKKTQLQLEHLLLDLQMILNGINNYKNPKLTRMLTFKFYMPKKATELKHLQCLEEELKPLEEVLNLAQSKNFHLRPRDL
ISNINVIVLELKGSETTFMCEYADETATIVEFLNRWITFCQSIISTLTGGGGSGGGGSGGGGSGGGGSDKTHTCPPCPAPEAAGGPSVFLFPP
KPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLWCLVKGFYPSDIAVEWESNGQPENNYKTTPPVLDSDGSFFLYSKLT
VDKSRWQQGNVFSCSVMHEALHNHYTQKSLSLSPGGGGSGGGGSGGGGSGGGGSALDTNYCFRNLEENCCVRPLYI
DFRQDLGWKWVHEPKGYYANFCSGPCPYLRSADTTHSTVLGLYNTLNPEASASPSCVPQDLEPLTILYYVGRTPKVEQLSNMV
VKSCKCS

APTSSSTKKTQLQLEHLLLDLQMILNGINNYKNPKLTRMLTFKFYMPKKATELKHLQCLEEELKPLEEVLNLAQSKNFHLRPRDLISNINVI
[hIL2(wt)]

VLELKGSETTFMCEYADETATIVEFLNRWITFCQSIISTLTGGGGSGGGGSGGGGSGGGGSDKTHTCPPCPAPEAAGGPSVFLFPPKPKDTLMISRT
[hIL2(wt)] [hIgG1 Fc (LALA) KiH, chain A]

PEVTCVVVDVSHEDPEVKFNWYVDGVEVHNAKTKPREEQYNSTYRVVSVLTVLHQDWLNGKEYKCKVSNKALPAPIEKTISKAKGQPREPQV
[hIgG1 Fc (LALA) KiH, chain A]

YTLPPSREEMTKNQVSLWCLVKGFYPSDIAVEWESNGQPENNYKTTPPVLDSDGSFFLYSKLTVDKSRWQQGNVFSCSVMHEALHNHYTQKS
[hIgG1 Fc (LALA) KiH, chain A]

LSLSPGGGGSGGGGSGGGGSGGGGSALDTNYCFRNLEENCCVRPLYIDFRQDLGWKWVHEPKGYYANFCSGPCPYLRSADTTHSTV
[hTGFbeta-3 (C77S)]

LGLYNTLNPEASASPSCVPQDLEPLTILYYVGRTPKVEQLSNMVVKSCKCS
[hTGFbeta-3 (C77S)]

FIG. 7E

APTSSSTKKTQLQLETLLLDLQMILNGINNYKNPKLTRMLTAKFYMPKKATELKHLQCLEEELKPLEEVLNLAQSKNFHLRPRDL
ISNINVIVLELKGSETTFMCEYADETATIVEFLNRWITFCQSIISTLT*GGGGSGGGGSGGGGS*DKTHTCPPCPAPE*AA*GGPSVFLPP
KPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSL*W*CLVKGFYPSDIAVEWESNGQPENNYKTTPPVLDSDGSFFLYSKLT
VDKSRWQQGNVFSCSVMHEALHNHYTQKSLSLSP*GGGGSGGGGSGGGGS*QLCKFCDVRFSTCDNQKSCMSNCSITSICEKPQ
EVCCAVWRKNDENITLETVCHDPKLPYHDFILEDAASPKCIMKEKKKPGETFFMCSCSSAECNDNIIFSEEYNTSNPD*GGGSGG
GGS*GGGGSGGGGSGGGGSALDTNYCFRNLEENCCVRPLYIDFRQDLGWKWVHEPKGYYANFCSGPCYLRSADTTHSTVLGL
YNTLNPEASASP*S*CVPQDLEPLTILYYVGRTPKVEQLSNMVVKSCKCS

APTSSSTKKTQLQLETLLLDLQMILNGINNYKNPKLTRMLTAKFYMPKKATELKHLQCLEEELKPLEEVLNLAQSKNFHLRPRDLISNINVI

VLELKGSETTFMCEYADETATIVEFLNRWITFCQSIISTLTGGGGSGGGGSGGGGSDKTHTCPPCPAPEAAGGPSVFLFPPKPKDTLMISRT

PEVTCVVVDVSHEDPEVKFNWYVDGVEVHNAKTKPREEQYNSTYRVVSVLTVLHQDWLNGKEYKCKVSNKALPAPIEKTISKAKGQPREPQV

YTLPPSREEMTKNQVSLWCLVKGFYPSDIAVEWESNGQPENNYKTTPPVLDSDGSFFLYSKLTVDKSRWQQGNVFSCSVMHEALHNHYTQKS

LSLSPGGGGSGGGGSGGGGSQLCKFCDVRFSTCDNQKSCMSNCSITSICEKPQEVCCAVWRKNDENITLETVCHDPKLPYHDFILEDAASP

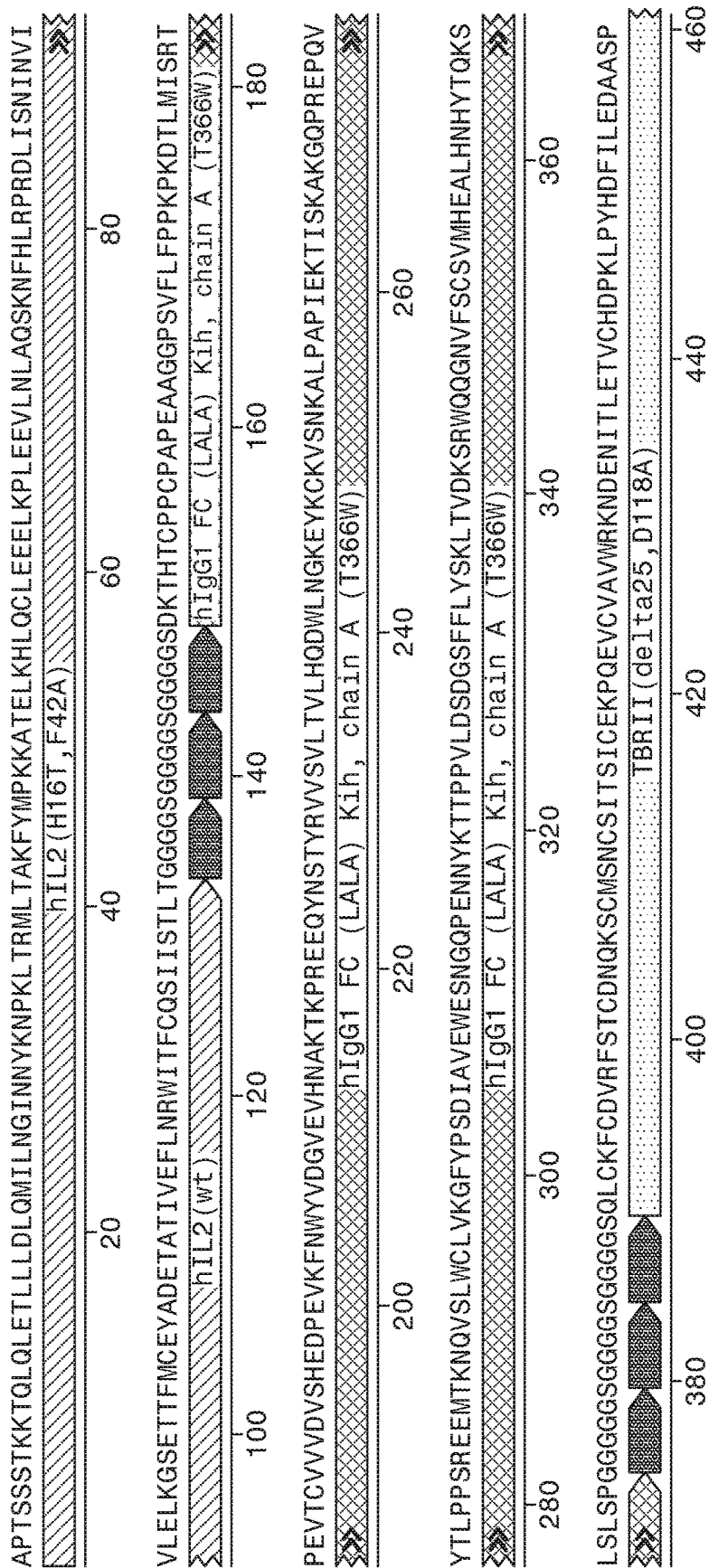

FIG. 7E (continued)

KCIMKEKKKPGETFFMCSCSSAECNDNIIFSEEYNTSNPDGGGGSGGGGSGGGGSGGGGSALDTNYCFRNLEENCCVRPLYIDFRQD

LGWKWWHEPKGYYANFCSGPCPYLRSADTTHSTVLGLYNTLNPEASASPSCVPQDLEPLTILYYVGRTPKVEQLSNMVVKSCKCS

3664

DKTHTCPPCPAPEAAGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEWESNGQPE
NNYKTTPPVLDSDGSFFLVSKLTVDKSRWQQGNVFSCSVMHEALHNHYTQKSLSLSPG

DKTHTCPPCPAPEAAGGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLSCAVKGFYPSDIAVEWESNGQPENNYKTTPPVLDSDGSF

FLVSKLTVDKSRWQQGNVFSCSVMHEALHNHYTQKSLSLSPG

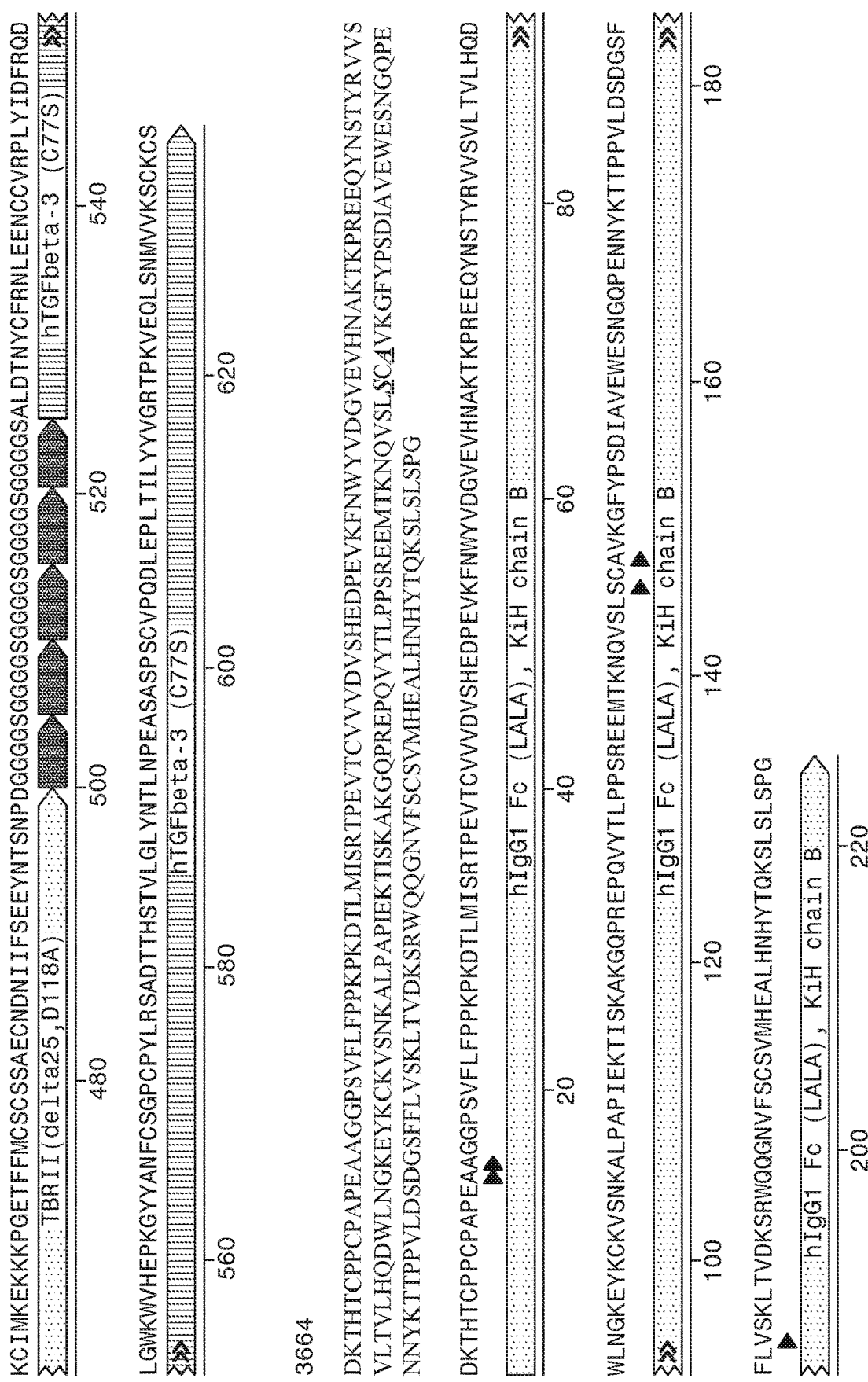

FIG. 7F (continued)

DKTHTCPPCPAPEAAGGPSVFLFPPKPKDTLMISRTPEVTCVVVDVSHEDPEVKFNWYVDGVEVHNAKTPREEQYNSTYRVVS
VLTVLHQDWLNGKEYKCKVSNKALPAPIEKTISKAKGQPREPQVYTLPPSREEMTKNQVSLWCLVKGFYPSDIAVEWESNGQPE
NNYKTTPPVLDSDGSFFLYSKLTVDKSRWQQGNVFSCSVMHEALHNHYTQKSLSLSPGGGGSGGGGSGGGGSAPTSSSTKKT
QLQLEHLLLDLQMILNGINNYKNPKLTRMLTFKFYMPKKATELKHLQCLEEELKPLEEVLNLAQSKNFHLRPRDLISNINVLEL
KGSETTFMCEYADETATIVEFLNRWITFCQSIISTLT

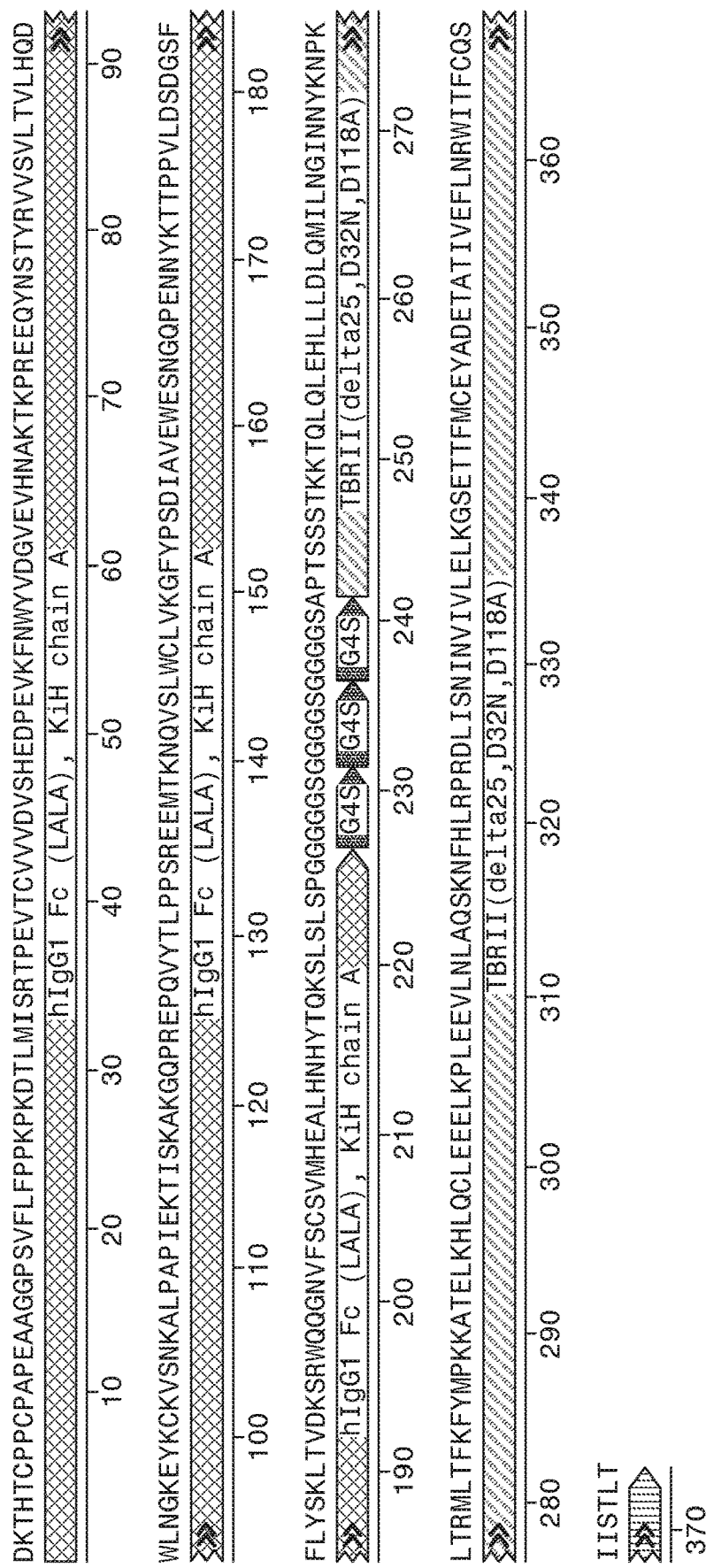

FIG. 7G

APTSSSTKKTQLQLEHLLLDLQMILNGINNYKNPKLTRMLTFKFYMPKKATELKHLQCLEEELKPLEEVLNLAQSKNFHLRPRDL
ISNINVIVLELKGSETTFMCEYADETATIVEFLNRWITFCQSIISTLTGGGGSGGGGSGGGGSAPEAAGGPSVFLFPPKDTLMISR
TPEVTCVVVDVSHEDPEVKFNWYVDGVEVHNAKTKPREEQYNSTYRVVSVLTVLHQDWLNGKEYKCKVSNKALPAPIEKTISK
AKGQPREPQVYTKPPSREEMTKNQVSLSCLVKGFYPSDIAVEWESNGQPENNYKTTVPLDSDGSFRLASYLTVDKSRWQQGN
VFSCSVMHEALHNHYTQKSLSLSPGGGGSGGGGSQLCKFCNVRFSTCDNQKSCMSNCSITSICEKPQEVCVAVWRKN
GSGGGGSALDTNYCFRNLEENCCVRPLYIDFRQDLGWKWVHEPKGYYANFCSGPCPYLRSADTTHSTVLGLYNTLNPEASASPS
CVPQDLEPLTILYYVGRTPKVEQLSNMVVKSCKCS

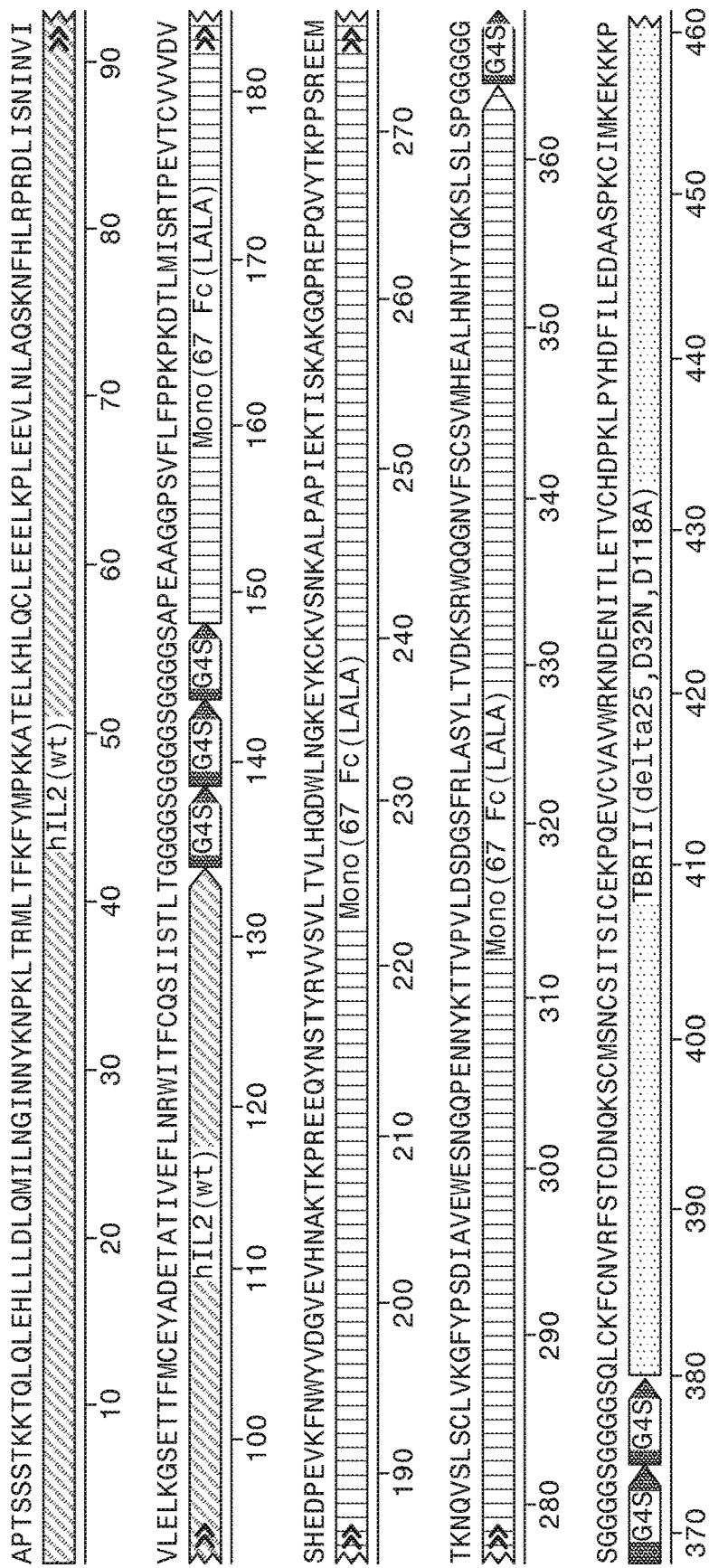

FIG. 7J

APTSSSTKKTQLQLEHLLLDLQMILNGINNYKNPKLTRMLTFKFYMPKKATELKHLQCLEEELKPLEEVLNLAQSKNFHLRPRDL
ISNINVIVLELKGSETTFMCEYADETATIVEFLNRWITFCQSIISTLTGGGSGGGGSGGGGSDKTHTCPPCPAPEAAGGPSVFLFPP
KPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLSCAVKGFYPSDIAVEWESNGQPENNYKTTPPVLDSDGSFFLVSKLTV
DKSRWQQGNVFSCSVMHEALHNHYTQKSLSLSPGGGGSGGGGSGGGGSQLCKFCNVRFSTCDNQKSCMSNCSITSICEKPQE
VCVAVWRKNDENITLETVCHDPKLPYHDFILEDAASPKCIMKEKKKPGETFFMCSCSSAECNDNIIFSEEYNTSNPD

APTSSSTKKTQLQLEHLLLDLQMILNGINNYKNPKLTRMLTFKFYMPKKATELKHLQCLEEELKPLEEVLNLAQSKNFHLRPRDLISNINVI
         hIL2(wt)
10        20        30        40        50        60        70        80        90

VLELKGSETTFMCEYADETATIVEFLNRWITFCQSIISTLTGGGSGGGGSGGGGSDKTHTCPPCPAPEAAGGPSVFLFPPKPKDTLMISRT
         hIL2(wt)              G4S  G4S  G4S       hIgG1 Fc (LALA), KiH chain B
100       110       120       130       140       150       160       170       180

PEVTCVVVDVSHEDPEVKFNWYVDGVEVHNAKTKPREEQYNSTYRVVSVLTVLHQDWLNGKEYKCKVSNKALPAPIEKTISKAKGQPREPQV
                    hIgG1 Fc (LALA), KiH chain B
190       200       210       220       230       240       250       260       270

YTLPPSREEMTKNQVSLSCAVKGFYPSDIAVEWESNGQPENNYKTTPPVLDSDGSFFLVSKLTVDKSRWQQGNVFSCSVMHEALHNHYTQKS
                    hIgG1 Fc (LALA), KiH chain B
280       290       300       310       320       330       340       350       360

LSLSPGGGGSGGGGSGGGGSQLCKFCNVRFSTCDNQKSCMSNCSITSICEKPQEVCVAVWRKNDENITLETVCHDPKLPYHDFILEDAASP
     G4S  G4S  G4S       TBRII(delta25,D32N,D118A)
370       380       390       400       410       420       430       440       450       460

KCIMKEKKKPGETFFMCSCSSAECNDNIIFSEEYNTSNPD
     TBRII(delta25,D32N,D118A)
470       480       490       500

| Mutation | Kd (µM) TGF-β1 | Kd (µM) TGF-β3 |
|---|---|---|
| Δ14 | 0.32 | 0.68 |
| L27A | 7.97 | 14.8 |
| F30A | 44.0 | 104 |
| D32A | 3.52 | 8.87 |
| D32N | 5.90 | 19.9 |
| S49A | 0.79 | 1.18 |
| I50A | 7.96 | 16.7 |
| T51A | 2.97 | 8.75 |
| S52A | 0.60 | 0.98 |
| S52L | 154 | 620 |
| I53A | 2.49 | 6.87 |
| E55A | 2.99 | 5.30 |
| V77A | 0.69 | 1.37 |
| D118A | 1.51 | 2.69 |
| E119A | 3.35 | 8.47 |
| E119Q | 5.95 | 10.6 |

PSM-4033-4039

FIG. 10B

Construct 4033 (SEQ ID NO:191)

APTSSSTKKTQLQLEALLLDLQMILNGINNYKNPKLTRMLTAKFYMPKKATELKHLQCLE
EELKPLEEVLNLAQSKNFHLRPRDLISNINVIVLELKGSETTFMCEYADETATIVEFLNRWIT
FCQSIISTLTGGGGSGGGGSGGGGSDKTHTCPPCPAPEAAGGPSVFLFPPKPKDTLMISRTPE
VTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPCREEMTKNQVSLWCLVKGFYPSDI
AVEWESNGQPENNYKTTPPVLDSDGSFFLYSKLTVDKSRWQQGNVFSCSVMHEALHNHY
TQKSLSLSPGGGGGSGGGGSGGGGSGGGGSGGGGSALDTNYCFRNLEENCCVRPLYIDFR
QDLGWKWVHEPKGYYANFCSGPCPYLRSADTTHSTVLGLYNTLNPEASASPSCVPQDLEP
LTILYYVGRTPKVEQLSNMVVKSCKCS

FIG. 10C

Construct 4039 (SEQ ID NO:192)

DKTHTCPPCPAPEAAGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKG
QPREPQVCTLPPSREEMTKNQVSLSCAVKGFYPSDIAVEWESNGQPENNYKTTPPVLDSDG
SFFLVSKLTVDKSRWQQGNVFSCSVMHEALHNHYTQKSLSLSPGGGGGSGGGGSGGGGS
QLCKFCDVRFSTCDNQKSCMSNCSITSICEKPQEVCVAVWRKNDENITLETVCHDPKLPYH
DFILEDAASPKCIMKEKKKPGETFFMCSCSSAECNDNIIFSEEYNTSNPD

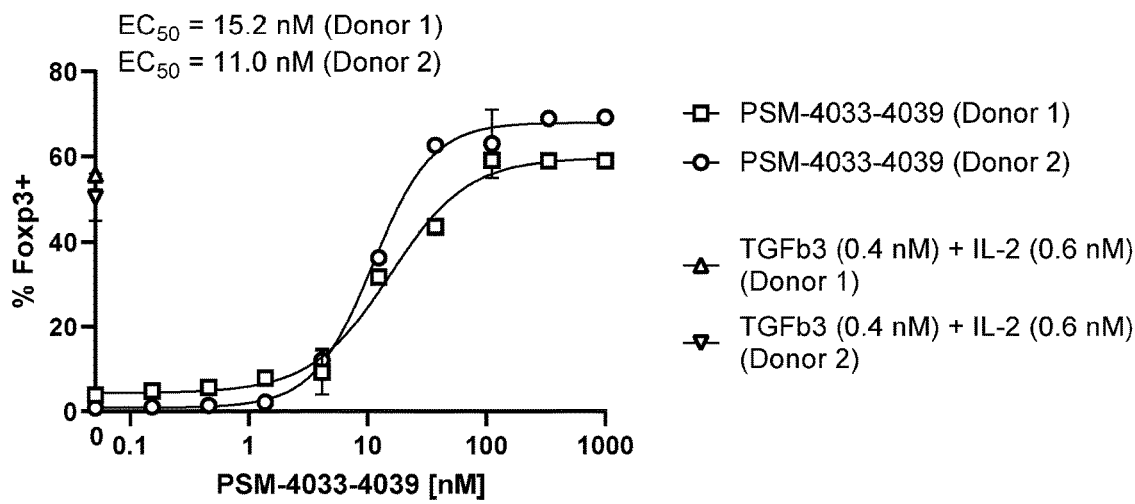

FIG. 11

TGF-β POLYPEPTIDES

CROSS-REFERENCE TO RELATED APPLICATIONS

This application is a continuation of International Application No. PCT/US2020/056937, filed Oct. 22, 2020, which claims the benefit of U.S. Provisional Application No. 62/925,227, filed Oct. 23, 2019.

INCORPORATION BY REFERENCE OF SEQUENCE LISTING

This application contains a sequence listing submitted electronically, which serves as both the paper copy and the computer readable form (CRF) and consists of a file entitled "2910-12_PCT-CON_seqlist.txt", which was created on Apr. 16, 2022, which is 342,012 bytes in size, and which is herein incorporated by reference in its entirety.

I. INTRODUCTION

A. TGF-β and its Actions

Transforming growth factor beta (TGF-β) is a cytokine belonging to the transforming growth factor superfamily that includes three mammalian (human) isoforms, TGF-β1, TGF-β2, and TGF-β3. TGF-βs are synthesized as precursor molecules containing a propeptide region in addition to the TGF-β sequences that homodimerize as an active form of TGF-β. TGF-β is secreted by macrophages and other cell types in a latent complex in which it is combined with two other polypeptides—latent TGF-β binding protein (LTBP) and latency-associated peptide (LAP). The latent TGF-β complex is stored in the extra cellular matrix (ECM), for example, bound to the surface of cells by CD36 via thrombospondin-1 (where it can be activated by plasmin) or to latent transforming growth factor beta binding proteins 1, 2, 3, and/or 4 (LTBP1-4).

The biological functions of TGF-β are seen after latent TGF-β activation, which is tightly regulated in response to ECM perturbations. TGF-β may be activated by a variety of cell or tissue specific pathways, or pathways observed in multiple cell or tissue types; however, the full mechanisms behind such activation pathways are not fully known. Activators include, but are not limited to, proteases, integrins, pH, and reactive oxygen species (ROS). In effect, the cell/tissue bound latent TGF-β complex functions, senses and responds to environmental perturbations releasing active TGF-β in a spatial and/or temporal manner. The released TGF-β acts to promote or inhibit cell proliferation depending on the context of its release. It also recruits stem/progenitor cells to participate in the tissue regeneration/remodeling process. Aberrations in TGF-β ligand expression, bioavailability, activation, receptor function, or post-transcriptional modifications disturb the normal function, and can lead to pathological consequences associated with many diseases, such as through the recruitment of excessive progenitors (e.g., in osteoarthritis or Camurati-Engelmann disease), or by the trans-differentiation of resident cells to unfavorable lineages (e.g., in epithelial to mesenchymal transition during cancer metastasis or tissue/organ fibrosis). Xu et al *Bone Research*, 6 (Article No. 2) (2018).

1 Integrin-Independent and Integrin-Dependent Activation a. Integrin-Independent Activation Among the integrin-independent means of TGF-β activation are those that work through the action of, among other things, proteases and/or metalloproteases, reactive oxygen species (ROS), and thrombospondin-1.

Plasmin and several matrix metalloproteinases (MMPs) promote tumor invasion and tissue remodeling by proteolysis of extracellular matrix components. The TGF-β may become activated by the action of such proteases that release the latent complex from the matrix, which is followed by proteolysis of the LAP to release TGF-β to its receptors. Both matrix metalloprotease −9 and −2 are known to cleave latent TGF-β.

TGF-β has been shown to be rapidly activated in vivo following radiation exposure to induce ROS release. ROS are thought to alter the interaction between LAP and TGF-β, leading to its activation.

Thrombospondin-1 (TSP-1), a glycoprotein found in plasma of healthy individuals, is known to increase in response to injury. TSP-1 is believed to activate latent TGF-β by forming direct interactions with the latent TGF-β complex and preventing it from binding to the matured TGF-β. Thrombospondin mediated activation is believed to be involved in wound (e.g., dermal wound) healing.

b. Activation by Alpha(V) Containing Integrins

Integrins, and particularly β6, αV, and β8 containing integrins, are understood to contribute to latent TGF-β (e.g., TGF-β1) activation. Activation appears to occur by inducing conformational changes to the latent TGF-β1 complex and hence releasing the active TGF-β1 or by an integrin-protease-dependent mechanism. Conformational changes leading to TGF-β1 activation without proteolysis, particularly in epithelial cells, are understood to occur through integrin binding an Arginyl-Glycyl-Aspartic cell adhesion motif (RGD motif) present in LAP-β1 or LAP-β3. LAPs containing the RGD motif are recognized by a majority of αV containing integrins. For example, αVβ6 integrin can activate/release TGF-β1 by binding to the RGD motif present in LAP-β1 and LAP-β3. In addition, integrin-protease-dependent activation of TGF-β can occur by creating a connection between the latent TGF-β complex and MMPs, such as MMP-2 and MMP-9, that can activate TGF-β by proteolytic degradation of the latent TGF-β complex.

2 TGF-β Signaling and Actions

Activated TGF-β plays a crucial role in cell differentiation as well as T-cell regulation. See, e.g., *Cold Spring Harbor Perspect. Biol.* 2017; 9:a022236 and citations therein. TGF-β promotes the thymic development of several T-cell lineages by supporting the survival of thymus-derived Treg (tTreg), invariant natural killer T (iNKT), and CD8α+ T-cell precursors, and accordingly promoting development of T-cells inducible by strong agonist ligands. TGF-β supports conventional CD8+T cells by promoting thymocyte expression of interleukin (IL)-7Rα. TGF-β also regulates peripheral T-cell homeostasis by promoting IL-7-dependent survival of low-affinity T cells, by controlling thymocyte IL-7Rα expression and by inhibiting T-cell receptor (TCR)-driven activation of autoreactive or high-affinity T cells. In early CD8+ T-cell differentiation, TGF-β inhibits cytotoxic T lymphocyte (CTL) formation and promotes the apoptosis of short-lived effector cells (SLECs) while promoting the differentiation of CD103-expressing tissue resident memory (TRM) cells. Although TGF-β inhibits T helper 1 and 2 (Th1 and Th2) cell differentiation, TGF-β acting with other factors promotes the development of various T-cells. TGF-β in conjunction with: IL-2 promotes production of peripheral Treg (pTreg), IL-6 promotes production of Th-17 cells, IL-4 promotes production of Th9 cells, and IL-21 and/or 23 promotes production of T follicular helper (Tfh) cells.

In addition to its action on T cells, a variety of other cells are regulated by TGF-β including B lymphocytes or "B cells," monocytes, and macrophages. TGF-β generally has inhibitory actions on B cells (Li et al., Annual Review of Immunology. 24 (1): 99-146 (2006) and Roes et al., *PNAS USA*, 100 (12): 7241-7246 (2003)); inhibiting B cell proliferation and inducing apoptosis of immature or resting B cells (Arsura, et al., *Immunity* 5(1): 31-40. (1996)). At least part of the action of TGF-β on B cells may be due to induction of IKBa, an inhibitor of NF-κB that regulates the production of cytokines including IL-1, TNF-a, and defensins. See, e.g., *Cold Spring Harbor Perspect. Biol.* 2017; 9:a022236 and citations therein.

In addition to its actions on B cells, TGF-β stimulates resting monocytes and inhibits activated macrophages. TGF-β displays inhibitory effects such as the proinflammatory response of macrophages that have been stimulated by Toll-Like-Receptor ("TLR") ligands. TGF-β stimulation, in the absence of TLR ligands or other cytokines, promotes production of several inflammatory cytokines by myeloid cells. TGF-β has been shown to induce peripheral blood monocytes and macrophages into tissues and enhance monocyte adherent properties. TGF-β can induce chemotaxis and enhance the adherent properties of mast cells. See, e.g., *Cold Spring Harbor Perspect. Biol.* 2017; 9:a022236 and citations therein.

Once TGF-β is activated, it is understood to act through cell surface signaling receptors. Signaling commences when an active TGF-β ligand binds to the transforming growth factor beta receptor II ("TβRII") on a cell surface. This interaction may result in the recruitment of transforming growth factor beta receptor I ("TβRI"). TβRII is capable of binding TGF-β1 alone, while TβRI can only bind the ligand in cooperation with TβRII. TβRII is phosphorylated and activated by TβRII, leading to signaling through the canonical signaling pathway via the recruitment and phosphorylation of the R-Smad proteins (Smad2 and Smad3). Those Smads subsequently bind to a co-Smad (Smad4), and together the complex drives the transcription of several genes. See Smith et al., *Clin. Cancer Res.;* 18(17): 4514-21 (2012). TGF-β can also signal through non-canonical (non-Smad) pathways that include various branches of MAP kinase pathways, Rho-like GTPase signaling pathways, and phosphatidylinositol-3-kinase/AKT pathways, that are activated by ligand-occupied receptors. Signaling through the non-canonical paths may reinforce, attenuate, or otherwise modulate downstream cellular responses. Zhang Ye, *Cell Res.* 19(1):128-39 (2009). In contrast to TβRI and TβRII, the transforming growth factor beta receptor III ("TβRIII" receptor or "beta glycan") does not participate in TGF-β signal transduction, but rather acts as a reservoir for TGF-β.

Perturbations of the activating factors, abnormal levels of activated TGF-β, and/or alterations in TGF-β signaling can lead to unregulated TGF-β signaling levels that can lead to several diseases or to complicated disease states. Indeed, TGF-β has been shown to have effects on conditions as diverse as inflammation, autoimmune disorders, fibrosis, cancer and cataracts.

TGF-β plays a pivotal role in maintaining hemostasis in the immune system as a factor involved in the induction of tolerance, and thereby affecting autoimmune responses. One mechanism by which TGF-β can bring about such effects is by driving T-cells (e.g., CD4+, CD8+, CD4 CD8+ and CD4 CD8 cells) to differentiate into T-regulatory cells or "T-Reg" cells (e.g., in the presence of IL-2). See e.g., Bettini and Vagnali, *Ann. N.Y. Acad. Sci.*, 1183:1-12 (2010). T-Reg cells are essential for the maintenance of immune tolerance. Josefowicz et al. *Annu Rev Immunol*, 30: 531-564. (2012). TGF-β's role in inducing tolerance to antigens, including self antigens, makes it a crucial factor in protecting against developing diseases such as arthritis (rheumatoid arthritis or "RA"), Type 1 diabetes mellitus ("T1D"), multiple sclerosis ("MS"), and systemic lupus erythematosus ("SLE"). For example, among TGF-β's key functions is regulation of autoimmune diseases and the related inflammatory processes. This is particularly true in the gut where it is believed to suppress macrophage cytokine production and mucosal inflammation in conditions such as inflammatory bowel disease or "IBD." Sanjab et al. *Cold Spring Harbor Perspect. Biol.* 2017; 9:a022236. Like IBD, RA is an autoimmune disorder with an inflammatory component directed at joints. RA results from aberrant responses in T and/or B cells. Systemic TGF-β appears to offer protection from RA development. See Schramm et al., *Arthritis Res. Ther.* 6:R114-R119 (2004) and Sanjab et al. *Cold Spring Harbor Perspect. Biol.* 2017; 9:a022236), and references cited therein.

A number of approaches to regulate TGF-β action at the level of the protein by sequestering it to effectively neutralize its action have been described in the literature. For example, monoclonal antibodies such as Metelimumab (CAT192) that is directed against TGF-β1, and Fresolimumab directed against multiple isoforms of TGF-β have been developed to bind, sequester, and neutralize TGF-β in vivo. In addition, receptor traps that tightly bind and sequester TGF-β thereby sequestering and neutralizing it have also been developed (see, e.g., Swaagrtra, et al., *Mol Cancer Ther;* 11(7): 1477-87 (2012) and U.S. Pat. Pub. No. 2018/0327477).

Unlike the molecules described above that are designed to bind and sequester the TGF-β and act as antagonists to TGF-β action, the masked TGF-β complexes described herein provide active TGF-polypeptides (e.g., TGF-β signaling pathway agonists) and a masking polypeptide (e.g., a TGF-β receptor fragment) that interact with each other to reversibly mask the TGF-β polypeptide sequence. The masked TGF-β complexes may include sequence variations in the TGF-β and/or in the masking polypeptides that can reduce their mutual affinity and contribute to TGF-β's unmasking, permitting its binding signaling through heteromeric cell surface receptors (e.g., binding to TβRII followed by TβRI to form a heteromeric receptor). Once formed the heteromeric TβRI-TβRII polypeptide complex, which has high affinity for TGF-β, can effectively compete with the masking polypeptide. Sequence variations in TGF-β and/or its masking polypeptide can also permit avoidance of undesirable interactions between the unmasked TGF-β polypeptide and other molecules. Such sequence variations include deletions of portions of the N-terminus of TβRII that attenuate binding to TβRI, and/or TGF-β sequence variations preventing its dimerization (e.g., C77S substitutions) that limit off target binding to the reservoir of non-signaling TβRIII molecules. In addition to the foregoing, the masked TGF-β constructs and complexes may also comprise additional wild type (wt.) and/or variant immunomodulatory polypeptide sequences (MODs) that can substantively impact the outcome of TGF-β binding to a target cell, including in vitro effects and in vivo effects such as therapeutic outcomes.

II. SUMMARY

The present disclosure describes the preparation of constructs in which TGF-β is masked by another polypeptide ("masked TGF-β constructs," see, e.g., FIG. 1 structure A with a single polypeptide chain), and complexes in which TGF-β is masked by another polypeptide ("TGF-β polypeptide complexes," see, e.g., FIG. 1 structures B-F showing complexes comprising two polypeptide chains), which constructs and complexes, that also may comprise additional elements, are referred herein to collectively as "masked TGF-β constructs and complexes." The masked TGF-β constructs and complexes are built around a scaffold polypeptide (e.g., an immunoglobulin Fc region) and contain masking polypeptide sequences that bind to TGF-β (a "masking polypeptide sequence," "masking polypeptide," or "masking sequence"). The masked TGF-β constructs and complexes may also contain one or more independently selected immunomodulatory polypeptide sequences such as wild type or variant IL-2 polypeptide sequences.

The masked TGF-β constructs and complexes can be expressed in numerous mammalian cell types as the masked untargeted TGF-β activity does not adversely impact the cells to the extent observed with unmasked TGF-β.

Masked TGF-β constructs may comprise as a first polypeptide:
i) a scaffold polypeptide sequence;
ii) a TGF-β polypeptide sequence;
iii) a masking polypeptide sequence optionally comprising a TGF-β receptor polypeptide sequence or an anti-TGF-β polypeptide sequence;
iv) optionally, one or more independently selected MOD polypeptide sequences;
and
v) optionally one or more independently selected linker polypeptide sequences;

a construct comprising these elements being collectively referred to herein as a "masked TGF-β construct," wherein the masking polypeptide sequence and the TGF-β polypeptide sequence bind to each other. That masked TGF-β construct may be organized in order (from N-terminus to C-terminus) as, e.g.:
i) the scaffold polypeptide sequence, the masking polypeptide sequence, and the TGF-β polypeptide sequence; or
ii) a first MOD polypeptide sequence, the scaffold polypeptide sequence, the masking polypeptide sequence, and the TGF-β polypeptide sequence; or
iii) a first independently selected MOD polypeptide sequence, a second independently selected MOD polypeptide sequence, optionally one or more additional MOD polypeptide sequences, the scaffold polypeptide sequence, the masking polypeptide sequence, and the TGF-β polypeptide sequence;

wherein masked TGF-β construct optionally comprise one or more independently selected linker polypeptide sequences.

The scaffold polypeptide of the above-mentioned masked TGF-β constructs may comprises interspecific or non-interspecific dimerization sequences that cause formation of a homodimer where the scaffold polypeptide sequences optionally have one or more covalent attachments to each other.

The scaffold polypeptides of the above-mentioned masked TGF-β constructs may also comprise an interspecific dimerization sequence, and further comprise a second polypeptide that dimerizes with a first polypeptide (as described above) through a counterpart interspecific dimerization sequence to form a masked TGF-β complex heterodimer. The second polypeptide may comprise one of the following structures: (i) a scaffold polypeptide sequence comprising the counterpart interspecific dimerization sequence; (ii) one or two (or more) independently selected MOD sequences and a scaffold polypeptide sequence comprising the counterpart interspecific dimerization sequence; (iii) a scaffold polypeptide sequence comprising the counterpart interspecific dimerization sequence, and an independently selected MOD sequence; or (iv) one or two (or more) independently selected MOD sequences and a scaffold polypeptide sequence comprising the counterpart interspecific dimerization sequence wherein the first and/or second polypeptides optionally comprises one or more independently selected linker polypeptide sequences. The second polypeptide thus may comprise one of the following structures, from N-terminus to C-terminus: (i) a scaffold polypeptide sequence comprising the counterpart interspecific dimerization sequence; (ii) one or two (or more) independently selected MOD sequences and a scaffold polypeptide sequence comprising the counterpart interspecific dimerization sequence; (iii) a scaffold polypeptide sequence comprising the counterpart interspecific dimerization sequence, and one or two (or more) independently selected MOD sequences; or (iv) one or two (or more) independently selected MOD sequences and a scaffold polypeptide sequence comprising the counterpart interspecific dimerization sequence; wherein first and/or second polypeptide optionally comprise one or more independently selected linker polypeptide sequences. Alternatively, the masked TGF-β complex heterodimer may comprise in order from N-terminus to C-terminus: (i) the scaffold polypeptide sequence comprising the counterpart interspecific dimerization sequence, the masking polypeptide sequence, and the TGF-β polypeptide sequence; (ii) a first MOD polypeptide sequence, the scaffold polypeptide sequence comprising the counterpart interspecific dimerization sequence, the masking polypeptide sequence, and the TGF-β polypeptide sequence; or (iii) a first independently selected MOD polypeptide sequence, a second independently selected MOD polypeptide sequence, the scaffold polypeptide sequence comprising the counterpart interspecific dimerization sequence, the masking polypeptide sequence, and the TGF-β polypeptide sequence.

Masked TGF-β complexes may also comprise a first polypeptide and a second polypeptide as a masked TGF-β complex heterodimer, wherein:
(i) the first polypeptide comprises
  a) a scaffold polypeptide sequence comprising an interspecific dimerization sequence,
  b) a masking polypeptide sequence optionally comprising a TGF-β receptor polypeptide sequence or an anti-TGF-β polypeptide sequence,
  c) optionally, one or more independently selected MOD polypeptide sequences, and
  d) optionally one or more independently selected linker polypeptide sequences;
(ii) the second polypeptide comprises
  a) a scaffold polypeptide sequence comprising a counterpart interspecific dimerization sequence to the interspecific dimerization sequence in the first polypeptide,
  b) a TGF-β polypeptide sequence,
  c) optionally, one or more independently selected MOD polypeptide sequences, and
  d) optionally one or more independently selected linker polypeptide sequences;

a complex comprising these elements being collectively referred to a "masked TGF-β complex," wherein the masking polypeptide sequence and the TGF-β polypeptide sequence are provided on different polypeptide chains and bind to each other;

wherein the interspecific binding sequence and the counterpart interspecific binding sequence interact with each other in the heterodimer; and wherein masked TGF-β first polypeptide and/or the second polypeptide optionally comprise one or more independently selected linker polypeptide sequences.

The TGF-β polypeptide sequences may be derived from any of the TGF-β isoforms, and may comprise substitutions that limit the ability of the TGF-β sequences from dimerizing. The masking sequences may be, for example, anti-TGF-β antibody sequences or TGF-β receptor (TβR) ectodomain sequences. Where TβR ectodomains are used to mask the TGF-β sequences, they may be modified to avoid inadvertent signaling by the masked molecule (e.g., by deletion of all or part of the ectodomain not necessary for interaction with the TGF-β sequence).

This disclosure also describes and provides for methods of producing the masked TGF-β constructs and complexes, and methods of their use in effecting various cell types and in treating a variety of diseases/disorders including autoimmune and inflammatory diseases. The methods of treatment described herein may include co-administration of the masked TGF-β constructs and complexes with other molecules including, but not limited to: immunomodulators (e.g., interleukins, cytokines, chemokines and the like); antibodies and antibody fragments (e.g., scFv, nanobodies, etc.); small molecule therapeutics (e.g., vitamin D or retinoic acids); and combinations thereof that may be beneficial to achieve the desired laboratory or therapeutic outcome.

III. BRIEF DESCRIPTION OF THE DRAWINGS

FIG. 1 depicts some formats for masked TGF-β constructs and complexes in which a TGF-β receptor sequence is used to mask a TGF-β polypeptide. Structure A depicts a monomeric construct with a single location for one or more independently selected MODs (e.g., a set of tandem independently selected MODs). Structure B depicts a symmetrical homodimer where the polypeptides interact by way of their respective Ig Fc sequences, which can spontaneously form disulfide bonds that link the two polypeptides. Structures C-F depict heterodimeric structures where the TGF-β and TGF-β receptor sequences are in "cis" (on the same polypeptide) or "trans" (on different polypeptides) of the heterodimer. Locations where one or more independently selected MODs may be placed are shown by circles filled with diagonal or vertical lines or a checkered pattern. Interspecific binding pairs are represented by knob-in-hole sequences, but may be any of the others as discussed below. The constructs may include no MODs, or may include one, two or more independently selected MOD sequences, including MOD sequences in tandem, which MODs may be provided in the indicated locations. Exemplary MODs include, e.g., wild type or mutant (e.g., with reduced affinity and/or selective affinity for a particular receptor or receptors) PD-L1, FAS-L, IL-1, IL-2, IL-4, IL-6, IL-7, IL-10, IL-15, IL-21 and IL-23 MOD sequences. In each instance where a TGF-β receptor sequence is used to mask a TGF-β polypeptide, the receptor polypeptide may be replaced with another masking polypeptide such as an antibody polypeptide (e.g., scFV or a nanobody) with affinity for the TGF-β polypeptide. Scaffold sequences may be joined (e.g., by disulfide bonds) to form covalently linked homodimers or covalently linked heterodimers. Any of the constructs shown in the figures may have sequence variations in the TGF-β polypeptide that limit its ability to dimerize (e.g., C77S substitutions).

FIGS. 2A-2H provide amino acid sequences of immunoglobulin Fc polypeptides (SEQ ID NOs:68-83).

FIG. 2I provides the amino acid sequences of a human J-chain with the signal peptide as 1-22 underlined (SEQ ID NO:84).

FIG. 2J provides a sequence of an Ig G1 heavy chain constant region CH1 domain. The serine residues at positions 70 and 72, which may be substituted by glutamic acid and valine respectively (S70E and S72V) for the formation of an MD13-like construct.

FIG. 2K provides a sequence of a light chain constant region "CL" domain from Ig κ and Ig λ chains. The serine at position 68 and the threonine at position 70 may be substituted by leucine and serine respectively (S68L and T70S) for the formation of an MD13-like construct.

FIG. 3 provides the sequences of three different isoforms of TGF-β as preproproteins and the mature form of TGF-β3 along with the C77S mutant of the mature protein.

FIG. 4 provides an alignment of TGF-β isoforms 1-3 with the residues corresponding to the mature form of TGF-β2 bolded, except aa residues Lys 25, Cys 77, Ile 92, and/or Lys 94 of TGF-β2 and their corresponding residues in the other forms of TGF-β isoforms 1 and 3 that are underlined and not bolded.

FIG. 5A provides the sequences of a type 1 TGF-β receptor (TβRI) and its ectodomain.

FIG. 5B provides the sequences of a type 2 TGF-β receptor (TβRII), its ectodomain, and fragments of the ectodomain. The locations indicated in bold and underlining in the isoform B are as F30, D32, S52, E55 and D118 of the mature polypeptide, any of which may be substituted with an aa other than the naturally occurring aa.

FIG. 5C provides the sequences of a type 3 TGF-β receptor (TβRIII).

FIG. 6 shows a plot showing the ability of different concentrations of various masked TGF-β constructs and complexes to stimulate the expression of FoxP3 on naïve CD4 T cells based on fluorescence cytometry analysis. Part A shows the induction of FoxP3 (as the percentage of CD4$^+$ cells) based on the indicated concentrations of TGF-β3 or a masked TGF-β3$_{WT}$ construct (see FIG. 1, structure A) in the absence and presence of 50 U/ml added IL-2 after 5 days in cell culture. Part B shows the distribution of FoxP3$^+$ cells (as the percentage of CD4 cells) in populations of naïve T cells treated for 5 days with various concentrations of TGF-β3 or one of three masked TGF-β3 constructs or a masked TGF-β3 complex bearing at least one N-terminal wt. or variant IL-2 MOD (see FIGS. 7G to 7I for the structures). Part C shows the induction of FoxP3$^+$ CD4$^+$ cells in the presence of a masked TGF-β3 polypeptide (structure (i) in part B of FIG. 6) at concentrations of 0.1 nM or 1000 nM.

FIG. 7A provides the aa sequence of a representative masked TGF-β (construct No.: 3470) SEQ ID NO:146, having the overall structure of FIG. 1 structure A. The polypeptide comprising, from N-terminus to C-terminus, wt. human IL-2 (hIL2), three repeats of G$_4$S linker, human mono IgG Fc with LALA substitutions, three repeats of G$_4$S linker, a human TβRII (hTβRII)$_{A25}$ sequence with a D118A substitution, five repeats of G$_4$S linker, and human TGF-β3 (hTGF-β3) sequence with a C77S substitution.

FIG. 7B provides the aa sequence of a representative masked TGF-β (construct No.: 3334) SEQ ID NO:147 having the overall structure of FIG. 1 structure B. The polypeptide, which forms a homodimer comprises, from N-terminus to C-terminus, hIL2 with H16T and F42A substitutions, three repeats of a $G_4S$, human IgG1 Fc with LALA substitutions, a $G_5S$ and two repeats of a $G_4S$ linker, a hTβ$RII_{\Delta25}$, D118A, five repeats of $G_4S$, and hTGF-β3 sequence.

FIG. 7C provides the aa sequences of a representative masked TGF-β construct having the overall structure of FIG. 1 structure D which comprises a first and second polypeptide. The first polypeptide construct No.: 3618 (SEQ ID NO:148) comprises from N-terminus to C-terminus, wt. hIL-2, three repeats of a $G_4S$ linker, human IgG1 Fc knob-in-hole (KiH) polypeptide chain A with LALA substitutions, a five repeats of $G_4S$ linker sequence, and hTGF-β3 sequence with a C77S substitution. The second polypeptide (construct No.: 3619), SEQ ID NO:149, comprises, from N-terminus to C-terminus, wt. hIL2, three repeats of $G_4S$ linker, human IgG1 Fc KiH polypeptide chain B with LALA substitutions, a $G_5S$ linker and two repeats of $G_4S$ linker, and a hTβ$RII_{\Delta25}$, D118A sequence.

FIG. 7D provides the aa sequences of a representative masked TGF-β construct having the overall structure of FIG. 1 structure E which comprises a first and second polypeptide. The first polypeptide (construct No.: 3618), SEQ ID NO:150 described above, comprises, from N-terminus to C-terminus, wt. hIL-2, three repeats of a $G_4S$ linker, human IgG1 Fc knob-in-hole (KiH) polypeptide chain A with LALA substitutions, a five repeats of $G_4S$ linker sequence, and hTGF-β3 sequence with a C77S substitution. The second polypeptide (construct No.: 3855), SEQ ID NO:151, comprises, from N-terminus to C-terminus, human IgG1 Fc KiH polypeptide chain B with LALA, T366S, L368A, and Y407V substitutions, three repeats of $G_4S$ linker, and a hTβ$RII_{\Delta25}$, D118A sequence.

FIG. 7E provides the aa sequences of a representative masked TGF-β construct having the overall structure of FIG. 1 structure F which comprises a first and second polypeptide. The first polypeptide (construct No.: 3891), SEQ ID NO:152, comprises, from N-terminus to C-terminus, hIL-2 with H16A, F42A, three repeats of $G_4S$ linker sequence, human IgG1 Fc knob-in-hole (KiH) polypeptide chain A with LALA and T366W substitutions, a $G_5S$ and two repeats of $G_4S$ linker, hTβ$RII_{\Delta25}$, D118A, five repeats of $G_4S$ linker, and hTGF-β3 with a C77S substitution. The second polypeptide (construct No.: 3664), SEQ ID NO:153, comprises, from N-terminus to C-terminus, human IgG1 Fc KiH polypeptide chain B with LALA substitutions.

FIG. 7F provides the aa sequences of a representative masked TGF-β construct having the overall structure of FIG. 1 structure F which comprises a first and second polypeptide. The first polypeptide (construct No.: 3715), SEQ ID NO:155, comprises from N-terminus to C-terminus, human IgG1 Fc KiH polypeptide chain A with LALA substitutions, three repeats of $G_4S$ linker, and human wt. IL2 sequences. The second polypeptide (construct No.: 3714), SEQ ID NO:156, comprises, from N-terminus to C-terminus, human IgG1 FcKiH polypeptide chain B with LALA substitutions, three repeats of a $G_4S$ linker, a hTβ$RII_{\Delta25}$, with D32N and D118A substitutions, five repeats of $G_4S$ linker sequence, and a hTGF-β3 sequence with a C77S substitution.

Any of the IL-2 sequence in FIGS. 7A to 7F may be substituted with a MOD or variant MOD other than IL-2, replaced by wt. IL-2, or replaced by an IL-2 sequence having substitutions at N88, H16 and/or F42, (e.g., a N88R, a substitution at H16 selected from H16A or H16T, and/or a substitution at F42 selected from F42A and F42T).

FIG. 7G provides the aa sequence of a representative masked TGF-β construct (construct No.: 3472), SEQ ID NO:157, having the overall structure of FIG. 1 structure A. The polypeptide comprising, from N-terminus to C-terminus, wt. hIL2, three repeats of $G_4S$ linker, human mono IgG Fc with LALA substitutions, three repeats of $G_4S$ linker, a human TβRII $(hTβRII)_{\Delta25}$ sequence with D32N and D118A substitutions, five repeats of $G_4S$ linker, and human TGF-β3 (hTGF-β3) sequence with a C77S substitution.

FIG. 7H provides the aa sequence of a representative masked TGF-β construct (construct No.: 3466), SEQ ID NO:158, having the overall structure of FIG. 1 structure A. The polypeptide comprising, from N-terminus to C-terminus, wt. hIL2, three repeats of $G_4S$ linker, human mono IgG Fc with LALA substitutions, three repeats of $G_4S$ linker, a human TβRII $(hTβRII)_{\Delta25}$ sequence with a D118A substitution, five repeats of $G_4S$ linker, and human TGF-β3 (hTGF-β3) sequence with a C77S substitution.

FIG. 7I provides the aa sequence of a representative masked TGF-β construct (construct No.: 3468), SEQ ID NO:159, having the overall structure of FIG. 1 structure A. The polypeptide comprising, from N-terminus to C-terminus hIL2 with H16T F42A substitutions, three repeats of $G_4S$ linker, human mono IgG Fc with LALA substitutions, three repeats of $G_4S$ linker, a human TβRII $(hTβRII)_{\Delta25}$ sequence with D32N and D118A substitutions, five repeats of $G_4S$ linker, and human TGF-β3 (hTGF-β3) sequence with a C77S substitution.

FIG. 7J provides the aa sequences of a representative masked TGF-β construct having the overall structure of FIG. 1 structure D which comprises a first and second polypeptide. The first polypeptide (construct No.: 3618), SEQ ID NO:148, comprises from N-terminus to C-terminus, wt. hIL-2, three repeats of a $G_4S$ linker, human IgG1 Fc knob-in-hole (KiH) polypeptide chain A with LALA substitutions, a five repeats of $G_4S$ linker sequence, and hTGF-β3 sequence with a C77S substitution. The second polypeptide (construct No.: 3621), SEQ ID NO:160, comprises, from N-terminus to C-terminus, wt. hIL2, three repeats of $G_4S$ linker, human IgG1 Fc KiH polypeptide chain B with LALA substitutions, three repeats of $G_4S$ linker, and a hTβ$RII_{\Delta25}$ sequence with D32N and D118A substitutions.

FIG. 8 shows a masked TGF-β construct (left) and two masked TGF-β complexes (center and right). Samples of the complexes were prepared by constructing nucleic acid vectors encoding the polypeptides, transfecting ExpiCHO cells and expressing the polypeptides. The polypeptides were purified by protein A chromatography followed by size exclusion chromatography. The purified proteins were subjected to SDS-PAGE and the resulting gels were stained with Coomassie blue. NR=not reducing or unreduced samples, and R=reduced samples (reduction with a disulfide reducing agent).

FIG. 9 shows the effect of various aa substitutions in mature TβRII polypeptide sequences (see FIG. 5B) on their affinity for TβRII and TGF-β3 or TGF-β1 (Table, top left). FIG. 9 also shows the effect of three of those substitutions, E55A, D32N, and S52L, on the binding interaction between a TβRII masked TGF-β construct and an immobilized TβRII-Fc receptor construct. The receptor construct is shown in a capture assay format with TGF-β3 in the top right of the figure where: mono-Fc is an Ig scaffold that does not form interspecific bonds to other scaffolds, and anti-IL-2 is an antibody against IL-2 labeled with biotin (B). Strep and HRP are streptavidin and horse radish peroxidase used for detection. The effect on binding was detected in a capture as binding curves developed for each of the four masked constructs (bottom). See Example 3.

FIG. 11 shows the results of an experiment in which PSM-4033-4039 is used to induce Foxp3+ iTregs from human peripheral naïve CD4+ T cells. See Example 4.

Figure 14A:
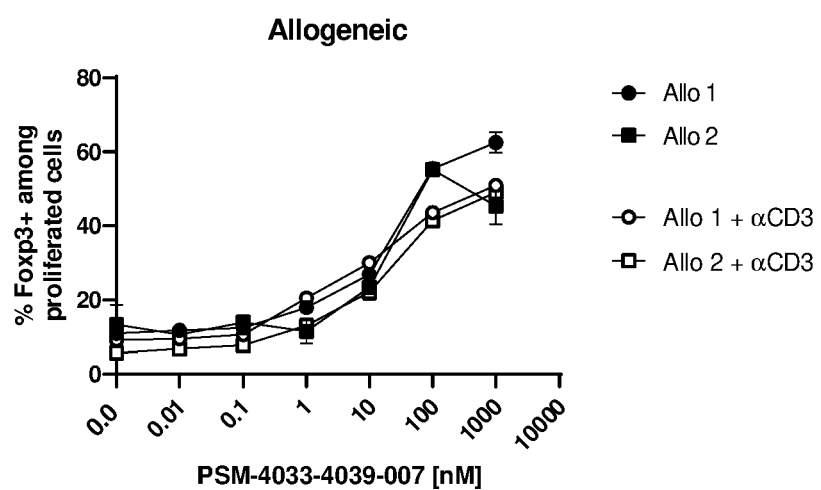
Figure 14B:
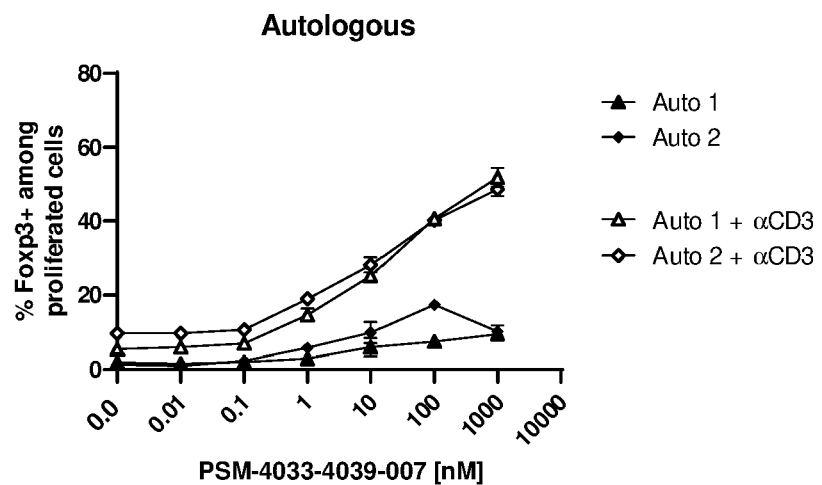

FIGS. 14A and B shows the results of an experiment in which PSM-4033-4039 is used to induce Foxp3+ iTregs from CD4+ T cells activated by an allogeneic lymphocyte reaction. See Example 4.

Figure 15:
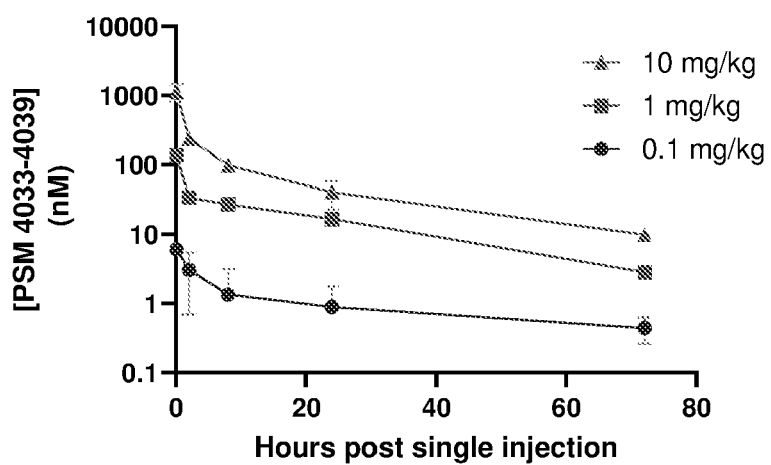

FIG. 15 shows the results of an experiment in which PSM-4033-4039 was administered intravenously to mice in various concentrations to determine serum concentrations in the mice at various intervals up to 72 hours post injection. See Example 4.

IV. DETAILED DESCRIPTION

A. Definitions

As used herein amino acid (abbreviated "aa" when singular unless the context dictates it can be plural, and as "aas" in the plural form) means the naturally occurring proteogenic alpha amino acids incorporated into polypeptides and proteins in mammalian cell translation. Unless stated otherwise: L (Leu, leucine), A (Ala, alanine), G (Gly, glycine), S (Ser, serine), V (Val, valine), F (Phe, phenylalanine), Y (Tyr, tyrosine), H (His, histidine), R (Arg, arginine), N (Asn, asparagine), E (Glu, glutamic acid), D (Asp, asparagine), C (Cys, cysteine), Q (Gln, glutamine), I (Ile, isoleucine), M (Met, methionine), P (Pro, proline), T (Thr, threonine), K (Lys, lysine), and W (Trp, tryptophan) Amino acid also includes the amino acids hydroxyproline and selenocysteine, which appear in some proteins found in mammalian cells.

The terms "polypeptide," "polypeptide sequence," and "protein" as used herein are synonyms and mean a sequence of aas joined together by peptide bonds between their C-1 carboxyl group and their alpha amine to form the backbone of the polypeptide. Accordingly, each polypeptide (e.g., a first polypeptide) that comprises any one or more of: a MOD polypeptide sequence, a scaffold polypeptide sequence, a TGF-β polypeptide sequence, and/or a masking polypeptide sequence (e.g., a TGF-β receptor polypeptide sequence or anti-TGF-β polypeptide sequence) comprises any one or more of those polypeptide sequences as a polypeptide chain with a single contiguous backbone. Such polypeptides (e.g., first polypeptides) may be linked to other polypeptides by covalent bonds (e.g., such as disulfide bonds between the side chains of cysteine residues). Furthermore, as used herein, the terms "polypeptide", "polypeptide sequence" and "protein" include modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

Where an embodiment, claim, or aspect is directed to a specific type of mammal (e.g., human or non-human subjects), nucleic acid and polypeptide sequences may be limited to sequences from those subjects. Unless stated otherwise the polypeptide sequence of proteins (e.g., TGF-β, TβRs, immunoglobulins, and MODs) are human (*Homo Sapiens*) sequences.

As used herein "masked" means that a molecule (e.g., masked polypeptide or masked protein) is bound or otherwise engaged by a masking molecule (e.g., polypeptide, protein or protein fragment) that limits the availability of the masked molecule to other proteins (e.g., cell surface receptors) that also have affinity for the molecule.

As used herein the term masked TGF-β construct refers to a single polypeptide that comprises both a TGF-β (e.g., TGF-β1, TGF-β2, or TGF-β) polypeptide sequence and a masking polypeptide sequence that binds to or otherwise interacts with the TGF-β polypeptide. Unless stated otherwise a masked TGF-β construct comprises a scaffold polypeptide sequence and optionally comprises one or more independently selected immunomodulatory (MOD) polypeptide sequences.

As used herein the term masked TGF-β complex refers to two or more polypeptides (typically two polypeptides designated a first and a second polypeptide arranged as a homodimer or heterodimer, but which can be a higher order multimer). Masked TGF-β complexes comprise a TGF-β (e.g., TGF-β1, TGF-β2, or TGF-β) polypeptide sequence, a masking polypeptide sequence that binds to or otherwise interacts with the TGF-β polypeptide, and a scaffold polypeptide that comprises a dimerization or multimerization sequence through which the polypeptides of the TGF-β complex associate. Any one or more of the TGF-β complex polypeptides optionally comprises one or more independently selected MOD polypeptide sequences.

The phrase "masked TGF-β construct or complex" is an abbreviation for a masked TGF-β construct or masked TGF-β complex. The abbreviation may be used in its plural form "masked TGF-β constructs or complexes."

The phrase "masked TGF-β constructs and complexes" is an abbreviation for both "masked TGF-β constructs" and "masked TGF-β complexes."

Dimerization and multimerization sequences as used herein are polypeptide sequences that permit the association of polypeptide sequences (e.g., separate polypeptides) as dimers (e.g., heterodimers or homodimers), or multimers (homo- or hetero-multimers of three, four five or more polypeptide sequences). Dimerization and multimerization sequences permit the association of sequences in a non-covalent fashion that may be converted into a covalent complex under some circumstances (e.g., disulfide bond formation between the polypeptides).

Interspecific binding sequences are dimerization sequences that permit an asymmetric paring of polypeptides (heterodimer formation). Interspecific binding sequences favor formation of heterodimers with their counterpart interspecific binding sequence(s) (as opposed to forming homodimers), which is their cognate binding partner. Key-in-hole (or key-into-hole) Fc polypeptide pairs represent one example of an interspecific binding sequence and its counterpart interspecific binding sequence.

Nanobodies® or nanobody as used herein refers to an antibody fragment consisting of a single monomeric variable antibody domain that, like a whole antibody, is able to bind selectively to a specific antigen.

Wild type (abbreviated as "wt.") with regard to aa sequences means a naturally occurring aa sequence, or a contiguous portion of a naturally occurring aa sequence as understood from the context, that has not been altered (does not have any substitutions, deletions, or insertions therein) relative to a sequence found naturally in a living organism. A specific naturally occurring sequence may be designated as the wt. sequence for reference.

As used herein, "T cell" includes all types of immune cells expressing CD3, including T-helper cells (CD4+ cells), cytotoxic T cells (CD8+ cells), T-regulatory cells (Treg), and NK-T cells.

The term "binding," as used herein refers to a non-covalent interaction between two molecules, e.g., the non-covalent interaction between a MOD and its co-MOD. Non-covalent binding refers to a direct association between two molecules, due to, for example, electrostatic, hydrophobic, ionic, and/or hydrogen-bond interactions, including interactions such as salt bridges and water bridges. Non-covalent binding interactions are generally characterized by a dissociation constant ($K_D$) of less than $10^{-6}$M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Specific binding" generally refers to binding with an affinity of at least about $10^{-7}$ M or greater, e.g., $5 \times 10^{-7}$ M, $10^{-8}$ M, $5 \times 10^{-8}$ M, $10^{-9}$ M, and greater. "Non-specific binding" generally refers to binding (e.g., the binding of a ligand to a moiety other than its designated binding site or receptor) with an affinity of less than about $10^{-7}$ M (e.g., binding with an affinity of $10^{-6}$ M, $10^{-5}$ M, $10^{-4}$ M). "Covalent binding" or "covalent bond," as used herein, refers to the formation of one or more covalent chemical bonds between two different molecules.

"Affinity" refers to the strength of non-covalent binding, increased binding affinity being correlated with a lower $K_D$. As used herein, the term "affinity" refers to the equilibrium constant for the reversible binding of two agents (e.g., an antibody and an antigen) and is expressed as a dissociation constant ($K_D$).

The term "immunomodulatory polypeptide" or MOD, as used herein, includes a polypeptide on an antigen presenting cell (APC) (e.g., a dendritic cell, a B cell, and the like), or a portion of the polypeptide on an APC, that specifically binds a cognate co-immunomodulatory polypeptide ("co-MOD") on a T cell, thereby providing a signal. For example, the bonding of an interleukin such as IL-2 or a fragment thereof (a MOD) to a cell surface IL-2 receptor (a co-MOD) provides a signal to the cell. MODs include, but are not limited to, IL-1, IL-2, IL-4, IL-6, IL-7, IL-10, IL-15, IL-21 and IL-23, PD-L1 and Fas ligand (FAS-L). MODs also encompass, inter alia, an antibody or an antibody sequence (e.g., a nanobody) that specifically binds with a co-MOD molecule present on a T cell that results in signaling by the coMOD. As discussed herein, MODs also include variants of wt. MODs including, e.g., variant MODs that have a reduced binding affinity for a co-MOD. Such reduced affinity can take multiple forms. For example, a variant IL-2 MOD can have reduced affinity for one or more of the α, ß, and/or γ chains of IL-2R. As discussed herein, variant IL-2 MODs comprising mutations at positions 16 and 42 can exhibit substantially no binding to the α chain of IL-2R and reduced affinity for the ß chain of IL-2R. Additionally, for MODs that have more than one co-MOD (e.g., CD80 binds to both CD28 and CTLA-4), a variant MOD can have reduced affinity for one of the co-MODs such that it preferentially or selectively binds the other co-MOD. For the purpose of this disclosure, TGF-β (e.g., TGF-β1, TGF-β2, or TGF-β3), and fragments thereof, are not considered MODs.

Unless indicated otherwise, the term "substantially" is intended to encompass both "wholly" and "largely but not wholly". For example, a variant IL-2 MOD that exhibits substantially no binding to the α chain of IL-2R is an IL-2 variant MOD that does not bind to the α chain of IL-2R at all or largely does not bind to the α chain of IL-2R.

As used herein the term "in vivo" refers to any process or procedure occurring inside of the body, e.g., of an autoimmune patient.

As used herein, "in vitro" refers to any process or procedure occurring outside of the body, including procedures that may be referred to as ex vivo.

"Tandem," as used herein to describe the placement of MOD polypeptide sequences means having two or more MODs arranged adjacent to each other on a polypeptide separated, at most, by a linker (e.g., no scaffold, masking polypeptide or TGF-β sequences interposed).

As used herein the term "ectodomain" means the part (domain) of a membrane protein that extends into the extracellular space and that does not include a sufficient portion of the transmembrane domain to cause it to be anchored in the cell membrane.

"Sequence identity" as used herein is a measure of the aa or nucleotide identity between two polynucleotide sequences or two polypeptide sequences. Stating that a protein or polynucleotide sequence has a certain percent "sequence identity" to another polynucleotide or polypeptide means that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), *J. Mol. Biol.* 215:403-10. Unless stated otherwise sequence identity is determined using alignments performed with NCBI BLAST algorithm version BLAST+ 2.9.0 released on Apr. 1, 2019 (for protein BLASTP 2.9.0+ and for nucleic acids BLASTN 2.9.0+).

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments, or from a series of synthetic oligonucleotides, to provide a synthetic nucleic acid which is capable of being expressed from a recombinant transcriptional unit contained in a cell or in a cell-free transcription and translation system. Recombinant used in reference to a peptide, polynucleotide, or protein indicates they have been prepared by expression from a recombinant nucleic acid.

As used herein, the term "about" used in connection with an amount indicates that the amount can vary by 10% of the stated amount. For example, "about 100" means an amount of from 90-110. Where about is used in the context of a range, the "about" used in reference to the lower amount of the range means that the lower amount includes an amount that is 10% lower than the lower amount of the range, and "about" used in reference to the higher amount of the range means that the higher amount includes an amount 10% higher than the higher amount of the range. For example, from about 100 to about 1000 means that the range extends from 90 to 1100.

The terms "treatment," "treating," and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; and/or (c) relieving the disease, i.e., causing regression of the disease. The therapeutic agent (e.g., a masked TGF-β construct or complex) may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. Therapeutic treatment may be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, rats, goats, sheep, horses, pigs and the like), canine (e.g., dogs), feline (e.g., cats) etc. (e.g., human, bovine, canine, feline, rodent, murine, caprine, simian, ovine, equine, lappine, porcine, etc.).

It must be noted that as used herein and in the appended aspects and claims, the singular forms "a," "an," and "the" include plural referents unless the context clearly dictates otherwise. Thus, for example, reference to "a Treg" includes a plurality of such Tregs and reference to "the TGF-β polypeptide" includes reference to one or more TGF-β polypeptides and equivalents thereof known to those skilled in the art, and so forth. It is further noted that the claims may be drafted to either include or exclude any optional element. As such, this statement is intended to serve as antecedent basis for either the use (inclusion) of such elements in claims (e.g., with terminology such as "solely," "only" and the like), or their removal from claims or as a basis for a "negative" limitation excluding any specific optional element.

It is appreciated that certain features of the invention, which are, for clarity, described in the context of separate aspects or embodiments, may also be provided in combination in a single aspect or embodiment including those subsequently claimed. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

B. Description

1 Introduction

The TGF-β superfamily includes endogenous proteins with growth inhibiting functions. Increases in the expression of TGF-β or defects in cellular mechanisms that inhibit TGF-β action have been correlated with, among other things, the malignancy of many cancers due to TGF-β's immunosuppressive actions. Dysregulation of TGF-β's immunosuppressive functions are also implicated in autoimmune diseases. Because TGF-β is a key regulator of immune function, it has been the target of numerous studies and both TGF-β and its signaling pathway are considered therapeutic targets for the treatment of a variety of diseases including inflammatory processes and autoimmune disorders.

The ability to effectively prepare and deliver TGF-β as a therapeutic is complicated by the molecule's toxicity and the complexity of TGF-β's receptor system. Production of TGF-β in large quantities in mammalian cell expression systems is limited by the toxicity of the protein to many mammalian cells. Cells subject to the cytotoxicity of TGF-β include many of those used for the production of biological molecules, such as Chinese Hamster Ovary or "CHO" cells, which are one of the most robust and commonly employed cells for commercial protein production. Use of TGF-β as a therapeutic is also complicated by the high pI of TGF-β1 with pI of about 8.59 (as opposed to the pI of about 6.1 for TGF-β3), its limited stability/solubility under conditions that are not acidic (such acidic conditions are not generally amenable for therapeutic use). In addition, the large amount of high affinity TβRIII receptor (e.g., on the order of 5 nM for TGF-β2) present in mammalian systems relative to the affinity of TβRII for TGF-β (on the order of 1-2 μM) represents a significant pharmacodynamic sink, limiting access of TGF-β-based biologics to target tissues. Similarly, TβRIII's role in recruiting TGF-β to TβRII/TβRI complexes may lead to significant off-target delivery of TGF-β, with unintended, undesirable and even toxic effects. Such off-target delivery may lead to non-specific activation, and could also lead to further production of active TGF-β, particularly where TGF-β signaling is under feed-forward control, thereby producing further unintended and undesirable effects. See, e.g., Jiang et al., *Redox Biol.* 2: 267-272 (2014).

The effective use of TGF-β as a therapeutic is further complicated by the need to provide additional stimuli to cells to direct the outcome of TGF-β stimulation. As noted above, cytokines such as, IL-1, IL-2, IL-4, IL-6, IL-7, IL-10, IL-15, IL-21 and IL-23, PD-L1 and Fas ligand (FAS-L) can have profound influences on the action of TGF-β. Accordingly, the ability to deliver TGF-β and additional stimuli in the form of cytokines etc. can be advantageous for achieving specific therapeutic or cell mediated outcomes (e.g., in vitro or in vivo) effects.

Figure 1:
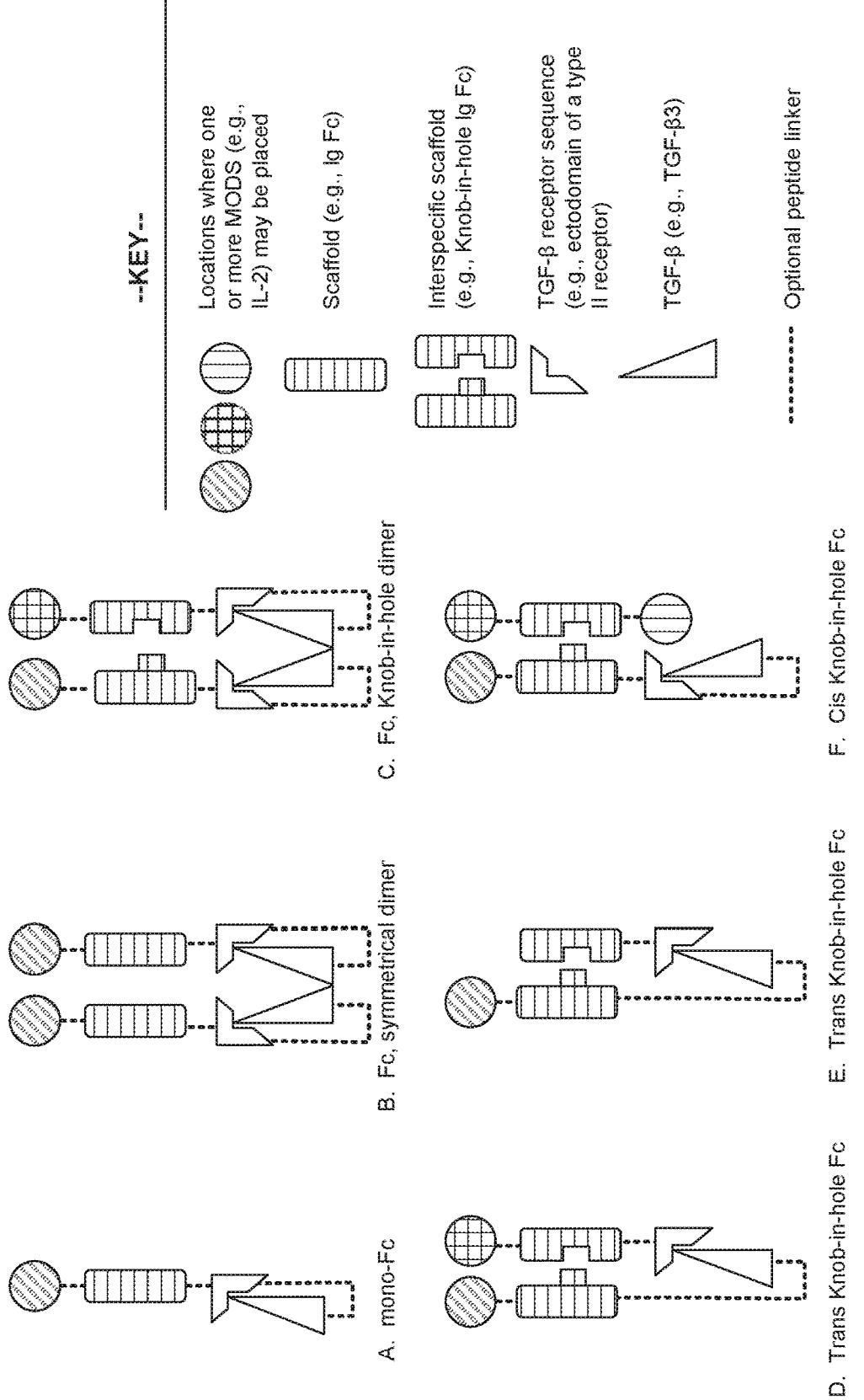

As discussed in more detail below, the current disclosure describes the use of a TGF-β polypeptide capable of interacting with and stimulating signaling on cells bearing TβRI and TβRII proteins. Advantageously, the TGF-β polypeptide is part of a masked TGF-β construct or complex, which is a fusion protein (a single polypeptide chain) or fusion protein complex (two or more polypeptide chains) that also contains a polypeptide that binds and masks the TGF-β polypeptide sequence (e.g., a TβRII sequence that functions as a masking sequence) built around a scaffold (e.g., one or two polypeptides such as immunoglobulin Fc polypeptides). Examples of such fusion proteins or fusion protein complexes are depicted in FIG. 1. In the event that the TGF-β polypeptide of the fusion protein interacts with, for example, a cellular TβRIII, the portion of the fusion protein that binds and masks TGF-β competes with the TβRIII, preventing the TGF-β from being sequestered in the TβRIII reservoir. In addition, the affinity of the masking polypeptide for the TGF-β polypeptide, which can be intentionally varied using aa substitutions, controls the overall potency of the masked polypeptide for its target receptor (e.g., TβRII) as demonstrated in FIG. 9. As TGF-β polypeptides principally bind TβRIII as a disulfide linked dimer, interactions with that receptor leading to sequestration can be attenuated by including aa substitutions that limit dimerization (e.g., C77S) or dimer stability as discussed below. Interaction of the TGF-β fusion protein or fusion protein complex with TβRII displaces the masking sequence, forming a cell surface bound TGF-β/TβRII complex. The subsequent recruitment of TβRI to form the heterodimeric TGF-β receptor provides a high affinity complex that binds TGF-β tightly (e.g., picomolar affinity) even in the presence of the masking polypeptide sequence. Accordingly, the masked TGF-β is still capable of binding to the heterodimeric TβRI/TβRII receptor complex and signaling through the canonical Smad protein pathway, the non-canonical Jun kinase pathway, and the p38 signaling path. In effect, the masking polypeptide delivers TGF-β to a cell and hands it off to a cell surface TβRII molecule that subsequently recruits the TβRI protein, forming a functional and active signaling complex that effectively holds the TGF-β polypeptide in place.

In addition to delivering TGF-β masked by a TGF-β binding protein (e.g., a fragment of a TGF-β receptor comprising all or part of its TGF-β binding ectodomain) in a form that avoids undesirable off target interactions, a masked TGF-β construct or complex may comprise one or more polypeptides that function as an immunomodulator (a "MOD" polypeptide) capable of affecting the result of TGF-β action on target cells. The ability to deliver both TGF-β and immunomodulators together not only allows the action of the TGF-β activating signal to be directed, but it reduces the amount of immunomodulator that would be required to produce the same effect on the target cells relative to administration of the immunomodulator alone. This is a result of the increased affinity (through avidity enhancement) obtained by having two polypeptide sequences with affinity for receptors on the same target cell. The increased avidity between masked TGF-β construct or complex bearing one or more MODs and target cells bearing receptors for both the TGF-β polypeptide and the one or more MODs (resulting from an increased free energy of binding, ΔG, due to MOD interactions with their receptors) provides for enhanced selectivity in the activation of target cells have both types of receptors, provided subsaturating amounts of the masked TGF-β construct or complex, are present. By way of example, a masked TGF-β construct, such as that in FIG. 1 structure A or FIG. 7G, having an IL-2 MOD is a more potent inducer of iTReg differentiation of naïve CD4+ cells than an otherwise identical masked TGF-β construct that lacks an IL-2 MOD even in the presence of an equivalent (equimolar) amount of the IL-2 MOD polypeptide. In addition, at subsaturating doses, and when similar numbers of cell types are present, a construct such as that in FIG. 1 structure A with an IL-2 MOD as shown in, for example, FIG. 7G, selectively binds to cells with both TGF-β and IL-2 receptors relative to the construct that lacks an IL-2 MOD.

The action of masked TGF-β constructs or complexes can be further specified by the incorporation of modifications that alter the actions of the individual polypeptide sequences. In some embodiments aa substitutions that alter the ability of TGF-β to dimerize (e.g., a C77S substitution in TGF-β3) may be incorporated. As the monomeric form of TGF-β displays little if any affinity for TβRIII, incorporation of mutations that limit TGF-β's ability to dimerize limit off target binding to TβRIII that can drag the complex into the TGF-β "reservoir" and limit its ability to stimulate target cells.

Modifications (e.g., substitutions, deletions, insertions etc.) may also be made to polypeptide sequences other than the TGF-β polypeptide sequence, including the masking polypeptide sequence, and the immunomodulatory polypeptide sequences.

Figure 9:
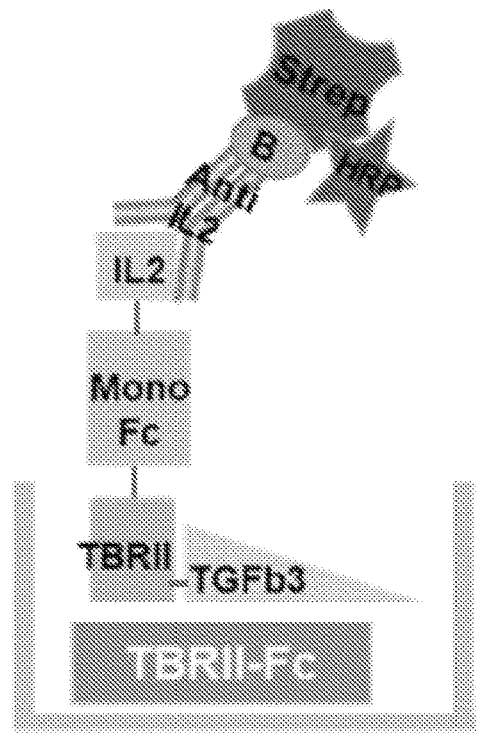

In addition to modifications of the TGF-β polypeptide sequence, modifications to the polypeptide that binds to TGF-β and masks it can be made. Such modifications can alter the availability of the TGF-β polypeptide sequence by changing the affinity of the masking polypeptide for TGF-β as well as the breathing rate (on and off rates) of the masking polypeptide and the TGF-β polypeptide. Although two different TGF-β polypeptide/masking polypeptide complexes may have the same binding association constant (ratio of kon to koff), the complex with a higher kon and koff can effectively be more available to cell surface TβRII binding depending on the rate constants, particularly the koff rate. FIG. 9 provides a list of some aa substitutions in TβRII that alter affinity for TGF-β1 and TGF-β3, along with a graph showing the affinity of otherwise identical TβRII masked TGF-β constructs either without or with one of three substitutions each having a different impact on TβRII binding to TGF-β3.

While it is possible to utilize various polypeptides to mask TGF-β including both single chain antibody sequences (e.g., humanized single chain antibody sequences), minimal TGF-β receptor sequences that bind TGF-β may be employed (e.g., the ectodomain of TβRI, TβRII, or TβRIII). TβRIII's ectodomain may be utilized as a masking polypeptide for dimeric TGF-β; however, its high affinity for TGF-β may cause it to antagonize the binding of TGF-β polypeptide sequences to TβRII. Nevertheless, TβRIII masking sequences could be effectively displaced by cell surface TβRI/TβRII complexes with higher affinity for TGF-β polypeptides, thereby permitting activation of those cell surface receptors.

TβRII's ectodomain may be utilized as a masking polypeptide. Deletion of N-terminal amino acids of TβRII (e.g., delta 14 or 25) can produce a protein (or polypeptide) suitable for masking TGF-β with a pI calculated to be about 4.5 to about 5.0 (e.g., about 4.7 to 4.85) in the presence or absence of D118A substitutions. The combination TGF-β1 polypeptides (which have high pI values) with TβRII masking polypeptides (e.g., including those with N-terminal deletions) can potentially neutralize the TGF-β1 polypeptide charge. The calculated pI of TβRII (delta25, D118A)/TGFβ1 is on the order of 6.23, where TGFβ1 has a pI of about 8.59. In contrast, complexes of delta 14 or delta 25 TβRII and TGF-β3 (with or without D118A and/or C77S substitutions) are calculated to have pI values of about 4.9 to about 5.3 (about pI of 5.06 to 5.17). In addition, although combining the TβRII ectodomain with an active TGF-β polypeptide could result in a complex capable of interacting with cell surface TβRI, thereby affecting TGF-β signaling (e.g., acting as an agonist, partial agonist, antagonist or partial antagonist) of TGF-β, the incorporation of aa substitutions limiting interactions with TβRI limits or blocks the masked complex's ability to participate in active signaling. Accordingly, as discussed below, incorporation TβRII ectodomain sequences with N-terminal deletions (e.g., deletion of 14 to 25aa, Δ14 to Δ25) or substitutions (e.g., substitutions at D118 by an aa other than aspartic acid such as D118A, D118R, etc.) that that reduced or ablate binding to TβRI can be used to mask TGF-β and prevent stimulation of cells by the TβRII ectodomain masked TGF-β polypeptide where the N-terminus of the TβRII is intact. Consequently, masked TGF-β complexes, including those where TGF-β is masked by N-terminal deletion mutants of TβRII, can act by unmasking of the TGF-β (dissociation from the masking peptide or opening of the folded molecule), binding to a target cell's TβRII and TβRI to form an active heterodimeric TβRI/TβRII signaling complex.

Masking of TGF-β permits its expression at high levels in mammalian cells (e.g., CHO cells) without reduction in the cell viability. This is particularly true where the masked TGF-β polypeptide is blocked from engaging TβRI by N-terminal aa deletions, substitutions, and/or other mutations. Blocking of TβRIII interactions (e.g., by blocking dimerization) can further reduce issues associated with cellular expression.

C. Masked TGF-B Constructs and Masked TGF-B Complexes

The present disclosure describes the preparation of masked TGF-β constructs (see, e.g., FIG. 1, structure A, with a single polypeptide chain) and masked TGF-β complexes (see, e.g., FIG. 1, structures B-F, having a complex of two polypeptide chains). The masked TGF-β constructs, and masked TGF-β complexes comprise as their components at least one TGF-β polypeptide sequence, at least one polypeptide that binds to and masks the TGF-β polypeptide(s), and optionally one or more (e.g., one, two or three) immunomodulatory polypeptides (MODs), all of which are assembled on a scaffold structure. Although masked TGF-β constructs, and masked TGF-β complexes, comprise portions of membrane bound proteins (e.g., TGF-β receptors), unless stated otherwise, they do not comprise portions of membrane anchoring domains (e.g., transmembrane domains sufficient to cause a majority of the expressed protein to become anchored in a cell membrane (e.g., expressed CHO cells).

Non-limiting examples of TGF-β constructs and complexes, including those of the forms shown in FIG. 1 are described below.

Components of the masked TGF-β constructs and complexes, including MODs, scaffolds, linkers, TGF-β polypeptides, and TGF-β masking polypeptides (e.g., a single chain antibody or a TGF-β receptor ectodomain) are each described in the sections that follow.

D. Immunomodulatory Polypeptide Sequences ("MODS")

1 The Incorporation of MODS into Masked TGF-β Constructs and Complexes

As discussed above, although immunomodulatory polypeptide (MODs) are not required for the delivery of masked TGF-β polypeptides or its ability to activate cells through the TβRI and TβRII heterodimeric receptor, MODs can substantially affect the outcome of TGF-β receptor activation. Accordingly, it can be desirable to incorporate wild type (wt.) or variant MODs (e.g., that display reduced affinity, increased affinity, or selectivity for specific receptors also referred to as "co-MODs," "co-immunomodulatory polypeptides" or cognate costimulatory receptors or their subtypes). Although TGF-β is an immunomodulatory polypeptide, because it is a central element in the masked TGF-β constructs and complexes described herein, the term "MOD (s)" as used herein does not include TGF-β or its polypeptides.

MODs that are suitable for inclusion into any of the masked TGF-β constructs and complexes (e.g., homodimer or heterodimer complexes) include, but are not limited to, as PD-L1, FAS-L, IL-1, IL-2, IL-4, IL-6, IL-7, IL-10, IL-15, IL-21 and IL-23.

In some cases, the MODs are selected independently from a mature PD-L1, FAS-L, IL-1, IL-2, IL-4, IL-6, IL-7, IL-10, IL-15, IL-21 and IL-23 polypeptides or a fragment of any thereof. The MOD polypeptide sequence(s) incorporated in masked TGF-β constructs and complexes can comprise only a portion of the secreted MOD polypeptide, or the extracellular portion of a full-length mature MOD protein if it is in a membrane anchored form. Thus, for example, the MOD polypeptide sequence in a masked TGF-β construct or complex can in some cases exclude one or more (e.g., each) of a signal peptide, a transmembrane domain, and/or an intracellular domain normally found in some naturally-occurring MODs.

In some cases, a MOD polypeptide sequence suitable for inclusion in masked TGF-β constructs and complexes of the present disclosure comprises all or a portion of (e.g., an extracellular portion of) the amino acid sequence of a naturally occurring MOD. In other instances, MODs suitable for inclusion in masked TGF-β constructs and complexes of the present disclosure include at least one (e.g., one, two, or three independently selected) variant MODs that comprises at least one amino acid insertion, substitution, and/or deletion compared to the amino acid sequence of a naturally-occurring MOD.

In some instances, a variant MOD exhibits a binding affinity for a co-MOD that is lower than the affinity of a corresponding naturally-occurring MOD (e.g., a MOD not comprising the amino acid substitution(s) present in the variant) for the co-MOD. Depending on the reduction in affinity, the use of MODs with reduced affinity for their co-MOD allows the TGF-β polypeptide to have more influence on, or even to dominate, the binding interactions. Where the binding affinity of the TGF-β polypeptide is higher than that of the MOD, it can drive the masked TGF-β construct or complex to associate with cells having a TGF-β receptor system (e.g., TGF-βR1 and TGF-βR2 that form a high affinity TGF-β binding heterodimer), while at the same time limiting off target binding to cells having even an abundance of co-MODs but lacking or having few TGF-β receptors. In essence, where the affinity (e.g. AG of binding) of the TGF-β polypeptide for its cellular receptor is greater than affinity of the MODs for their co-MODs (e.g. their ΔG of binding), the TGF-β drives the binding and specificity of the masked TGF-β construct or complex.

In an embodiment, any one or more MODs associated with masked TGF-β constructs and complexes are selected independently from the group consisting of wt. or variant:

PD-L1; FAS-L; IL-1; IL-2; IL-4; IL-6; IL-7; IL-10; IL-15; IL-21; IL-23; and combinations thereof.

In some cases, such as where it is desirable to stimulate the production of Treg cells, at least one MOD polypeptide (e.g., one, two or three independently selected MODs) present in masked TGF-β constructs and complexes is an IL-2 polypeptide or an IL-2 variant polypeptide. Sequence variations in IL-2 may be selected to bias binding of the IL-2 polypeptide, and the masked TGF-β constructs or complexes, to target cells bearing different combinations of IL-2R receptor subunits. The IL-2 receptor is comprised of a common IL-2Rγ and two additional IL-2Rα and/or IL-2Rβ subunits to form trimeric (IL-2Rα)$_2$-IL-2Rγ, (IL-2R β)$_2$-IL-2Rγ, or high affinity (Kd about 10 picomolar) IL-2Rα-IL-2Rβ-IL-2Rγ receptors. The α chain (CD25) is unique to IL-2 whereas the β chain (CD122) is shared with the IL-15 receptor, and the γ chain (CD132), which is critical for signaling, can be partnered with other cytokine receptor chains. Substitutions at H16 (e.g., H16A or H16T) or F42 (e.g., F42A or F42T) can bias binding in favor of receptors with IL-2Rβ subunits; and accordingly, their incorporation biases binding to memory T cells and NK cells which display β-γ receptors ((IL-2R β)$_2$-IL-2Rγ), or activated T-cells and T regs displaying high affinity α-β-γ (IL-2Rα-IL-2Rβ-IL-2Rγ) receptors. In contrast, substitutions at N88 (e.g., N88R) decrease binding to IL-2Rβ and can bias binding in favor of receptors with IL-2Rα subunits; and accordingly, substitutions at N88 biases binding to cells with α-γ ((IL-2Rα)$_2$—IL-2Rγ)) and α-β-γ (IL-2Rα-IL-2Rβ-IL-2Rγ) receptors, while avoiding binding and activation of cells with β-γ receptors. See, e.g., Skrombolas and Frelinger, *Expert Rev Clin Immunol.*, 10(2): 207-217 (2014). Biasing, as used in the context of binding a substituted MOD (such as an IL-2 polypeptide with an aa substitution) to its co-MOD or a cell displaying a co-MOD, means that the presence of a substitution changes the amount of interaction of the substituted MOD and co-MOD relative to the interaction between the wt. MOD and the same co-MOD. For example, IL-2 sequences with substitutions at N88 (e.g., N88R), which have a lower side effect profile (e.g., safer) and are better tolerated by human subjects, may be included with the above-mentioned substitutions at H16 and/or F42.

In some cases, such as where it is desirable to stimulate the production of iTreg cells (CD4+ FoxP3+ cells) (e.g., to induce peripheral tolerance to actively suppress effector T cells and/or inhibit immune-mediated tissue damage), at least one MOD polypeptide (e.g., one, two or three independently selected MODs) present in masked TGF-β constructs or complexes is an independently selected wt. or variant PD-L1 MOD polypeptide. See e.g., Francisco et al., *J. Exp. Med.*, 206(13): 3015-3029 (2009). In addition to the wt. or variant PD-L1 sequences, the masked TGF-β constructs or complexes can comprise one or more independently selected wt. or variant IL-2 polypeptides. Sequence variations in IL-2 may be selected to bias binding of the IL-2 polypeptide, and the masked TGF-β constructs, to target cells bearing different combinations IL-2R receptor subunits. As discussed above, the IL-2 variants include substitutions at H16 (e.g., H16A or H16T) and/or F42 (e.g., F42A or F42T) that can bias binding in favor of receptors with IL-2Rβ subunits; and/or IL-2 with substitutions at N88 (e.g., N88R) that decrease binding to IL-2Rβ are that better tolerated by human subjects. In an embodiment, masked TGF-β construct/-β complex comprise both H16T and F42A, or both H16A and F42 substitutions, either pair of which may be combined with an N88 (e.g., N88R) substitution.

In some cases, such as where it is desirable to stimulate the production of Th17 cells, at least one MOD polypeptide (e.g., one, two or three independently selected MODs) present in masked TGF-β constructs and complexes is an IL-6 polypeptide or an IL-6 variant polypeptide.

In some cases, such as where it is desirable to stimulate the production of Th9 cells, at least one MOD polypeptide (e.g., one, two or three independently selected MODs) present in masked TGF-β constructs and complexes is an IL-4 polypeptide or an IL-4 variant polypeptide. See, e.g., Elyaman et al., *Immunity.*, 36(4): 623-634, *Immunity.* (2012).

In some cases, such as where it is desirable to promote IL-7-dependent survival of low-affinity T cells, by control of thymocyte IL-7Ra expression, at least one MOD polypeptide (e.g., one, two or three independently selected MODs) present in masked TGF-β constructs and complexes is an IL-7 polypeptide or an IL-7 variant polypeptide.

In some cases, such as where it is desirable to stimulate the production of T follicular helper (Tfh) cells, at least one MOD polypeptide (e.g., one, two or three independently selected MODs) present in masked TGF-β construct masked TGF-β constructs and complexes is an IL-21 or an IL-23 polypeptide, or a variant of an IL-21 or an IL-23 polypeptide.

In some cases, such as where it is desirable to induce tolerance, at least one MOD polypeptide (e.g., one, two or three independently selected MODs) present in masked TGF-β constructs and, or a variant of a Fas ligand (FasL) polypeptide.

In some cases, such as where it is desirable to inhibit type II innate lymphoid cells (ILC2 cells) (e.g., to suppress asthma and allergic inflammation) at least one MOD polypeptide (e.g., one, two or three independently selected MODs) present in masked TGF-β constructs and complexes is an IL-10 polypeptide, or a variant of an IL-10 polypeptide. See, e.g., Rajas et al., *J Allergy Clin Immunol*, 139(5):1468 (2017); and Ogasawara et al., *J Allergy Clin Immunol*, 141(3): 1147-1151 (2018). Inhibition of ILC2 cells may be assessed by the reduction in their production of type-2 cytokines IL-5 and IL-13 in vivo (in a tissue or body fluid) or in vitro (in culture media). The IL-10 polypeptide may be a monomeric isomer such as the IL-10M1 molecule described by Josephson et al., *J. Biol. Chem.*, 275:13552-13557 (2000), or a variant thereof, both of which are discussed below. In contrast to wild type IL-10 whose biologically active form is an intertwined pair of IL-10 peptides that forms a complex consisting of 2 IL-10 molecules and 4 IL-10Ra receptor chains, IL-10M1 forms a 1:1 complex with the soluble IL-10Ra with a dissociation constant of 30 nm that is biologically active in cellular proliferation assays. Id.

2 MODs and Variant MODs with Reduced Affinity

Suitable MODS that exhibit reduced affinity for their co-MODs can have from 1 amino acid (aa) to 20 aa differences from a wild-type MOD sequence. For example, in some cases, a variant MOD polypeptide sequence present in a masked TGF-β construct complex may differ in amino acid sequence by 1 aa, 2 aa, 3 aa, 4 aa, 5 aa, 6 aa, 7 aa, 8 aa, 9 aa, or 10 aa from the corresponding wild-type MOD polypeptide sequence. As another example, in some cases, a variant MOD polypeptide present in a masked TGF-β construct or complex differs in amino acid sequence by 11 aa, 12 aa, 13 aa, 14 aa, 15 aa, 16 aa, 17 aa, 18 aa, 19 aa, or 20 aa from the corresponding wild-type MOD polypeptide. As an example, in some cases, a variant MOD polypeptide present in a masked TGF-β construct or complex includes 1, 2, 3, 4, 5, 6, 7, 8, 9, or 10 aa substitutions, compared to the corresponding reference (e.g., wild-type) MOD sequence. In some cases, a variant MOD present in a masked TGF-β construct or complex includes a single aa substitution compared to the corresponding reference (e.g., wild-type) MOD sequence. In some cases, a variant MOD present in a masked TGF-β construct or complex includes 2 aa substitutions (e.g., no more than 2 aa substitutions) compared to the corresponding reference (e.g., wild-type) MOD sequence. In some cases, a variant MOD present in a masked TGF-β construct or complex includes 3 aa substitutions (e.g., no more than 3 aa substitutions) compared to the corresponding reference (e.g., wild-type) MOD sequence. In some cases, a variant MOD present in a masked TGF-β construct or complex includes 4 aa or 5 aa substitutions compared to the corresponding reference (e.g., wild-type) MOD sequence. In some cases, a variant MOD present in a masked TGF-β construct or complex includes 6 aa or 7 aa substitutions compared to the corresponding reference (e.g., wild-type) MOD sequence. In some cases, a variant MOD present in a masked TGF-β construct or complex includes 8 aa or 9aa substitutions compared to the corresponding reference (e.g., wild-type) MOD sequence. In some cases, a variant MOD present in a masked TGF-β construct or complex includes 10 aa or 11 aa substitutions (e.g., no more than 10 aa substitutions) compared to the corresponding reference (e.g., wild-type) MOD sequence.

In some cases, a variant MOD present in a masked TGF-β construct or complex includes 11 aa or 12 aa substitutions compared to the corresponding reference (e.g., wild-type) MOD sequence. In some cases, a variant MOD present in a masked TGF-β construct or complex includes 13 aa or 14 aa substitutions compared to the corresponding reference (e.g., wild-type) MOD sequence. In some cases, a variant MOD present in a masked TGF-β construct or complex includes 15 aa or 16 aa substitutions compared to the corresponding reference (e.g., wild-type) MOD sequence. In some cases, a variant MOD present in a masked TGF-β construct or complex includes 17 aa or 18 aa substitutions compared to the corresponding reference (e.g., wild-type) MOD sequence. In some cases, a variant MOD present in a masked TGF-β construct or complex includes 19 aa or 20 aa substitutions compared to the corresponding reference (e.g., wild-type) MOD sequence.

As discussed above, variant MODs suitable for inclusion in a masked TGF-β construct or complex may exhibit reduced affinity for their cognate co-MOD, compared to the affinity of a corresponding wild-type MOD for the cognate co-MOD.

In some cases, a variant MOD polypeptide sequence present in a masked TGF-β construct or complex has a binding affinity for a cognate co-MOD that is from 1 nM to 100 μM. For example, in some cases, a variant MOD polypeptide present in a masked TGF-β construct or complex has a binding affinity for a cognate co-MOD that is from about 1 nM to about 5 nM, from about 5 nM to about 10 nM, from about 10 nM to about 50 nM, from about 50 nM to about 100 nM, from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

3 Determining Binding Affinity

Binding affinity between a MOD (e.g., a MOD polypeptide) and its cognate co-MOD can be determined by biolayer interferometry (BLI) using purified MOD and purified cognate co-MOD. Binding affinity between masked TGF-β constructs or complexes that comprise a MOD and the MOD's cognate co-MOD can also be determined by BLI using purified masked TGF-β construct or complex and the MOD's cognate co-MOD. BLI methods are well known to those skilled in the art. See, e.g., Lad et al. (2015) *J. Biomol. Screen.* 20(4):498-507; and Shah and Duncan (2014) *J. Vis. Exp.* 18:e51383. The specific and relative binding affinities described in this disclosure between a MOD and its cognate co-MOD, or between a masked TGF-β construct or complex having a MOD and its cognate co-MOD, can be determined using the following procedures.

To determine binding affinity between a MOD-containing masked TGF-β construct or complex and the MOD's cognate co-MOD, a BLI assay can be carried out using an Octet RED 96 (Pal FortéBio) instrument, or a similar instrument, as follows. A control masked TGF-β construct or complex (e.g., a masked TGF-β construct or complex comprising a wild-type MOD) is immobilized onto an insoluble support (a "biosensor"). The immobilized masked TGF-β construct or complex is the "target." Immobilization can be effected by immobilizing a capture antibody onto the insoluble support, where the capture antibody immobilizes the masked TGF-β construct or complex. For example, where the masked TGF-β construct or complex comprises an Ig Fc scaffold, immobilization can be effected by immobilizing anti-Ig Fc (e.g., anti-human IgG Fc) antibodies onto the insoluble support, where the immobilized anti-Ig Fc antibodies bind to and immobilize the masked TGF-β construct or complex. A co-MOD is applied, at several different concentrations, to the immobilized masked TGF-β construct or complex, and the instrument's response is recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-MOD to the immobilized masked TGF-β construct or complex is conducted at 30° C.

As a positive control for binding and binding affinity, an antibody (e.g., a monoclonal antibody) can be used. The antibody may be selected based on the specific structure of the masked TGF-β construct or complex (see, e.g., FIG. 1). For example, a monoclonal antibody (mAb) directed against the TGF-β, TGF-β receptor, scaffold or MOD polypeptide sequences can be used as a positive control provided the antibody does not cause the masked TGF-β construct or complex to become dissociated from the support (biosensor). A standard curve can be generated using serial dilutions of the anti-MHC Class I or Class II monoclonal antibody. The co-MOD, or the anti-MHC mAb, is the "analyte." BLI analyzes the interference pattern of white light reflected from two surfaces: i) the immobilized polypeptide ("target"); and ii) an internal reference layer. A change in the number of molecules ("analyte"; e.g., co-MOD; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_{d/a}$) gives rise to the affinity constant $K_D$.

As noted above, determining binding affinity between a MOD (e.g., IL-2 or an IL-2 variant) and its cognate co-MOD (e.g., IL-2R) also can be determined by BLI. The assay is similar to that described above for the masked TGF-β construct or complex. A BLI assay can be carried out using an Octet RED 96 (Pal FortéBio) instrument, or a similar instrument, as follows. A component MOD of a masked TGF-β construct or complex (e.g., a variant IL-2 polypeptide of the present disclosure); and a control MOD (where a control MOD comprises a wild-type MOD, e.g. wild-type IL-2) are immobilized separately onto insoluble supports (a "biosensor"). Each MOD is the "target" Immobilization can be effected by immobilizing a capture antibody onto the insoluble support, where the capture antibody immobilizes the MOD. For example, if the target is fused to an immuno-affinity tag (e.g. FLAG, human IgG Fc, etc.), immobilization can be effected by immobilizing the appropriate antibody to the immuno-affinity tag (e.g. anti-human IgG Fc) on the insoluble support, where the immobilized antibodies bind to and immobilize the MOD (where the MOD comprises an IgFc polypeptide). A co-MOD (or polypeptide) is applied, at several different concentrations, to the immobilized MOD, and the instrument's response is recorded. Alternatively, a co-MOD (or polypeptide) is immobilized to the biosensor (e.g., for the IL-2 receptor heterotrimer, as a monomeric subunit, heterodimeric subcomplex, or the complete heterotrimer), the MOD is applied, at several different concentrations, to the immobilized co-MOD(s), and the instrument's response is recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-MOD to the immobilized MOD is conducted at 30° C. BLI analyzes the interference pattern of white light reflected from two surfaces: i) the immobilized polypeptide ("target"); and ii) an internal reference layer. A change in the number of molecules ("analyte"; e.g., co-MOD) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/k_a$) gives rise to the affinity constant $K_D$. Determining the binding affinity of both a wild-type MOD (e.g., IL-2) for its co-MOD (e.g., its cognate binding partner or receptor; in the case of IL-2, the IL-2R), and a variant MOD (e.g., an IL-2 variant as disclosed herein) for its co-MOD (e.g., in the case of an IL-2 variant, the IL-2R), thus allows one to determine the relative binding affinity of the variant co-MOD, as compared to the wild-type co-MOD, for the co-MOD. That is, one can determine whether the binding affinity of a variant MOD for its co-MOD is reduced as compared to the binding affinity of the wild-type MOD for the same cognate co-MOD, and, if so, what is the percentage reduction from the binding affinity of the wild-type co-MOD.

The BLI assay is carried out in a multi-well plate. To run the assay, the plate layout is defined, the assay steps are defined, and biosensors are assigned in Octet Data Acquisition software. The biosensor assembly is hydrated. The hydrated biosensor assembly and the assay plate are equilibrated for 10 minutes on the Octet instrument. Once the data are acquired, the acquired data are loaded into the Octet Data Analysis software. The data are processed in the Processing window by specifying method for reference subtraction, y-axis alignment, inter-step correction, and Savitzky-Golay filtering. Data are analyzed in the Analysis window by specifying steps to analyze (Association and Dissociation), and selecting curve fit model (1:1), fitting method (global), and window of interest (in seconds). The quality of fit is evaluated. $K_D$ values for each data trace (analyte concentration) can be averaged if within a 3-fold range. $K_D$ error values should be within one order of magnitude of the affinity constant values; $R^2$ values should be above 0.95. See, e.g., Abdiche et al. (2008) *J. Anal. Biochem.* 377:209.

In some cases, the ratio of: i) the binding affinity of a control masked TGF-β construct or complex (where the control masked TGF-β construct or complex comprises a wild-type MOD) to a cognate co-MOD to ii) the binding affinity of a masked TGF-β construct or complex comprising a variant of the wild-type MOD to the cognate co-MOD, when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5 \times 10^2$:1, at least $10^3$:1, at least $5 \times 10^3$:1, at least $10^4$:1, at least $10^5$:1, or at least $10^6$:1. In some cases, the ratio of: i) the binding affinity of a control masked TGF-β construct or complex (where the control masked TGF-β construct or complex comprises a wild-type MOD) to a cognate co-MOD to ii) the binding affinity of a masked TGF-β construct or complex comprising a variant of the wild-type MOD to the cognate co-MOD, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

In some cases, a variant MOD present in a masked TGF-β construct or complex has a binding affinity for a cognate co-MOD that is from 1 nM to 100 nM, or from 100 nM to 100 μM. For example, in some cases, a variant MOD present in a masked TGF-β construct or complex has a binding affinity for a cognate co-MOD that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM. In some cases, a variant MOD present in a masked TGF-β construct or complex has a binding affinity for a cognate co-MOD that is from about 1 nM to about 5 nM, from about 5 nM to about 10 nM, from about 10 nM to about 50 nM, or from about 50 nM to about 100 nM.

4 PD-L1 and its Variants

As one non-limiting example, a MOD or variant MOD present in a masked TGF-β construct or complex is a PD-L1 or variant PD-L1 polypeptide. Wild-type PD-L1 binds to PD1.

A wild-type human PD-L1 polypeptide can comprise the following amino acid sequence: MRIFAVFIFM TYWHLLNAFT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKICLT LSPST (SEQ ID NO:1); where aas 1-18 form the signal sequence, aas 19-127 form the Ig-like V-type or IgV domain, and 133-225 for the Ig-like C2 type domain.

A wild-type human PD-L1 ectodomain can comprise the following amino acid sequence: FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:2); where aas 1-109 form the Ig-like V-type or "IgV" domain, and aas 115-207 for the Ig-like C2 type domain.

A wild-type PD-L1 IgV domain, suitable for use as a MOD may comprise aa 18, aas IgV aas 19-127 of SEQ D No. 1, and a carboxyl terminal stabilization sequences, such as for instance the last seven amino acids (bolded and italicized) of the sequence: A FTVTVPKDLY VVEYGSNMTI ECKFPVEKQL DLAALIVYWE MEDKNIIQFV HGEEDLKTQH SSYRQRARLL KDQLSLGNAA *LQ*ITDVKLQD AGVYRCMISY GGADYKRITV KVNAPY *AAAL HEH* SEQ ID NO:β8. Where the carboxyl stabilizing sequence comprises a histidine (e.g., a histidine approximately 5 residues to the C-terminal side of the Tyr (Y) appearing as aa 117 of SEQ ID NO:β8) at about aa 122, the histidine may form a stabilizing electrostatic bond with the backbone amide at aas 82 and 83 (bolded and italicized in SEQ ID NO:β8 (Q107 and L106 of SEQ ID NO:1). As an alternative, a stabilizing disulfide bond may be formed by substituting one of aas 82 or 83) (Q107 and L106 of SEQ ID NO:1) and one of aa residues 121, 122, or 123 (equivalent to aa positions 139-141 of SEQ ID NO:1).

A wild-type PD-1 polypeptide can comprise the following amino acid sequence:

```
                                              (SEQ ID NO: 3)
PGWFLDSPDR PWNPPTFSPA LLVVTEGDNA TFTCSFSNTS

ESFVLNWYRM SPSNQTDKLA AFPEDRSQPG QDCRFRVTQL

PNGRDFHMSV VRARRNDSGT YLCGAISLAP KAQIKESLRA

ELRVTERRAE VPTAHPSPSP RPAGQFQTLV VGVVGGLLGS

LVLLVWVLAV ICSRAARGTI GARRTGQPLK EDPSAVPVFS

VDYGELDFQW REKTPEPPVP CVPEQTEYAT IVFPSGMGTS

SPARRGSADG PRSAQPLRPE DGHCSWPL.
```

In some cases, a variant PD-L1 polypeptide (e.g. a variant of SEQ ID NO:2 or PD-L1's IgV domain) exhibits reduced binding affinity to PD-1 (e.g., a PD-1 polypeptide comprising the amino acid sequence set forth in SEQ ID NO:3), compared to the binding affinity of a PD-L1 polypeptide comprising the amino acid sequence set forth in SEQ ID NO:1 or SEQ ID NO:2. For example, in some cases, a variant PD-L1 polypeptide binds PD-1 (e.g., a PD-1 polypeptide comprising the amino acid sequence set forth in SEQ ID NO:3) with a binding affinity that is at least 10% less, at least 20% less, at least 30% less, at least 40% less, at least 50% less, at least 60% less, at least 70% less, at least 80% less, at least 90% less, at least 95% less, or more than 95% less than the binding affinity of a PD-L1 polypeptide comprising the amino acid sequence set forth in SEQ ID NO:1 or SEQ ID NO:2.

In some cases, a variant PD-L1 polypeptide (e.g. a variant of SEQ ID NO:2 or its IgV domain) has a binding affinity to PD-1 (e.g. of SEQ ID NO:3) that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant PD-L1 polypeptide (e.g. a variant of SEQ ID NO:2) has a binding affinity for PD1 (e.g., a PD1 polypeptide comprising the amino acid sequence set forth in SEQ ID NO:3) that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

A number of aa substitutions may be made in the PD-L1 ectodomain sequences used as MODs, including substitutions to sequences having greater than 90% (95%, 98% or 99%) sequence identity to at least 85 contiguous aas (e.g., at least 90, at least 95, at least 100, or at least 105 contiguous aas) of any one of SEQ ID NO:1, SEQ ID NO:2, aas 19-127 (the IgV domain) of SEQ ID NO:1, and SEQ ID NO:β8. The substitutions may include (a) disulfide bond substitution pairs D103C and G33C, or V104 and S34C; (b) salt bridge forming substitution pairs Q107D and K62R or Q107D and S80R; and/or (c) Pi stacking substitutions M36Y or M36F (based on SEQ ID NO:1). A PD-L1 MOD sequence may comprise a sequence having at least 85 contiguous aas (e.g., at least 90, at least 95, at least 100, or at least 105 contiguous aas) of SEQ ID NO:2, and at least one disulfide, salt bridge, or Pi stacking substitution. A PD-L1 MOD sequence may comprise a sequence having at least 85 contiguous aas (e.g., at least 90, at least 95, at least 100, or at least 105 contiguous aas) of aas 19-127 (the IgV domain) of SEQ ID NO:1, and at least one disulfide, salt bridge, or Pi stacking substitution. A PD-L1 MOD sequence may comprise a sequence having at least 85 contiguous aas (e.g., at least 90, at least 95, at least 100, or at least 105 contiguous aas) of aas SEQ ID NO:β8, and at least one disulfide, salt bridge, or Pi stacking substitution.

In some cases, a variant PD-L1 polypeptide has a single aa substitution compared to the PD-L1 amino acid sequence set forth in SEQ ID NO:1, SEQ ID NO:2 or PD-L1's IgV domain. In some cases, a variant PD-L1 polypeptide has from 2 aa to 10 aa substitutions compared to the PD-L1 amino acid sequence set forth in SEQ ID NO:1, SEQ ID NO:2 or PD-L1's IgV domain. In some cases, a variant PD-L1 polypeptide has 2 aa substitutions compared to the PD-L1 amino acid sequence set forth in SEQ ID NO:1, SEQ ID NO:2 or PD-L1's IgV domain. In some cases, a variant PD-L1 polypeptide has 3 aa or 4 aa substitutions compared to the PD-L1 amino acid sequence set forth in SEQ ID NO:1, SEQ ID NO:2 or PD-L1's IgV domain. In some cases, a variant PD-L1 polypeptide has 5 aa or 6 aa substitutions compared to the PD-L1 amino acid sequence set forth in SEQ ID NO:1, SEQ ID NO:2 or PD-L1's IgV domain. In some cases, a variant PD-L1 polypeptide has 7 aa or 8 aa substitutions compared to the PD-L1 amino acid sequence set forth in SEQ ID NO:1, SEQ ID NO:2 or PD-L1's IgV domain. In some cases, a variant PD-L1 polypeptide has 9 aa or 10 aa substitutions compared to the PD-L1 amino acid sequence set forth in SEQ ID NO:1, SEQ ID NO:2 or PD-L1's IgV domain.

Suitable variant PD-L1 polypeptide sequences include polypeptide sequences having at least 80%, at least 85%, at least 90%, at least 95%, at least 98%, or at least 99% aa sequence identity to at least 170 contiguous aa (e.g., at least 180, 190 or 200 contiguous aa) of SEQ ID NO:2 (e.g. which have at least one aa insertion, deletion or substitution). Suitable variant PD-L1 IgV polypeptide sequences include polypeptide sequences having at least 80%, at least 85%, at least 90%, at least 95%, at least 98%, or at least 99% aa sequence identity to at least 70 contiguous aa (e.g., at least 80, 90, 100 or 105 contiguous aas) of aas 1-109 of SEQ ID NO:2 (e.g. which have at least one aa insertion, deletion or substitution).

In an instance, variant PD-L1 polypeptide sequences include polypeptide sequences having at least 90% (e.g., at least 95%, 98%, or 99%), or 100%, aa sequence identity to SEQ ID NO:2, wherein the residue at position 8 is an aa other than D; in one such instance that residue is an A, and in another, R. Variant PD-L1 polypeptide sequences include polypeptide sequences having at least 90% (e.g., at least 95%, 98%, or 99%), or 100%, aa sequence identity to SEQ ID NO:2, wherein the residue at position 36 is an aa other than I; in one such instance that residue is an A, and in another, D. Variant PD-L1 polypeptide sequences also include polypeptide sequences having at least 90% (e.g., at least 95%, 98%, or 99%), or 100%, aa sequence identity to SEQ ID NO:2, wherein the residue at position 54 is an aa other than E; in one such instance that residue is an A, and in another, R.

5 IL-1 and its Variants

As one non-limiting example, a MOD or variant MOD present in a masked TGF-β construct or complex is an IL-1 or variant IL-1 polypeptide. Wild-type IL-1 has two isoforms, IL-1α and IL-1β, both of which bind to the IL-1 receptor.

A wild-type human IL-1α precursor polypeptide can comprise the following amino acid sequence: MAKVPDM-FEDL KNCYSENEEDS SSIDHLSLNQK SFYHVSYG-PLH EGCMDQSVSLS ISETSKTSKLT FKESMVVVATN GKVLKKRRLSL SQSITDDDLEA IANDSEEEIIK PRSAPFSFLSN VKYNFMRIIKY EFILNDALNQS IIRANDQYLTA AALHNLDEAVK FDMGAYKSSKD DAKITVILRIS KTQLYVTAQDE DQPVLLKEMPE IPKTITGSETN LLFFWETHGTK NYFTSVAHPNL FIATKQDYWVC LAGGPPSITDF QILENQA (SEQ ID NO:4) UniProtKB—P01583, NCBI Ref. Seq. NP_000566.3, that can have one or more of the following naturally occurring variations R85Q, A114S, N125D, D138N, and D176H.

A mature wild-type human IL-1α polypeptide can comprise the following amino acid sequence:

(SEQ ID NO: 5)
PRSAPFSFLS NVKYNFMRII KYEFILNDAL NQSIIRANDQ

YLTAAALHNL DEAVKFDMGA YKSSKDDAKI TVILRISKTQ

LYVTAQDEDQ PVLLKEMPEI PKTITGSETN LLFFWETHGT

KNYFTSVAHP NLFIATKQDY WVCLAGGPPS ITDFQILENQ A.

A wild-type human IL-1β precursor polypeptide can comprise the following amino acid sequence: MAEVPE-LASE MMAYYSGNED DLFFEADGPK QMKCSFQDLD LCPLDGGIQL RISDHHYSKG FRQAASVVVA MDKLRKMLVP CPQTFQENDL STFFPFIFEE EPIFFDTWDN EAYVHDAPVR SLNCTLRDSQ QKSLVMSGPY ELKALHLQGQ DMEQQVVFSM SFVQGEESND KIPVALGLKE KNLYLSCVLK DDKPTLQLES VDPKNYPKKK MEKRFVFNKI EINN- KLEFES AQFPNWYIST SQAENMPVFL GGTKGGQDIT DFTMQFVSS (SEQ ID NO:6) UniProtKB—P0158, NCBI Ref. Seq. NP_000567.1.

A mature wild-type human IL-1β polypeptide can comprise the following amino acid sequence (SEQ ID NO: 7)
APVRSLNCTLRDSQQKSLVMSGPYELKALHLQGQDMEQQVVFSMSFVQGE

ESNDKIPVALGLKEKNLYLSCVLKDDKPTLQLESVDPKNYPKKKMEKRFV

FNKIEINNKLEFESAQFPNWYISTSQAENMPVFLGGTKGGQDITDFTMQF

VSS.

Both IL-1α and IL-1β bind to the IL-1 receptor, which can have the sequence: MKVLLRLICF IALLISSLEA DKCK-EREEKI ILVSSANEID VRPCPLNPNE HKGTITWYKD DSKTPVSTEQ ASRIHQHKEK LWFVPAKVED SGHYYCVVRN SSYCLRIKIS AKFVENEPNL CYN-AQAIFKQ KLPVAGDGGL VCPYMEFFKN ENNELPKLQW YKDCKPLLLD NIHFSGVKDR LIVMNVAEKH RGNYTCHASY TYLGKQYPIT RVIEFITLEE NKPTRPVIVS PANETMEVDL GSQIQLICNV TGQLSDIAYW KWNGSVIDED DPVLGEDYYS VENPANKRRS TLITVLNISE IESRFYKHPF TCFAKNTHGI DAAYIQLIYP VTNFQKHMIG ICVTLTVIIV CSVFIYKIFK IDI-VLWYRDS CYDFLPIKAS DGKTYDAYIL YPKTVGEGST SDCDIFVFKV LPEVLEKQCG YKLFIYGRDD YVGEDIVEVI NENVKKSRRL IIIL-VRETSG FSWLGGSSEE QIAMYNALVQ DGIKVVL-LEL EKIQDYEKMP ESIKFIKQKH GAIRWSGDFT QGPQSAKTRF WKNVRYHMPV QRRSPSSKHQ LLSPATKEKL QREAHVPLG, (SEQ ID NO:8), NCBI Ref. Seq. NP_000868.1, with aas 21 to 569 forming the mature polypeptide, the ectodomain of which can be used to determine binding affinity to IL-1α and IL-1β.

In some cases, a variant IL-1α and IL-1β polypeptide exhibits reduced binding affinity to an IL-1 receptor having the sequence set forth in SEQ ID NO:8 or its ectodomain, compared to the binding affinity of an IL-1 polypeptide comprising the amino acid sequence set forth in SEQ ID NO:5 or SEQ ID NO:7. For example, in some cases, a variant IL-1α and IL-1β polypeptide binds the IL-1 receptor set forth in SEQ ID NO:8 or the mature proteins of the ectodomain) with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of a IL-1α or IL-1β polypeptide comprising the amino acid sequence set forth in SEQ ID NO:5 or SEQ ID NO:7.

In some cases, a variant IL-1α or IL-1β polypeptide (e.g., a variant of SEQ ID NOs:5 or 7) has a binding affinity to an IL-1 receptor having the sequence set forth in SEQ ID NO:8 that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant IL-1α or IL-1β polypeptide (e.g., a variant of SEQ ID NOs:5 or 7) has a binding affinity for the IL-1 receptor set forth in SEQ ID NO:8 or its ectodomain that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, from about 1 µM to about 5 µM, from about 5 µM to about 10 µM, from about 10 µM to about 20 µM, from about 20 µM to about 30 µM, from about 30 µM to about 50 µM, from about 50 µM to about 75 µM, or from about 75 µM to about 100 µM.

In some cases, a variant IL-1α or IL-1β polypeptide has a single aa substitution compared to the IL-1α or IL-1β amino acid sequence set forth in SEQ ID NO:5 or SEQ ID NO:7. In some cases, a variant IL-1α or IL-1β polypeptide has from 2 aa to 10 aa substitutions compared to the IL-1α or IL-1β amino acid sequence set forth in SEQ ID NO:5 or SEQ ID NO:7. In some cases, a variant IL-1α or IL-1β polypeptide has 2 aa substitutions compared to the IL-1α or IL-1β amino acid sequence set forth in SEQ ID NO:5 or SEQ ID NO:7. In some cases, a variant IL-1α or IL-1β polypeptide has 3 aa or 4 aa substitutions compared to the IL-1α or IL-1β amino acid sequence set forth in SEQ ID NO:5 or SEQ ID NO:7. In some cases, a variant IL-1α or IL-1β polypeptide has 5 aa or 6 aa substitutions compared to the IL-1α or IL-1β amino acid sequence set forth in SEQ ID NO:5 or SEQ ID NO:7. In some cases, a variant IL-1α or IL-1β polypeptide has 7 aa or 8 aa substitutions compared to the IL-1α or IL-1β amino acid sequence set forth in SEQ ID NO:5 or SEQ ID NO:7. In some cases, a variant IL-1α or IL-1β polypeptide has 9 aa or 10 aa substitutions compared to the IL-1α or IL-1β amino acid sequence set forth in SEQ ID NO:5 or SEQ ID NO:7.

Suitable variant IL-1α or IL-1β polypeptide sequences include polypeptide sequences having at least 80%, at least 85%, at least 90%, at least 95%, at least 98%, or at least 99% aa sequence identity to at least 100 contiguous aa of the amino acid sequence set forth in SEQ ID NO:5 or SEQ ID NO:7 (e.g., which have at least one aa substitution, deletion or insertion).

6 IL-2 and its Variants

As one non-limiting example, a MOD or variant MOD present in a masked TGF-β construct or complex is an IL-2 or variant IL-2 polypeptide. In some cases, a variant MOD present in a masked TGF-β construct or complex is a variant IL-2 polypeptide. Wild-type IL-2 binds to an IL-2 receptor (IL-2R). A wild-type IL-2 amino acid sequence can be as follows: APTSSSTKKT QLQL EH LLL D LQMILNGINN YKNPKLTRML T FKF YMPKKA TELKHLQCLE EELKPLEEVL NLAQSKNFHL RPRDLIS NIN VIVLELKGSE TTFMCEYADE TATIVEFLNR WITFC Q SIIS TLT (aa 21-153 of UniProt P60568, SEQ ID NO:9).

Wild-type IL-2 binds to an IL-2 receptor (IL-2R) on the surface of a cell. An IL-2 receptor is in some cases a heterotrimeric polypeptide comprising an alpha chain (IL-2Rα; also referred to as CD25), a beta chain (IL-2Rβ; also referred to as CD122) and a gamma chain (IL-2Rγ; also referred to as CD132). Amino acid sequences of human IL-2Rα, IL-2Rβ, and IL-2Rγ can be as follows.

Human IL-2Rα:
(SEQ ID NO: 10)
ELCDDDPPE IPHATFKAMA YKEGTMLNCE CKRGFRRIKS

GSLYMLCTGN SSHSSWDNQC QCTSSATRNT TKQVTPQPEE

QKERKTTEMQ SPMQPVDQAS LPGHCREPPP WENEATERIY

HFVVGQMVYY QCVQGYRALH RGPAESVCKM THGKTRWTQP

QLICTGEMET SQFPGEEKPQ ASPEGRPESE TSCLVTTTDF

QIQTEMAATM ETSIFTTEYQ VAVAGCVFLL ISVLLLSGLT

WQRRQRKSRR TI.

Human IL-2Rβ:
(SEQ ID NO: 11)
VNG TSQFTCFYNS RANISCVWSQ DGALQDTSCQ VHAWPDRRRW

NQTCELLPVS QASWACNLIL GAPDSQKLTT VDIVTLRVLC

REGVRWRVMA IQDFKPFENL RLMAPISLQV VHVETHRCNI

SWEISQASHY FERHLEFEAR TLSPGHTWEE APLLTLKQKQ

EWICLETLTP DTQYEFQVRV KPLQGEFTTW SPWSQPLAFR

TKPAALGKDT IPWLGHLLVG LSGAFGFIIL VYLLINCRNT

GPWLKKVLKC NTPDPSKFFS QLSSEHGGDV QKWLSSPFPS

SSFSPGGLAP EISPLEVLER DKVTQLLLQQ DKVPEPASLS

SNHSLTSCFT NQGYFFFHLP DALEIEACQV YFTYDPYSEE

DPDEGVAGAP TGSSPQPLQP LSGEDDAYCT FPSRDDLLLF

SPSLLGGPSP PSTAPGGSGA GEERMPPSLQ ERVPRDWDPQ

PLGPPTPGVP DLVDFQPPPE LVLREAGEEV PDAGPREGVS

FPWSRPPGQG EFRALNARLP LNTDAYLSLQ ELQGQDPTHL V.

Human IL-2Rγ:
(SEQ ID NO: 12)
LNTTILTP NGNEDTTADF FLTTMPTDSL SVSTLPLPEV

QCFVFNVEYM NCTWNSSSEP QPTNLTLHYW YKNSDNDKVQ

KCSHYLFSEE ITSGCQLQKK EIHLYQTFVV QLQDPREPRR

QATQMLKLQN LVIPWAPENL TLHKLSESQL ELNWNNRFLN

HCLEHLVQYR TDWDHSWTEQ SVDYRHKFSL PSVDGQKRYT

FRVRSRFNPL CGSAQHWSEW SHPIHWGSNT SKENPFLFAL

EAVVISVGSM GLIISLLCVY FWLERTMPRI PTLKNLEDLV

TEYHGNFSAW SGVSKGLAES LQPDYSERLC LVSEIPPKGG

ALGEGPGASP CNQHSPYWAP PCYTLKPET.

In some cases, where a masked TGF-β construct or complex comprises a variant IL-2 polypeptide, a cognate co-MOD is an IL-2R comprising polypeptides comprising the amino acid sequences of any one of SEQ ID NO:10, SEQ ID NO:11, and SEQ ID NO:12.

In some cases, a variant IL-2 polypeptide exhibits reduced binding affinity to IL-2R, compared to the binding affinity of an IL-2 polypeptide comprising the amino acid sequence set forth in SEQ ID NO:9. For example, in some cases, a variant IL-2 polypeptide binds IL-2R with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-2 polypeptide comprising the amino acid sequence set forth in SEQ ID NO:9 for an IL-2R (e.g., an IL-2R comprising polypeptides comprising the amino acid sequence set forth in SEQ ID NOs:10-12), when assayed under the same conditions.

In some cases, a variant IL-2 polypeptide (e.g., a variant of SEQ ID NO:9) has a binding affinity to IL-2R (e.g., of SEQ ID NOs:10-12) that is from 100 nM to 100 μM. As another example, in some cases, a variant IL-2 polypeptide (e.g., a variant of SEQ ID NO:9) has a binding affinity for IL-2R (e.g., an IL-2R comprising polypeptides comprising the amino acid sequence set forth in SEQ ID NOs: 10-12) that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, from about 1 µM to about 5 µM, from about 5 µM to about 10 µM, from about 10 µM to about 20 µM, from about 20 µM to about 30 µM, from about 30 µM to about 50 µM, from about 50 µM to about 75 µM, or from about 75 µM to about 100 µM.

In some cases, a variant IL-2 polypeptide has a single aa substitution compared to the IL-2 amino acid sequence set forth in SEQ ID NO:9. In some cases, a variant IL-2 polypeptide has from 2 to 10 aa substitutions compared to the IL-2 amino acid sequence set forth in SEQ ID NO:9. In some cases, a variant IL-2 polypeptide has 2 aa substitutions compared to the IL-2 amino acid sequence set forth in SEQ ID NO:9. In some cases, a variant IL-2 polypeptide has 3 aa substitutions compared to the IL-2 amino acid sequence set forth in SEQ ID NO:9. In some cases, a variant IL-2 polypeptide has 4 aa substitutions compared to the IL-2 amino acid sequence set forth in SEQ ID NO:9. In some cases, a variant IL-2 polypeptide has 5 aa substitutions compared to the IL-2 amino acid sequence set forth in SEQ ID NO:9. In some cases, a variant IL-2 polypeptide has 6 aa substitutions compared to the IL-2 amino acid sequence set forth in SEQ ID NO:9. In some cases, a variant IL-2 polypeptide has 7 aa substitutions compared to the IL-2 amino acid sequence set forth in SEQ ID NO:9. In some cases, a variant IL-2 polypeptide has 8 aa substitutions compared to the IL-2 amino acid sequence set forth in SEQ ID NO:9. In some cases, a variant IL-2 polypeptide has 9 aa substitutions compared to the IL-2 amino acid sequence set forth in SEQ ID NO:9. In some cases, a variant IL-2 polypeptide has 10 aa substitutions compared to the IL-2 amino acid sequence set forth in SEQ ID NO:9.

Suitable variant IL-2 polypeptide sequences include polypeptide sequences comprising an aa sequence having at least 80%, at least 85%, at least 90%, at least 95%, at least 98%, at least 99%, or 100%, aa sequence identity to at least 80 (e.g., 90, 100, 110, 120, 130 or 133) contiguous aas of SEQ ID NO:9. In addition, IL-2 variants include polypeptides that comprises an aa sequence having at least 80%, at least 85%, at least 90%, at least 95%, at least 98%, at least 99%, or 100%, aa sequence identity to at least 80 (e.g., 90, 100, 110, 120, 130 or 133) contiguous aas of any one of the variant IL-2 aa sequences that follow (see SEQ ID NOs: 13-27).

APTSSSTKKT QLQL $\underline{X}$HLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:13), where X is any amino acid other than Glu. In some cases, X is Ala.

APTSSSTKKT QLQLEHLLL $\underline{X}$ LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:14), where X is any amino acid other than Asp. In some cases, X is Ala.

APTSSSTKKT QLQLE $\underline{X}$LLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:15), where X (H16) is any amino acid other than His. In some cases, X is Ala (H16A). In some cases, X is Arg. In some cases, X is Asn. In some cases, X is Asp. In some cases, X is Cys. In some cases, X is Glu. In some cases, X is Gln. In some cases, X is Gly. In some cases, X is Ile. In some cases, X is Lys. In some cases, X is Leu. In some cases, X is Met. In some cases, X is Phe. In some cases, X is Pro. In some cases, X is Ser. In some cases, X is Thr (H16T). In some cases, X is Tyr. In some cases, X is Trp. In some cases, X is Val.

APTSSSTKKT QLQLEHLLLD LQMILNGINN YKNPKLTRML T $\underline{X}$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:16), where X (F42) is any amino acid other than Phe. In some cases, X is Ala (F42A). In some cases, X is Thr (F42T).

APTSSSTKKT QLQLEHLLLD LQMILNGINN YKNPKLTRML TFKF $\underline{X}$MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:17), where X is any amino acid other than Tyr. In some cases, X is Ala;

APTSSSTKKT QLQLEHLLLD LQMILNGINN YKNPKLTRML TFKFYMPKKA TELKHLQCLE EELKPLEEVL NLAQSKNFHL RPRDLIS$\underline{X}$IN VIVLELKGSE TTFMCEYADE TATIVEFLNR WITFCQSIIS TLT (SEQ ID NO:18), where X (N88) is any amino acid other than Asn. In some cases, X is Ala; in some cases, X is Arg.

APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFC$\underline{X}$SIIS TLT (SEQ ID NO:19), where X is any amino acid other than Gln. In some cases, X is Ala.

APTSSSTKKT QLQLE $\underline{X_1}$LLLD LQMILNGINN YKNPKLTRML T $\underline{X_2}$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:20), where $X_1$ (H16) is any amino acid other than His, and where $X_2$ (F42) is any amino acid other than Phe. In some cases, $X_1$ is Ala. In some cases, $X_2$ is Ala. In some cases, $X_1$ is Ala; and $X_2$ is Ala (H16A, F42A). In some cases, $X_1$ is Thr; and $X_2$ is Ala (H16T, F42A). In some cases, $X_1$ is Ala; and $X_2$ is Thr (H16A, F42T). In some cases, $X_1$ is Thr; and $X_2$ is Thr (H16T, F42T).

APTSSSTKKT QLQLE $\underline{X_1}$LLLD LQMILNGINN YKNPKLTRML T $\underline{X_2}$KFYMPKKA TELKHLQCLE EELKPLEEVL NLAQSKNFHL RPRDLIS $\underline{R}$IN VIVLELKGSE TTFMCEYADE TATIVEFLNR WITFCQSIIS TLT (SEQ ID NO:21), which comprises an N88R substitution, and where $X_1$ (H16) is any amino acid other than His, and where $X_2$ (F42) is any amino acid other than Phe. In some cases, $X_1$ is Ala. In some cases, $X_2$ is Ala. In some cases, $X_1$ is Ala; and $X_2$ is Ala. In some cases, $X_1$ is Thr; and $X_2$ is Ala. In some cases, $X_1$ is Ala; and $X_2$ is Thr. In some cases, $X_1$ is Thr; and $X_2$ is Thr.

APTSSSTKKT QLQLEHLLL $\underline{X_1}$ LQMILNGINN YKNPKLTRML T $\underline{X_2}$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:22), where $X_1$ is any amino acid other than Asp; and where $X_2$ is any amino acid other than Phe. In some cases, $X_1$ is Ala. In some cases, $X_2$ is Ala. In some cases, $X_1$ is Ala; and $X_2$ is Ala.

APTSSSTKKT QLQL $\underline{X_1}$HLLL $\underline{X_2}$ LQMILNGINN YKNPKLTRML T $\underline{X_3}$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:23), where $X_1$ is any amino acid other than Glu; where $X_2$ is any amino acid other than Asp; and where $X_3$ is any amino acid other than Phe. In some cases, $X_1$ is Ala. In some cases, $X_2$ is Ala. In some cases, $X_3$ is Ala. In some cases, any two or all three of $X_1$ is Ala; $X_2$ is Ala; and $X_3$ is Ala.

APTSSSTKKT QLQLE $\underline{X_1}$LLL $\underline{X_2}$ LQMILNGINN YKNPKLTRML T $\underline{X_3}$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:24), where $X_1$ is any amino acid other than His; where $X_2$ is any amino acid other than Asp; and where $X_3$ is any amino acid other than Phe. In some cases, $X_1$ is Ala. In some cases, $X_2$ is Ala. In some cases, $X_3$ is Ala. In some cases, $X_1$ is Ala; $X_2$ is Ala; and $X_3$ is Ala.

APTSSSTKKT QLQLEHLLL $\underline{X_1}$LQMILNGINN YKNPKLTRML T $\underline{X_2}$KFYMPKKA TELKHLQCLE EELKPLEEVL NLAQSKNFHL RPRDLISNIN VIVLELKGSE TTFMCEYADE TATIVEFLNR WITFC $\underline{X_3}$SIIS TLT (SEQ ID NO:25), where $X_1$ is any amino acid other than Asp; where $X_2$ is any amino acid other than Phe; and where $X_3$ is any amino acid other than Gln. In some cases, $X_1$ is Ala. In some cases, $X_2$ is Ala. In some cases, $X_3$ is Ala. In some cases, $X_1$ is Ala; $X_2$ is Ala; and $X_3$ is Ala.

APTSSSTKKT QLQLEHLLL $\underline{X_1}$ LQMILNGINN YKNPKLTRML T $\underline{X_2}$KF $\underline{X_3}$MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:26), where $X_1$ is any amino acid other than Asp; where $X_2$ is any amino acid other than Phe; and where $X_3$ is any amino acid other than Tyr. In some cases, $X_1$ is Ala. In some cases, $X_2$ is Ala. In some cases, $X_3$ is Ala. In some cases, $X_1$ is Ala; $X_2$ is Ala; and $X_3$ is Ala.

APTSSSTKKT QLQLE $\underline{X_1}$LLL $\underline{X_2}$ LQMILNGINN YKNPKLTRML T $\underline{X_3}$KF $\underline{X_4}$MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:27), where $X_1$ is any amino acid other than His; where $X_2$ is any amino acid other than Asp; where $X_3$ is any amino acid other than Phe; and where $X_4$ is any amino acid other than Tyr. In some cases, $X_1$ is Ala. In some cases, $X_2$ is Ala. In some cases, $X_3$ is Ala. In some cases, $X_4$ is Ala. In some cases, $X_1$ is Ala; $X_2$ is Ala; $X_3$ is Ala; and $X_4$ is Ala.

APTSSSTKKT QLQLEHLLL $\underline{X_1}$ LQMILNGINN YKNPKLTRML T $\underline{X_2}$KF $\underline{X_3}$MPKKA TELKHLQCLE EELKPLEEVL NLAQSKNFHL RPRDLISNIN VIVLELKGSE TTFMCEYADE TATIVEFLNR WITFC $\underline{X_4}$SIIS TLT (SEQ ID NO:139), where $X_1$ is any amino acid other than Asp; where $X_2$ is any amino acid other than Phe; where $X_3$ is any amino acid other than Tyr; and where $X_4$ is any amino acid other than Gln. In some cases, $X_1$ is Ala. In some cases, $X_2$ is Ala. In some cases, $X_3$ is Ala. In some cases, $X_4$ is Ala. In some cases, $X_1$ is Ala; $X_2$ is Ala; $X_3$ is Ala; and $X_4$ is Ala.

APTSSSTKKT QLQLE $\underline{X_1}$LLL $\underline{X_2}$ LQMILNGINN YKNPKLTRML T $\underline{X_3}$KF $\underline{X_4}$MPKKA TELKHLQCLE EELKPLEEVL NLAQSKNFHL RPRDLISNIN VIVLELKGSE TTFMCEYADE TATIVEFLNR WITFC $\underline{X_5}$SIIS TLT (SEQ ID NO:140), where $X_1$ is any amino acid other than His; where $X_2$ is any amino acid other than Asp; where $X_3$ is any amino acid other than Phe; where $X_4$ is any amino acid other than Tyr; and where $X_5$ is any amino acid other than Gln. In some cases, $X_1$ is Ala. In some cases, $X_2$ is Ala. In some cases, $X_3$ is Ala. In some cases, $X_4$ is Ala. In some cases, $X_5$ is Ala. In some cases, any two, three, four, or all five of $X_1$ is Ala; $X_2$ is Ala; $X_3$ is Ala; $X_4$ is Ala; and/or $X_5$ is Ala.

APTSSSTKKT QLQLE $\underline{X_1}$LLLD LQMILNGINN YKNPKLTRML T $\underline{X_2}$KFYMPKKA TELKHLQCLE EELKPLEEVL NLAQSKNFHL RPRDLISNIN VIVLELKGSE TTFMCEYADE TATIVEFLNR WITFC $\underline{X_3}$SIIS TLT (SEQ ID NO:141), where $X_1$ is any amino acid other than His; where $X_2$ is any amino acid other than Phe; and where $X_3$ is any amino acid other than Gln. In some cases, $X_1$ is Ala. In some cases, $X_2$ is Ala. In some cases, $X_3$ is Ala. In some cases, any two or all three of $X_1$ is Ala; $X_2$ is Ala; and/or $X_3$ is Ala.

7 IL-4 and its Variants

As one non-limiting example, a MOD or variant MOD present in a masked TGF-β construct or complex is an IL-4 or variant IL-4 polypeptide. Wild-type IL-4 has two isoforms, IL-4a and IL-413, both of which bind to the membrane bound IL-4 receptor (isoform 1) or its soluble counterpart (isoform 2).

A wild-type human IL-4 isoform 1 precursor polypeptide can comprise the following amino acid sequence: MGLTSQLLPP LFFLLACAGN FVHGHKCDIT LQEIIKTLNS LTEQKTLCTE LTVTDIFAAS KNTTEKETFC RAATVLRQFY SHHEKDTRCL GATAQQFHRH KQLIRFLKRL DRNLWGLAGL NSCPVKEANQ STLENFLERL KTIMREKYSK CSS (SEQ ID NO:28) NCBI Ref. Seq. NP_000580.1.

A mature wild-type human IL-4 isoform 1 polypeptide can comprise the following amino acid sequence: KCDIT LQEIIKTLNS LTEQKTLCTE LTVTDIFAAS KNTTEKETFC RAATVLRQFY SHHEKDTRCL GATAQQFHRH KQLIRFLKRL DRNLWGLAGL NSCPVKEANQ STLENFLERL KTIMREKYSK CSS (SEQ ID NO:29).

A wild-type human IL-4 isoform 2 precursor polypeptide can comprise the following amino acid sequence: MGLTSQLLPP LFFLLACAGN FVHGHKCDIT LQEIIKTLNS LTEQKNTTEK ETFCRAATVL RQFYSHHEKD TRCLGATAQQ FHRHKQLIRF LKRLDRNLWG LAGLNSCPVK EANQSTLENF LERLKTIMRE KYSKCSS, NCBI Ref. Seq: NP_758858.1, (SEQ ID NO:30).

A mature wild-type human IL-4 isoform 2 polypeptide can comprise the following amino acid sequence KCDIT LQEIIKTLNS LTEQKNTTEK ETFCRAATVL RQFYSHHEKD TRCLGATAQQ FHRHKQLIRF LKRLDRNLWG LAGLNSCPVK EANQSTLENF LERLKTIMRE KYSKCSS (SEQ ID NO:31).

Both IL-4 isoform 1 and isoform 2 bind to the membrane bound IL-4 receptor (IL-4R) and/or its soluble isoform 2. Membrane bound IL-4 can have the sequence MGWLCSGLLF PVSCLVLLQV ASSGNMKVLQ EPTCVSDYMS ISTCEWKMNG PTNCSTELRL LYQLVFLLSE AHTCIPENNG GAGCVCHLLM DDVVSADNYT LDLWAGQQLL WKGSFKPSEH VKPRAPGNLT VHTNVSDTLL LTWSNPYPPD NYLYNHLTYA VNIWSENDPA DFRIYNVTYL EPSLRIAAST LKSGISYRAR VRAWAQCYNT TWSEWSPSTK WHNSYREPFE QHLLLGVSVS CIVILAVCLL CYVSITKIKK EWWDQIPNPA RSRLVAIIIQ DAQGSQWEKR SRGQEPAKCP HWKNCLTKLL PCFLEHNMKR DEDPHKAAKE MPFQGSGKSA WCPVEISKTV LWPESISVVR CVELFEAPVE CEEEEEVEEE KGSFCASPES SRDDFQEGRE GIVARLTESL FLDLLGEENG GFCQQDMGES CLLPPSGSTS AHMPWDEFPS AGPKEAPPWG KEQPLHLEPS PPASPTQSPD NLTCTETPLV IAGNPAYRSF SNSLSQSPCP RELGPDPLLA RHLEEVE- PEM PCVPQLSEPT TVPQPEPETW EQILRRNVLQ HGAAAAPVSA PTSGYQEFVH AVEQGGTQAS AVVGLGPPGE AGYKAFSSLL ASSAVSPEKC GFGASSGEEG YKPFQDLIPG CPGDPAPVPV PLFTGFLDRE PPRSPQSSHL PSSSPEHLGL EPGEKVEDMP KPPLPQEQAT DPLVDSLGSG IVY-SALTCHL CGHLKQCHGQ EDGGQTPVMA SPCCGCCCGD RSSPPTTPLR APDPSPGGVP LEA-SLCPASL APSGISEKSK SSSSFHPAPG NAQSSSQTPK IVNFVSVGPT YMRVS, (SEQ ID NO:32), NCBI Ref. Seq. NP_000409.1, with aas 26 to 825 forming the mature polypeptide, and aas 233-256 the transmembrane region; the ectodomain of the protein can be used to determine binding affinity to IL-4 isoform 1 or 2.

The soluble isoform 2, having the sequence MGWLCSGLLF PVSCLVLLQV ASSGNMKVLQ EPTCVSDYMS ISTCEWKMNG PTNCSTELRL LYQLVFLLSE AHTCIPENNG GAGCVCHLLM DDVVSADNYT LDLWAGQQLL WKGSFKPSEH VKPRAPGNLT VHTNVSDTLL LTWSNPYPPDN YLYNHLTYAVN IWSENDPADF RIYNVTYLEP SLRI-AASTLK SGISYRARVRA WAQCYNTTWSE WSP-STKWHNS NIC, (SEQ ID NO:33), UniProtKB—P24394, can also be used for determining binding affinity of both IL-4 isoforms.

In some cases, a variant IL-4 isoform 1 or 2 polypeptide (e.g., a variant of SEQ ID NOs:29 or 31) exhibits reduced binding affinity to a mature IL-4 receptor sequence set forth in SEQ ID NO:32 or its ectodomain, or the soluble IL-4 receptor set forth in SEQ ID NO:33, compared to the binding affinity of an IL-4 polypeptide comprising the amino acid sequence set forth in SEQ ID NO:29 or SEQ ID NO:31. For example, in some cases, a variant IL-4 isoform 1 or 2 polypeptide binds the mature IL-4 receptor set forth in SEQ ID NO:32 (or its ectodomain) or in SEQ ID NO:33 with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of a IL-4 isoform 1 or 2 polypeptide comprising the amino acid sequence set forth in SEQ ID NO:29 or SEQ ID NO:31.

In some cases, a variant IL-4 isoform 1 or 2 polypeptide (e.g., a variant of SEQ ID NOs:29 or 31) has a binding affinity that is from 1 nM to 1 mM to a mature IL-4 receptor set forth in SEQ ID NO:32 (or its ectodomain) or in SEQ ID NO:33 (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant IL-4 isoform 1 or 2 polypeptide (e.g., a variant of SEQ ID NOs:29 or 31) has a binding affinity for the mature IL-4 receptor set forth in SEQ ID NO:32 (or its ectodomain) or in SEQ ID NO:33 that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-4 isoform 1 or 2 polypeptide has a single aa substitution compared to the IL-4 isoform 1 or 2 amino acid sequence set forth in SEQ ID NO:29 or SEQ ID NO:31. In some cases, a variant IL-4 isoform 1 or 2 polypeptide has from 2 aa to 10 aa substitutions compared to the IL-4 isoform 1 or 2 amino acid sequence set forth in SEQ ID NO:29 or SEQ ID NO:31. In some cases, a variant IL-4 isoform 1 or 2 polypeptide has 2 aa substitutions compared to the IL-4 isoform 1 or 2 amino acid sequence set forth in SEQ ID NO:29 or SEQ ID NO:31. In some cases, a variant IL-4 isoform 1 or 2 polypeptide has 3 aa or 4 aa substitutions compared to the IL-4 isoform 1 or 2 amino acid sequence set forth in SEQ ID NO:29 or SEQ ID NO:31. In some cases, a variant IL-4 polypeptide has 5 aa or 6 aa substitutions compared to the IL-4 isoform 1 or 2 amino acid sequence set forth in SEQ ID NO:29 or SEQ ID NO:31. In some cases, a variant IL-4 isoform 1 or 2 polypeptide has 7 aa or 8 aa substitutions compared to the IL-4 isoform 1 or 2 amino acid sequence set forth in SEQ ID NO:29 or SEQ ID NO:31. In some cases, a variant IL-4 isoform 1 or 2 polypeptide has 9 aa or 10 aa substitutions compared to the IL-4 isoform 1 or 2 amino acid sequence set forth in SEQ ID NO:29 or SEQ ID NO:31.

Suitable variant IL-4 isoform 1 or 2 polypeptide sequences include polypeptide sequences having at least 80%, at least 85%, at least 90%, at least 95%, at least 98%, or at least 99% aa sequence identity to at least 80 contiguous aa (e.g., at least 100, or 110 contiguous aa) of SEQ ID NO:29 or SEQ ID NO:31 (e.g., which have at least one aa substitution, deletion or insertion).

8 IL-6 and its Variants

As one non-limiting example, a MOD or variant MOD present in a masked TGF-β construct or complex is an IL-6 or variant IL-6 polypeptide. Wild-type IL-6 binds to the IL-6 receptor that is comprised of an alpha and beta (gp130) subunit, which forms a signaling hexamer of two trimers having an IL-6 molecule and each subunit. See, e.g., Lacroix et al., *J. Biol. Chem.,* 290(45)26943-953 (2015).

A wild-type human IL-6 precursor polypeptide can comprise the following amino acid sequence: MNSFSTSAFG PVAFSLGLLL VLPAAFPAPV PPGEDSKDVA APHRQPLTSS ERIDKQIRYI LDGISALRKE TCNKSNMCES SKEALAENNL NLPKMAEKDG CFQSGFNEET CLVKIITGLL EFEVYLEYLQ NRFESSEEQA RAVQMSTKVL IQFLQKKAKN LDAITTPDPT TNASLLTKLQ AQNQWLQDMT THLILRSFKE FLQSSLRALR QM (SEQ ID NO:34) NCBI Ref. Seq. NP_000591.1.

A mature wild-type human IL-6 polypeptide can comprise the following amino acid sequence:

```
                                          (SEQ ID NO: 35)
VPPGEDSKDVA APHRQPLTSS ERIDKQIRYI LDGISALRKE

TCNKSNMCES SKEALAENNL NLPKMAEKDG CFQSGFNEET

CLVKIITGLL EFEVYLEYLQ NRFESSEEQA RAVQMSTKVL

IQFLQKKAKN LDAITTPDPT TNASLLTKLQ AQNQWLQDMT

THLILRSFKE FLQSSLRALR QM.
```

IL-6 binds to the membrane bound IL-6 receptor, which is comprised of an alpha and beta subunit. The human IL-6R alpha subunit can have the sequence MLAVGCALLA ALLAAPGAAL APRRCPAQEV ARGVLTSLPG DSVTLTCPGV EPEDNATVHW VLRKPAAGSH PSRWAGMGRR LLLRSVQLHD SGNYSCYRAG RPAGTVHLLV DVPPEEPQLS CFRKSPLSNV VCEWGPRSTP SLTTKAVLLV RKFQNSPAED FQEPCQYSQE SQKFSCQLAV PEGDSSFYIV SMCVASSVGS KFSKTQTFQG CGILQPDPPA NITVTAVARN PRWLSVTWQD PHSWNSSFYR LRFELRYRAE RSKTFTTWMV KDLQHHCVIH DAWSGLRHVV QLRAQEEFGQ GEWSEWSPEA MGTPWTESRS PPAENEVSTP MQALTTNKDD DNILFRDSAN ATSLPVQDSS SVPLPTFLVA GGSLAFGTLL CIAIVLRFKK TWKLRALKEG KTSMHPPYSL GQLVPERPRP TPVLVPLISP PVSPSSLGSD NTSSHNRPDA RDPRSPYDIS NTDYFFPR, (SEQ ID NO:36), NCBI Ref. Seq: NP_000556.1, with aas 26 to 825 forming the mature polypeptide, and aas 233-256 the transmembrane region. After binding IL-6, the IL6 alpha subunit binds the IL-6 beta subunit.

The human IL-6R beta subunit can have the sequence MLTLQTWLVQ ALFIFLTTES TGELLDPCGY ISPESPVVQL HSNFTAVCVL KEKCMDYFHV NANYIVWKTN HFTIPKEQYT IINRTASSVT FTDIASLNIQ LTCNILTGFQ LEQNVYGITI ISGLPPEKPK NLSCIVNEGK KMRCEWDGGR ETHLETNFTL KSEWATHKFA DCKAKRDTPT SCTVDYSTVY FVNIEVWVEA ENALGKVTSD HINFDPVYKV KPNPPHNLSV INSEELSSIL KLTWTNPSIK SVIILKYNIQ YRTKDASTWS QIPPEDTAST RSSFTVQDLK PFTEYVFRIR CMKEDGKGYW SDWSEEASGI TYEDRPSKAP SFWYKIDPSH TQGYRTVQLV WKTLPPFEAN GKILDYEVTL TRWKSHLQNY TVNATKLTVN LTNDRYLATL TVRNLVGKSD AAVLTIPACD FQATHPVMDL KAFPKDNMLW VEWTTPRESV KKYILEWCVL SDKAPCITDW QQEDGTVHRT YLRGNLAESK CYLITVTPVY ADGPGSPESI KAYLKQAPPS KGPTVRTKKV GKNEAVLEWD QLPVDVQNGF IRNYTIFYRT IIGNETAVNV DSSHTEYTLS SLTSDTLYMV RMAAYTDEGG KDGPEFTFTT PKFAQGEIEA IVVPVCLAFL LTTLLGVLFC FNKRDLIKKH IWPNVPDPSK SHIAQWSPHT PPRHNFNSKD QMYSDGNFTD VSVVEIEAND KKPFPEDLKS LDLFKKEKIN TEGHSSGIGG SSCMSSSRPS ISSSDENESS QNTSSTVQYS TVVHSGYRHQ VPSVQVFSRS ESTQPLLDSE ERPEDLQLVD HVDGGDGILP RQQYFKQNCS QHESSPDISH FERSKQVSSV NEEDFVRLKQ QISDHISQSC GSGQMKMFQE VSAADAFGPG TEGQVERFET VGMEAATDEG MPKSYLPQTV RQGGYMPQ, (SEQ ID NO:37), UniProtKB—P40189, with aas 23 to 918 forming the mature polypeptide, and aas 620-641 the transmembrane region.

As an alternative to IL-6 binding to the membrane bound IL-6R alpha subunit, it can bind the mature soluble form of the IL-6R alpha subunit having the sequence MLAVGCALLA ALLAAPGAAL APRRCPAQEV ARGVLTSLPG DSVTLTCPGV EPEDNATVHW VLRKPAAGSH PSRWAGMGRR LLLRSVQLHD SGNYSCYRAG RPAGTVHLLV DVPPEEPQLS CFRKSPLSNV VCEWGPRSTP SLTTKAVLLV RKFQNSPAED FQEPCQYSQE SQKFSCQLAV PEGDSSFYIV SMCVASSVGS KFSKTQTFQG CGILQPDPPA NITVTAVARN PRWLSVTWQD PHSWNSSFYR LRFELRYRAE RSKTFTTWMV KDLQHHCVIH DAWSGLRHVV QLRAQEEFGQ GEWSEWSPEA MGTPWTESRS PPAENEVSTP MQALTTNKDD DNILFRDSAN ATSLPVQDSS SVPLPTFLVA GGSLAFGTLL CIAIVLRFKK TWKLRALKEG KTSMHPPYSL GQLVPERPRP TPVLVPLISP PVSPSSLGSD NTSSHNRPDA RDPRSPYDIS NTDYFFPR, (SEQ ID NO:38) with the mature peptide comprising aas 20 to 468, UniProtKB—P08887.1. The soluble subunit can take the place of the membrane bound IL-6R alpha subunit and can be used in binding affinity assays.

In some cases, a variant IL-6 polypeptide (e.g., a variant of SEQ ID NO:35) exhibits reduced binding affinity to a mature IL-6 receptor set forth in SEQ ID NOs:36 and 37, or SEQ ID NOs:37 and 38, compared to the binding affinity of an IL-6 polypeptide comprising the amino acid sequence set forth in SEQ ID NO:35. For example, in some cases, a variant IL-6 polypeptide binds a mature IL-6 receptor set forth in SEQ ID NOs:36 and 37, or SEQ ID NOs:37 and 38, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-6 polypeptide comprising the amino acid sequence set forth in SEQ ID NO:35.

In some cases, a variant IL-6 polypeptide (e.g., a variant of SEQ ID NO:35) has a binding affinity that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM) to a mature IL-6 receptor set forth in SEQ ID NOs:36 and 37 or SEQ ID NOs:37 and 38. As another example, in some cases, a variant IL-6 polypeptide (e.g., a variant of SEQ ID NO:35) has an affinity to a mature IL-6 receptor set forth in SEQ ID NOs:36 and 37, or SEQ ID NOs:37 and 38, that is from 100 nM to 100 μM (e.g., from 100 nM to 1 μM, from 1 μM to 10 μM, or from 10 μM to 100 μM). As another example, in some cases, a variant IL-6 polypeptide (e.g., a variant of SEQ ID NO:35) has a binding affinity for the mature IL-6 receptor set forth in SEQ ID NOs:36 and 37, or SEQ ID NOs:37 and 38, that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-6 polypeptide has a single aa substitution compared to the IL-6 amino acid sequence set forth in SEQ ID NO:35. In some cases, a variant IL-6 polypeptide has from 2 aa to 10 aa substitutions compared to the IL-6 amino acid sequence set forth in SEQ ID NO:35. In some cases, a variant IL-6 polypeptide has 2 aa substitutions compared to the IL-6 amino acid sequence set forth in SEQ ID NO:35. In some cases, a variant IL-6 polypeptide has 3 aa or 4 aa substitutions compared to the IL-6 amino acid sequence set forth in SEQ ID NO:35. In some cases, a variant IL-6 polypeptide has 5 aa or 6 aa substitutions compared to the IL-6 amino acid sequence set forth in SEQ ID NO:35. In some cases, a variant IL-6 polypeptide has 7 aa or 8 aa substitutions compared to the IL-6 amino acid sequence set forth in SEQ ID NO:35. In some cases, a variant IL-6 polypeptide has 9 aa or 10 aa substitutions compared to the IL-6 amino acid sequence set forth in SEQ ID NO:35.

Suitable variant IL-6 polypeptide sequences include polypeptide sequences having at least 80%, at least 85%, at least 90%, at least 95%, at least 98%, or at least 99% aa sequence identity to at least 80 contiguous aa (e.g., at least 100, or 110 contiguous aa) of SEQ ID NO:35 (e.g., which have at least one aa substitution, deletion or insertion).

9 IL-7 and its Variants

As one non-limiting example, a MOD or variant MOD present in a masked TGF-β construct or complex is an IL-7 or variant IL-7 polypeptide. Wild-type IL-7 has four isoforms all of which bind to the membrane bound IL-7 receptor, which has two subunits, alpha (a) and the common gamma (common-γ) chain.

A wild-type human IL-7 isoform 1 precursor polypeptide can comprise the following amino acid sequence: MFHVSFRYIF GLPPLILVLL PVASSDCDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ VKGRKPAALG EAQPTKSLEE NKSLKEQKKL NDLCFLKRLL QEIKTCWNKI LMGTKEH (SEQ ID NO:39) UniProtKB—P13232, NCBI Ref Seq. NP_000871.1.

A mature wild-type human IL-7 isoform 1 polypeptide can comprise the following amino acid sequence: DCDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ VKGRKPAALG EAQPTKSLEE NKSLKEQKKL NDLCFLKRLL QEIKTCWNKI LMGTKEH (SEQ ID NO:40).

A wild-type human IL-7 isoform 2 precursor polypeptide can comprise the following amino acid sequence: MFHVSFRYIF GLPPLILVLL PVASSDCDIE GKDGKQYESV LMVSIDQLLD SMKEIGSNCL NNEFNFFKRH ICDANKVKGR KPAALGEAQP TKSLEENKSL KEQKKLNDLC FLKRLLQEIK TCWNKILMGT KEH, (SEQ ID NO:41) NCBI Ref. Seq: NP_001186815.1.

A mature wild-type human IL-7 isoform 2 polypeptide can comprise the following amino acid sequence: SDCDIE GKDGKQYESV LMVSIDQLLD SMKEIGSNCL NNEFNFFKRH ICDANKVKGR KPAALGEAQP TKSLEENKSL KEQKKLNDLC FLKRLLQEIK TCWNKILMGT KEH (SEQ ID NO:42).

A wild-type human IL-7 isoform 3 precursor polypeptide can comprise the following amino acid sequence: MFHVSFRYIF GLPPLILVLL PVASSDCDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ EENKSLKEQK KLNDLCFLKR LLQEIKTCWN KILMGTKEH, (SEQ ID NO:43) NCBI Ref. Seq: NP_001186816.1.

A mature wild-type human IL-7 isoform 3 polypeptide can comprise the following amino acid sequence: CDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ EENKSLKEQK KLNDLCFLKR LLQEIKTCWN KILMGTKEH (SEQ ID NO:44).

A wild-type human IL-7 isoform 4 precursor polypeptide can comprise the following amino acid sequence: MFHVSFRYIF GLPPLILVLL PVASSDCDIE GKDGKQYESV LMVSIDQLLD SMKEIGSNCL NNEFNFFKRH ICDANKEENK SLKEQKKLND LCFLKRLLQE IKTCWNKILM GTKEH, NCBI Ref. Seq: NP_001186817.1 (SEQ ID NO:45).

A mature wild-type human IL-7 isoform 4 polypeptide can comprise the following amino acid sequence: SDCDIE GKDGKQYESV LMVSIDQLLD SMKEIGSNCL NNEFNFFKRH ICDANKEENK SLKEQKKLND LCFLKRLLQE IKTCWNKILM GTKEH (SEQ ID NO:46).

The IL-7 receptor alpha subunit can have the sequence: MTILGTTGFM VFSLLQVVSG ESGYAQNGDL EDAEL-DDYSF SCYSQLEVNG SQHSLTCAFE DPDVNITNLE FEICGALVEV KCLNFRKLQE IYFIETKKFL LIGKSNICVK VGEKSLTCKK IDLTTIVKPE APFDLSV-VYR EGANDFVVTF NTSHLQKKYV KVLMHDVAYR QEKDENKWTH VNLSSTKLTL LQRKLQPAAM YEIKVRSIPD HYFKGFWSEW SPSYYFRTPE INNSSGEMDP ILLTISILSF FSVALLVILA CVLWKKRIKP IVWPSLPDHK KTLEHLCKKP RKNLNVSFNP ESFLDCQIHR VDDIQARDEV EGFLQDTFPQ QLEESEKQRL GGDVQSPNCP SEDV-VITPES FGRDSSLTCL AGNVSACDAP ILSSSRSLDC RESGKNGPHV YQDLLLSLGT TNSTLPPPFS LQSGILTLNP VAQGQPILTS LGSNQEEAYV TMSSFYQNQ (SEQ ID NO:47), NCBI Ref. Seq. NP_002176.2, with aas 21 to 459 forming the mature polypeptide, and aas 240-264 the transmembrane region. All or part of the receptor subunit (e.g., the ectodomain (aas 21-239) of the protein can be used to determine binding affinity to IL-7 isoforms along with IL-7 receptor gamma subunit.

The common-γ subunit (IL-7RG or IL-R7γ) can have the sequence MLKPSLPFTS LLFLQLPLLG VGLNTTILTP NGNEDTTADF FLTTMPTDSL SVSTLPLPEV QCFVFN-VEYM NCTWNSSSEP QPTNLTLHYW YKNSDNDKVQ KCSHYLFSEE ITSGCQLQKK EIHLYQTFVV QLQDPREPRR QATQMLKLQN LVIPWAPENL TLHKLSESQL ELNWNNRFLN HCLEHLVQYR TDWDHSWTEQ SVDYRHKFSL PSVDGQKRYT FRVRSRFNPL CGSAQHWSEW SHPIHWGSNT SKENP-FLFAL EAVVISVGSM GLIISLLCVY FWLERTMPRI PTLKNLEDLV TEYHGNFSAW SGVSKGLAES LQPDY-SERLC LVSEIPPKGG ALGEGPGASP CNQHSPYWAP PCYTLKPET, NCBI Ref. Seq. NP_000197.1, (SEQ ID NO:48) with aas 23 to 369 forming the mature polypeptide, and aas 263-283 the transmembrane region. All or part of the receptor subunit (e.g., the ectodomain (aas 23-262) of the protein can be used to determine binding affinity to IL-7 along with the alpha subunit.

In some cases, a variant IL-7 isoform 1, 2, 3, or 4 polypeptide (e.g. of SEQ ID NOs:40, 42, 44, or 46) exhibits reduced binding affinity to a mature IL-7 receptor sequence (e.g., an IL-7 receptor comprising all or part of the polypeptides set forth in SEQ ID NOs: 47 and 48, such as their ectodomains), compared to the binding affinity of an IL-7 polypeptide comprising the amino acid sequence set forth in SEQ ID NOs:40, 42, 44, or 46. For example, in some cases, a variant IL-7 isoform 1, 2, 3, or 4 polypeptide binds an IL-7 receptor comprising all or part of the polypeptides set forth in SEQ ID NOs: 47 and 48, such as their ectodomains, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-7 isoform 1, 2, 3, or 4 polypeptide comprising the amino acid sequence set forth in SEQ ID NOs:40, 42, 44, or 46.

In some cases, a variant of IL-7 isoform 1, 2, 3, or 4 polypeptide (e.g. a variant of SEQ ID NOs:40, 42, 44, or 46) has a binding affinity for an IL-7 receptor comprising all or part of the polypeptides set forth in SEQ ID NOs: 47 and 48, such as their ectodomains, that is from 1 nM to 1 mM. In some cases, a variant IL-7 isoform 1, 2, 3, or 4 polypeptide (e.g. a variant of SEQ ID NOs:40, 42, 44, or 46) has a binding affinity to a mature IL-7 receptor comprising all or part of the polypeptides set forth in SEQ ID NOs: 47 and 48, such as their ectodomains, that is from 100 nM to 100 μM (e.g., from 100 nM to 1 μM, from 1 μM to 10 μM, or from 10 μM to 100 μM). As another example, in some cases, a variant IL-7 isoform 1, 2, 3, or 4 polypeptide has a binding affinity for a mature IL-7 receptor comprising all or part of the polypeptides set forth in SEQ ID NOs:47 and 48, such as their ectodomains, that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, from about 1 µM to about 5 µM, from about 5 µM to about 10 µM, from about 10 µM to about 20 µM, from about 20 µM to about 30 µM, from about 30 µM to about 50 µM, from about 50 µM to about 75 µM, or from about 75 µM to about 100 µM.

In some cases, a variant IL-7 isoform 1, 2, 3, or 4 polypeptide has a single aa substitution compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has from 2 aa to 10 aa substitutions compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has 2 aa substitutions compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has 3 aa or 4 aa substitutions compared to the IL-7 isoform 1, 2, 3, or 4 amino acid sequence set forth in SEQ ID NOs:40, 42, 44, or 46. In some cases, a variant IL-7 polypeptide has 5 aa or 6 aa substitutions compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has 7 aa or 8 aa substitutions compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has 9 aa or 10 aa substitutions compared to the IL-7 isoform 1, 2, 3, or 4 amino acid sequence set forth in SEQ ID NOs:40, 42, 44, or 46.

Suitable variant IL-7 isoform 1, 2, 3, or 4 polypeptide sequences include polypeptide sequences having at least 80%, at least 85%, at least 90%, at least 95%, at least 98%, or at least 99% aa sequence identity to at least 50 contiguous aa (e.g., at least 60, at least 70, at least 80, at least 90, at least 100, or at least 110 contiguous aa) of SEQ ID NOs:40, 42, 44, or 46 (e.g., which have at least one aa substitution, deletion or insertion).

10 IL-10 and its Variants

As one non-limiting example, a MOD or variant MOD present in a masked TGF-β construct or complex is an IL-10 or variant IL-10 polypeptide, such as monomeric IL-10 variants having an insertion in the hinge region between the D and E helices described by Josephson et al., *J. Biol. Chem.* 275:13552-13557 (2000). Wild-type IL-10 has isoforms, all of which bind to the membrane bound IL-10 receptor, which has both alpha (α) IL-10RA and beta (β) IL-10RB subunits. The receptor exists as a tetramer on the surface of cells (e.g., B cells, T cells, NK cells, mast cells, and dendritic cells).

A wild-type human IL-10 isoform 1 precursor polypeptide can comprise the following amino acid sequence: MHSSALLCCL VLLTGVRASP GQGTQSENSC THFPGNLPNM LRDLRDAFSR VKTFFQMKDQ LDNLLLKESL LEDFKGYLGC QALSEMIQFY LEEVMPQAEN QDPDIKAHVN SLGENLKTLR LRLRRCHRFL PCENKSKAVE QVKNAFNKLQ EKGIYKAMSE FDIFINYIEA YMTMKIRN (SEQ ID NO:49) UniProtKB—P22301, NCBI Ref Seq. NP_000563.1, which may have an H227L sequence variation.

A mature wild-type human IL-10 polypeptide can comprise the following amino acid sequence (SEQ ID NO: 50)
SP GQGTQSENSC THFPGNLPNM LRDLRDAFSR VKTFFQMKDQ

LDNLLLKESL LEDFKGYLGC QALSEMIQFY LEEVMPQAEN

QDPDIKAHVN SLGENLKTLR LRLRRCHRFL PCENKSKAVE

QVKNAFNKLQ EKGIYKAMSE FDIFINYIEA YMTMKIRN.

A human IL-10 polypeptide can comprise the following amino acid sequence MIQFYLEEVM PQAENQDPDI KAHVNSLGEN LKTLRLRLRR CHRFLPCENK SKAVEQVKNA FNKLQEKGIY KAMS, UniProtKB—A0A286YEX3 1 (SEQ ID NO:51).

An IL-10 polypeptide can comprise an insertion in the hinge region between the D and E helices of the IL-10 polypeptide (e.g., a 5-7 aa insertion adjacent to any of E48, N49, K50, or S51 of SEQ ID NO:51, or the equivalent location of in SEQ ID NOs:49 or 50) that render it a monomeric form. A monomeric IL-10 polypeptide can comprise a 5-7 aa insertion between N49 and K50 of SEQ ID NO:51 (or the equivalent location of in SEQ ID NOs:49 or 50). In an instance the 5-7 amino acids comprise Ala, Gly and/or Ser. In an instance the 5-7 amino acids are selected from Ala or Ser. In an instance the 5-7 aas are selected from Gly and Ser. In one instance the insertion comprises the IL-10M1 aa insertion (GGGGSGGG SEQ ID NO:142) between N49 and K50 of SEQ ID NO:51 (or the equivalent location in SEQ ID NOs:49 or 50). In one instance the IL-10 variant consists of the IL-10M1 (SEQ ID NO:189) GGGSGG inserted into SEQ ID NO:51 between aa 49 and 50. See e.g., Josephson et al., *J. Biol. Chem.* 275:13552-13557 (2000).

The IL-10 receptor alpha subunit can have the sequence: MLPCLVVLLA ALLSLRLGSD AHGTELPSPP SVWFEAEFFH HILHWTPIPN QSESTCYEVA LLRYGIESWN SISNCSQTLS YDLTAVTLDL YHSNGYRARV RAVDGSRHSN WTVTNTRFSV DEVTLTVGSV NLEIHNGFIL GKIQLPRPKM APANDTYESI FSHFREYEIA IRKVPGNFTF THKKVKHENF SLLTSGEVGE FCVQVKPSVA SRSNKGMWSK EECISLTRQY FTVTNVIIFF AFVLLLSGAL AYCLALQLYV RRRKKLPSVL LFKKPSPFIF ISQRPSPETQ DTIHPLDEEA FLKVSPELKN LDLHGSTDSG FGSTKPSLQT EEPQFLLPDP HPQADRTLGN REPPVLGDSC SSGSSNSTDS GICLQEPSLS PSTGPTWEQQ VGSNSRGQDD SGIDLVQNSE GRAGDTQGGS ALGHHSPPEP EVPGEEDPAA VAFQGYLRQT RCAEEKATKT GCLEEESPLT DGLGPKFGRC LVDEAGLHPP ALAKGYLKQD PLEMTLASSG APTGQWNQPT EEWSLLALSS CSDLGISDWS FAHDLAPLGC VAAPGGLLGS FNSDLVTLPL ISSLQSSE, (SEQ ID NO:52), NCBI Ref. Seq. NP_001549.2, with aas 21 to 587 forming the mature polypeptide, and aas 236-256 the transmembrane region. All or part of the receptor subunit (e.g., the ectodomain (aas 21-235) of the protein can be used to determine binding affinity to IL-10 isoforms along with IL-10 receptor beta subunit.

The IL-10 receptor beta subunit can have the sequence MAWSLGSWLG GCLLVSALGM VPPPENVRMN SVNFKNILQW ESPAFAKGNL TFTAQYLSYR IFQDKCMNTT LTECDFSSLS KYGDHTLRVR AEFADEHSDW VNITFCPVDD TIIGPPGMQV EVLADSLHMR FLAPKIENEY ETWTMKNVYN SWTYNVQYWK NGTDEKFQIT PQYDFEVLRN LEPWTTYCVQ VRGFLPDRNK AGEWSEPVCE QTTHDETVPS WMVAVILMAS VFMVCLALLG CFALLWCVYK KTKYAFSPRN SLPQHLKEFL GHPHHNTLLF FSFPLSDEND VFDKLSVIAE DSESGKQNPG DSCSLGTPPG QGPQS, NCBI Ref. Seq. NP_000619.3, (SEQ ID NO:53) with aas 20 to 325 forming the mature polypeptide, and aas 221-242 the transmembrane region. All or part of the receptor subunit (e.g., the ectodomain (aas 20-220) of the protein can be used to determine binding affinity to IL-10 along with the alpha subunit.

In some cases, a variant IL-10 isoform polypeptide (e.g., a variant of SEQ ID NOs: 50, 51, or an monomeric IL-10 variant of those sequences bearing a 5-7 aa insertion into the hinge between the D and E helices described above) exhibits reduced binding affinity to a mature IL-10 receptor sequence (e.g., an IL-10 receptor comprising all or part of the polypeptides set forth in SEQ ID NOs: 52 or 53, such as their ectodomains), compared to the binding affinity of an IL-10 polypeptide comprising the amino acid sequence set forth in SEQ ID NOs: 50 or 51. For example, in some cases, a variant of an IL-10 polypeptide (e.g., a variant of SEQ ID NOs: 50 or 51) binds an IL-10 receptor comprising all or part of the polypeptides set forth in SEQ ID NOs: 52 and 53, such as their ectodomains, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-10 isoform (e.g., of SEQ ID NOs: 50 or 51) to an IL-10 receptor comprising all or part of the polypeptides set forth in SEQ ID NOs: 52 or 53 (such as their ectodomains).

In some cases, a variant IL-10 polypeptide (e.g., a variant of SEQ ID NOs: 50 or 51 which may comprise one of the above-mentioned insertions in the hinge region between the D and E helices) has a binding affinity for an IL-10 receptor (e.g., comprising all or part of the polypeptides set forth in SEQ ID NOs: 52 and 53, such as their ectodomains), that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). In some cases, a variant IL-10 polypeptide (e.g., a variant of SEQ ID NOs: 50 or 51) has a binding affinity to a mature IL-10 receptor (e.g., comprising all or part of the polypeptides set forth in SEQ ID NOs:52 and 53, such as their ectodomains), that is from 100 nM to 100 μM (e.g., from 100 nM to 1 μM, from 1 μM to 10 μM, or from 10 μM to 100 μM). As another example, in some cases, a variant IL-10 polypeptide (e.g., a variant of SEQ ID NOs:50 or 51) has a binding affinity for a mature IL-10 receptor (e.g., comprising all or part of the polypeptides set forth in SEQ ID NOs:52 and 53, such as their ectodomains), that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-10 polypeptide has a single aa substitution compared to an IL-10 polypeptide sequence set forth in SEQ ID NOs:50 or 51. In some cases, a variant IL-10 polypeptide has from 2 aa to 10 aa substitutions compared to an IL-10 polypeptide sequence set forth in SEQ ID NOs:50 or 51. In some cases, a variant IL-10 polypeptide has 2 aa substitutions compared to an IL-10 polypeptide sequence set forth in SEQ ID NOs:50 or 51. In some cases, a variant IL-10 polypeptide has 3 aa or 4 aa substitutions compared to an IL-10 polypeptide sequence set forth in SEQ ID NOs:50 or 51. In some cases, a variant IL-10 polypeptide has 5 aa or 6 aa substitutions compared to an IL-10 polypeptide sequence set forth in SEQ ID NOs:50 or 51. In some cases, a variant IL-10 polypeptide has 7 aa or 8 aa substitutions compared to an IL-10 polypeptide sequence set forth in SEQ ID NOs:50 or 51. In some cases, a variant IL-10 polypeptide has 9 aa or 10 aa substitutions compared to an IL-10 polypeptide sequence set forth in SEQ ID NOs:50 or 51. In some cases, a variant IL-10 polypeptide has 1-10 aa substitutions, and comprises a 5-7 aa substitution in hinge region between the D and E helices (e.g., K49 and N50 of SEQ ID NO:50) compared to an IL-10 polypeptide sequence set forth in SEQ ID NOs:50 or 51.

Suitable variant IL-10 polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, at least 110, at least 120, at least 130, at least 140, at least 150, or at least 160) contiguous aa of SEQ ID NOs: 50 or 51 (e.g. which have at least one aa substitution, deletion or insertion).

11 IL-15 and its Variants

In some cases, the MOD present in a masked TGF-β construct or complex of the present disclosure is an IL-15 polypeptide. The sequences of IL-15 polypeptides, including two isoforms formed by alternative splicing giving rise to different precursor proteins, are known in the art. In an embodiment, a wt. IL-15 polypeptide has the sequence: MRISKPHLRS ISIQCYLCLL LNSHFLTEAG IHV-FILGCFS AGLPKTEANW VNVISDLKKI EDLIQSMHID ATLYTESDVH PSCKVTAMKC FLLELQVISL ESG-DASIHDT VENLIILANN SLSSNGNVTE SGCKECEELE EKNIKEFLQS FVHIVQMFIN TS, (SEQ ID NO. 54), UniProtKB—P40933, NCBI Ref. NP_000576.1, IL-15 preprotein with aa 1 to 29 as the signal peptide, and 30-48 as the propeptide.

A mature IL-15 polypeptide, denoted as isoform 1 for the purpose of this disclosure, can have the form NW VNVIS-DLKKI EDLIQSMHID ATLYTESDVH PSCKVTAMKC FLLELQVISL ESGDASIHDT VENLIILANN SLSSNG-NVTE SGCKECEELE EKNIKEFLQS FVHIVQMFIN TS, (SEQ ID NO:55).

IL-15 is structurally similar to IL-2 and signals through a cell surface trimeric receptor having the same beta and gamma chains as the IL-2 receptor but having distinct IL-15 receptor alpha (IL-15Rα) subunit. An amino acid sequence of human an IL-15Rα isoform 1 precursor protein can be MAPRRARGCR TLGLPALLLL LLLRPPATRG ITCPPPMSVE HADIWVKSYS LYSRERYICN SGFKRK-AGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEIS-SHES SHGTPSQTTA KNWELTASAS HQPPGVYPQG HSDTTVAIST STVLLCGLSA VSLLACYLKS RQTP-PLASVE MEAMEALPVT WGTSSRDEDL ENCSHHL (SEQ ID NO:56) NCBI Ref NP_002180, with aas 1-30 forming the signal sequence, and aas peptide 31-267 the mature polypeptide. The sequences of the IL-2Rβ, and IL-2Rγ are provided as SEQ ID NOs: 11 and 12.

In some cases, a variant IL-15 isoform 1 polypeptide (e.g., a variant of SEQ ID NO:55) exhibits reduced binding affinity to a mature IL-15 receptor sequence (e.g., an IL-15 receptor comprising all or part of the polypeptides set forth in SEQ ID NOs:11, 12, and 56, such as their ectodomains), compared to the binding affinity of an IL-15 polypeptide comprising the amino acid sequence set forth in SEQ ID NO:55. For example, in some cases, a variant of an IL-15 polypeptide (e.g., a variant of SEQ ID NO:55) binds an IL-15 receptor comprising all or part of the polypeptides set forth in SEQ ID NOs:11, 12, and 56, such as their ectodomains, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of a IL-15 polypeptide comprising the amino acid sequence set forth in SEQ ID NO:55.

In some cases, a variant IL-15 polypeptide (e.g., a variant of SEQ ID NO:55) has a binding affinity for an IL-15 receptor comprising all or part of the polypeptides set forth in SEQ ID NOs:11, 12, and 56, such as their ectodomains, that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant IL-15 polypeptide (e.g., a variant of SEQ ID NO:55) has a binding affinity for a mature IL-15 receptor comprising all or part of the polypeptides set forth in SEQ ID NOs:11, 12, and 56, such as their ectodomains, that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-15 polypeptide (e.g., a variant of SEQ ID NO:55) has a single aa substitution compared to the IL-15 polypeptide sequence set forth in SEQ ID NO:55. In some cases, a variant IL-15 polypeptide (e.g., a variant of SEQ ID NO:55) has from 2 aa to 10 aa substitutions compared to the IL-15 polypeptide sequence set forth in SEQ ID NO:55. In some cases, a variant IL-15 polypeptide has 2 aa substitutions compared to the IL-15 polypeptide sequence set forth in SEQ ID NO:55. In some cases, a variant IL-15 polypeptide has 3 aa or 4 aa substitutions compared to the IL-15 polypeptide sequence set forth in SEQ ID NO:55. In some cases, a variant IL-15 polypeptide has 5 aa or 6 aa substitutions compared to the IL-15 polypeptide sequence set forth in SEQ ID NO:55. In some cases, a variant IL-15 polypeptide has 7 aa or 8 aa substitutions compared to the IL-15 polypeptide sequence set forth in SEQ ID NO:55. In some cases, a variant IL-15 polypeptide has 9 aa or 10 aa substitutions compared to the IL-15 polypeptide sequence set forth in SEQ ID NO:55.

Suitable variant IL-15 polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, or at least 110 contiguous aa) of SEQ ID NO:55, and which have at least one aa substitution, deletion or insertion.

12 IL-21 and its Variants

In some cases, the MOD present in a masked TGF-β construct or complex of the present disclosure is an IL-21 polypeptide. The sequences of IL-21 polypeptides, including two isoforms formed by alternative splicing giving rise to different precursor proteins, are known in the art.

In an embodiment, a wild type (wt.) IL-21 isoform 1 polypeptide has the sequence MRSSPGNMER IVICLMVIFL GTLVHKSSSQ GQDRHMIRMR QLIDIVDQLK NYVNDLVPEF LPAPEDVETN CEWSAFSCFQ KAQLKSANTG NNERIINVSI KKLKRKPPST NAGRRQKHRL TCPSCDSYEK KPPKEFLERF KSLLQKMIHQ HLSSRTHGSE DS, (SEQ ID NO:57), UniProtKB—Q9HBE4, NCBI Ref. NP_068575.1, IL-21 protein with aa 1 to 29 as the signal peptide.

A mature IL-21 isoform 1 polypeptide can have the aa sequence Q GQDRHMIRMR QLIDIVDQLK NYVNDLVPEF LPAPEDVETN CEWSAFSCFQ KAQLKSANTG NNERIINVSI KKLKRKPPST NAGRRQKHRL TCPSCDSYEK KPPKEFLERF KSLLQKMIHQ HLSSRTHGSE DS, (SEQ ID NO:58).

In an embodiment, a wild type (wt.) IL-21 isoform 2 polypeptide has the sequence MRSSPGNMER IVICLMVIFL GTLVHKSSSQ GQDRHMIRMR QLIDIVDQLK NYVNDLVPEF LPAPEDVETN CEWSAFSCFQ KAQLKSANTG NNERIINVSI KKLKRKPPST NAGRRQKHRL TCPSCDSYEK KPPKEFLERF KSLLQKMIHQ HLSSRTHGSE DS, (SEQ ID NO:59), NP_001193935.1, IL-21 protein with aa 1 to 29 as the signal peptide.

A mature IL-21 isoform 2 polypeptide can have the aa sequence MRSSPGNMER IVICLMVIFL GTLVHKSSSQ GQDRHMIRMR QLIDIVDQLK NYVNDLVPEF LPAPEDVETN CEWSAFSCFQ KAQLKSANTG NNERIINVSI KKLKRKPPST NAGRRQKHRL TCPSCDSYEK KPPKEFLERF KSLLQKVSTL SFI, (SEQ ID NO:60).

IL-21 signals through a dimeric cell surface receptor having the same gamma chains as the IL-2 receptor but having distinct IL-21R receptor subunit. An aa sequence of a human IL-21R isoform 1 precursor protein can be MPRGWAAPLL LLLLQGGWGC PDLVCYTDYL QTVICILEMW NLHPSTLTLT WQDQYEELKD EATSCSLHRS AHNATHATYT CHMDVFHFMA DDIFSVNITD QSGNYSQECG SFLLAESIKP APPFNVTVTF SGQYNISWRS DYEDPAFYML KGKLQYELQY RNRGDPWAVS PRRKLISVDS RSVSLLPLEF RKDSSYELQV RAGPMPGSSY QGTWSEWSDP VIFQTQSEEL KEGWNPHLLL LLLLVIVFIP AFWSLKTHPL WRLWKKIWAV PSPERFFMPL YKGCSGDFKK WVGAPFTGSS LELGPWSPEV PSTLEVYSCH PPRSPAKRLQ LTELQEPAEL VESDGVPKPS FWPTAQNSGG SAYSEERDRP YGLVSIDTVT VLDAEGPCTW PCSCEDDGYP ALDLDAGLEP SPGLEDPLLD AGTTVLSCGC VSAGSPGLGG PLGSLLDRLK PPLADGEDWA GGLPWGGRSP GGVSESEAGS PLAGLDMDTF DSGFVGSDCS SPVECDFTSP GDEGPPRSYL RQWVVIPPPL SSPGPQAS (SEQ ID NO:61) NCBI Ref Seq. NP_068570.1, with aas 1-19 forming the signal sequence, aas 20-538 the mature polypeptide, aas 233 . . . 253 the transmembrane domain, and aas 20-232 the ectodomain.

In some cases, a variant IL-21 polypeptide exhibits reduced binding affinity to a mature IL-21 receptor sequence (e.g., an IL-21 receptor comprising all or part of the polypeptides set forth in SEQ ID NOs:12 and 61, such as their ectodomains), compared to the binding affinity of a wt. IL-21 polypeptide comprising the amino acid sequence set forth in SEQ ID NO:58 or 60. For example, in some cases, a variant of an IL-21 polypeptide comprising SEQ ID NO:58 or 60 binds an IL-21 receptor comprising all or part of the polypeptides set forth in SEQ ID NOs:12 and 61, such as their ectodomains, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of a wt. IL-21 polypeptide comprising the amino acid sequence set forth in SEQ ID NO:58 or 60.

In some cases, a variant IL-21 polypeptide (e.g., a variant of SEQ ID NO:58 or 60) has a binding affinity for an IL-21 receptor (e.g., comprising all or part of the polypeptides set forth in SEQ ID NOs:12 and 61, such as their ectodomains) that is from 1 nM to 1 mM (e.g., from 1 nM to 10 nM, from 10 nM to 100 nM, from 100 nM to 1 µM, from 1 µM to 10 µM, from 10 µM to 100 µM, or from 100 µM to 1 mM). In some cases, a variant IL-21 polypeptide (e.g., a variant of SEQ ID NO:58 or 60) has a binding affinity to all or part of a mature IL-21 receptor (e.g., comprising all or part of the polypeptides set forth in SEQ ID NOs:12 and 61, such as their ectodomains), that is from 100 nM to 100 µM (e.g., from 100 nM to 1 µM, from 1 µM to 10 µM, or from 10 µM to 100 µM). As another example, in some cases, a variant IL-21 polypeptide (e.g., a variant of SEQ ID NO:58 or 60) has a binding affinity for all or part of an IL-21 receptor (e.g., comprising all or part of the polypeptides set forth in SEQ ID NOs:12 and 61, such as their ectodomains) that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, from about 1 µM to about 5 µM, from about 5 µM to about 10 µM, from about 10 µM to about 20 µM, from about 20 µM to about 30 µM, from about 30 µM to about 50 µM, from about 50 µM to about 75 µM, or from about 75 µM to about 100 µM.

In some cases, a variant IL-21 polypeptide (e.g., a variant of SEQ ID NO:58 or 60) has a single aa substitution compared to the IL-21 polypeptide sequence set forth in SEQ ID NO:58 or 60. In some cases, a variant IL-21 polypeptide (e.g., a variant of SEQ ID NO:58 or 60) has from 2 aa to 10 aa substitutions compared to the IL-21 polypeptide sequence set forth in SEQ ID NO:58 or 60. In some cases, a variant IL-21 polypeptide has 2 aa substitutions compared to the IL-21 polypeptide sequence set forth in SEQ ID NO:58 or 60. In some cases, a variant IL-21 polypeptide has 3 aa or 4 aa substitutions compared to the IL-21 polypeptide sequence set forth in SEQ ID NO:58 or 60. In some cases, a variant IL-21 polypeptide has 5 aa or 6 aa substitutions compared to the IL-21 polypeptide sequence set forth in SEQ ID NO:58 or 60. In some cases, a variant IL-21 polypeptide has 7 aa or 8 aa substitutions compared to the IL-21 polypeptide sequence set forth in SEQ ID NO:58 or 60. In some cases, a variant IL-21 polypeptide has 9 aa or 10 aa substitutions compared to the IL-21 polypeptide sequence set forth in SEQ ID NO:58 or 60.

Suitable IL-21 polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, or at least 110 contiguous aa) of SEQ ID NO:58 or 60, and which have at least one aa substitution, deletion or insertion.

13 IL-23 and its Variants

In some cases, the MOD present in a masked TGF-β construct or complex of the present disclosure is an IL-23 polypeptide. IL-23 is a heterodimeric cytokine composed of an IL-23A (IL-23p19) subunit and an IL-12B (IL-12p40) subunit (that is shared with IL-12).

In an embodiment, a wild type (wt.) IL-23A polypeptide has the sequence: MLGSRAVMLL LLLLPWTAQGR AVPGGSSPAW TQCQQLSQKL CTLAWSAHPL VGHMDLREEG DEETTNDVPH IQCGDGCDPQ GLRDNSQFCL QRIHQGLIFY EKLLGSDIFT GEPSLLPDSP VGQLHASLLG LSQLLQPEGH HWETQQIPSL SPSQPWQRLL LRFKILRSLQ AFVA-VAARVF AHGAATLSP, (SEQ ID NO:62), NCBI Ref. Seq. NP_057668.1 protein with aa 1 to 19 as the signal peptide, and 20-189 as the mature peptide.

A mature IL-23A polypeptide can have the aa sequence: R AVPGGSSPAW TQCQQLSQKL CTLAWSAHPL VGHMDLREEG DEETTNDVPH IQCGDGCDPQ GLRDNSQFCL QRIHQGLIFY EKLLGSDIFT GEPSLLPDSP VGQLHASLLG LSQLLQPEGH HWETQQIPSL SPSQPWQRLL LRFKILRSLQ AFVA-VAARVF AHGAATLSP, (SEQ ID NO:63).

In an embodiment, a wild type (wt) IL-12B polypeptide has the sequence: MCHQQLVISW FSLVFLASPL VAI-WELKKDV YVVELDWYPD APGEMVVLTC DTPEED-GITW TLDQSSEVLG SGKTLTIQVK EFGDAGQYTC HKGGEVLSHS LLLLHKKEDG IWSTDILKDQ KEPKNKTFLR CEAKNYSGRF TCWWLTTIST DLTFSVKSSR GSSDPQGVTC GAATLSAERV RGDN-KEYEYS VECQEDSACP AAEESLPIEV MVDAVHKLKY ENYTSSFFIR DIIKPDPPKN LQLKPLKNSR QVEVSWEYPD TWSTPHSYFS LTFCVQVGK SKREKKDRVF TDKTSATVIC RKNA-SISVRA QDRYYSSSWS EWASVPCS, (SEQ ID NO:64), UniProtKB—P29460 protein with aa 1 to 22 as the signal peptide, and 23 to 328 as the mature peptide.

A mature IL-12B polypeptide can have the aa sequence: IWELKKDV YVVELDWYPD APGEMVVLTC DTPEED-GITW TLDQSSEVLG SGKTLTIQVK EFGDAGQYTC HKGGEVLSHS LLLLHKKEDG IWSTDILKDQ KEPKNKTFLR CEAKNYSGRF TCWWLTTIST DLTFSVKSSR GSSDPQGVTC GAATLSAERV RGDN-KEYEYS VECQEDSACP AAEESLPIEV MVDAVHKLKY ENYTSSFFIR DIIKPDPPKN LQLKPLKNSR QVEVSWEYPD TWSTPHSYFS LTFCVQVGK SKREKKDRVF TDKTSATVIC RKNA-SISVRA QDRYYSSSWS EWASVPCS, (SEQ ID NO:65).

IL-23 signals through a dimeric cell surface receptor comprised of an IL-23 receptor polypeptide (IL-23R) and a subunit it has in common with the IL-12 receptor, denoted 12RB1 or 12Rβ1.

An IL-23R isoform 1 precursor protein sequence can be: MNQVTIQWDA VIALYILFSW CHGGITNINC SGHIWVEPAT IFKMGMNISI YCQAAIKNCQ PRKLHFYKNG IKERFQITRI NKTTARLWYK NFLE-PHASMY CTAECPKHFQ ETLICGKDIS SGYPPDIPDE VTCVIYEYSG NMTCTWNAGK LTYIDTKYVV HVKS-LETEEE QQYLTSSYIN ISTDSLQGGK KYLVWVQAAN ALGMEESKQL QIHLDDIVIP SAAVISRAET INATVPKTII YWDSQTTIEK VSCEMRYKAT TNQTWNVKEF DTNFTYVQQS EFYLEPNIKY VFQVRCQETG KRYWQPWSSL FFHKTPETVP QVTSKAFQHD TWNSGLTVAS ISTGHLTSDN RGDIGLLLGM IVFAVMLSIL SLIGIFNRSF RTGIKR-RILL LIPKWLYEDI PNMKNSNVVK MLQENSELMN NNSSEQVLYV DPMITEIKEI FIPEHKPTDY KKENTG-PLET RDYPQNSLFD NTTVVYIPDL NTGYKPQISN FLPEGSHLSN NNEITSLTLK PPVDSLDSGN NPRLQKHPNF AFSVSSVNSL SNTIFLGELS LILNQGECSS PDIQNSVEEE TTMLLENDSP SETI- PEQTLL PDEFVSCLGI VNEELPSINT YFPQNILESH FNRISLLEK, (SEQ ID NO:66) NCBI Ref. Seq. NP_653302.2, with aas 1-23 forming the signal sequence, aas 24-629 the mature polypeptide, aas 356 to 376 the transmembrane domain, and aas 24-355 the ectodomain.

An 12RB1 isoform 1 precursor protein aa sequence can be: MEPLVTWVVP LLFLFLLSRQ GAACRTSECC FQDPPYPDAD SGSASGPRDL RCYRISSDRY ECSWQYEGPT AGVSHFLRCC LSSGRCCYFA AGSATRLQFS DQAGVSVLYT VTLWVESWAR NQTEKSPEVT LQLYNSVKYE PPLGDIKVSK LAGQLRMEWE TPDNQVGAEV QFRHRTPSSP WKLGDCGPQD DDTESCLCPL EMNVAQEFQL RRRQLGSQGS SWSKWSSPVC VPPENPPQPQ VRFS-VEQLGQ DGRRRLTLKE QPTQLELPEG CQGLAPGTEV TYRLQLHMLS CPCKAKATRT LHLGKMPYLS GAAYNVAVIS SNQFGPGLNQ TWHI-PADTHT EPVALNISVG TNGTTMYWPA RAQSMTYCIE WQPVGQDGGL ATCSLTAPQD PDPAG-MATYS WSRESGAMGQ EKCYYITIFA SAHPEKLTLW STVLSTYHFG GNASAAGTPH HVSVKNHSLD SVSVDWAPSL LSTCPGVLKE YVVRCRDEDS KQVSEHPVQP TETQVTLSGL RAGVAYTVQV RAD-TAWLRGV WSQPQRFSIE VQVSDWLIFF ASLGSFLSIL LVGVLGYLGL NRAARHLCPP LPTPCASSAI EFPGGKETWQ WINPVDFQEE ASLQEALVVE MSWDKGERTE PLEKTELPEG APELALDTEL SLEDGDRCKA KM, (SEQ ID NO:67) NCBI Ref Seq. NP_005526.1 with aas 1-23 forming the signal sequence, aas 24-662 the mature polypeptide, aas 546 to 570 the transmembrane domain, and aas 24-545 the ectodomain.

In some cases, a variant IL-23 (e.g., comprising a variant of SEQ ID NO:63 and/or 65) polypeptide exhibits reduced binding affinity to a mature IL-23 receptor sequence (e.g., an IL-23 receptor comprising all or part of the polypeptides set forth in SEQ ID NOs:66 and 67, such as their ectodomains), compared to the binding affinity of an IL-23 polypeptide comprising the amino acid sequence set forth in SEQ ID NO:63 or 65. For example, in some cases, a variant of an IL-23 polypeptide (e.g., comprising a variant of SEQ ID NO:63 and/or 65) binds an IL-23 receptor (e.g., comprising all or part of the polypeptides set forth in SEQ ID NOs:66 and 67, such as their ectodomains), with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-23 polypeptide comprising the amino acid sequence set forth in SEQ ID NO:63 or 65.

In some cases, a variant IL-23 polypeptide (e.g., comprising a variant of SEQ ID NO:63 and/or 65) has a binding affinity for an IL-23 receptor (e.g., comprising all or part of the polypeptides set forth in SEQ ID NOs:66 and 67, such as their ectodomains), that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant IL-23 polypeptide (e.g., comprising a variant of SEQ ID NO:63 and/or 65) has a binding affinity for a mature IL-23 receptor (e.g., comprising all or part of the polypeptides set forth in SEQ ID NOs:66 and 67, such as their ectodomains) that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-23 polypeptide (e.g., comprising a variant of SEQ ID NO:63 and/or 65) has a single aa substitution compared to the IL-23 polypeptide sequence set forth in SEQ ID NO:63 and/or 65. In some cases, a variant IL-23 polypeptide (e.g., comprising a variant of SEQ ID NO:63 and/or 65) has from 2 aa to 10 aa substitutions compared to the IL-23 polypeptide sequence set forth in SEQ ID NO:63 and/or 65. In some cases, a variant IL-23 polypeptide has 2 aa substitutions compared to the IL-23 polypeptide sequence set forth in SEQ ID NO:63 and/or 65. In some cases, a variant IL-23 polypeptide has 3 aa or 4 aa substitutions compared to the IL-23 polypeptide sequence set forth in SEQ ID NO:63 and/or 65. In some cases, a variant IL-23 polypeptide has 5 aa or 6 aa substitutions compared to the IL-23 polypeptide sequence set forth in SEQ ID NO:63 and/or 65. In some cases, a variant IL-23 polypeptide has 7 aa or 8 aa substitutions compared to the IL-23 polypeptide sequence set forth in SEQ ID NO:63 and/or 65. In some cases, a variant IL-23 polypeptide has 9 aa or 10 aa substitutions compared to the IL-23 polypeptide sequence set forth in SEQ ID NO:63 and/or 65.

Suitable variant IL-23 polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, at least 110, at least 120, at least 140, at least 160, at least 180, at least 200, at least 220, at least 240, at least 260, at least 280, at least 300, at least 320, or at least 340 contiguous aas) of SEQ ID NO:63 and/or 65, and which have at least one aa substitution, deletion or insertion.

14 Fas Ligand (FasL) and its Variants

In some cases, the MOD present in a masked TGF-β construct or complex of the present disclosure is a Fas Ligand (FasL). FasL is a homomeric type-II transmembrane protein in the tumor necrosis factor (TNF) family. FasL signals by trimerization of the Fas receptor in a target cell, which forms a death-inducing complex leading to apoptosis of the target cell. Soluble FasL results from matrix metalloproteinase-7 (MMP-7) cleavage of membrane-bound FasL at a conserved site.

In an embodiment, a wt. *Homo sapiens* FasL protein has the sequence MQQPFNYPYP QIYWVDSSAS SPWAPPGTVL PCPTSVPRRP GQRRPPPPPP PPPLPPPPPP PPLPPLPLPP LKKRGNHSTG LCLL-VMFFMV LVALVGLGLG MFQLFHLQKE LAEL-RESTSQ MHTASSLEKQ IGHPSPPPEK KELRKVAHLT GKSNSRSMPL EWEDTYGIVL LSGVKYKKGG LVI-NETGLYF VYSKVYFRGQ SCNNLPLSHK VYMRN-SKYPQ DLVMMEGKMM SYCTTGQMWA RSSYL-GAVFN LTSADHLYVN VSELSLVNFE ESQTFFGLYK L, (SEQ ID NO:143), NCBI Ref. Seq. NP_000630.1, UniProtKB—P48023 where residues 1-80 are cytoplasmic, 810102 are the transmembrane domain and aas 103-281 are extracellular (ectodomain).

A suitable FasL polypeptide comprises all or part of the ectodomain of FasL QLFHLQKE LAELRESTSQ MHTASSLEKQ IGHPSPPPEK KELRKVAHLT GKSN-SRSMPL EWEDTYGIVL LSGVKYKKGG LVINETGLYF VYSKVYFRGQ SCNNLPLSHK VYMRNSKYPQ DLVMMEGKMM SYCTTGQMWA RSSYLGAVFN LTSADHLYVN VSELSLVNFE ESQTFFGLYK L. (SEQ ID NO144).

A Fas receptor can have the sequence MLGIWTLLPL VLTSVARLSS KSVNAQVTDI NSKGLELRKT VTTVETQNLE GLHHDGQFCH KPCPPGERKA RDCTVNGDEP DCVPCQEGKE YTDKAHFSSK CRR-CRLCDEG HGLEVEINCT RTQNTKCRCK PNFFCN-STVC EHCDPCTKCE HGIIKECTLT SNTKCKEEGS RSNLGWLCLL LLPIPLIVWV KRKEVQKTCR KHRKENQGSH ESPTLNPETV AINLSDVDLS KYITTI-AGVM TLSQVKGFVR KNGVNEAKID EIKNDNVQDT AEQKVQLLRN WHQLHGKKEA YDTLIKDLKK ANLCTLAEKI QTIILKDITS DSENSNFRNE IQSLV, (SEQ ID NO:145) NCBI Reference Sequence: NP_000034.1, UniProtKB—P25445, where aas 26-173 form the ectodomain (extracellular domain), aas 174-190 form the transmembrane domain, and 191-335 the cytoplasmic domain. The ectodomain may be used to determine binding affinity with FasL.

In some cases, a variant FasL polypeptide (e.g., comprising a variant of SEQ ID NO144) exhibits reduced binding affinity to a mature Fas receptor sequence (e.g., a FasL receptor comprising all or part of the polypeptides set forth in SEQ ID NO:145, such as its ectodomain), compared to the binding affinity of an FasL polypeptide comprising the amino acid sequence set forth in SEQ ID NO:144. For example, in some cases, a variant FasL polypeptide (e.g., comprising a variant of SEQ ID NO:144) binds an Fas receptor (e.g., comprising all or part of the polypeptides set forth in SEQ ID NO:145, such as its ectodomains), with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an FasL polypeptide comprising the amino acid sequence set forth in SEQ ID NO:144.

In some cases, a variant FasL polypeptide (e.g., comprising a variant of SEQ ID NO:144) has a binding affinity for an Fas receptor (e.g., comprising all or part of the polypeptides set forth in SEQ ID NO:145, such as its ectodomain), that is from 1 nM to 1 mM (e.g., from 1 nM to 10 nM, from 10 nM to 100 nM, from 100 nM to 1 µM, from 1 µM to 10 µM, from 10 µM to 100 µM, or from 100 µM to 1 mM). As another example, in some cases, a variant FasL polypeptide (e.g., comprising a variant of SEQ ID NO:144) has a binding affinity for a mature Fas receptor (e.g., comprising all or part of the polypeptides set forth in SEQ ID NO:145, such as its ectodomains), that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, from about 1 µM to about 5 µM, from about 5 µM to about 10 µM, from about 10 µM to about 20 µM, from about 20 µM to about 30 µM, from about 30 µM to about 50 µM, from about 50 µM to about 75 µM, or from about 75 µM to about 100 µM.

In some cases, a variant FasL polypeptide (e.g., comprising a variant of SEQ ID NO:144) has a single aa substitution compared to the FasL polypeptide sequence set forth in SEQ ID NO:144. In some cases, a variant FasL polypeptide (e.g., comprising a variant of SEQ ID NO:144) has from 2 aa to 10 aa substitutions compared to the FasL polypeptide sequence set forth in SEQ ID NO:144. In some cases, a variant FasL polypeptide has 2 aa substitutions compared to the FasL polypeptide sequence set forth in SEQ ID NO:144. In some cases, a variant FasL polypeptide has 3 aa or 4 aa substitutions compared to the FasL polypeptide sequence set forth in SEQ ID NO:144. In some cases, a variant FasL polypeptide has 5 aa or 6 aa substitutions compared to the FasL polypeptide sequence set forth in SEQ ID NO:144. In some cases, a variant FasL polypeptide has 7 aa or 8 aa substitutions compared to the FasL polypeptide sequence set forth in SEQ ID NO:144. In some cases, a variant FasL polypeptide has 9 aa or 10 aa substitutions compared to the FasL polypeptide sequence set forth in SEQ ID NO:144.

Suitable variant FasL polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, at least 110, at least 120, at least 140, at least 160, or at least 180 contiguous aa) of SEQ ID NO:144 (e.g., which have at least one aa substitution, deletion or insertion).

E. Scaffolds

Scaffold polypeptides serve, among other things, as structural elements providing a framework upon which other components of a masked TGF-β construct or complex are organized (see, e.g., FIG. 1, structure A, with an IgFc scaffold). Where the polypeptide sequence that masks a TGF-β polypeptide and the TGF-β polypeptide are located in trans (on different polypeptides of the complex), the scaffolds sequences that form interspecific and non-interspecific duplexes (or higher order structures) can keep the masking polypeptide sequence associated with the TGF-β polypeptide even during periods where the complex is in an open form with TGF-β polypeptide sequence being available to interact with other molecules (when the TGF-β sequence is not in direct contact with the masking sequence). Depending on the nature of the scaffold, it can also act as an organizational element providing higher order structure in terms of protein folding and dimerization or multimerization (e.g., homodimerization or heterodimerization accomplished through dimerization sequences). The scaffold can also contribute to serum stability, particularly where it is an immunoglobulin heavy chain constant region (e.g., an Ig Fc). Suitable scaffold polypeptides will, in some cases, be half-life extending polypeptides. In some cases, a suitable scaffold polypeptide increases the in vivo half-life (e.g., the serum half-life) of a masked TGF-β construct or complex, compared to a control masked TGF-β construct or complex having a scaffold polypeptide with a different, non-immunoglobulin sequence, by at least about 10%, at least about 15%, at least about 25%, at least about 50%, at least about 2-fold, at least about 5-fold, at least about 10-fold, at least about 25-fold, at least about 50-fold, at least about 100-fold, or more than 100-fold. As an example, in some cases an Ig Fc polypeptide sequence (e.g., including interspecific Ig sequence such as a knob-in-hole sequence pairs) increases the stability and/or in vivo half-life (e.g., the serum half-life) of a masked TGF-β construct or complex, compared to a control masked TGF-β construct or complex having the Ig Fc polypeptide sequence replaced by a linker (e.g., a GGGS aa repeat of equal sequence length). The increase in in vivo half-life can be by at least about 10%, at least about 15%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. Where an Ig Fc polypeptide is employed in the masked TGF-β construct, the Ig Fc can contain mutations that will prevent the spontaneous formation of dimers of the masked TGF-β construct (See, e.g., Tianlei Ying et al., J. Biol. Chem., 287 (23), pp 19399-19408 (Jun. 1, 2012)), and additionally may include mutations (e.g., the LALA mutations discussed below) that substantially reduce or eliminate the ability of the Ig polypeptide to induce cell lysis, e.g., though complement-dependent cytotoxicity (CDC) and/or antibody-dependent cellular cytotoxicity (ADCC).

Where scaffold polypeptide sequences of a masked TGF-β construct comprise one or more sequences that permit scaffolds to interact (specifically bind) with other scaffold molecules, the masked TGF-β constructs can form homodimer complexes (see, e.g., FIG. 1, structure B) or heterodimer complexes (see, e.g., FIG. 1, structures C-F). Masked TGF-β constructs may also comprise one or more aa sequences that permit scaffolds to interact (specifically bind) with other scaffold molecules forming higher order structures. Sequences that form higher order multimer structures permit the formation of masked TGF-β construct or complexes of higher order (e.g., trimers, tetramers, pentamers etc.). By way of example, scaffold polypeptides comprising IgM Fc regions (e.g., SEQ ID NO:83) permit formation of pentameric (particularly when j-chain sequences are also expressed e.g., SEQ ID NO:84) or hexameric masked TGF-β construct or complexes. Petrušić et al., *Med Hypotheses.* 77(6):959-61 (2011). Masked TGF-β constructs in the form of homo- and hetero-dimers, trimers, tetramers, pentamers etc. are referred to as masked TGF-β complexes.

Where it is desirable to bring together a masked TGF-β with one or more other polypeptide sequences (such as one or more specific MODs or copies of MODs), scaffold polypeptide sequences may comprise interspecific dimerization sequences that tend to form a heterodimer with their counterpart interspecific binding (dimerization) sequence. Interspecific binding sequences may in some instance form homodimers, but preferentially dimerize (bind more strongly) with their counterpart interspecific binding sequence. Accordingly, specific heterodimers may be (tend to be) formed when an interspecific dimerization sequence and its counterpart interspecific binding sequence are incorporated into a pair of polypeptides. By way of example, where an interspecific dimerization sequence and its counterpart are incorporated into a pair of polypeptides to selectively form heterodimers, greater than 60%, 70%, 80%, 90%, 95%, 98% or 99% of an equimolar mixture of the peptides are engaged in heterodimer formation, with the remainder of the peptides present as monomers or homodimers.

A variety of aa sequences that specifically bind to each other or themselves with sufficient affinity may be utilized as dimerization sequences in a masked TGF-β construct or complex (see, e.g., U.S. Patent Publication No. 2003/0138440). The sequences may be of relatively compact size (e.g., such as less than about 300, 250, 225, 200, 175, 150, 125, 100, 75, or 50 aa). Dimerization/multimerization sequences include, but are not limited to immunoglobulin heavy chain constant region (Ig Fc) polypeptide sequences (sequences comprising CH2-CH3 regions of immunoglobulins; see, e.g., FIGS. 2A-2H and SEQ ID NOs: 68 to 83); Fc knob-in-hole sequences (e.g., SEQ ID NOs:77 and 78); polypeptides of the collectin family (e.g., ACRP30 or ACRP30-like proteins) that contain collagen domains consisting of collagen repeats Gly-Xaa-Yaa; coiled-coil domains; leucine-zipper domains; Fos/Jun binding pairs; Ig heavy chain region 1 (CH1) and light chain constant region CL sequences (CH1/CL pairs such as a CH1 sequence paired with a κ or λ Ig light chain constant region sequence).

In some embodiments, the scaffold polypeptide sequence comprises an immunoglobulin heavy chain constant region (CH2-CH3) polypeptide sequence that functions as a dimerization or multimerization sequence (see, e.g., FIGS. 2A-2H and SEQ ID NOs: 68 to 83). In embodiments, the Ig polypeptide substantially will not induce cell lysis, e.g., through activation of complement-dependent cytotoxicity (CDC) and/or antibody-dependent cellular cytotoxicity (ADCC), and thus may include mutations that substantially reduce or eliminate the ability of the Ig polypeptide to induce cell lysis. In some cases, the Fc sequence has at least about 70%, at least about 80%, at least about 90%, at least about 95%, at least about 98%, at least about 99%, or 100% aa sequence identity to an aa sequence of an Fc region depicted in FIGS. 2A-2H. Such immunoglobulin sequences can covalently link the polypeptides of a masked TGF-β complex together by forming one or two interchain disulfide bonds. As discussed below, an additional disulfide bond can be introduced to stabilize dimers, particularly where a pair of interspecific Ig sequence such knob-in-hole polypeptide pairs are employed.

In an embodiment, the scaffold polypeptide sequence of a masked TGF-β complex comprises a sequence that has at least about 70%, at least about 80%, at least about 90%, at least about 95%, at least about 98%, at least about 99%, or 100% aa sequence identity to at least 150 contiguous aas (at least 175, at least 200, at least 225, at least 250, at least 275, at least 300, at least 325, or at least 350 contiguous aas), or all aas, of the IgA Fc sequence depicted in FIG. 2A (SEQ ID NO:68). In an embodiment, the scaffold polypeptide sequence comprises a sequence that has at least about 70%, at least about 80%, at least about 90%, at least about 95%, at least about 98%, at least about 99%, or 100% aa sequence identity to at least 150 contiguous aas (at least 175, at least 200, at least 225, at least 250, at least 275, at least 300, at least 325, or at least 350 contiguous aas), or all aas, of the IgD Fc sequence depicted in FIG. 2B (SEQ ID NO:69). In an embodiment, the scaffold polypeptide sequence comprises a sequence that has at least about 70%, at least about 80%, at least about 90%, at least about 95%, at least about 98%, at least about 99%, or 100% aa sequence identity to least 125 contiguous aas (at least 150, at least 175, or at least 200 contiguous aas), or all aas, of the IgE Fc sequence depicted in FIG. 2C (SEQ ID NO:70). In an embodiment, the scaffold polypeptide sequence comprises a sequence that has at least about 70%, at least about 80%, at least about 90%, at least about 95%, at least about 98%, at least about 99%, or 100% aa sequence identity to least 125 contiguous aas (at least 150, at least 175, or at least 200 contiguous aas), or all aas, of the wt. IgG Fc polypeptide sequence, such as the IgG1 Fc sequence depicted in FIG. 2D (SEQ ID NOs: 71-78). In an embodiment, the scaffold polypeptide sequence comprises a sequence that has at least about 70%, at least about 80%, at least about 90%, at least about 95%, at least about 98%, at least about 99%, or 100% aa sequence identity to at least 125 contiguous aas (at least 150, at least 175, at least 200, at least 225, at least 250, at least 275, or at least 300), or all aas, of the IgG2 Fc polypeptide sequence depicted in FIG. 2E (SEQ ID NO:79). In an embodiment, the scaffold polypeptide sequence comprises a sequence that has at least about 70%, at least about 80%, at least about 90%, at least about 95%, at least about 98%, at least about 99%, or 100% aa sequence identity to at least 125 contiguous aas (at least 150, at least 175, at least 200, or at least 225), or all aas, of the IgG3 Fc sequence depicted in FIG. 2F (SEQ ID NO:80). In an embodiment, the scaffold polypeptide sequence comprises a sequence that has at least about 70%, at least about 80%, at least about 90%, at least about 95%, at least about 98%, at least about 99%, or 100% aa sequence identity to at least 125 contiguous aas (at least 150, at least 175, at least 200, at least 225, or at least 250), or all aas, of the IgG4 Fc sequence depicted in FIG. 2G (SEQ ID NO:81 or 82). In an embodiment, the scaffold polypeptide sequence comprises a sequence that has at least about 70%, at least about 80%, at least about 90%, at least about 95%, at least about 98%, at least about 99%, or 100% aa sequence identity to at least 125 contiguous aas (at least 150, at least 175, at least 200, at least 225, or at least 250), or all aas, of the IgM Fc polypeptide sequence depicted in FIG. 2H (SEQ ID NO:83). The above-recited polypeptides of a masked TGF-β complex comprising immunoglobulin scaffold polypeptide sequences (e.g., depicted in FIGS. 2A-2H) can be covalently linked together by formation of one or two interchain disulfide bonds between cysteines adjacent to their hinge regions.

In some cases, the dimerization sequence of a scaffold polypeptide present in a masked TGF-β construct or complex has at least about 70% (e.g., at least about 80%, 90%, 95%, 98%, 99% or 100%) aa sequence identity to the human IgG1 Fc polypeptide depicted in FIG. 2D, and comprises a substitution of N297 with an alanine (N297A substitution, or N77 as numbered in FIG. 2D, SEQ ID NO:74) substitution. In some cases, the dimerization sequence of a scaffold polypeptide present in masked TGF-β construct or complex comprises an aa sequence depicted in FIG. 2D (human IgG1 Fc), except for a substitution of N297 (N77 of the aa sequence depicted in FIG. 2D) with an aa other than asparagine. Substitutions at N297 lead to the removal of carbohydrate modifications and result antibody sequences with reduced complement component 1q ("C1q") binding compared to the wt. protein, and accordingly a reduction in complement-dependent cytotoxicity.

In some cases, the dimerization sequence of a scaffold polypeptide present in a masked TGF-β construct or complex comprises an aa sequence depicted in FIG. 2D (human IgG1 Fc), except for a substitution of L234 (L14 of the aa sequence depicted in FIG. 2D) with an aa other than leucine. L234 and other aas in the lower hinge region (e.g., aas 234-LLGGPS-239, which correspond to aas 14-19 of SEQ ID NO:71) of IgG are involved in binding to the Fc lambda receptor (FR), and accordingly, mutations at that location reduce binding to the receptor (relative to the wt. protein). In some cases, the dimerization sequence of a scaffold polypeptide present in a masked TGF-β construct or complex comprises an aa sequence depicted in FIG. 2D (human IgG1 Fc), except for a substitution of L235 (L15 of the aa sequence depicted in FIG. 2D) with an aa other than leucine. In some cases, the dimerization sequence of a scaffold polypeptide present in a masked TGF-β construct or complex comprises an aa sequence depicted in FIG. 2D (e.g., the wt. human IgG1 sequence) with L234A and L235A ("LALA") substitutions (the positions corresponding to positions 14 and 15 of the wt. aa sequence depicted in FIG. 2D; see, e.g., SEQ ID NO:75).

In some cases, the dimerization sequence of a scaffold polypeptide present in a masked TGF-β construct or complex comprises an aa sequence depicted in FIG. 2D (human IgG1 Fc), having a substitution of P331 (P111 of the aa sequence depicted in FIG. 2D) with an aa other than proline; in some cases, the substitution is a P331S substitution. Substitutions at P331, like those at N297, lead to reduced binding to C1q relative to the wt. protein, and thus a reduction in complement-dependent cytotoxicity. Substitutions of D270, K322, and/or P329 (corresponding to D50, K122, and P119 of SEQ ID NO:71 in FIG. 2D), for example with alanine, may be utilized alone or in place of a P331 substitution to reduce binding to C1q. In some cases, the dimerization sequence of a scaffold polypeptide present in a masked TGF-β construct or complex is an IgG1 Fc polypeptide that comprises L234A and/or L235A substitutions (substitutions of leucines at L14 and/or L15 of the aa sequences depicted in FIG. 2D with Ala). In some cases, the dimerization sequence of a scaffold polypeptide present in a masked TGF-β construct or complex comprises the aa sequence depicted in FIG. 2D (wt. human IgG1 Fc), except for substitutions at L234 and/or L235 (L14 and/or L15 of the aa sequence depicted in FIG. 2D) with aas other than leucine, and a substitution of P331 (P111 of the aa sequence depicted in FIG. 2D) with an aa other than proline. In some cases, the dimerization sequence of a scaffold polypeptide present in a masked TGF-β construct or complex comprises the "Triple Mutant" aa sequence (SEQ ID NO:73) depicted in FIG. 2D (human IgG1 Fc) comprising L234F, L235E, and P331S substitutions (corresponding to aa positions 14, 15, and 111 of the aa sequence depicted in FIG. 2D).

Where an asymmetric pairing between two polypeptides of a masked TGF-β complex is desired, the dimerization sequence of a scaffold polypeptide present in a masked TGF-β construct or complex comprises, consist essentially of, or consist of an interspecific binding sequence. Interspecific binding sequences favor formation of heterodimers with their cognate polypeptide sequence (i.e., the interspecific sequence and its counterpart interspecific sequence), particularly those based on immunoglobulin Fc sequence variants. Such interspecific polypeptide sequences include knob-in-hole without (KiH) or with (KiH)s-s a stabilizing disulfide bond, HA-TF, ZW-1, 7.8.60, DD-KK, EW-RVT, EW-RVTs-s, and A107 sequences. One interspecific binding pair comprises a T366Y and Y407T mutant pair in the CH3 domain interface of IgG1, or the corresponding residues of other immunoglobulins. See Ridgway et al., *Protein Engineering*, 9:7, 617-621 (1996), (substitutions are denoted by EU numbering scheme of Kabat et al. (1991)). A second interspecific binding pair involves the formation of a knob by a T366W substitution, and a hole by the triple substitutions T366S, L368A and Y407V on the complementary Fc sequence. See Xu et al. mAbs 7:1, 231-242 (2015). Another interspecific binding pair has a first Fc polypeptide with Y349C, T366S, L368A, and Y407V substitutions and a second Fc polypeptide with S354C, and T366W substitutions (disulfide bonds can form between the Y349C and the S354C). Brinkmann and Konthermann, *mAbs*, 9:2, 182-212 (2015). Fc polypeptide sequences, either with or without knob-in-hole modifications, can be stabilized by the formation of disulfide bonds between the Fc polypeptides (e.g., the hinge region disulfide bonds). Several interspecific polypeptide binding sequences are summarized in Table 1, with cross reference to the numbering of the aa positions as they appear in the wt. IgG1 sequence (SEQ ID NO:71) set forth in FIG. 2D shown in brackets "{ }".

TABLE 1

Interspecific Sequences and their cognate counterpart interspecific sequences

| Interspecific Pair Name | Substitutions in the first interspecific polypeptide sequence | Substitutions in the second (counterpart) interspecific polypeptide sequence | Comments |
|---|---|---|---|
| KiH | T366W {T146W} | T366S/L368A/Y407V {T146S/L148A/Y187V} | Hydrophobic/steric complementarity |
| KiHs-s | T366W/S354C* {T146W/S134C*} | T366S/L368A/Y407V/Y349C {T146S/L148A/Y187V/Y129C} | KiH + inter-CH3 domain S-S bond |
| HA-TF | S364H/F405A {S144H/F185A} | Y349T/T394F {Y129T/T174F} | Hydrophobic/steric complementarity |
| ZW1 | T350V/L351Y/F405A/Y407V {T130V/L131Y/F185A/Y187V} | T350V/T366L/K392L/T394W {T130V/T146L/K172L/T174W} | Hydrophobic/steric complementarity |
| 7.8.60 | K360D/D399M/Y407A {K140D/D179M/Y187A} | E345R/Q347R/T366V/K409V {E125R/Q127R/T146V/K189V} | Hydrophobic/steric complementarity + electrostatic complementarity |
| DD-KK | K409D/K392D {K189D/K172D} | D399K/E356K {D179K/E136K} | Electrostatic complementarity |
| EW-RVT | K360E/K409W {K140E/K189W} | Q347R/D399V/F405T {Q127R/D179V/F185T} | Hydrophobic/steric complementarity & long-range electrostatic interaction |
| EW-RVTs-s | K360E/K409W/Y349C* {K140E/K189W/Y129C*} | Q347R/D399V/F405T/S354C {Q127R/D179V/F185T/S134C} | EW-RVT + inter-CH3 domain S-S bond |
| A107 | K370E/K409W {K150E/K189W} | E357N/D399V/F405T {E137N/D179V/F185T} | Hydrophobic/steric complementarity + hydrogen bonding complementarity |

Table 1 modified from Ha et al., Frontiers in Immunol. 7:1-16 (2016).
*aa forms a stabilizing disulfide bond.

In addition to the interspecific pairs of sequences in Table 1, interspecific "SEED" sequences having 45 residues derived from IgA in an IgG1 CH3 domain of the interspecific sequence and 57 residues derived from IgG1 in the IgA CH3 on the counterpart interspecific sequence. See Ha et al., *Frontiers in Immunol.*, 7:1-16 (2016).

In an embodiment, the scaffold sequences found in a masked TGF-β construct or complex comprise an interspecific binding sequence or its counterpart interspecific binding sequence selected from the group consisting of: knob-in-hole (KiH); knob-in-hole with a stabilizing disulfide (KiHs-s); HA-TF; ZW-1; 7.8.60; DD-KK; EW-RVT; EW-RVTs-s; A107; or SEED sequences.

In an embodiment, a masked TGF-β complex comprises a first polypeptide comprising an IgG1 scaffold with a T146W KiH sequence substitution, and a second polypeptide comprising an IgG1 scaffold with T146W, L148A, and Y187V KiH sequence substitutions, where the scaffolds comprises a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71. One or both scaffold aa sequences optionally comprising substitutions at one of more of L234 and L235 (e.g., L234A/L235A "LALA" or L234F/L235E), N297 (e.g., N297A), P331 (e.g. P331S), L351 (e.g., L351K), T366 (e.g., T366S), P395 (e.g., P395V), F405 (e.g., F405R), Y407 (e.g., Y407A), and K409 (e.g., K409Y) using Kabat numbering. Those substitutions appear at L14 and L15 (e.g., L14A/L15A "LALA" or L14F/L15E), N77 (e.g., N77A), P111 (e.g. P111S), L131 (e.g., L131K), T146 (e.g., T146S), P175 (e.g., P175V), F185 (e.g., F185R), Y187 (e.g., Y187A), and K189 (e.g., K189Y) in the IgG1 sequence of SEQ ID NO:71.

In an embodiment, a masked TGF-β complex comprises a first polypeptide comprising an IgG1 scaffold with a T146W KiH sequence substitution, and a second polypeptide comprising an IgG1 scaffold with T146S, L148A, and Y187V KiH sequence substitutions, where the scaffolds comprises a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering). See, e.g., FIG. 2D, SEQ ID NOs:77 and 78.

In an embodiment, the first and second polypeptide of a masked TGF-β complex comprise in the first scaffold sequence T146W and S134C KiHs-s substitutions, and in the second scaffold sequence T146S, L148A, Y187V and Y129C KiHs-s substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptide of a masked TGF-β complex comprise in the first scaffold sequence S144H and F185A HA-TF substitutions, and in the second scaffold sequence Y129T and T174F HA-TF substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptides of a masked TGF-β complex comprise in the first scaffold sequence T130V, L131Y, F185A, and Y187V ZW1 substitutions, and in the second scaffold sequence T130V, T146L, K172L, and T174W ZW1 substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptides of a masked TGF-β complex comprise in the first scaffold sequence K140D, D179M, and Y187A 7.8.60 substitutions, and in the second scaffold sequence E125R, Q127R, T146V, and K189V 7.8.60 substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second β polypeptides of a masked TGF-β complex comprise in the first scaffold sequence K189D, and K172D DD-KK substitutions, and in the second scaffold sequence D179K and E136K DD-KK substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering), In an embodiment, the first and second polypeptides of a masked TGF-β complex comprise in the first scaffold sequence K140E and K189W EW-RVT substitutions, and in the second scaffold sequence Q127R, D179V, and F185T EW-RVT substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptides of a masked TGF-β complex comprise in the first scaffold sequence K140E, K189W, and Y129C EW-RVTs-s substitutions, and in the second scaffold sequence Q127R, D179V, F185T, and S134C EW-RVTs-s substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptides of a masked TGF-β complex comprise in the first scaffold sequence K150E and K189W A107 substitutions, and in the second scaffold sequence E137N, D179V, and F185T A107 substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

As an alternative to the use of immunoglobulin heavy chain constant regions as scaffolds, immunoglobulin light chain constant regions can be paired with heavy chain CH1 sequences as dimerization sequences that form, or are a part of, scaffold polypeptide sequences. In an embodiment, the first and second polypeptides of a masked TGF-β complex comprise in the first scaffold sequence an Ig CH1 domain (e.g., the polypeptide of SEQ ID NO:85), and in the second scaffold sequence Ig κ chain constant region sequence SEQ ID NO:86), where the scaffolds comprise a sequence having at least 80%, 85%, 90%. 95%, 98%, 99%, or 100% sequence identity to at least 70, at least 80, at least 90, at least 100, or at least 110 contiguous aas of SEQ ID NOs: 85 and/or 86 respectively). See FIGS. 2J and 2K. The CH1 and Ig κ sequences may be modified to increase their affinity for each other, and accordingly the stability of any heterodimer formed utilizing them as a dimerization sequences. Among the substitutions that increase the stability of CH1-Ig κ heterodimers are those identified as the MD13 combination in Chen et al., *MAbs,* 8(4):761-774 (2016). In MD13 two substitutions are introduced into to each of the CH1 and Ig κ sequences. The CH1 sequence is modified to contain S64E and S66V substitutions (S70E and S72V in SEQ ID NO:85 shown in FIG. 2J). The Ig κ sequence is modified to contain S69L and T71S substitutions (S68L and T70S in SEQ ID NO:86 shown in FIG. 2K).

In another embodiment, the first and second polypeptide of a masked TGF-β complex comprise in the first scaffold sequence an Ig CH1 domain (e.g., the polypeptide of SEQ ID NO:85), and in the second scaffold sequence Ig λ chain constant region sequence SEQ ID NO:87), where the scaffolds comprise a sequence having at least 80%, 85%, 90%. 95%, 98%, 99%, or 100% sequence identity to at least 70, at least 80, at least 90, at least 100, or at least 110 contiguous aas of SEQ ID NOs:85 and/or 87 respectively. See FIGS. 2J and 2K.

In some cases, the scaffold polypeptide sequence of a first and a second polypeptide of a masked TGF-β complex each comprise a leucine zipper polypeptide as a dimerization sequence. The leucine zipper polypeptides bind to one another to form dimer (e.g., homodimer). Non-limiting examples of leucine-zipper polypeptides include, for example, a peptide of any one of the following aa sequences:

RMKQIEDKIEEILSKIYHIENEIARIKKLIGER (SEQ ID NO:88); LSSIEKKQEEQTSW LIWISNELTLIRNELAQS (SEQ ID NO:89); LSSIEKKLEEITSQLIQISNELTLIRNELAQ (SEQ ID NO:90; LSSIEKKLEEITSQLIQIRNELTLIRNELAQ (SEQ ID NO:91); LSSIEKKLEEITSQLQQIR NELTLIRNELAQ (SEQ ID NO:92); LSSLEKKLEELTSQLIQLRNELTLLRNELAQ (SEQ ID NO:93); ISSLEKKIEELTSQIQQLRNEITLLRNEIAQ (SEQ ID NO:94). In some cases, a leucine zipper polypeptide comprises the following aa sequence: LEIEAAFLERENTALETRVAELRQRVQR LRNRVSQYRTRYGPLGGGK (SEQ ID NO:95). Additional leucine-zipper polypeptides are known in the art, any of which is suitable for use as scaffold or incorporation into a scaffold as a dimerization sequence.

In some cases, the scaffold polypeptide sequence of a first and a second polypeptide of a masked TGF-β complex each comprise a coiled-coil peptide that forms a dimer (e.g., homodimer). Non-limiting examples of coiled-coil polypeptides include, for example, a peptide of any one of the following aa sequences: LKSVENRLAVVENQLKTVIEELKTVKDLLSN (SEQ ID NO:96); LARIEEKLKTIKA QLSEIASTLNMIREQLAQ (SEQ ID NO:97); VSRLEEKVKTLKSQVTELASTVSLLREQ VAQ (SEQ ID NO:98); IQSEKKIEDISSLIGQIQSEITLIRNEIAQ (SEQ ID NO:99); LMSLEKKLEELTQTLMQL QNELSMLKNELAQ (SEQ ID NO:100).

In some cases, a scaffold polypeptide sequence that permits dimerization (homodimerization) of a first and a second polypeptide of a masked TGF-β complex each comprise a polypeptide sequence having at least one cysteine residue that can form a disulfide bond. Examples of such polypeptide sequences include: a human FasL polypeptide VDLEGSTSNGRQCAGIRL (SEQ ID NO:101); EDDVTTTEELAPALVPPPKGTCAGWMA (SEQ ID NO:102); and GHDQETTTQGPGVLLPLP KGACTGQMA (SEQ ID NO:103).

Peptides suitable as multimerization (oligomerization) sequences permit formation of masked TGF-β complexes greater than dimers (e.g., trimers tetramers, pentamers, hexamers, etc.) include, but are not limited to, IgM constant regions (see, e.g., FIG. 2 H) which forms hexamer, or pentamers (particularly when combined with a mature j-chain peptide lacking a signal sequence such as that provided in FIG. 2I). Collagen domains, which form trimers, can also be employed. Collagen domains can comprise (Gly-Xaa-Xaa)n, where Xaa is any aa, or and where n is an integer (e.g., from 10 to 40); where Xaa and Yaa are independently any aa and n is an integer from 10 to 40. In Gly-Xaa-Yaa sequences, Xaa and Yaa are frequently proline and hydroxyproline respectively in greater than 25%, 50%, 75%, 80% 90% or 95% of the Gly-Xaa-Yaa occurrences, or in each of the Gly-Xaa-Yaa occurrences. In some cases, a collagen domain comprises the sequence (Gly-Xaa-Pro)n, where n is an integer (e.g., from 10 to 40). A collagen oligomerization peptide can comprise the following aa sequence: VTAFSNMDDMLQKAHLVIEGTFIYLRDSTEFFIRVRDGWKKLQLGELIPIPADSPPP PALSSNP (SEQ ID NO:104).

F. TGF-β Polypeptides

As noted above, a masked TGF-β construct or complex comprises at least one TGF-β polypeptide (e.g., one or more independently selected TGF-β polypeptides) Amino acid sequences of TGF-β polypeptides are known in the art. In some cases, the TGF-β polypeptide present in a masked TGF-β construct or complex is a TGF-β1 polypeptide. In some cases, the TGF-β polypeptide present in a masked TGF-β construct or complex is a TGF-β2 polypeptide. In some cases, the TGF-β polypeptide present in a masked TGF-β construct or complex is a TGF-β3 polypeptide.

While TGF-β1, TGF-β2, or TGF-β3 polypeptide sequences may be incorporated into a masked TGF-β construct or complex, a variety of factors may influence the choice of the specific TGF-β polypeptide, and the specific sequence and aa substitutions that will be employed. For example, TGF-β1 and TGF-β3 are subject to "clipping" of their amino acid sequences when expressed in a number of mammalian cell systems (e.g., CHO cell). In addition, dimerized TGF-β (e.g., TGF-β2) has a higher affinity for the TβR3 (beta glycan receptor) than for the TβR2 receptor, which could lead to off target binding and loss of biological active masked protein to the large in vivo pool of non-signaling TβR3 molecules. In order to minimize high-affinity off target binding to TβR3, it may be desirable to substitute the residues leading to dimeric TGF-β molecules, which are joined by a disulfide bond. Accordingly, cysteine 77 (C77) may be substituted by an amino acid other than cysteine (e.g., a serine forming a C77S substitution).

A suitable TGF-β polypeptide can have a length from about 70 aas to about 125 aas; for example, a suitable TGF-β polypeptide can have a length from about 70 aas to about 80 aas from about 80 aas to about 90 aas; from about 90 aas to about 100 aas; from about 100 aas to about 105 aas, from about 105 aas to about 110 aas, from about 110 aas to about 112 aas, from about 113 aas to about 120 aas, or from about 120 aas to about 125 aas. A suitable TGF-β polypeptide can comprise an amino acid sequence having at least 60%, at least 70%, at least 80%, at least 80%, at least 85%, at least 90%, at least 95%, at least 98%, at least 99%, or 100%, aa sequence identity to at least 80, at least 90, at least 100, or at least 110 contiguous aas of the mature form of a human TGF-β1 polypeptide, a human TGF-β2 polypeptide, or a human TGF-β3 polypeptide.

1 TGF-β1 Polypeptides

A suitable TGF-β1 polypeptide can comprise an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β1 amino acid sequence: AL DTNYCFSSTE KNCCVRQLYI DF *R*KDLGWKW IHEPKGYHAN FCLGPCPYIW SLDTQYSKVL ALYNQHNPGA SAAPCCVPQA LEPLPIVYYV G *R*KPKVEQLS NMIVRSCKCS (SEQ ID NO:105, 112 aas in length); where the TGF-β1 polypeptide has a length of about 112 aas. A TGF-β1 preproprotein is provided in FIG. 3 as SEQ ID NO:106 Amino acids R25, C77, V92 and R94 are bolded and italicized see FIG. 4.

In some cases, a suitable TGF-β1 polypeptide comprises a C77S substitution. Thus, in some cases, a suitable TGF-β1 polypeptide comprises an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β1 amino acid sequence: AL DTNYCFSSTE KNCCVRQLYI DF *R*KDLGWKW IHEPKGYHAN FCLGPCPYIW SLDTQYSKVL ALYNQHNPGA SAAPSCVPQA LEPLPIVYYV G *R*KPKVEQLS NMIVRSCKCS (SEQ ID NO:107), where amino acid 77 is Ser. Positions 25, 77, 92 and 94 are bolded and italicized.

2 TGF-β2 Polypeptides A suitable TGF-β2 polypeptide can comprise an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β2 amino acid sequence: ALDAAYCFR NVQDNCCLRP LYIDF *K*RDLG WKWIHEPKGY NANFCAGACP YLWSSDTQHS RVLSLYNTIN PEASASPCCV SQDLEPLTIL YYIG *K*TPKIE QLSNMIVKSC KCS (SEQ ID NO:108), where the TGF-β2 polypeptide has a length of about 112 aas. A TGF-β2 preproprotein is provided in FIG. 3 as SEQ ID NO:109. Residues Lys 25, Ile 92, and/or Lys 94 are bolded and italicized.

In some cases, a suitable TGF-β2 polypeptide comprises a C77S substitution. Thus, in some cases, a suitable TGF-β2 polypeptide comprises an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β2 amino acid sequence: ALDAAYCFR NVQDNCCLRP LYIDFKRDLG WKWIHEPKGY NANFCAGACP YLWSSDTQHS RVLSLYNTIN PEASASPSCV SQDLEPLTIL YYIGKTPKIE QLSNMIVKSC KCS (SEQ ID NO:110), where amino acid 77 is Ser.

3 TGF-β3 Polypeptides

A suitable TGF-β3 polypeptide can comprise an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β3 amino acid sequence: ALDTNYCFRN LEENCCVRPL YIDF *R*QDLGW KWVHEPKGYY ANFCSGPCPY LRSADTTHST VLGLYNTLNP EASASPCCVP QDLEPLTILY YVG *R*TPKVEQ LSNMVVKSCK CS (SEQ ID NO:111), where the TGF-β3 polypeptide has a length of about 112 aas. A TGF-β3 isoform 1 preproprotein is provided in FIG. 3 as SEQ ID NO:112. Positions 25, 92 and 94 are bolded and italicized.

In some cases, a suitable TGF-β3 polypeptide comprises a C77S substitution. In some cases, a suitable TGF-β3 polypeptide comprises an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β3 amino acid sequence: ALDTNYCFRN LEENCCVRPL YIDF *R*QDLGW KWVHEPKGYY ANFCSGPCPY LRSADTTHST VLGLYNTLNP EASASPSCVP QDLEPLTILY YVG *R*TPKVEQ LSNMVVKSCK CS (SEQ ID NO:113), where amino acid 77 is Ser. Positions 25, 92 and 94 are bolded and italicized.

4 Additional TGF-β Polypeptide Sequence Variations

In addition to sequence variations that alter TGF-β molecule dimerization (e.g., cysteine 77 substitutions such as C77S), TGF-β1-3 polypeptides having sequence variations that affect affinity and other properties may be incorporated into a masked TGF-β construct or complex. When a masked TGF-γ construct or complex comprises a TGF-β variant with reduced affinity for the masking polypeptide (e.g. TβR polypeptide such as a TβRII polypeptide) those components dissociate more readily, making the masked TGF-β polypeptide more available to cellular TβR proteins. Because the TβRII protein is generally the first peptide of the heteromeric TβR signaling complex to interact with TGF-β, interactions with TβRII effectively controls entry of TGF-β into active signaling complexes. Accordingly, variants controlling the affinity of TGF-β for TβRII effectively control entry of masked TGF-β constructs and complexes into active signaling complexes.

The present disclosure includes and provides for masked TGF-β constructs and complexes comprising a variant masking TβR (e.g., TβRII) polypeptide sequence and/or a variant TGF-β polypeptide having altered (e.g., reduced) affinity for each other (relative to an otherwise identical masked TGF-β construct or complex without the sequence variation(s)). Affinity between a TGF-β polypeptide and a TβR (e.g., TβRII) polypeptide may be determined using (BLI) as described above for MODs and their co-MODs.

a. Additional TGF-β2 Sequence Variants

The present disclosure includes and provides for masked TGF-β2 constructs and complexes comprising a masking TβR (e.g., TβRII) polypeptide sequence and either a wt. or a variant TGF-β2 polypeptide; where the variant polypeptide has a reduced affinity for the masking TβR (relative to an otherwise identical wt. TGF-β polypeptide sequence without the sequence variations).

The disclosure provides for a masked TGF-β construct or complex comprises a masking TβRII receptor sequence and a variant TGF-β2 polypeptide having greater than 85% (e.g., greater than 90%, 95%, 98% or 99%) sequence identity to at least 100 contiguous aa of SEQ ID NO:108, and comprising a substitution reducing the affinity of the variant TGF-β2 polypeptide for the TβRII receptor sequence.

In some cases, a masked TGF-β construct or complex comprises a masking TβRII polypeptide and a variant TGF-β (e.g. TGF-β2) polypeptide comprising a substitution at one or more, two or more, or all three of Lys 25, Ile 92, and/or Lys 94 (see SEQ ID NO:108 for the location of the residues, and FIG. 4 for the corresponding residues in TGF-β1 and TGF-β3). Those aa residues have been shown to affect the affinity of TGF-β2 for TβRII polypeptides (see Crescenzo et al., *J. Mol. Biol.*, 355: 47-62 (2006)). The masked TGF-β construct or complex optionally comprises one or more independently selected MODs such as IL-2 or a variant thereof. In one instance, the masked TGF-β construct or complex comprises a masking TβRII polypeptide and a TGF-β2 polypeptide having an aa other than Lys or Arg at position 25 of SEQ ID NO:108; and optionally comprises one or more independently selected MODs (e.g., one or more IL-2 MOD polypeptide or reduced affinity variant thereof). A masked TGF-β construct or complex with a masking TβRII polypeptide may comprises a TGF-β2 polypeptide having an aa other than Ile or Val at position 92 of SEQ ID NO:108 (or an aa other than Ile, Val, or Leu at position 92); and optionally comprises one or more independently selected MODs (e.g., one or more IL-2 MOD polypeptide or reduced affinity variant thereof). A masked TGF-β construct or complex with a masking TβRII polypeptide may comprise a TGF-β2 polypeptide having an aa other than Lys or Arg at position 94 of SEQ ID NO:108; and optionally comprises one or more independently selected MODs (e.g., one or more IL-2 MOD polypeptide or reduced affinity variant thereof). A masked TGF-β construct or complex with a masking TβRII polypeptide may comprise a TGF-β2 polypeptide comprising a substitution at one or more, two or more or all three of Lys 25, Ile 92, and/or Lys 94, and further comprises one or more independently selected MODs. A masked TGF-β construct or complex with a masking TβRII polypeptide may comprise a TGF-β2 polypeptide comprising a substitution at one or more, two or more or all three of Lys 25, Ile 92, and/or Lys 94, and further comprises one or more independently selected IL-2 MODs or reduced affinity variants thereof b. Additional TGF-β1 and TGF-β3 Sequence Variants In some cases, a masked TGF-β construct or complex comprises a masking TβRII polypeptide and a variant TGF-β1 or TGF-β3 polypeptide comprising a substitution at one or more, two or more or all three aa positions corresponding to Lys 25, Ile 92, and/or Lys 94 in TGF-β2 SEQ ID NO:108. In TGF-β1 or TGF-β3, the aa that corresponds to: Lys 25 is an Arg 25, Ile 92 is Val 92, and Lys 94 is Arg 94, each of which is a conservative substitution. See, e.g., SEQ ID NOs:106 and 107 for TGF-β1 and SEQ ID NOs:112 and 113 for TGF-β3.

As noted above, the masked TGF-β construct or complex optionally comprises one or more independently selected MODs such as IL-2 or a variant thereof. In one instance, the masked TGF-β construct or complex with a masking TβRII polypeptide comprises a TGF-β1 or 133 polypeptide having an aa other than Arg or Lys at position 25; and optionally comprises one or more independently selected MODs (e.g., one or more IL-2 MOD polypeptide or reduced affinity variant thereof). In one instance, the masked TGF-β construct or complex with a masking TβRII polypeptide comprises a TGF-β1 or 133 polypeptide having an aa other than Val or Ile at position 92 (or an aa other than Ile, Val, or Leu at position 92); and optionally comprises one or more independently selected MODs (e.g., one or more IL-2 MOD polypeptide or reduced affinity variant thereof). In another instance, the masked TGF-β construct or complex with a masking TβRII polypeptide comprises a TGF-β2 polypeptide having an aa other than Arg or Lys; and optionally comprises one or more independently selected MODs (e.g., one or more IL-2 MOD polypeptide or reduced affinity variant thereof). In one specific instance, a masked TGF-β construct or complex with a masking TβRII polypeptide comprises a TGF-β1 or 133 polypeptide comprising a substitution at one or more, two or more or all three of Arg 25, Val 92, and/or Arg 94, and further comprises one or more independently selected MODs. In another specific instance, a masked TGF-β construct or complex with a masking TβRII polypeptide comprises a TGF-β1 or 133 polypeptide comprising a substitution at one or more, two or more or all three of Arg 25, Val 92, and/or Arg 94, and further comprises one or more independently selected IL-2 MODs, or reduced affinity variants thereof.

G. TGF-β Receptor Polypeptides and Other Polypeptides that Bind and Mask TGF-β

In any of the above-mentioned TGF-β polypeptides or polypeptide complexes the polypeptide that binds to and masks the TGF-β polypeptide (a "masking polypeptide") can take a variety of forms, including fragments of TβRI, TβRII, TβRIII and anti TGF-β antibodies or fragments thereof (e.g., Fab., single chain antibodies, etc.).

1 TGF-β Receptor Polypeptides

The masking of TGF-β in masked TGF-β constructs and complexes may be accomplished by utilizing a TGF-β receptor fragment (e.g., the ectodomain sequences of TβRI, TβRII or TβRIII) that comprises polypeptide sequences sufficient to bind a TGF-β polypeptide (e.g., TGF-β1, TGF-β2 or TGF-β3). In an embodiment, the masking sequence comprises all or part of the TβRI, TβRII, or TβRIII ectodomain.

a. TGF-β Receptor I (TβRI)

In an embodiment the polypeptide sequence masking TGF-β in a masked TGF-β construct or complexes may be derived from a TβRI (e.g., isoform 1 SEQ ID NO:114) and may comprises all or part of the TβRI ectodomain (aas 34-126). In some cases, a suitable TβRI polypeptide for masking TGF-β comprises an amino acid sequence having at least 60%, at least 70%, at least 80%, at least 90%, at least 95%, at least 98%, at least 99%, or 100%, aa sequence identity to at least 70, at least 80, at least 90, at least 100, or 103 aas of the following TβRI ectodomain aa sequence: LQCFCHL CTKDNFTCVT DGLCFVSVTE TTDKVIHNSM CIAEIDLIPR DRPFVCAPSS KTGSVTT-TYC CNQDHCNKIE LPTTVKSSPG LGPVEL (SEQ ID NO:115).

b. TGF-β Receptor II (TβRII)

In embodiments, the polypeptide sequence masking TGF-β in a masked TGF-β construct or complex may be derived from a TβRII (e.g., isoform A SEQ ID NO:116), and may comprises all or part of the TβRII ectodomain sequence (aas 24 to 177). In an embodiment, a suitable TβRII isoform A polypeptide for masking TGF-β may comprise an amino acid sequence having at least 60%, at least 70%, at least 80%, at least 90%, at least 95%, at least 98%, at least 99%, or 100%, aa sequence identity to at least 70, at least 80, at least 90, at least 100, at least 110, at least 120, at least 130, at least 140, at least 150 or at least 154 aas of the following TβRII isoform A ectodomain aa sequence: IPPHVQK SDVEMEAQKD EIICPSCNRT AHPLRHINND MIVTDNNGAV KFPQLCKFCD VRFSTCDNQK SCMSNCSITS ICEKPQEVCV AVWRKNDENI TLETVCHDPK LPYHDFILED AASPKCIMKE KKKPGETFFM CSCSS *D*ECND NIIFSEE (SEQ ID NO:117). The location of the aspartic acid residue corresponding to D118 in the B isoform is bolded, underlined, and italicized.

In an embodiment, the polypeptide sequence masking TGF-β in a masked TGF-β construct or complex may be derived from TβRII isoform B SEQ ID NO:118) and may comprises all or part of the TβRII ectodomain sequence (aas 24 to 166). In embodiment, a suitable TβRII isoform B polypeptide for masking TGF-β comprises an amino acid sequence having at least 60%, at least 70%, at least 80%, at least 90%, at least 95%, at least 98%, at least 99%, or 100%, aa sequence identity to at least 70, at least 80, at least 90, at least 100, or 103 aas of the TβRII isoform B ectodomain aa sequence: IPPHVQKSVN NDMIVTDNNG AVKFPQLCK *F* C *D*VRFSTCDN QKSCMSNCSI TSIC *E*KPQEV CVAVWRKNDE NITLETVCHD PKLPYHDFIL EDAASPKCIM KEKKKPGETF FMCSCSS *D*EC NDNIIFSEEY NTSNPDLLLV IFQ (SEQ ID NO:119). As discussed below, any one or more of F30, D32, S52, E55, or D118 (italicized and bolded) may be substituted by an amino acid other than the naturally occurring aa at those positions (e.g., alanine). A polypeptide sequence masking TGF-β may comprise the polypeptide of SEQ ID NO:119 bearing a D118A or D118R substitution. A sequence masking TGF-β may comprise the peptide of SEQ ID NO:119 bearing a D118A or D118R substitution and one or more of a F30A, D32N, S52L and/or E55A substitution.

Although TβRII's ectodomain may be utilized as a masking polypeptide, that region of the protein has charged and hydrophobic patches that can lead to an unfavorable pI and can be toxic to cell expressing the polypeptide. In addition, combining a TβRII ectodomain with the an active TGF-β polypeptide can result in a complex that could combine with cell surface TβRI and cause activation of that signaling receptor (e.g., signaling through the Smad pathway). Modifying TβRII ectodomain sequences used to mask TGF-β by removing or altering sequences involved in TβRI association can avoid the unintentional stimulation of cells by the masked TGF-β except through their own cell surface heterodimeric TβRI/TβRII complex. Modifications of TβRII may also alter (e.g., reduce) the affinity of the TβRII for TGF-β (e.g., TGF-β3), thereby permitting control of TGF-β unmasking and its availability as a signaling molecule. Masked TGF-β construct or complexes comprising TβR (e.g., TβRII) peptides with the highest affinity for TGF-β (e.g., TGF-β3) most tightly mask the TGF-β sequence and require higher doses to achieve the same effect. In contrast, aa substitutions in TβRII that lower the affinity unmask the TGF-β polypeptide and are biologically effective at lower doses. See, e.g., Example 3.

Accordingly, where it is desirable to block/limit signaling by the masked TGF-β polypeptide through TβRI and/or modify (e.g., reduce) the affinity of a masking TβRII polypeptide for TGF-β a number of alterations to TβRII may be incorporated into the TβRII polypeptide sequence. Modifications that can be made include the above-mentioned deletions of N-terminal 25 amino acids from 1 to 25 aa in length (e.g. Δ14, Δ25) and/or substitutions at one or more of L27, F30, D32, S49, I50, T51, S52, I53, E55, V77, D118, and/or E119. Some specific modifications resulting in a reduction in TβRI association with TβRII and reduced affinity for TGF-β include any one or more of L27A, F30A, D32A, D32N, S49A, I50A, T51A, S52A, S52L, I53A, E55A, V77A, D118A, D118R, E119A, and/or E119Q based on SEQ ID NO:119. See, e.g., J. Groppe et al., *Mol Cell*, 29, 157-168, (2008) and De Crescenzo et al., *JMB*, 355, 47-62 (2006). See FIG. 9 for the effects of those substitutions on TGF-β3-TβRII and TβRI-TβRII complexes. Modifications of TβRII the including an N-terminal Δ25 deletion and/or substitutions at F24 (e.g., an F24A substitution) substantially or completely block signal through the canonical SMAD signaling pathway). In one aspect, the aspartic acid at position 118 (D118) of the mature TβRII B isoform (SEQ ID NO:119) is replaced by an amino acid other than Asp or Glu, such as Ala giving rise to a "D118A" substitution or by an Arg giving rise to a D118R substitution. The Asp residues corresponding to D118 are indicated in SEQ ID NOs:117-123 (with bold and underlining in FIG. 5B). N-terminal deletions of from 1 to 25 aa in length (e.g., a Δ25 deletions) and/or substitutions at F24 (e.g., an F24A substitution) may be combined with D118 substitutions (e.g., D118A or D118R). N-terminal deletions of from 1 to 25 aa in length (e.g., a Δ25 deletions) and/or substitutions at F24 (e.g., an F24A substitution) may also be combined with substitutions at any of L27, F30, D32, S49, I50, T51, S52, I53, E55, V77, D118, and/or E119 (e.g., D118A) substitutions, and particularly any of the specific substitutions recited for those locations in SEQ ID NO:119 described above to alter the affinity.

Deletions of the N-terminus of the TβRII polypeptides may also result in loss of TβRI interactions and prevent masked TGF-β constructs and complexes comprising a TβRII polypeptide from acting as a constitutively active complex that engages and activates TβRI signaling. A 14 aa deletion (Δ14) of the TβRII polypeptide substantively reduces the interaction of the protein with TβRI, and a Δ25 aa deletion of TβRII appears to completely abrogate the interaction with TβRI. N-terminal deletions also substantially alter the pI of the protein, with the Δ14 TβRII ectodomain mutant displaying a pI of about 4.5-5.0 (e.g., about 4.74). Accordingly, TGF-β constructs or complexes may comprise TβRII ectodomain polypeptides (e.g., polypeptides of SEQ ID NOs:117 or 118) with N-terminal deletions, such as from 14 to 25 aas (e.g., 14, 15, 16, 17, 18, 19, 20, 21, 22, 23, 24, or 25 aa). Modified ectodomain sequences, including those that limit interactions with TβRI, that may be utilized to mask TGF-β polypeptides in a masked TGF-β construct or complex are described in the paragraphs that follow.

In an embodiment, the sequence masking TGF-β in a masked TGF-β construct or complex comprises sequence having at least 60%, at least 70%, at least 80%, at least 90%, at least 95%, at least 98%, at least 99%, or 100%, aa sequence identity to at least 70, at least 80, at least 90, at least 100, or 103 aas of the TβRII isoform B ectodomain sequence: IPPHVQKSVN NDMIVTDNNG AVKFPQLCK *F* C *D*VRFSTCDN QKSCMSNCSI T*S*IC *E*KPQEV CVAVWRKNDE NITLETVCHD PKLPYHDFIL EDAASPKCIM KEKKKPGETF FMCSCSS *D*EC NDNIIFSEE (SEQ ID NO:120). Any one or more of F30, D32, S52, E55, or D118 (italicized and bolded) may be substituted by an amino acid other than the naturally occurring aa at those positions (e.g., alanine). In an embodiment, the sequence masking TGF-β comprises the peptide of SEQ ID NO:120 bearing a D118A substitution. In an embodiment, the sequence masking TGF-β comprises the polypeptide of SEQ ID NO:120 bearing a D118A substitution and one or more of a F30A, D32N, S52L and/or E55A substitution.

Combinations of N-terminal deletions of TβRII, such as from 14 to 25 aas (e.g., 14, 15, 16, 17, 18, 19, 20, 21, 22, 23, 24, or 25 aa), that block inadvertent cell signaling due to the masked TGF-β/TβRII complex interacting with TβRI may be combined with other TβRII ectodomain substitutions, including those at any one or more of F30, D32, S52, E55, and/or D118. The combination of deletions and substitutions ensures the masked TGF-β construct or complex does not cause cell signaling except through the cell's membrane bound TβRI & TβRII receptors.

In an embodiment, the sequence masking TGF-β in a masked TGF-β construct or complex comprises sequence having at least 60%, at least 70%, at least 80%, at least 90%, at least 95%, at least 98%, at least 99%, or 100%, aa sequence identity to at least 70, at least 80, at least 90, at least 100, or 103 aas of the TβRII isoform B ectodomain sequence: TDNNG AVKFPQLCK*F* C *D*VRFSTCDN QKSCMSNCSI TSIC *E*KPQEV CVAVWRKNDE NITLETVCHD PKLPYHDFIL EDAASPKCIM KEKKKPGETF FMCSCSS *D*EC NDNIIFSEE (SEQ ID NO:121), which has aas 1-14 (Δ14) deleted. Any one or more of F30, D32, S52, E55, or D118 (italicized and bolded) may be substituted by an amino acid other than the naturally occurring aa at those positions (e.g., alanine). In an embodiment, the sequence masking TGF-β comprises the peptide of SEQ ID NO:121 bearing a D118A substitution. In an embodiment, the sequence masking TGF-β comprises the polypeptide of SEQ ID NO:121 bearing a D118A substitution and one or more of a F30A, D32N, S52L and/or E55A substitution.

In an embodiment, the sequence masking TGF-β in a masked TGF-β construct or complex comprises sequence having at least 60%, at least 70%, at least 80%, at least 90%, at least 95%, at least 98%, at least 99%, or 100%, aa sequence identity to at least 70, at least 80, at least 90, at least 100, or 103 aas of the sequence: QLCK *F* C *D*VRF-STCDN QKSCMSNCSI TSIC *E* KPQEV CVAVWRKNDE NITLETVCHD PKLPYHDFIL EDAASPKCIM KEKKKPGETF FMCSCSS *D*EC NDNIIFSEE (SEQ ID NO:122), which has aas 1-25 (Δ25) deleted. Any one or more of F30, D32, S52, E55, or D118 (italicized and bolded) may be substituted by an amino acid other than the naturally occurring aa at those positions (e.g., alanine). In an embodiment, the sequence masking TGF-β comprises the polypeptide of SEQ ID NO:122 bearing a D118A substitution (shown as SEQ ID NO:123 in FIG. 5B). In an embodiment, the sequence masking TGF-β in a masked TGF-β construct or complex comprises the peptide of SEQ ID NO:122 bearing a D118A substitution and one or more of a F30A, D32N, S52L and/or E55A substitution. In an embodiment, the sequence masking TGF-β in a masked TGF-β construct or complex comprises the peptide of SEQ ID NO:122 (see FIG. 5B) bearing D118A and F30A substitutions. In an embodiment, the sequence masking TGF-β in a masked TGF-β construct or complex comprises the peptide of SEQ ID NO:122 (see FIG. 5B) bearing D118A and D32N substitutions. In an embodiment, the sequence masking TGF-β in a masked TGF-β construct or complex comprises the peptide of SEQ ID NO:122 (see FIG. 5B) bearing D118A and S52L substitutions. In an embodiment, the sequence masking TGF-β in a masked TGF-β construct or complex comprises the peptide of SEQ ID NO:122 (see FIG. 5B) bearing D118A and E55A.

c. TGF-β Receptor III (TβRIII)

In an embodiment, the polypeptide sequence masking TGF-β in a masked TGF-β construct or complexes may be derived from a TβRIII (e.g., isoform A SEQ ID NO:124 and isoform B 125), and may comprise all or part of a TβRIII ectodomain (aas 27-787 of the A isoform or 27-786 of the B isoform). In some cases, a suitable TβRIII polypeptide for masking TGF-β comprises an amino acid sequence having at least 60%, at least 70%, at least 80%, at least 90%, at least 95%, at least 98%, at least 99%, or 100%, aa sequence identity to at least 70, at least 80, at least 90, at least 100, or 120 aas of a TβRIII A isoform or B isoform ectodomain sequences (e.g., provided in FIG. 5C as SEQ ID NO:124 or SEQ ID NO:125).

2 Antibodies

Although TGF-β receptor polypeptides (e.g., ectodomain sequences) can function to bind and mask TGF-β polypeptides in masked TGF-β constructs or complexes, other polypeptide sequences (protein sequences) that bind to TGF-β sequences can also be employed as masking polypeptides. Among the suitable polypeptide or protein sequences that can be used to mask TGF-β are antibodies with affinity for TGF-β (e.g., antibodies specific for an one or more of TGF-β1, TGF-β2, or TGF-β3) or their fragments, nanobodies with affinity for TGF-β polypeptides, and particularly single chain anti-TGF-β antibodies (e.g., any of which may be humanized). Some antibodies, including scFV antibodies, that bind and neutralize TGF-β have been described. See e.g., U.S. Pat. No. 9,090,685. Throughout the embodiments and/or aspects of the invention described in this disclosure, TβR (e.g., TβRII) sequences used to mask TGF-β polypeptides may be replaced with masking antibody sequences (e.g., a scFV or a nanobody) with affinity for the TGF-β polypeptide. For instance, in each of the masked TGF-β constructs or complexes in FIG. 1 where a TGF-β receptor sequence is used to mask a TGF-β polypeptide, the receptor polypeptide may be replaced with a masking antibody polypeptide (e.g., scFV or a nanobody) with affinity for the TGF-β polypeptide.

One potential advantage of using an antibody (e.g., a single chain antibody) as a masking polypeptide is the ability to limit it to the isoform of the TGF-β polypeptide(s) to be masked. By way of example, single chain antibody sequences based on Metelimumab (CAT192) directed against TGF-β1 (e.g., Lord et al., mAbs 10(3): 444-452 (2018)) can be used to mask that TGF-β isoform when present in TGF-β constructs or complexes. In another embodiment, a single chain antibody sequence specific for TGF-β2 is used to mask that TGF-β isoform when present in TGF-β constructs or complexes. In another embodiment, a single chain antibody sequence specific for TGF-β3 is used to mask that TGF-β isoform when present in TGF-β constructs or complexes. Single chain antibodies can also be specific for a combination of TGF-β isoforms (e.g., ectodomain sequences appearing in masked TGF-β constructs or complexes selected from the group consisting of: TGF-β1 & TGF-β2; TGF-β1 & TGF-β3; and TGF-β2 & TGF-β3. The single chain antibodies may also be pan-specific for TGF-β1, TGF-β2, and TGF-β3 ectodomain sequences appearing in masked TGF-β constructs or complexes. See, e.g., WO 2014/164709. Antibodies and single chain antibodies that have the desired specificity and affinity for TGF-β isoforms can be prepared by a variety of methods, including screening hybridomas and/or modification (e.g., combinatorial modification) to the variable region sequence of antibodies that have affinity for a target TGF-β polypeptide sequence.

In an embodiment, a masked TGF-β construct or complex comprises a single chain antibody to mask a TGF-β sequence (e.g., a TGF-β3 sequence). In one such embodiment the single chain amino acid sequence is specific for the TGF-β3 set forth in SEQ ID NO:111 comprising a C77S substitution (see SEQ ID NO:112).

H. Linkers

As noted above, a masked TGF-β construct or complex can include a linker peptide/polypeptide sequence interposed between any two elements of a masked TGF-β construct or complex. Although the term "linker" is employed, the same sequences described below as linkers may also be placed at the N- and/or C-terminus of a polypeptide of a masked TGF-β construct or complex for example as protection against proteolytic degradation.

Suitable linkers (also referred to as "spacers") can be readily selected and can be any of a number of suitable lengths, such as from 1 aa to 25 aa, from 3 aa to 20 aa, from 2 aa to 15 aa, from 3 aa to 12 aa, from 4 aa to 10 aa, from 5 aa to 9 aa, from 6 aa to 8 aa, or from 7 aa to 8 aa. A suitable linker can be 1, 2, 3, 4, 5, 6, 7, 8, 9, 10, 11, 12, 13, 14, 15, 16, 17, 18, 19, 20, 21, 22, 23, 24, or 25 aa in length. A suitable linker can be from 25 to 35 aa in length. A suitable linker can be 25, 26, 27, 28, 29, 30, 31, 32, 33, 34, or 35 aa in length. A suitable linker can also be from 35 to 45 aa in length. A suitable linker can be 35, 36, 37, 38, 39, 40, 41, 42, 43, 44, or 45 aa in length. A suitable linker can be from 45 to 50 aa in length. A suitable linker can be 45, 46, 47, 48, 49, or 50 aa in length.

Exemplary linkers include those comprising glycine, or a polyglycine containing sequence from about 2 to about 50 (e.g., 2-4, 4-7, 7-10, 10-20, 20-35, or 35-50) contiguous glycine residues; glycine-serine polymers (including, for example, $(GS)_n$, $(GSGGS)_n$ (SEQ ID NO:126) and $(GGGS)_n$ (SEQ ID NO:127), where n is an integer of at least one (e.g., 1-10, 10-20, or 20-30); glycine-alanine polymers or alanine-serine polymers (e.g., having a length of 1-10, 10-20, or 20-30aa); and other flexible linkers known in the art. Glycine and glycine-serine polymers can be used; both Gly and Ser are relatively unstructured, and therefore can serve as a neutral tether between components. Glycine polymers can be used; glycine assesses significantly more phi-psi space than even alanine, and is much less restricted than residues with longer side chains (see Scheraga, *Rev. Computational Chem.*, 11173-142 (1992)). Exemplary linkers can comprise amino acid sequences including, but not limited to, GGSG (SEQ ID NO:128), GGSGG (SEQ ID NO:129), GSGSG (SEQ ID NO:130), GSGGG (SEQ ID NO:131), GGGSG (SEQ ID NO:132), GSSSG (SEQ ID NO:133), and the like. Exemplary linkers can comprise, e.g., GGSG (SEQ ID NO:134) which may be repeated 2, 3, 4, 5, 6, 7, 8, 9, or 10 ten times. In some cases, a linker comprises the amino acid sequence (GSSSS) (SEQ ID NO:135) that may be repeated 2, 3, or 4 times. In some cases, a linker comprises the amino acid sequence (GSSSS) (SEQ ID NO:135) repeated four or five times. Exemplary linkers can include, e.g., (GGGGS) (SEQ ID NO:β6), which can be repeated 2, 3, 4, 5, 6, 7, 8, 9, or 10 ten times. In some cases, a linker comprises the amino acid sequence (GGGGS) (SEQ ID NO:β6) once or repeated 2 times. In some cases, a linker comprises the amino acid sequence (GGGGS) (SEQ ID NO:β6) repeated 3 or 4 times. In some cases, a linker comprises the amino acid sequence (GGGGS) (SEQ ID NO:β6) repeated 5, 6, or 7 times. In some cases, a linker comprises the amino acid sequence (GGGGS) (SEQ ID NO:β6) repeated 8, 9, or 10 times.

In some cases, a linker polypeptide present in a first polypeptide of a masked TGF-β complex includes a cysteine residue that can form a disulfide bond with a cysteine residue present in a second polypeptide of the masked TGF-β construct or complex. In some cases, for example, a suitable linker comprises the amino acid sequence GCGASGGGSGGGS (SEQ ID NO:137).

I. Exemplary Masked TGF-β Constructs and Complexes

As discussed above, in any of the masked TGF-β constructs and complexes described in the present disclosure, the masking polypeptide that binds to and masks the TGF-β polypeptide sequences can take a variety of forms. The masking peptide may be an antibody, binding fragment of an antibody, a single chain antibody or portion thereof that binds TGF-β (e.g., an scFv), or nanobody; any of which may be humanized. The masking polypeptide may also be a TGF-β receptor fragment (e.g., the ectodomain sequences of TβRI, TβRII or TβRIII) that comprises polypeptide sequences sufficient to bind a TGF-β polypeptide (e.g., TGF-β1, TGF-β2 or TGF-β3).

In any of the above-mentioned masked TGF-β constructs and complexes, the TGF-β polypeptide sequence employed may be based upon TGF-β1, TGF-β2 or TGF-β3. In an embodiment the TGF-β polypeptide comprises a TGF-β3 sequence. Full length mature TGF-β protein sequence is not required in the masked TGF-β constructs and complexes, only the portion of TGF-β needed to interact with cell surface TβRII and permit the masked TGF-β complexes with cell surface TβRII to recruit TβRI and thereby initiate signaling (e.g. signaling through the Smad and non-Smad pathways).

Although immunomodulatory polypeptide (MODs) are not required for the delivery of masked TGF-β or its ability to activate cells bearing TβRI and TβRII, as noted above, the presence of MODs can substantially affect the outcome of TGF-β cell activation. Consequently, the incorporation of MODs in any of the above-mentioned masked TGF-β constructs and complexes can be used to drive various outcomes, including therapeutic outcomes, from the use of the masked TGF-β constructs and complexes described herein.

In an embodiment, the MODs present in a masked TGF-β construct or complex are selected from the group consisting of PD-L1, Fas-L, IL-2, IL-4, IL-6, IL-7, IL-21, IL-23, and variants of any thereof including those with reduced affinity for their co-MOD.

While it may be desirable to incorporate MODs into masked TGF-β constructs and complexes, their presence is not necessary in all cases, particularly where the masked TGF-β constructs and complexes are administered along with other materials, including cytokines (e.g., one or more independently selected interleukin, lymphokine, interferon, chemokine, and/or tumor necrosis factor). For example, where it is desirable to support the development of conventional CD8+ T cells (or the survival of low affinity CD8+ T cells) by promoting thymocyte expression of the interleukin 7 receptor (e.g., IL-7Ra), masked TGF-β constructs and complexes without a MOD polypeptide ("MOD-less") may be employed. Similarly, where it is desirable to promote the development of T-cell populations that are induced by strong agonist ligands, MOD-containing or MOD-less masked TGF-β constructs and complexes may be employed to support the survival of thymus-derived Treg (tTreg), invariant natural killer T (iNKT), and CD8αα+ T-cell precursors.

The following are non-limiting examples of masked TGF-β constructs and complexes.

1 Masked TGF-β Constructs

In the case of masked TGF-β constructs, all of the components (e.g., TGF-β, scaffold, a masking polypeptide such as a TβRII sequence, and optionally one or more MODs) are part of a single polypeptide chain (see, e.g., FIG. 1, structure A). In such an embodiment, the scaffold polypeptide does not form a dimer or higher order structure with other scaffold polypeptides, and accordingly the masked TGF-β constructs are not in the form of homodimers, heterodimers or higher order multimer structures (trimers etc.).

In the case of the masked TGF-β construct in FIG. 1, Structure A the polypeptide may comprise, from N-terminus to C-terminus: optionally one or more MODs; a scaffold polypeptide (without an interspecific binding sequence); a polypeptide that binds to and masks the TGF-β polypeptide; and a TGF-β polypeptide sequence. Such masked TGF-β constructs include those where:

(i) the polypeptide comprises from N-terminus to C-terminus: optionally one or more independently selected wt. or reduced affinity variant MODs; a scaffold polypeptide (without an interspecific binding sequence); a TβR polypeptide that binds to and masks the TGF-β polypeptide; and a TGF-β polypeptide sequence;

(ii) the polypeptide comprises from N-terminus to C-terminus: optionally one or more independently selected wt. or reduced affinity variant MODs; a scaffold polypeptide (without an interspecific binding sequence); a TβRII polypeptide that binds to and masks the TGF-β polypeptide; and a TGF-β polypeptide sequence;

(iii) the polypeptide comprises from N-terminus to C-terminus: one or more independently selected wt. or reduced affinity variant MODs; a scaffold polypeptide (without an interspecific binding sequence); a TβR polypeptide that binds to and masks the TGF-β polypeptide; and a TGF-β polypeptide sequence;

(iv) the polypeptide comprises from N-terminus to C-terminus: one or more independently selected wt. or reduced affinity variant IL-2 MODs; a scaffold polypeptide (without an interspecific binding sequence); a TβR polypeptide that binds to and masks the TGF-β polypeptide; and a TGF-β polypeptide sequence;

(v) the polypeptide comprises from N-terminus to C-terminus: one or more independently selected wt. or reduced affinity variant MODs; a scaffold polypeptide (without an interspecific binding sequence); a TβR polypeptide that binds to and masks a TGF-β3 polypeptide; and a TGF-β3 polypeptide sequence;

(vi) the polypeptide comprises from N-terminus to C-terminus: one or more independently selected wt. or reduced affinity variant MODs; a scaffold polypeptide (without an interspecific binding sequence); a TβRII polypeptide that binds to and masks a TGF-β3 polypeptide; and a TGF-β3 polypeptide sequence; and (vii) the polypeptide comprises from N-terminus to C-terminus: one or more independently selected wt. or reduced affinity variant IL-2 MODs; a scaffold polypeptide (without an interspecific binding sequence); a TβRII polypeptide that binds to and masks a TGF-β3 polypeptide; and a TGF-β3 polypeptide sequence.

In any instance of the masked TGF-β constructs described herein, C77 of the TGF-β polypeptide sequence may be substituted to prevent dimerization (e.g., a C77S substitution), and the TGF-β polypeptide may further comprise variations to reduce their affinity for the masking TβR polypeptide (e.g., at one, two or all three of aas 25, 92 and/or 94), along with modifications in the MODs and the TβR polypeptide sequences. Exemplary TβR polypeptide sequences that may be incorporated into masked TGF-β constructs include Δ14 or Δ25 TβRII polypeptides optionally having a D118A or D118R substitution to attenuate TβRI engagement. MODs variants are described along with their polypeptide sequences and additional modifications of TβRI, TβRII, and TβRIII are described above.

Figure 7A:
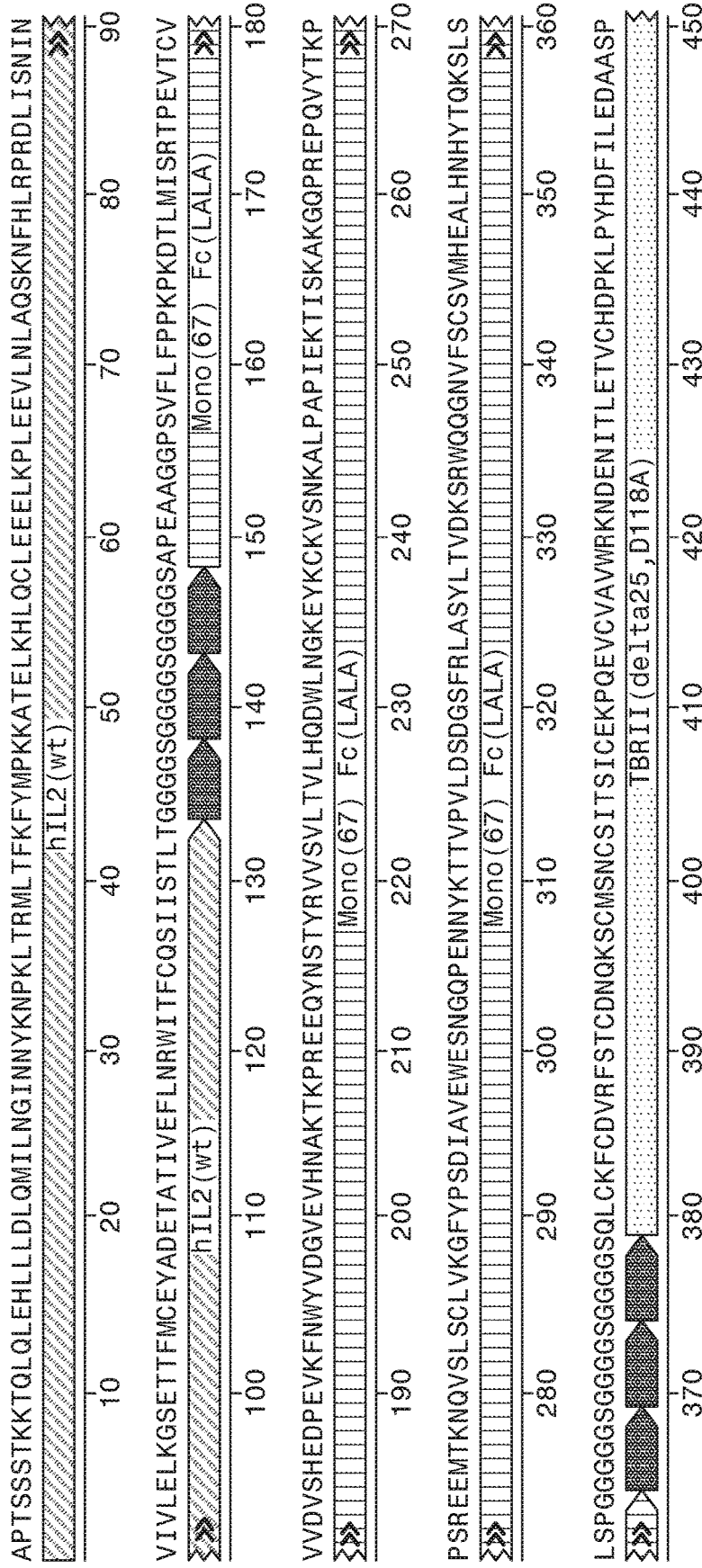
Figure 7A:
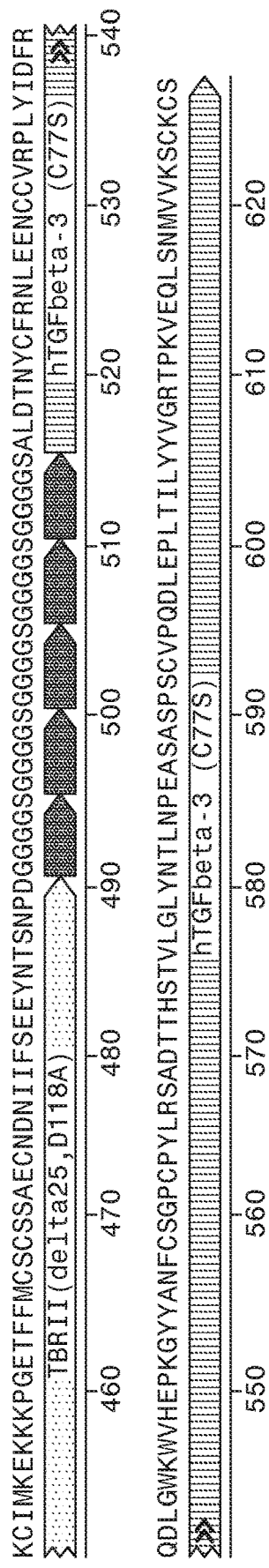
Figure 7B:
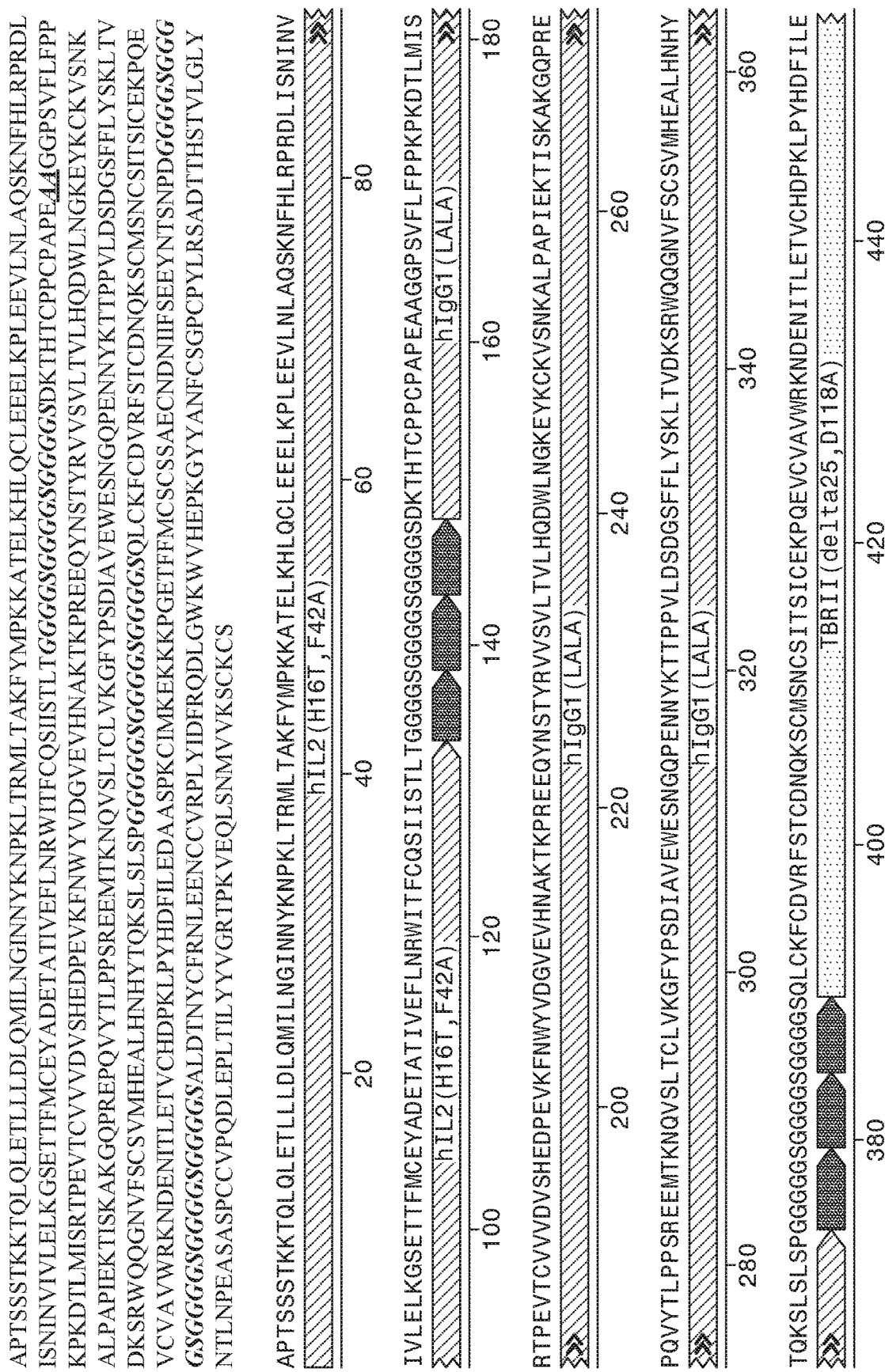
Figure 7B:
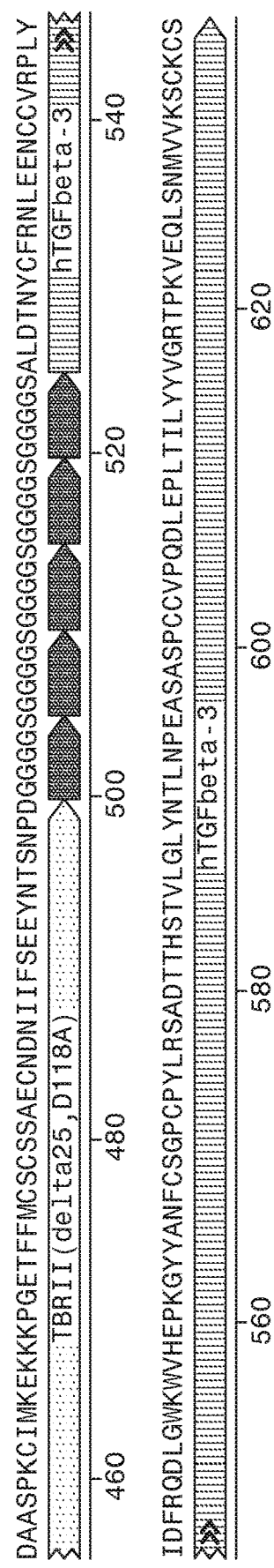

In an embodiment, a masked TGF-β construct has the sequence set forth in SEQ ID NO:146 (see FIG. 7A). In an embodiment, a masked TGF-β construct has the sequence set forth in SEQ ID NO:147 (see FIG. 7B). In an embodiment, a masked TGF-β construct has the sequence set forth in SEQ ID NO157 (see FIG. 7G). In an embodiment, a masked TGF-β construct has the sequence set forth in SEQ ID NO:158 (see FIG. 7H). In an embodiment, a masked TGF-β construct has the sequence set forth in SEQ ID NO:159 (see FIG. 7I).

2 Masked TGF-β Complexes

Masked TGF-β complexes comprise at least two polypeptides, a first and a second polypeptide, each of which contains a scaffold polypeptide that associates with another scaffold polypeptide, bringing the first and second polypeptides together into a complex. Consequently, TGF-β polypeptide complexes form homodimers, heterodimers, or higher order multimeric structures:

(i) in a first instance, the masked TGF-β complex comprises at least one TGF-β polypeptide sequence, at least one polypeptide that binds to and masks the one or more TGF-β polypeptides (e.g., a masking sequence for each TGF-β polypeptide sequence), and optionally one or more immunomodulatory polypeptides (MODs) assembled on a scaffold structure that can dimerize to form a homodimer (e.g., a symmetrical dimer) as in FIG. 1, structure B. In such homodimers, the Ig Fc polypeptides can permit the spontaneous formation of disulfide bonds between the Ig Fc polypeptides in the scaffold of each construct, and may include mutations (e.g., the LALA mutations discussed herein) that substantially reduce or eliminate the ability of the Ig polypeptide to induce cell lysis, e.g., though complement-dependent cytotoxicity (CDC) and antibody-dependent cellular cytotoxicity (ADCC).

(ii) in a second instance, a masked TGF-β complex comprises (a) a first polypeptide comprising at least one TGF-β polypeptide sequence, at least one polypeptide that binds to and masks the one or more TGF-β polypeptides (e.g., a masking sequence for each TGF-β polypeptide sequence), and optionally one or more immunomodulatory polypeptides (MODs) assembled on a scaffold structure comprising an interspecific dimerization sequence, and (b) a second polypeptide comprising at least one TGF-β polypeptide sequence, at least one polypeptide that binds to and masks the at least one TGF-β polypeptide, and optionally one or more immunomodulatory polypeptides (MODs) assembled on a scaffold structure comprising a counterpart to the interspecific dimerization sequence of the first polypeptide;

where the first and second polypeptides form a heterodimer through interaction of the interspecific dimerization sequences as in FIG. 1, structure C.

(iii) in a third instance, a masked TGF-β complex comprises (a) a first polypeptide comprising at least one TGF-β polypeptide sequence, at least one polypeptide that binds to and masks the at least one or more TGF-β polypeptides (e.g., a masking sequence for each TGF-β polypeptide sequence), and optionally one or more immunomodulatory polypeptides (MODs) assembled on a scaffold structure comprising an interspecific dimerization sequence, and (b) a second polypeptide comprising a scaffold structure comprising a counterpart to the interspecific dimerization sequence of the first polypeptide, and optionally one or more immunomodulatory polypeptides (MODs);

where the first and second polypeptides form a heterodimer through interaction of the interspecific dimerization sequences as in FIG. 1, structure F, and (iv) in a fourth instance, a masked TGF-β complex comprises (a) a first polypeptide comprising at least one TGF-β polypeptide sequence, and optionally one or more immunomodulatory polypeptides (MODs) assembled on a scaffold structure comprising an interspecific dimerization sequence, and (b) a second polypeptide comprising at least one polypeptide that binds to and masks the at least one or more TGF-β polypeptides, and optionally one or more immunomodulatory polypeptides (MODs) assembled on a scaffold structure comprising a counterpart to the interspecific dimerization sequence of the first polypeptide;

where the first and second polypeptides form a heterodimer through interaction of the interspecific dimerization sequences as in FIG. 1, structures D and E.

In some instances, the masked TGF-β complexes (FIG. 1, structures B, C and F), the sequence comprising the TGF-β polypeptide (the first polypeptide) may comprise, from N-terminus to C-terminus: optionally one or more MODs; a scaffold polypeptide (with or without an interspecific binding sequence); a polypeptide that binds to and masks the TGF-β polypeptide; and a TGF-β polypeptide sequence. The polypeptide not containing a TGF-β sequence in FIG. 1, structure F, (the second polypeptide) comprises a scaffold polypeptide with an interspecific binding sequence and optionally comprises a MOD on the N-terminus, C-terminus, or both the N- and C-termini.

In some instances, the masked TGF-β complexes in FIG. 1, structures D and E, the TGF-β polypeptide sequence-containing polypeptide (the first polypeptide) may comprise, from N-terminus to C-terminus: one or more optional MODs; a scaffold polypeptide (with interspecific binding sequence); and a TGF-β polypeptide sequence. The polypeptide not containing a TGF-β sequence in FIG. 1, structures D and E, (the second polypeptide) may comprise, from N-terminus to C-terminus: optionally one or more MODs, a scaffold polypeptide with an interspecific binding sequence, and a polypeptide that binds to and masks the TGF-β polypeptide. Although not illustrated in FIG. 1, the first polypeptide comprising the TGF-β polypeptide sequence may not comprise one or more MODs and the second polypeptide comprising the masking sequence may comprise one or more MODs.

The above-described instances of masked TGF-β complexes include those where the first polypeptide comprises, from N-terminus to C-terminus:

(i) optionally one or more MODs; a scaffold polypeptide (with an interspecific binding sequence); and a TGF-β polypeptide sequence;

(ii) optionally one or more independently selected wt. or reduced affinity variant MODs; a scaffold polypeptide (with an interspecific binding sequence); and a TGF-β polypeptide sequence;

(iii) one or more independently selected wt. or reduced affinity variant MODs; a scaffold polypeptide (with an interspecific binding sequence); and a TGF-β1 or 2 polypeptide sequence;

(iv) one or more independently selected wt. or reduced affinity variant IL-2 MODs; a scaffold polypeptide (without an interspecific binding sequence); and a TGF-β polypeptide sequence;

(v) one or more independently selected wt. or reduced affinity variant MODs; a scaffold polypeptide (with an interspecific binding sequence); and a TGF-β3 polypeptide sequence;

(vi) one or more independently selected wt. or reduced affinity variant MODs; a scaffold polypeptide (with an interspecific binding sequence); and a TGF-β3 polypeptide sequence; or (vii) one or more independently selected wt. or reduced affinity variant IL-2 MODs; a scaffold polypeptide (with an interspecific binding sequence); and a TGF-β3 polypeptide sequence. In each instance, the second polypeptide comprises from N-terminus to C-terminus a scaffold polypeptide comprising the counterpart to the interspecific binding (dimerization sequence) of the first polypeptide followed by a TβR (e.g., a TβRII) polypeptide that binds to and masks the TGF-β polypeptide of the first polypeptide. In the case of a masked TGF-β complex as in FIG. 1, structure F, a TβR (e.g., a TβRII) polypeptide may be interposed between the N-terminal MOD (if present) and the scaffold of the first polypeptide and the second polypeptide comprises the counterpart to the interspecific binding (dimerization sequence) of the first polypeptide to which one or more independently selected wt. or reduced affinity variant MODs (e.g., wt. or variant IL-2 MODs) may be attached at the N- or C-termini.

In any instance of the masked TGF-β complexes described herein, C77 of the TGF-β polypeptide sequence may be substituted to prevent dimerization (e.g., a C77S substitution), and the TGF-β polypeptide may further comprise variations to reduce their affinity for the masking TβR polypeptide (e.g., at one, two or all three of aas 25, 92 and/or 94), along with modifications in the MODs and the TβR polypeptide sequences. Exemplary TβR polypeptide sequences that may be incorporated into masked TGF-β constructs include Δ14 or Δ25 TβRII polypeptides optionally having a D118A substitution. MODs variants are described along with their polypeptide sequences and additional modifications of TβRI, TβRII, and TβRIII are described above.

Figure 7C:
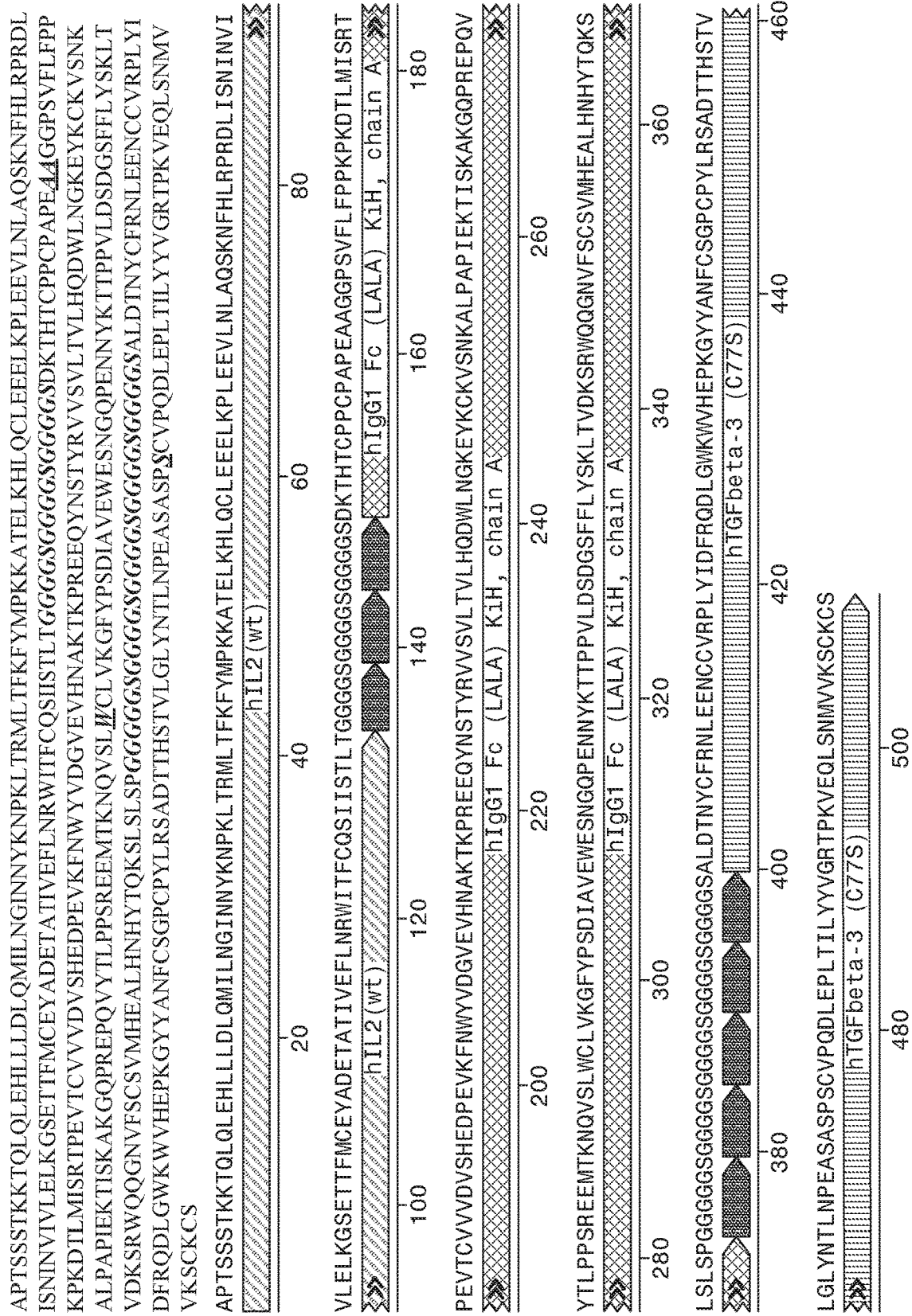
Figure 7C:
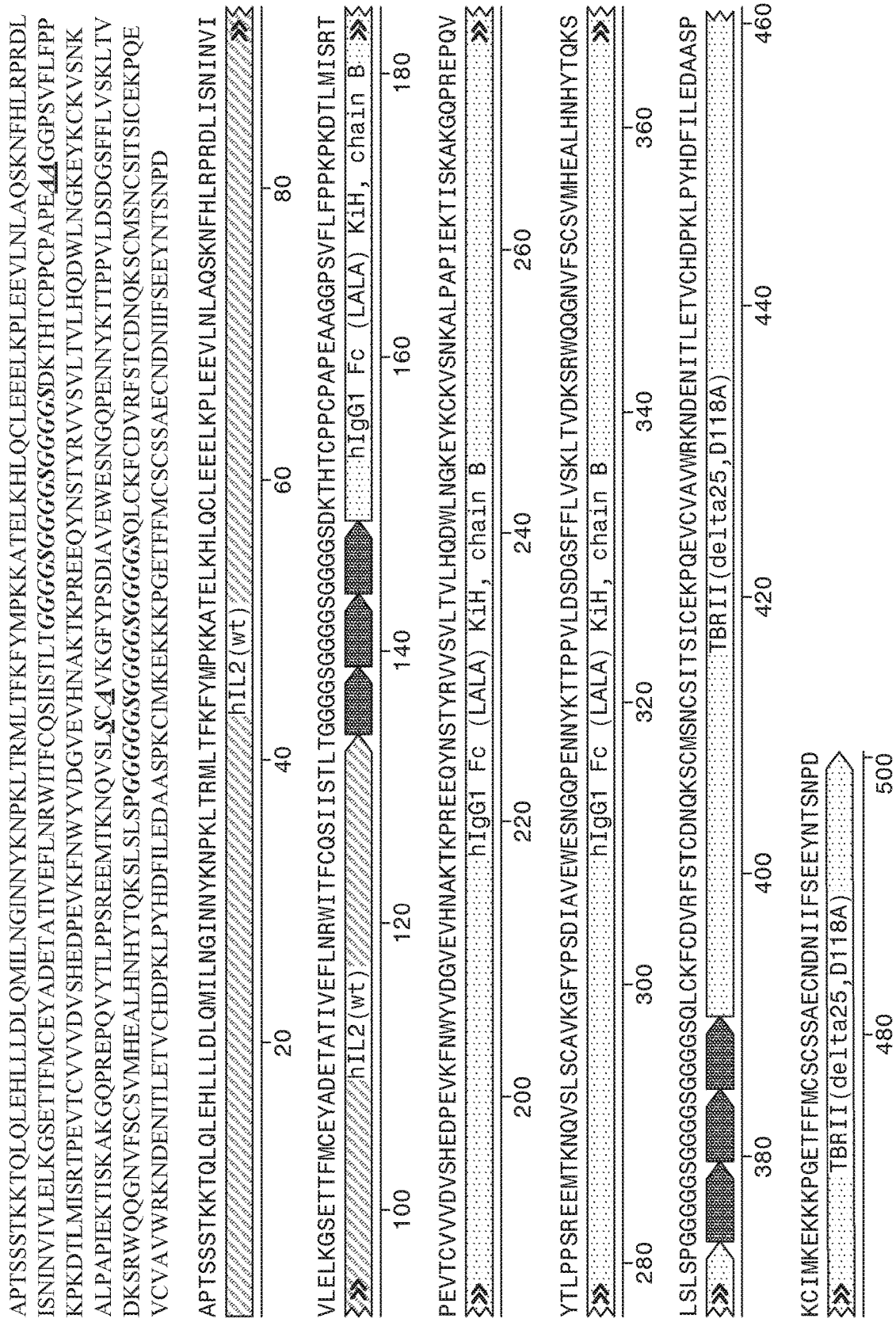
Figure 7D:
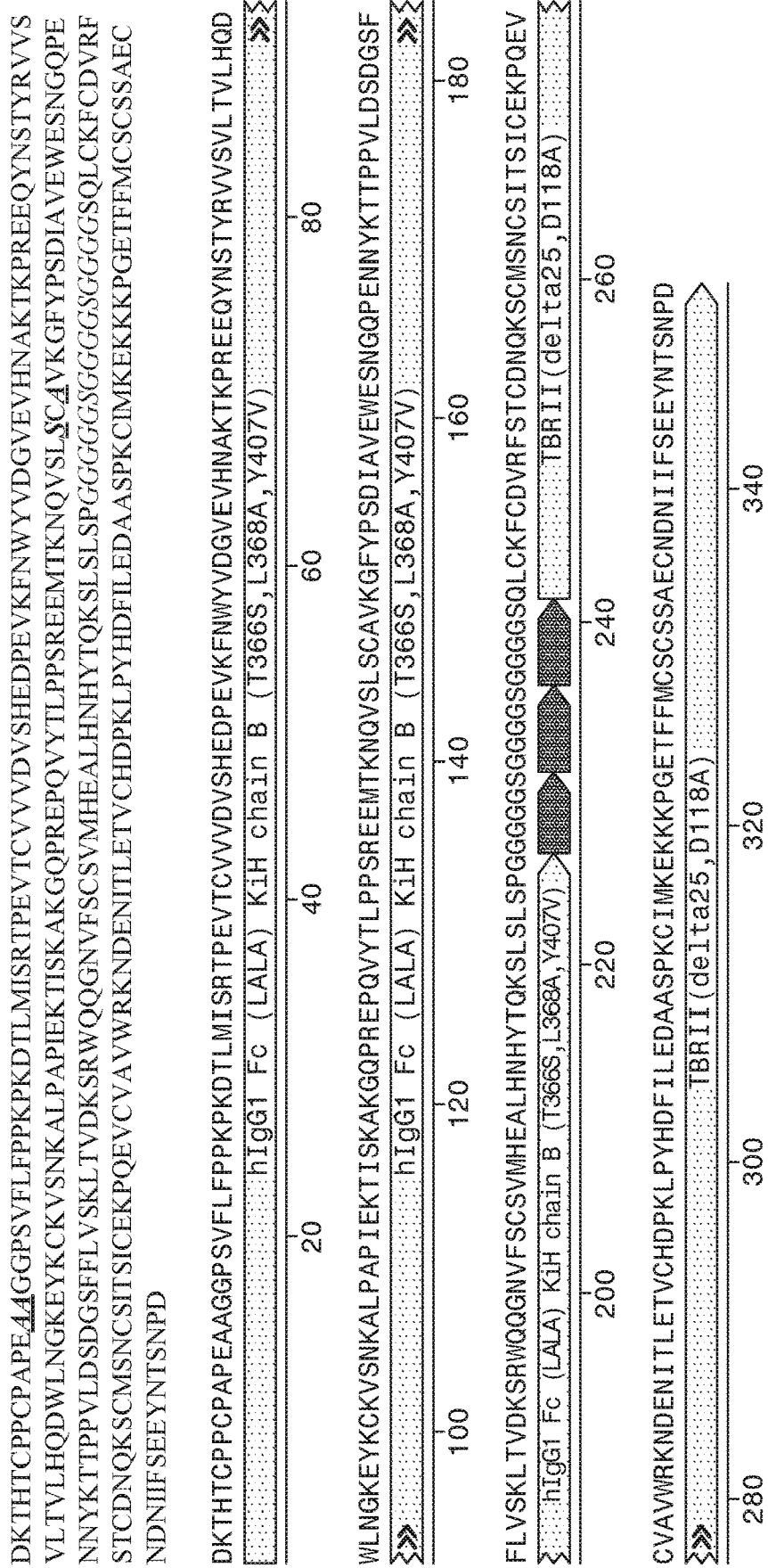
Figure 7F:
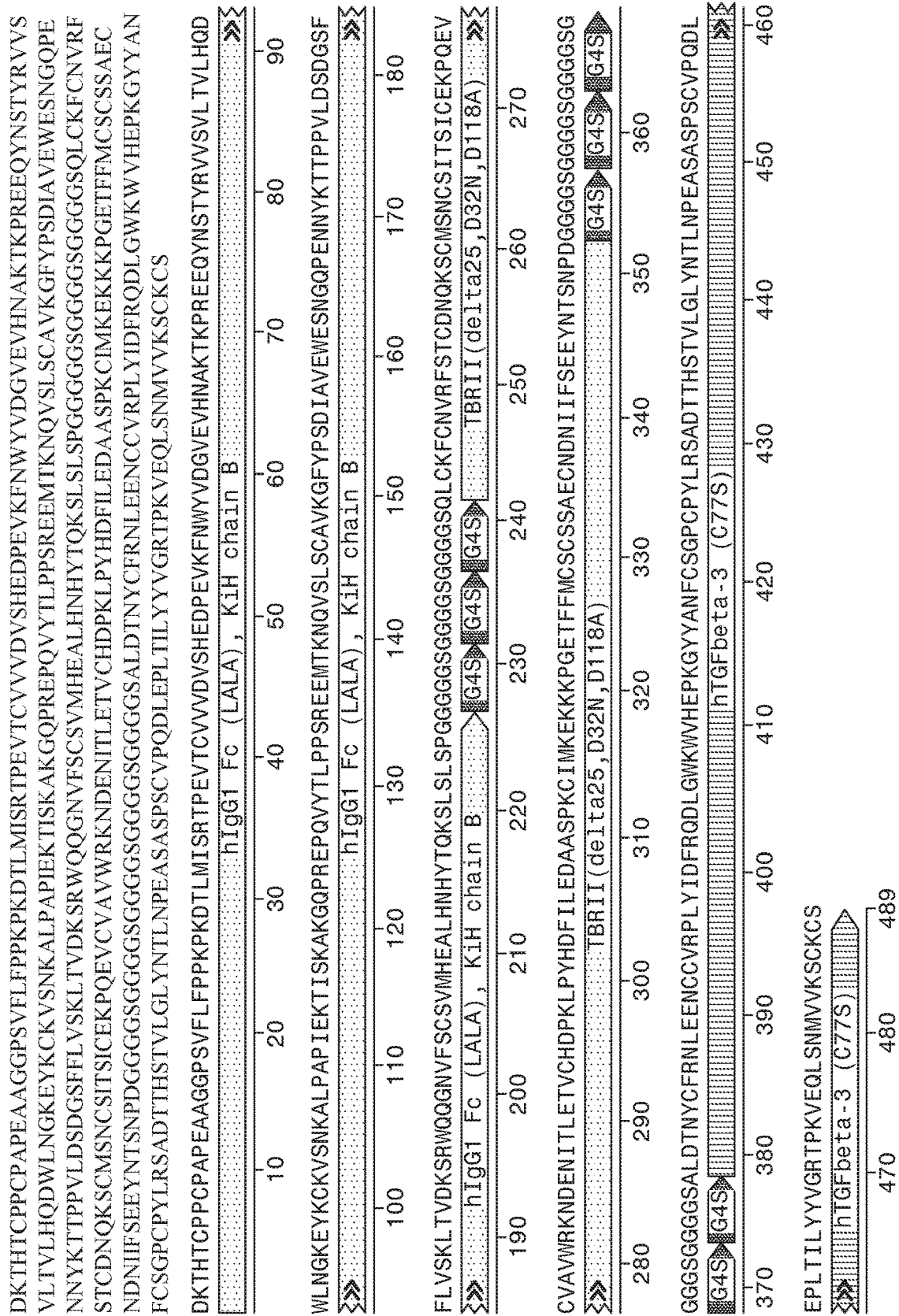

In an embodiment, a masked TGF-β complex comprise polypeptides having the sequences set forth in SEQ ID NOs:148 and 149 (see FIG. 7C). In an embodiment, a masked TGF-β complex comprise polypeptides having the sequences set forth in SEQ ID NOs:150 and 151 (see FIG. 7D). In an embodiment, a masked TGF-β complex comprise polypeptides having the sequences set forth in SEQ ID NOs:152 and 153 (see FIG. 7E). In an embodiment, a masked TGF-β complex comprise polypeptides having the sequences set forth in SEQ ID NOs:155 and 156 (see FIG. 7F). In an embodiment, a masked TGF-β complex comprise polypeptides having the sequences set forth in SEQ ID NOs:148 and 160 (see FIG. 7J).

J. Nucleic Acids

The present disclosure provides a nucleic acid comprising a nucleotide sequence encoding masked TGF-β constructs and complexes. In some cases, the nucleic acid is a recombinant expression vector; thus, the present disclosure provides a recombinant expression vector comprising a nucleotide sequence encoding a masked TGF-β construct or complex. In some cases, the nucleic acid is a recombinant expression vector; thus, the present disclosure provides a recombinant expression vector comprising a nucleotide sequence encoding masked TGF-β constructs and complexes. The discussion, of nucleic acids that follows refers to nucleic acids encoding masked TGF-β constructs and complexes of the present disclosure.

Nucleic Acids Encoding Single-Chain Antigen-Presenting Polypeptides

As described above, a masked TGF-β construct comprises a single polypeptide chain. Thus, the present disclosure provides a nucleic acid comprising a nucleotide sequence encoding a single-chain masked TGF-β construct. A nucleic acid comprising a nucleotide sequence encoding a single-chain masked TGF-β construct can be operably linked to a transcription control element(s), e.g., a promoter.

Nucleic Acid(s) Encoding Masked TGF-β Complexes

As noted above, in some cases, a masked TGF-β complex comprises at least two separate polypeptide chains (a first polypeptide chain and a second polypeptide chain). The present disclosure provides nucleic acids comprising nucleotide sequences encoding a masked TGF-β complex. In some cases, the individual polypeptide chains of a masked TGF-β complex are encoded in separate nucleic acids. In some cases, all polypeptide chains of a masked TGF-β construct or complex are encoded in a single nucleic acid. In some cases, a first nucleic acid comprises a nucleotide sequence encoding the first polypeptide of a masked TGF-β complex; and a second nucleic acid comprises a nucleotide sequence encoding the second polypeptide of a masked TGF-β complex. In some cases, single nucleic acid comprises a nucleotide sequence encoding the first and the second polypeptide of a masked TGF-β complex, which may be operably linked and under the transcriptional control of a single promoter or two independently selected promoters.

Separate Nucleic Acids Encoding Individual Polypeptide Chains of a Masked TGF-β Construct or Complex As noted above, in some cases, the individual polypeptide chains of a masked TGF-β complex are encoded by separate nucleic acids. In some cases, nucleotide sequences encoding the separate polypeptide chains of a masked TGF-β complex are operably linked to transcriptional control elements, e.g., promoters, such as promoters that are functional in a eukaryotic cell, where the promoter can be a constitutive promoter or an inducible promoter.

For example, the present disclosure provides a first nucleic acid and a second nucleic acid, where the first nucleic acid comprises a nucleotide sequence encoding the first polypeptide of a masked TGF-β complex, and where the second nucleic acid comprises a nucleotide sequence encoding the second polypeptide of the masked TGF-β complex. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

Nucleic Acid Encoding Two or More Polypeptides Present in a Masked TGF-β Complex The present disclosure provides a nucleic acid comprising nucleotide sequences encoding at least the first polypeptide and the second polypeptide of a masked TGF-β complex. In some cases, where a masked TGF-β complex includes a first, second, and third polypeptide, the nucleic acid includes a nucleotide sequence encoding the first, second, and third polypeptides. In some cases, the nucleotide sequences encoding the first polypeptide and the second polypeptide of a masked TGF-β complex encode a proteolytically cleavable site or linker interposed between the encoded first polypeptide and second polypeptide. In some cases, the nucleotide sequences encoding the first polypeptide and the second polypeptide of a masked TGF-β complex includes a nucleotide encoding an internal ribosome entry site (IRES) interposed between the encoded the first polypeptide and second polypeptides. In some cases, the nucleotide sequences encoding the first polypeptide and the second polypeptide of a masked TGF-β complex includes a sequence encoding a ribosome skipping signal (or cis-acting hydrolase element, CHYSEL) interposed between the nucleotide sequence encoding the first polypeptide and the nucleotide sequence encoding the second polypeptide.

In some cases, the first nucleic acid (e.g., a recombinant expression vector, an mRNA, a viral RNA, etc.) comprises a nucleotide sequence encoding a first polypeptide chain of a masked TGF-β complex; and a second nucleic acid (e.g., a recombinant expression vector, an mRNA, a viral RNA, etc.) comprises a nucleotide sequence encoding a second polypeptide chain of a masked TGF-β complex. In some cases, the nucleotide sequence encoding the first polypeptide, and the second nucleotide sequence encoding the second polypeptide, are each operably linked to independently selected transcriptional control elements, e.g., promoters, such as promoters that are functional in a eukaryotic cell, where the promoter can be a constitutive promoter or an inducible promoter.

Recombinant Expression Vectors

The present disclosure provides recombinant expression vectors comprising nucleic acids. In some cases, the recombinant expression vector is a non-viral vector. In some cases, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, a non-integrating viral vector, etc.

Suitable expression vectors include, but are not limited to, viral vectors (e.g. viral vectors based on vaccinia virus; poliovirus; adenovirus (see, e.g., Li et al., *Invest Opthalmol Vis Sci,* 35:2543 2549, 1994; Borras et al., *Gene Ther,* 6:515 524, 1999; Li and Davidson, *PNAS,* 92:7700 7704, 1995; Sakamoto et al., H *Gene Ther,* 5:1088 1097, 1999; WO 94/12649, WO 93/03769; WO 93/19191; WO 94/28938; WO 95/11984 and WO 95/00655); adeno-associated virus (see, e.g., Ali et al., *Hum Gene Ther,* 9:81 86, 1998, Flannery et al., *PNAS,* 94:6916 6921, 1997; Bennett et al., *Invest Opthalmol Vis Sci,* 38:2857 2863, 1997; Jomary et al., *Gene Ther,* 4:683 690, 1997, Rolling et al., *Hum Gene Ther,* 10:641 648, 1999; Ali et al., *Hum Mol Genet,* 5:591 594, 1996; Srivastava in WO 93/09239, Samulski et al., *J. Vir.* (1989) 63:3822-3828; Mendelson et al., *Virol.* (1988) 166: 154-165; and Flotte et al., *PNAS* (1993) 90:10613-10617); SV40; herpes simplex virus; human immunodeficiency virus (see, e.g., Miyoshi et al., *PNAS,* 94:10319 23, 1997; Takahashi et al., *J Virol,* 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Numerous suitable expression vectors are known to those of skill in the art, and many are commercially available.

Depending on the host/vector system utilized, any of a number of suitable transcription and translation control elements, including constitutive and inducible promoters, transcription enhancer elements, transcription terminators, etc. may be used in the expression vector (see, e.g., Bitter et al; (1987) *Methods in Enzymology,* 153:516-544).

In some cases, a nucleotide sequence encoding the polypeptides of masked TGF-β constructs and complexes are operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some cases, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

Preparation of Genetically Modified Host Cells Expressing Masked TGF-β Constructs and Complexes and Purification of Masked TGF-β Constructs and Complexes The present disclosure provides a genetically modified host cell, where the host cell is genetically modified with one or more nucleic acid(s) encoding a masked TGF-β construct or complex.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Genetically modified host cells can be used to produce a masked TGF-β construct or complex. For example, a genetically modified host cell can be used to produce a masked TGF-β complex, or a single-chain masked TGF-β construct by introducing expression vector(s), such as those described above, comprising nucleotide sequences encoding the polypeptide(s) into a host cell, generating thereby producing a genetically modified host cell. The host cell may constitutively express the masked TGF-β construct or complex, or express it in response to exposure to an inducer where the promoters driving expression are inducible (e.g., a CMV promoter and a tetracycline resistance operon induced by exposure to tetracycline).

The masked TGF-β construct or complex is obtained from the cells, or if the polypeptide(s) are targeted to the secretory pathway by incorporation of signal sequences, from the cell culture media. The protein may be purified by any means known in the art including, for example, one or more of precipitation (e.g., ammonium sulfate or ethanol), isoelectric focusing, and one or more types of chromatography. Suitable chromatographic methods include, but are not limited to, size-based chromatographic separation (e.g., size exclusion or gel permeation), hydrophobic interaction chromatography, ion-exchange chromatography, and affinity chromatography. Where the masked TGF-β construct or complex comprises an immunoglobulin polypeptide sequence (e.g., as a scaffold) the protein A or protein G may be used to affinity purify the masked TGF-β construct or complex. In the absence of an immunoglobulin polypeptide, the complex may be affinity purified using an antibody directed a polypeptide present in the masked TGF-β construct or complex; or alternatively, by incorporation of an affinity tag such as a myc epitope (CEQKLISEEDL SEQ ID NO:154), “HIS” tag (for divalent metal ion resin binding), or a “FLAG” tag. A purification and/or concentration step that may be combined with any of the foregoing methods employs size limited semipermeable membrane (e.g., a dialysis membrane or pressure cell), which may be used to remove contaminants having a substantially different molecular weight and/or to concentrate the purified protein.

In an embodiment, a masked TGF-β construct or complex is expressed from a nucleic acid sequence introduced into a mammalian cell (e.g., a CHO cell) and targeted to the secretory pathway such that it is excreted from the cell into its culture media (e.g., a serum free media). The masked TGF-β construct or complex is purified from the cell culture media using affinity chromatography alone or in combination with sized-based separation (e.g., size-based chromatographic or membrane separation). In a specific example of such an embodiment, the masked TGF-β construct or complex comprises an immunoglobulin scaffold (e.g., an IgG polypeptide sequence), and purification is accomplished by affinity chromatography (e.g., protein A or G) alone or in combination with sized based separation (size-based chromatography).

K. Compositions

The present disclosure provides compositions, including pharmaceutical compositions, comprising a masked TGF-β construct or complex. The present disclosure also provides compositions, including pharmaceutical compositions, comprising a nucleic acid or a recombinant expression vector.

1 Compositions Comprising a Masked TGF-β Construct or Complex

A composition of the present disclosure can comprise, in addition to a masked TGF-β construct or complex, one or more of: a salt, e.g., NaCl, $MgCl_2$, KCl, $MgSO_4$, etc.; a buffering agent, e.g., a Tris buffer, N-(2-hydroxyethyl)piperazine-N'-(2-ethanesulfonic acid) (HEPES), 2-(N-morpholino) ethanesulfonic acid (MES), 2-(N-Morpholino)ethanesulfonic acid sodium salt (MES), 3-(N-morpholino) propanesulfonic acid (MOPS), N-tris[hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have ‘been amply described in a variety of publications, including, for example, “Remington: The Science and Practice of Pharmacy”, $19^{th}$ Ed. (1995), or latest edition, Mack Publishing Co; A. Gennaro (2000) “Remington: The Science and Practice of Pharmacy”, 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise: i) a masked TGF-β construct or complex; and ii) a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is substantially free of detectable pyrogens and/or other toxins, or where such detectable pyrogens and/or other toxins are present at a level within acceptable limits set by an applicable regulatory agency, e.g., the USF&DA.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a masked TGF-β construct or complex is utilized (e.g., introduced into a cell culture system) or administered (e.g., subcutaneously, intraperitoneally, intramuscularly, intralymphatically, and/or intravenously) as an injectable directly into a tissue, a formulation can be provided as a ready-to-use dosage form, or as non-aqueous form (e.g. a storage-stable powder that can be reconstituted) or aqueous form, such as liquid composed of pharmaceutically acceptable carriers and excipients. The protein-containing formulations may also be provided in a form that enhances serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 Ann. Rev. Biophys. Bioeng. 9:467, U.S. Pat. Nos. 4,235,871, 4,501,728 and 4,837,028. The preparations may also be provided in controlled release or slow-release forms.

In some cases, a composition comprises: a) a masked TGF-β construct or complex; and b) saline (e.g., 0.9% NaCl). In some cases, the composition is sterile. In some cases, the composition is suitable for administration to a human subject, e.g., where the composition is sterile and is substantially free of detectable pyrogens and/or other toxins, or where such detectable pyrogens and/or other toxins are present in an amount within acceptable limits. Thus, the present disclosure provides a composition comprising: a) a masked TGF-β construct or complex; and b) saline (e.g., 0.9% NaCl), where the composition is sterile and is substantially free of detectable pyrogens and/or other toxins, or where such detectable pyrogens and/or other toxins are present in an amount within acceptable limits.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a masked TGF-β construct or complex in a formulation can vary widely such as from less than about 0.1% (usually at or at least about 2%) to as much as 20% to 50% or more by weight (e.g., from 0.1% to 1%, 1% to 5%, 5% to 10%, 10% to 20%, or 20% to 50% by weight) and will usually be selected primarily based on fluid volumes, viscosities, and patient-based factors in accordance with the particular mode of administration selected and the patient's needs.

The present disclosure provides a container comprising a composition, e.g., a liquid composition. The container can be, e.g., a syringe, an ampoule, and the like. In some cases, the container is sterile. In some cases, both the container and the composition are sterile.

2 Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

A composition of the present disclosure can include: a) one or more nucleic acids or one or more recombinant expression vectors comprising nucleotide sequences encoding a masked TGF-β construct or complex; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glycylglycine, N-2-hydroxyethylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethane-sulfonic acid (TES), N-tris(hydroxymethyl)methyl-glycine (Tricine), tris(hydroxymethyl)-aminomethane (Tris), etc.). Suitable salts include, e.g., NaCl, MgCl2, KCl, MgSO4, etc.

A pharmaceutical formulation can include a nucleic acid or recombinant expression vector in an amount of from about 0.001% to about 99% (w/w) (e.g., 0.001-0.1, 0.1-1.0, 1.0-10, 10-20, 20-40, 40-80, or 80-100 percent w/w). In the description of formulations, below, "subject nucleic acid or recombinant expression vector" will be understood to include a nucleic acid or recombinant expression vector. For example, in some cases, a subject formulation comprises a nucleic acid or recombinant expression vector.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanolamine, N,N-dimethylacetamide, N,N-dimethylformamide, 2-pyrrolidone and derivatives thereof, tetrahydrofurfuryl alcohol, and AZONE™.

L. Formulations

Suitable formulations are described above, where the compositions are of pharmaceutically acceptable grade (e.g., the compositions include a pharmaceutically acceptable excipient(s) and active molecules). In some cases, a suitable formulation comprises: a) a masked TGF-β construct or complex; and b) a pharmaceutically acceptable excipient. In some cases, a suitable formulation comprises: a) a nucleic acid comprising a nucleotide sequence encoding a masked TGF-β construct or complex; and b) a pharmaceutically acceptable excipient; in some instances, the nucleic acid is an mRNA. In some cases, a suitable formulation comprises: a) a first nucleic acid comprising a nucleotide sequence encoding the first polypeptide of a masked TGF-β construct or complex; b) a second nucleic acid comprising a nucleotide sequence encoding the second polypeptide of a masked TGF-β construct or complex; and c) a pharmaceutically acceptable excipient. In some cases, a suitable formulation comprises: a) a recombinant expression vector comprising a nucleotide sequence encoding a masked TGF-β construct or complex; and b) a pharmaceutically acceptable excipient. In some cases, a suitable formulation comprises: a) a first recombinant expression vector comprising a nucleotide sequence encoding the first polypeptide of a masked TGF-β construct or complex; b) a second recombinant expression vector comprising a nucleotide sequence encoding the second polypeptide of a masked TGF-β construct or complex; and c) a pharmaceutically acceptable excipient.

Suitable pharmaceutically acceptable excipients are described above.

M. Methods

A masked TGF-β construct or complex is useful for modulating an activity of a T cell. Thus, the present disclosure provides methods of modulating an activity of a T cell, the methods generally involving contacting a target T cell with a masked TGF-β construct or complex.

1 Methods of Modulating Immune Cell Activity Including Generating, Stimulating or Inhibiting Specific Immune Cell Types.

The present disclosure provides a method of selectively modulating the activity of cells that express TβRI and TβRII, the method comprising contacting the cell (e.g., T cells, B cells, and innate cells, including natural killer (NK) cells, macrophages, dendritic cells, and granulocytes) with a masked TGF-β construct or complex, where contacting the T cell with a masked TGF-β construct or complex selectively modulates the activity of the epitope-specific T cell. In some cases, the contacting occurs in vitro. In some cases, the contacting occurs in vivo. Wherein the activity of the cells (e.g., signaling through canonical pathway, non-canonical pathways, and/or downstream gene expression) subject to a masked TGF-β construct or complex may be assessed relative to treatment groups (e.g., cells subjects) that have not been exposed to TGF-β or a masked TGF-β construct or complex.

The present disclosure provides a method of reducing the number and/or activity of T cells or B cells (e.g., pathogenic autoreactive T cells and/or pathogenic autoreactive B cells); the method comprising administering (e.g., to a subject in need thereof) one or more masked TGF-β constructs or complexes. In some cases, the method increases the number and/or activity of a regulatory T cell (Treg), resulting in reduced number and/or activity of T cells or B cells (e.g., one or more autoreactive T cells and/or one or more autoreactive B cells), wherein the reduction in the number and/or activity of T cells or B cells subjected to one or more masked TGF-β constructs or complexes is assessed relative to treatment groups (e.g., cells subjects) that have not been exposed to TGF-β or one or more masked TGF-β constructs or complexes.

Administration of one or more masked TGF-β constructs or complexes, optionally comprising one or more (e.g., one, two or more or three or more) independently selected wildtype or variant MODs may directly or indirectly effect various cell populations. By way of example, administration of masked TGF-β constructs or complexes, optionally comprising one or more wild type or variant IL-2 MODs may directly stimulate the development and/or survival of FoxP3+ Treg cells (in vivo or in vitro). In addition to any direct action that a TGF-β/IL-2 complex has on various immune cells, the resultant Treg cells can suppress immune responses by, for example, blocking induction of T cell activation and/or the effector phase of T cell responses, suppressing B cell activation, and/or inhibiting the differentiation and/or proliferation of natural killer cells.

a. Tregs (i) tTregs, pTregs, iTregs and TGF-β Constructs or Complexes Comprising IL-2

The present disclosure provides a method of promoting the development (e.g. expansion) and/or survival of thymus-derived Treg (tTreg) and/or peripheral Treg (pTreg) (Tregs are $CD4^+$, $FoxP3^+$, and $CD25^+$ cells that can suppress autoreactive T cells and B cells); the method comprising administering (e.g., to one or more subjects in need thereof), or contacting CD4+ T cells (e.g., naïve CD4+ T cells) with, one or more masked TGF-β constructs or complexes; (e.g., in tissue culture, blood, or in a specific tissue location such as a wound). The one or more masked TGF-β constructs or complexes administered or contacted in the method may comprise one or more (e.g., one, two or three) independently selected IL-2 MOD polypeptide sequences and/or variant IL-2 MOD polypeptide sequences. Administration or contacting may be conducted in conjunction with the administration or contacting of the cells with vitamin D (e.g., Vitamin D3 or an analog thereof), retinoic acid (e.g., all trans retinoic acid), and/or an inhibitor of the mammalian target of rapamycin (mTOR) (e.g., rapamycin or a functional analog thereof such as sirolimus, everolimus or temsirolimus). Accordingly, the present disclosure provides a method of promoting the development and/or survival of induced regulatory T cells (iTregs), which are FoxpP3+, FoxP3+ thymus derived Treg (tTreg) and/or FoxP3+ peripheral Treg (pTreg), the method comprising administering (e.g., to a subject in need thereof), or contacting CD4+ T cells (e.g., naïve CD4+ T cells) with, one or more masked TGF-β constructs or complexes that comprises one or more IL-2 MOD polypeptide sequences and/or variant IL-2 MOD polypeptide sequences, optionally in the presence of vitamin D or an analog thereof, retinoic acid (e.g., all trans retinoic acid) or an analog thereof, and/or rapamycin or an analog thereof. The effects of administration or treatment with one or more masked TGF-β constructs or complexes may be assessed relative the baseline value (e.g., number of cells prior to treatment) or relative to a treatment group (e.g., cells or subjects) that are matched with a test group (e.g., otherwise identical to), but that have not been exposed to TGF-β or one or more masked TGF-β constructs or complexes.

The present disclosure provides a method of increasing the induction/proliferation of Tregs, maintaining Tregs and/or sustaining their function, the method comprising contacting T cells (e.g., CD4+ T cell in vivo or in vitro) with one or more masked TGF-β constructs or complexes comprising one or more (e.g., one, two or three) independently selected IL-2 MOD polypeptide sequences and/or variant IL-2 MOD polypeptide sequences. The contacting increases the induction/proliferation of Tregs, maintains the Tregs, and/or sustains their function either relative to a baseline value determined prior to the contacting or relative to a control group of otherwise identical cells that have not been contacted with the one or more masked TGF-β constructs or complexes. The disclosure includes and provides for masked TGF-β constructs or complexes comprising one or more (e.g., one, two or three) independently selected IL-2 MOD polypeptide sequences and/or variant IL-2 MOD polypeptide sequences for use in the method. In an embodiment, the masked TGF-β constructs or complexes comprising one or more (e.g., one, two or three) independently selected IL-2 MOD polypeptide sequences and/or variant IL-2 MOD polypeptide sequences has the structural organization described in FIG. 1 structures A, B or C. In an embodiment, the masked TGF-β constructs or complexes comprising one or more (e.g., one, two or three) independently selected IL-2 MOD polypeptide sequences and/or variant IL-2 MOD polypeptide sequences has the structural organization described in FIG. 1 structures D or E. In an embodiment, the masked TGF-β constructs or complexes comprising one or more (e.g., one, two or three) independently selected IL-2 MOD polypeptide sequences and/or variant IL-2 MOD polypeptide sequences has the structural organization described in FIG. 1 structure F.

The present disclosure provides a method of increasing the induction/proliferation of Tregs, maintaining Tregs and/or sustaining their function, the method comprising contacting T cells (e.g., CD4+ T cell in vivo or in vitro) with one or more masked TGF-β constructs or complexes comprising one or more (e.g., one, two or three) independently selected PD-L1 or PD-L2 MOD polypeptide sequences and/or variant PD-L1 or PD-L2 MOD polypeptide sequences. The contacting increases the induction/proliferation of Tregs, maintains the Tregs, and/or sustains their function either relative to a baseline value determined prior to the contacting or relative to a control group of otherwise identical cells that have not been contacted with the one or more masked TGF-β constructs or complexes. The disclosure includes and provides for masked TGF-β constructs or complexes comprising one or more (e.g., one, two or three) independently selected PD-L1 or PD-L2 MOD polypeptide sequences and/or variant PD-L1 or PD-L2 MOD polypeptide sequences for use in the method. In an embodiment, the masked TGF-β constructs or complexes comprising one or more (e.g., one, two or three) independently selected PD-L1 or PD-L2 MOD polypeptide sequences and/or variant PD-L1 or PD-L2 MOD polypeptide sequences has the structural organization described in FIG. 1 structures A, B or C. In an embodiment, the masked TGF-β constructs or complexes comprising one or more (e.g., one, two or three) independently selected PD-L1 MOD polypeptide sequences and/or variant PD-L1 or PD-L2 MOD polypeptide sequences has the structural organization described in FIG. 1 structures D or E. In an embodiment, the masked TGF-β constructs or complexes comprising one or more (e.g., one, two or three) independently selected PD-L1 or PD-L2 MOD polypeptide sequences and/or variant PD-L1 or PD-L2 MOD polypeptide sequences has the structural organization described in FIG. 1 structure F. Masked TGF-β constructs or complexes comprising one or more (e.g., one, two or three) independently selected PD-L1 or PD-L2 MOD polypeptide sequences and/or variant PD-L1 or PD-L2 MOD polypeptide sequences may be administered with IL-2 (e.g. recombinant IL-2 such as Proleukin (aldesleukin)) for the induction/proliferation of Tregs (e.g., Tbet+ FoxP3+ iTreg cells), maintaining Tregs, and/or sustaining their function.

The present disclosure provides a method for increasing the induction/proliferation of Tregs, maintaining Tregs (e.g. Treg numbers), and/or sustaining their function, the method comprising contacting T cells (e.g., CD4+ cells in vivo or in vitro) with one or more masked TGF-β constructs or complexes comprising one or more (e.g., one, two or three) independently selected IL-2 and/or variant IL-2 MOD polypeptide sequences, and one or more independently selected wt. or variant PD-L1 and/or PD-L2 MOD polypeptide sequences. The contacting increases the induction/proliferation of Tregs, maintains the Tregs, and/or sustains their function either relative to a baseline value determined prior to the contacting or relative to a control group of otherwise identical cells that have not been contacted with the one or more masked TGF-β constructs or complexes. The disclosure includes and provides for masked TGF-β constructs or complexes comprising one or more (e.g., one, two or three) independently selected IL-2 MOD and/or variant IL-2 MOD polypeptide sequences and one or more independently selected wt. or variant PD-L1 and/or PD-L2 polypeptide sequences for use in the method. In an embodiment, the masked TGF-β constructs or complexes comprising one or more (e.g., one, two or three) independently selected IL-2 MOD and/or variant IL-2 MOD polypeptide sequences and one or more independently selected wt. or variant PD-L1 and/or PD-L2 polypeptide sequences has the structural organization described in FIG. 1 structures A, B or C. In an embodiment, the masked TGF-β constructs or complexes comprising one or more (e.g., one, two or three) independently selected IL-2 MOD and/or variant IL-2 MOD polypeptide sequences and one or more independently selected wt. or variant PD-L1 and/or PD-L2 polypeptide sequences has the structural organization described in FIG. 1 structures D or E. In an embodiment, the masked TGF-β constructs or complexes comprising one or more (e.g., one, two or three) independently selected IL-2 MOD and/or variant IL-2 MOD polypeptide sequences and one or more independently selected wt. or variant PD-L1 and/or PD-L2 polypeptide sequences has the structural organization described in FIG. 1 structure F.

Contacting T cells (e.g., naïve CD4+ cells) with masked TGF-β constructs or complexes (e.g., in vivo or in vitro) comprising one or more (e.g., one, two or three) independently selected IL-2 MOD and/or variant IL-2 MOD polypeptide sequences, alone or in combination with one or more independently selected wt. or variant PD-L1 and/or PD-L2 MOD polypeptide sequences can increase the expression of FoxP3 and Treg cell induction (e.g., Tbet+ FoxP3+ iTreg cells). Similarly, contacting T cells (e.g., naïve CD4+ cells) with masked TGF-β constructs or complexes (e.g., in vitro or in vivo) comprising one or more (e.g., one, two or three) independently selected PD-L1 or PDL2 and/or variant PD-L1 or PD-L2 MOD polypeptide sequences, alone or in combination with IL-2 (e.g., recombinant human IL-2) can increase the expression of FoxP3 and Treg cell induction (e.g., Tbet+ FoxP3+ iTreg cells). Where both IL-2 and either PD-L1 or PD-L2 are provided to the cells the contacting may reduce T reg endolysosomal asparaginyl endopeptidase. Reduction in endolysosomal asparaginyl endopeptidase, which is responsible for destabilizing Foxp3 in Tregs, results in maintenance of Tregs (e.g., iTregs) and sustains their function. See, e.g., Francsisco et al., J Exp. Med., 206(13) 3015-3029 (2018) and Stathopoulou et al. Immunity 49(2): 247-263 (2018). Accordingly, where the masked TGF-β constructs or complexes comprise both IL-2 and either PD-L1 or PD-L2, contacting the T-cells may result not only in increased numbers of Treg, but also increased stability and function of those cells.

Where contacting of masked TGF-β constructs or complexes comprising IL-2 MOD (wt. and/or variant) and/or PD-L1 and/or PD-L2 (wt. and/or variant) polypeptide sequences occurs in vivo (or in vitro with the treated cells administered to patient), the contacting may constitute treatment. Such treatments result in increased Treg cell levels (e.g., total number of iTregs or their fraction in a tissue or circulating in blood) in an individual or population of individuals. The treatment may also result in elevated levels of FoxP3 in Tregs.

Where the masked TGF-β constructs or complexes comprise wt. and/or variant IL-2 MOD polypeptide sequence(s) in combination with wt. or variant PD-L1 and/or PD-L2 MOD polypeptide sequence(s) the increased Treg cell levels (e.g., total number of iTregs or their fraction in a tissue or circulating in blood) in an individual or population of individuals persists for a longer period of time than is observed when treating an individual or population of individuals (e.g., matched for age, gender, weight, and/or disease status) with an otherwise identical masked TGF-β construct or complex lacking the PD-L1 sequence(s). Treatment with masked TGF-β constructs or complexes comprising wt. and/or variant IL-2 MOD polypeptide sequences in combination with wt. or variant PD-L1 and/or PD-L2 MOD polypeptide sequences may also result in persistently elevated levels of FoxP3 in Tregs relative to the levels observed when the treatment is conducted with an otherwise identical masked TGF-β construct or complex that lacks PD-L1 polypeptide sequences. Treatment with masked TGF-β constructs or complexes comprising wt. and/or variant IL-2 MOD polypeptide sequences in combination with wt. or variant PD-L1 and/or PD-L2 MOD polypeptide sequences may also result in reduced activity of endolysosomal asparaginyl endopeptidase in Treg cells relative to the activity of that enzyme in T-cells of an individual (or group of individuals on average) that have been treated with an otherwise identical masked TGF-β construct or complex that lacks PD-L1 MOD polypeptide sequences.

The process of contacting T-cells, with masked TGF-β constructs or complexes comprising wt. and/or variant IL-2 MOD polypeptide sequences alone or in combination with wt. or variant PD-L1 and/or PD-L2 MOD polypeptide sequences (e.g., in vitro, ex vivo or in vivo such as in a process of treating an individual), may further comprise contacting the T cells presence of vitamin D or an analog thereof, retinoic acid (e.g., all trans retinoic acid) or an analog thereof, and/or an mTOR inhibitor such as rapamycin or an analog thereof). Contacting in the presences of those agents may increase level of Tregs (e.g., number or relative number of Tregs in an individual or tissue due to proliferation or maintenance of cells with the Treg phenotype) either relative to a baseline value determined prior to the contacting or relative to a the value determine in a control group (e.g., a group of individuals) that have not been contacted with the one or more masked TGF-β constructs or complexes. Where control groups of individuals are employed the individual may be matched for one or more of age, sex, and weight. The individuals may also be matched for ethnicity, alcohol consumption, and/or smoking status.

The present disclosure provides a method of increasing the number of Tregs in one or more subjects (e.g., individuals or patients), the method comprising administering to the one or more subjects one or more masked TGF-β constructs or complexes comprising one or more (e.g., one, two or three) independently selected IL-2 MOD polypeptide sequences and/or variant IL-2 MOD polypeptide sequences and optionally comprising one or more independently selected wt. or variant PD-L1 or PD-L2 MOD polypeptide sequences, where the administering results in an increase in the number of Tregs in the one or more subjects. For example, the average number of Tregs (e.g., in blood or a tissue or a location such as a wound) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold relative to the number of Tregs in the individual prior to administration of the one or more masked TGF-β constructs or complexes or relative to a control group that did not receive the one or more masked TGF-β constructs or complexes.

The present disclosure provides a method of increasing the number of Tregs in one or more subjects (e.g., individuals or patients), the method comprising administering to the one or more subjects one or more masked TGF-β constructs or complexes comprising one or more (e.g., one, two or three) independently selected wt. or variant PD-L1 and/or PD-L2 polypeptide sequences optionally in combination with IL-2 (e.g., recombinant IL-2 such as Proleukin (aldesleukin)), where the administering results in an increase in the number of Tregs in the one or more subjects. For example, the average number of Tregs (e.g., in blood or a tissue or a location such as a wound) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold relative to the number of Tregs in the individual prior to administration of the one or more masked TGF-β constructs or complexes or relative to a control group that did not receive the one or more masked TGF-β constructs or complexes b. T Helper Cells (i) Th9 Cells and Masked TGF-β Constructs or Complexes Comprising IL-4

The present disclosure provides a method of promoting the development and/or survival of thymus-derived Th9 cells (CD4+ cells characterized by expression of CD4 and CCR6 and the lack of CCR4); the method comprising administering (e.g., to a subject in need thereof), or contacting CD4+ T cells (e.g., naïve CD4+ T cells or Th2 cells) with, one or more masked TGF-β constructs or complexes. The one or more masked TGF-β constructs or complexes administered or contacted in the method may comprise one or more (e.g., one, two or three) independently selected IL-4 MOD polypeptide sequences and/or variant IL-4 MOD polypeptide sequences. Accordingly, the present disclosure provides a method of promoting the development and/or survival of Th9 cells comprising administering (e.g., to a subject in need thereof), or contacting naïve T cells with, one or more masked TGF-β constructs or complexes that comprises one or more IL-4 MOD polypeptide sequences and/or variant IL-4 MOD polypeptide sequences, where the administering results in an increase in the number of Th9 cells in the individual. For example, the number of Th9 cells (e.g., in tissue culture, blood, or in a specific tissue location) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold.

(ii) Th17 Cells and TGF-β Constructs or Complexes Comprising IL-17

The present disclosure provides a method of stimulating the production of Th17 cells (T cells defined by their production of IL-17), the method comprising administering (e.g., to a subject in need thereof), or contacting CD4+ T cells (e.g., naïve CD4+ T cells) with one or more masked TGF-β constructs or complexes comprising at least one IL-6 or variant IL-6 MOD polypeptide (e.g., one, two or three IL-6 and/or variant IL-6 MOD polypeptides). For example, the number of Th17 cells (e.g., in tissue culture, blood, or in a specific tissue location) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold relative to either the number present prior to administration of the one or more masked TGF-β constructs or complexes, or relative to a control group that did not receive the one or more masked TGF-β constructs or complexes. The method may be useful for maintaining the gut mucosal barrier function and may be needed for protection against pathogenic bacteria (e.g., against *Citrobacter*) and for recruiting neutrophils and monocytes and neutrophils to attack and destroy extracellular fungi (e.g., mucocutaneous *Candida*).

(iii) Tfh Cells and Masked TGF-β Constructs or Complexes Comprising IL-21 and IL-23

The present disclosure provides a method of stimulating the production of T follicular helper (Tfh) cells (T cells which are defined by CXCR5 expression), the method comprising administering (e.g., to a subject in need thereof), or contacting macrophages with, one or more masked TGF-β constructs or complexes comprising at least one MOD polypeptide (e.g., one, two or three) independently selected from an IL-21 MOD polypeptide, an IL-23 MOD polypeptide, a variant of an IL-21 or a variant of an IL-23 MOD polypeptide. For example, the number of Tfh cells (e.g., in tissue culture, blood, or in a specific tissue location such as a lymphoid follicle) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold relative to either the number present prior to administration of the one or more masked TGF-β constructs or complexes, or relative to a control group that did not receive the one or more masked TGF-β constructs or complexes. The method may be useful in supporting the development of antigen-specific antibody responses.

c. T Effector Cells and Masked TGF-β Constructs or Complexes Comprising IL-7 (i) IL-7 and CD8+ T Cells The present disclosure provides a method of promoting the development (lineage commitment) and/or survival of CD4+ and/or CD8+ T-cell (e.g., by promoting thymocyte expression of the IL-7R (e.g., IL-7Rα); the method comprising administering (e.g., to a subject in need thereof), or contacting precursor CD4+CD8+ T-cells with, one or more masked TGF-β constructs or complexes. The one or more masked TGF-β constructs or complexes administered or contacted in the method may comprise one or more (e.g., one, two or three) independently selected IL-7 MOD polypeptide sequences and/or variant IL-7 MOD polypeptide sequences. Accordingly, the present disclosure provides a method of promoting the development of cells committed to CD4+ or CD8+ lineages (e.g., by promoting thymocyte expression of interleukin (IL)-7Rα), the method comprising administering (e.g., to a subject in need thereof), or contacting CD 4+ and or CD8+ cell precursors (e.g., CD4+8+ T-cells) with one or more masked TGF-β constructs or complexes comprising one or more (e.g., one, two or three) independently selected IL-7 MOD polypeptide sequences and/or variant IL-7 MOD polypeptide sequences; wherein the development and/or survival of CD4+ and/or CD8+ cells is assessed by monitor peripheral blood or specific tissue (e.g., thymus) CD4+ and/or CD8+ cell numbers.

(i) IL-7 and Low Affinity T-Cells

The present disclosure provides a method of regulating peripheral T-cell homeostasis by promoting IL-7-dependent survival of CD4+ T cells and CD8+ T cells with T-cell receptors having low affinity for peptides being presented by MHC proteins. See e.g., *Cold Spring Harbor Perspect. Biol.* 2017; 9:a022236 and citations therein. The method may operate by controlling thymocyte IL-7Rα expression. The method promoting IL-7-dependent survival comprises administering (e.g., to a subject in need thereof) one or more masked TGF-β constructs or complexes. The one or more masked TGF-β constructs or complexes administered may comprise one or more (e.g., one, two or three) independently selected IL-7 MOD polypeptide sequences and/or variant IL-7 MOD polypeptide sequences. Accordingly, the present disclosure provides a method of regulating peripheral T-cell homeostasis; the method comprising administering (e.g., to a subject in need thereof) one or more masked TGF-β constructs or complexes comprising one or more (e.g., one, two or three) independently selected IL-7 MOD polypeptide sequences and/or variant IL-7 MOD polypeptide sequences, wherein administration of the TGF-β construct or complex increases the number of peripheral CD4+ T cells and CD8+ T cells in a subject, or group of subjects, relative to the number of those cells prior to administration.

d. Masked TGF-β Constructs or Complexes and IL-10

The present disclosure provides a method of inhibiting type 2 innate lymphoid cells (ILC2 cells) (e.g., to suppress asthma and allergic inflammation, see e.g., Rajas et al., *J Allergy Clin Immunol,* 139(5):1468 (2017); and Ogasawara, et al., *J Allergy Clin Immunol,* 141(3): 1147-1151 (2018)), using one or more masked TGF-β constructs or complexes comprising at least one (e.g. at least two) independently selected wild type or variant IL-10 MOD polypeptide (e.g., one, two or three independently selected MODs). Variant IL-10 MOD polypeptides may include all or part of a monomeric IL-10 polypeptide (e.g., all or part of SEQ ID NO:50 or 51 substituted with a 5-7 aa insertion in the hinge region between helices D and E mentioned above). See e.g., Josephson et al., *J. Biol. Chem.* 275:13552-13557 (2000). The method of inhibiting type II innate lymphoid cells comprising administering (e.g., to a subject in need thereof), or contacting type II innate lymphoid cells with, one or more masked TGF-β constructs or complexes optionally comprising one or more (e.g., one, two or more or three or more) independently selected wild type or variant IL-10 MODs. The inhibition of ILC2 cells is assessed by suppression of type 2 cytokine (e.g., IL-3 and/or IL-13) expression by ILC2 cells relative to either the amount if type 2 cytokines prior to administration of the one or more masked TGF-β constructs or complexes, or relative to the amount of type 2 cytokines in a control group (e.g., in cells, tissue, or bodily fluid from a subject) that have not been exposed to TGF-β or the one or more masked TGF-β constructs or complexes.

TGF-β and IL-10 have nonredundant roles in maintaining gastrointestinal homeostasis, with IL-10 functioning both upstream and downstream of TGF-β. For example, IL-10 can induce TGF-β expression and secretion by lamina propria T cells and it acts cooperatively with TGF-b to promote differentiation of Treg cells. Accordingly, the present disclosure provides methods of maintaining intestinal homeostasis and differentiation of Treg cells in a subject comprising administering one or more masked TGF-β constructs or complexes comprising a wt. or variant IL-10 sequence or both an IL-2 and IL-10 aa sequence, either or both of which may be an independently selected wt. or a variant sequence. See e.g., *Cold Spring Harbor Perspect. Biol.* 2017; 9:a022236 and citations therein.

In some case, such as where it is desirable to induce tolerance, at least one MOD polypeptide (e.g., one, two or three independently selected MODs) present in one or more masked TGF-β constructs or complexes comprising at least one (e.g. at least two) independently selected wild type or variant IL-10 MOD polypeptides. See e.g., *Am J Physiol Gastrointest Liver Physiol* 306: G575-G581 (2014), and Levings et al. *Int Arch Allergy Immunol.* 129(4):263-76 (2002). The variant IL-10 MOD polypeptides may include all or part of a monomeric IL-10 polypeptide (e.g., all or part of SEQ ID NO:50 or 51 substituted with a 5-7 aa insertion in the hinge region between helices D and E to form an active monomeric IL-10 as mentioned above. Accordingly, the present disclosure provides methods of inducing tolerance in a subject comprising administering one or more masked TGF-β constructs or complexes comprising a wt. or variant IL-10 sequence or both an IL-2 and IL-10 polypeptide sequence. Alternatively, one or more masked TGF-β constructs or complexes comprising a wt. or variant IL-10 (e.g., monomeric IL-10) sequence may be administered with (concurrently or combined) one or more masked TGF-β constructs or complexes comprising a wt. or variant IL-2 polypeptide sequence.

e. Masked TGF-β Constructs or Complexes and FasL

In some case, such as where it is desirable to induce tolerance or suppress T-effector cells, at least one MOD polypeptide (e.g., one, two or three independently selected MODs) present in one or more masked TGF-β constructs or complexes may comprise a Fas ligand (FasL) polypeptide, or a variant of a Fas ligand polypeptide. (see e.g., Qiu et. al. *J Surg Res.* 218:180-193 (2017). As discussed above, IL-10 or variant IL-10 polypeptides may also be utilized to induce tolerance.

Accordingly, the present disclosure provides methods of inducing tolerance or suppressing T-effector cells in a subject comprising administering one or more masked TGF-β constructs or complexes comprising a wt. or variant FasL polypeptide sequence or both an IL-2 and a FasL polypeptide sequence. The present disclosure also provides for induction of tolerance. Alternatively, one or more masked TGF-β constructs or complexes comprising a wt. or variant FasL sequence may be administered with (concurrently or combined) one or more masked TGF-β constructs or complexes comprising a wt. or variant IL-2 polypeptide sequence.

f. Methods of Modulating Other Cells

The present disclosure provides a method of supporting the development and/or survival of invariant natural killer T (iNKT) cells; the method comprising administering (e.g., to a subject in need thereof), or contacting iNKT cell precursor cells with a masked TGF-β construct or complex, optionally comprising one or more (e.g., one, two or more or three or more) independently selected wild type or variant MODs. Where the development and/or survival is assessed relative to treatment groups (e.g., cells or subjects) that have not been exposed to TGF-β or a masked TGF-β construct or complex.

The present disclosure provides a method of inhibiting macrophages (e.g., macrophages activated by a Toll Like Receptor Ligand or cytokine stimulation); the method comprising administering (e.g., to a subject in need thereof), or contacting macrophages with, one or more masked TGF-β constructs or complexes optionally comprising one or more (e.g., one, two or more or three or more) independently selected wildtype or variant MODs; wherein the inhibition is assessed relative to treatment groups (e.g., cells or subjects) that have not been exposed to TGF-β and/or a one or more masked TGF-β constructs or complexes. Activation, and inhibition of macrophage activation is assessed by methods known in the art, such as nitric oxide production by activated macrophages.

TGF-β inhibits $H_2O_2$ production by monocytes, and is a chemoattractant for monocytes that inhibits fibronectin adherence. See e.g., Warwick Davies and Cole, *J Immunol.* 155(6): 3186-3193 (1995). Accordingly, the present disclosure provides a method of stimulating monocytes (e.g., resting monocytes) to undergo migration; the method comprising administering (e.g., to a subject in need thereof), or contacting monocytes with one or more masked TGF-β constructs or complexes optionally comprising one or more (e.g., one, two or more or three or more) independently selected wildtype or variant MODs; wherein the stimulation is assessed relative to treatment groups (e.g., cells or subjects) that have not been exposed to TGF-β and/or one or more masked TGF-β constructs or complexes. Activation, and inhibition of monocytes activation is assessed by methods known in the art, including measurement of $H_2O_2$ production and fibronectin adherence. $H_2O_2$ production (e.g., in response to a monocyte stimulus) may be decreased by at least 5% (e.g., at least 10%, at least 15%, at least 20%, at least 25%, at least 30%, at least 40%, at least 50%, at least 60%, at least 70%, at least 80%, at least 90%, 10-fold, 20-fold, 30-fold, or more).

The present disclosure provides a method of altering peripheral blood monocyte and/or macrophage migration (e.g., assessed by time-lapse microscopy or Boyden chamber assay) into tissues (e.g., injured or inflamed tissue), and/or to enhance macrophage and/or monocyte adherent properties; the method comprising administering (e.g., to a subject in need thereof), or contacting myeloid cells with a masked TGF-β construct or complex, optionally comprising one or more (e.g., one, two or more or three or more) independently selected wildtype or variant MODs; wherein the migration and/or adherent properties are assessed relative to treatment groups (e.g., cells or subjects) that have not been exposed to TGF-β or a masked TGF-β construct or complex. For example, some instances short term interaction of cells or tissue with TGF-β (e.g., TGF-β1) stimulated the migration of macrophages or monocytes, whereas long-term exposure decreased their migration. See, e.g., Kim et al., Blood 108:1821-1829 (2006), and Xu et al Bone Research, 6 (Article No. 2) (2018).

The present disclosure provides a method of inducing chemotaxis (e.g., assessed by time-lapse microscopy or Boyden chamber assay) and/or enhancing the adherent properties of mast cells; the method comprising administering (e.g., to a subject in need thereof), or contacting mast cells with, a masked TGF-β construct or complex, optionally comprising one or more (e.g., one, two or more or three or more) independently selected wildtype or variant MODs; wherein the chemotaxis and/or adherent properties are assessed relative to treatment groups (e.g., cells or subjects) that have not been exposed to TGF-β or a masked TGF-β construct or complex.

The present disclosure includes and provides methods of modulating auto reactive and/or inflammatory T cells (e.g., Th1, Th2, Th17 and/or Th22 cells). The methods comprise administering (e.g., to a subject in need thereof), or contacting the T cells (e.g., in vivo or in vitro) with, one or more masked TGF-β constructs or complexes, optionally comprising one or more (e.g., one, two or more or three or more) independently selected wildtype and/or variant MODs. The TGF-β constructs or complexes that optionally comprise one or more wildtype and/or variant MODs may directly interact with such inflammatory T cells, and/or indirectly affect such cells through released molecules (e.g., cytokines/interleukins) or through other cell populations. By way of example, administration of masked TGF-β constructs or complexes optionally comprising one or more wild type and/or variant IL-2 MODs (a TGF-β/IL-2 complex) may directly stimulate the development and/or survival of FoxP3+T reg cells (in vitro or in vivo). In addition to the direct interactions of a TGF-β/IL-2 complexes with cells resulting in $FoxP3^+$ T reg cells, the resultant T regs may influence other cells such as by, for example, blocking induction of T cell activation and/or the effector phase of T cell responses, suppressing B cell activation, and inhibiting the differentiation and/or proliferation of natural killer cells. Such actions by T regs may be carried out through various means including, but not limited to, production of IL-10, TGF-β, and/or the binding of CTLA-4 on the T reg to B7 (B7-1 or CD80/B7-2 or CD86) on antigen presenting cells thereby competing with CD28 costimulation of those cells. Accordingly, this disclosure includes and provides for methods of modulating autoreactive T cells and inflammatory T cells belonging to lineages such as Th1, Th2, Th17, Th22 etc. The autoreactive cells may be a population of bystander T cells (e.g., bystander Th1, Th2, and/or Th17 cells). For example, in celiac disease the T cells that are modulated may include Th17 cells found in the intestinal mucosa resulting in reduced expression, secretion, and/or mucosal tissue levels of IL-17A, IL-17F, IL-21, and/or IL-22.

The present disclosure includes and provides a method of inhibiting the action of CD4+Th1 cells (e.g., reduce their secretion of interferon γ and/or TNF) and thereby activation of macrophages (e.g., phagocytosis and the macrophage involvement in delayed type hypersensitivity or "DTH" that is a component of inflammatory disease including granulomatous inflammation). The method comprising administering (e.g., to a subject in need thereof), or contacting CD4+ Th1 cells with, a one or more masked TGF-β constructs or complexes, optionally comprising one or more (e.g., one, two or more or three or more) independently selected wildtype or variant MODs; wherein the inhibition of Th1 cell action is assessed by the production of interferon γ and/or TNF relative to a treatment group (e.g., cells or subjects) that have not been exposed to TGF-β and/or one or more masked TGF-β constructs or complexes.

The present disclosure includes and provides a method of inhibiting the action (activation) of CD4+Th2 cells (e.g., reduced IgE, mast cell, and eosinophil mediated reactions); the method comprising administering (e.g., to a subject in need thereof), or contacting CD4+Th2 cells with, one or more masked TGF-β constructs or complexes, optionally comprising one or more (e.g., one, two or more or three or more) independently selected wildtype or variant MODs; wherein the inhibition of Th2 cell action (the degree of Th2 cell activation) is assessed by the production of IL-4, IL-5, and/or IL-13 relative to a treatment group (e.g., cells or subjects) that have not been exposed to TGF-β and/or one or more masked TGF-β constructs or complexes.

2 Methods of Selectively Delivering a Costimulatory Polypeptide

The present disclosure provides a method of delivering TGF-β in a masked form along with one or more (e.g., one, two or more, three or more, or four or more) independently selected MODs and/or variant MODs using one or more masked TGF-β constructs or complexes. Delivery of MODs to cells comprising TβRs can be complicated due to the interact actions of MODs with their receptors (co-MODs) on cells that contain or do not contain TβRs. Masked TGF-β constructs or complexes may be targeted to cells by varying the number MODs and the affinity for their corresponding co-MODs relative to the effective affinity of the masked TGF-β polypeptide for the TβR. Incorporating variant MODs with reduced affinity into masked TGF-β constructs or complexes allows the TGF-β polypeptide to more strongly influence, or even dominate, the binding interactions. Incorporating a combination of variant MODs with reduced affinity (provided they can still stimulate their co-MODs) and TGF-β polypeptides with relatively strong affinity for the TβR permits the masked TGF-β constructs and complexes comprising one or more MOD(s) to be biased (or even selective) in their binding to cells with both TβRs and the corresponding co-MOD(s). Such a combination also avoids the off-target stimulation of cell bearing the co-MODs without TβR.

The present disclosure provides for the selective delivery of both a TGF-β polypeptide and at least one variant MOD selectively to target cells (e.g., in vitro or in vivo) expressing on their surface membrane a TβR (e.g., TβRII and/or TβRI) and co-MODs corresponding to the at least one variant MOD. When used in this context, "selective delivery" means that the MOD of the masked TGF-β construct or complex is delivered to a co-MOD on a higher number of cells that express a TβR (e.g., TβRII and/or TβRI), i.e., the "target cells", than to cells that do not comprise a TβR, i.e., "non-target cells."

In view of the foregoing, the present disclosure provides for the delivery of both a TGF-β polypeptide and at least one variant MOD selectively to target cells (e.g., in vitro or in vivo) expressing on their surface membrane a TβR (e.g., TβRII and/or TβRI) and co-MODs corresponding to the at least one variant MOD; the method comprising: contacting a population of cells with an amount of a masked TGF-β construct or complex comprising at least one reduced affinity variant MOD that is insufficient to saturate the TβRs present on the cells (e.g., occupy less than 70%, 60%, 50%, 40% or 30% of the TβRs present on the cells); and permitting the masked TGF-β construct or complex comprising at least one reduced affinity variant MOD to interact with the cells (e.g., for a time sufficient to bind). In such a method the ratio of (i) number of cells expressing both the TβR and a co-MOD bound by the masked TGF-β construct or complex comprising at least one reduced affinity variant MOD divided by the number of cells expressing the co-MOD bound by the masked TGF-β construct or complex comprising at least one reduced affinity variant MOD is greater than (ii) the ratio of number of cells expressing both the TβR and a co-MOD bound by the masked TGF-β construct or complex comprising the wt. MOD divided by the number of cells expressing the co-MOD bound by the masked TGF-β construct or complex comprising the wt. MOD.

The present disclosure provides for the delivery to target cells (e.g., in vitro or in vivo) of both a masked TGF-β polypeptide and at least one wt. and/or variant IL-2 MOD polypeptide, comprising contacting the target cell with a masked TGF-β construct or complex comprising at least one wt. and/or variant IL-2 MOD polypeptide optionally in the presence of vitamin D, retinoic acid (e.g., all trans retinoic acid), and/or rapamycin. In one case masked TGF-β polypeptide comprising at least one wt. or variant IL-2 MOD polypeptide are delivered in the presence of any one, any two, or all three of vitamin D, retinoic acid (e.g., all trans retinoic acid), and/or rapamycin.

The present disclosure provides for the delivery and optionally the selective delivery to target cells (e.g., in vitro or in vivo) of a masked TGF-β construct or complex comprising at least one wild type and/or variant IL-6 MOD polypeptide.

The present disclosure provides for the delivery and optionally the selective delivery to target cells (e.g., in vitro or in vivo) of both a masked TGF-β construct or complex comprising at least one wild type and/or variant IL-7 MOD polypeptide.

The present disclosure provides for the delivery and optionally the selective delivery to target cells (e.g., in vitro or in vivo) of both a masked TGF-β construct or complex comprising at least one wild type and/or variant IL-10 MOD polypeptide.

The present disclosure provides for the delivery and optionally the selective delivery to target cells (e.g., in vitro or in vivo) of both a masked TGF-β construct or complex comprising at least one wild type and/or variant IL-15 MOD polypeptide.

The present disclosure provides for the delivery and optionally the selective delivery to target cells (e.g., in vitro or in vivo) of both a masked TGF-β construct or complex comprising at least one wild type and/or variant IL-21 MOD polypeptide.

The present disclosure provides for the delivery and optionally the selective delivery to target cells (e.g., in vitro or in vivo) of both a masked TGF-β construct or complex comprising at least one wild type and/or variant IL-23 MOD polypeptide.

The present disclosure provides for the delivery and optionally the selective delivery to target cells (e.g., in vitro or in vivo) of both a masked TGF-β construct or complex comprising at least one wild type and/variant PD-L1 MOD polypeptide.

The present disclosure provides for the delivery and optionally the selective delivery to target cells (e.g., in vitro or in vivo) of both a masked TGF-β construct or complex comprising at least one wild type and/or variant FasL MOD polypeptide.

3 Methods of Treatment or Prophylaxis

The present disclosure provides treatment and prophylaxis methods, the methods may comprise contacting a target population of cells from an individual (e.g., in vitro or in vivo) and/or administering to the individual, an effective amount of a masked TGF-β construct or complex (e.g., PSM-4033-4039), or one or more nucleic acids or expression vectors encoding the masked TGF-β construct or complex, effective to selectively modulate the activity of the target cell population of cells and/or to treat the individual. Where target cells are treated separately from the individual (i.e., in vitro), all or a portion of the cells or their progeny may be administered to individual. In some cases, a method of treatment or prophylaxis comprises administering to an individual in need thereof an effective amount of one or more recombinant expression vectors comprising nucleotide sequences encoding a masked TGF-β construct or complex. In some cases, a method of treatment or prophylaxis comprises administering to an individual in need thereof one or more mRNA molecules comprising nucleotide sequences encoding a masked TGF-β construct or complex. In some cases, a method of treatment or prophylaxis comprises contacting a target population of cells from an individual (i.e., in vitro) in need thereof with an effective amount of a masked TGF-β construct or complex (e.g., PSM-4033-4039) and thereby forming a contacted target population of cells, the method further comprising administering all or part of the contacted target population of cells (and/or their progeny) to the individual. In some cases, a method of treatment or prophylaxis comprises administering to an individual in need thereof an effective amount of a masked TGF-β construct or complex (e.g., PSM-4033-4039), or a pharmaceutically acceptable composition comprising an effective amount of a masked TGF-β construct or complex (e.g., PSM-4033-4039). Conditions that can be treated (e.g., to cure and/or ameliorate symptoms) with a composition comprising an effective amount of a masked TGF-β construct or complex (e.g., PSM-4033-4039) include: conditions associated with an insufficient number of Treg cells or insufficiently active Treg cells, autoimmune diseases or disorders, allergic reaction(s), wounds (e.g., dermal and/or mucosal wounds), and/or burns. In addition, individuals undergoing organ transplantation may also benefit from treatment.

A method of treatment or prophylaxis comprising administering to an individual with an insufficient number of FoxP3+ Treg cells or insufficiently active FoxP3+ Treg cells an effective amount of a masked TGF-β construct or complex (e.g., PSM-4033-4039) and/or one or more nucleic acids (e.g., recombinant expression vectors) encoding the masked TGF-β construct or complex. In one instance, the masked TGF-β construct or complex comprises PSM-4033-4039. In one instance, the masked TGF-β construct or complex comprises one or more (e.g., one, two or three) independently selected IL-2 or variant IL-2 MOD polypeptide sequences. The masked TGF-β construct or complex and/or one or more nucleic acids (e.g., recombinant expression vectors) encoding the masked TGF-β construct or complex, with or without an IL-2 or variant IL-2 MOD, may be administered before, during (concurrent or combined administration) or after administration of any one or more of vitamin D (e.g., 1α,25-dihydroxyvitamin D3 or 1α,25-Dihydroxycholecalciferol) or a vitamin D analog, rapamycin, and/or a retinoic acid (e.g., all trans retinoic acid).

A method of treatment or prophylaxis may comprise administering to an individual with an autoimmune disease or disorder which is in need thereof an effective amount of a masked TGF-β construct or complex and/or one or more nucleic acids (e.g., recombinant expression vectors) comprising nucleotide sequences encoding a masked TGF-β construct or complex. In one instance, the masked TGF-β construct or complex comprise one or more (e.g., one, two or three) independently selected IL-2 or variant IL-2 MOD polypeptide sequences (e.g., PSM-4033-4039). In a second instance, the masked TGF-β construct or complex comprise one or more (e.g., one, two or three) independently selected IL-10 or variant IL-10 MOD polypeptide sequences. In one instance, the masked TGF-β construct or complex comprises at least one independently selected IL-2 or variant IL-2 MOD polypeptide sequence and at least one independently selected IL-10 or variant IL-10 MOD polypeptide sequence. In a second instance, the masked TGF-β construct or complex comprise one or more (e.g., one, two or three) independently selected IL-10 or variant IL-10 MOD polypeptide sequences. Autoimmune diseases that can be treated with a method of the present disclosure include, but are not limited to, Addison's disease, alopecia areata, ankylosing spondylitis, autoimmune encephalomyelitis, autoimmune hemolytic anemia, autoimmune hepatitis, autoimmune-associated infertility, autoimmune thrombocytopenic purpura, bullous pemphigoid, Crohn's disease, Goodpasture's syndrome, glomerulonephritis (e.g., crescentic glomerulonephritis, proliferative glomerulonephritis), Grave's disease, Hashimoto's thyroiditis, mixed connective tissue disease, multiple sclerosis, myasthenia gravis (MG), pemphigus (e.g., pemphigus vulgaris), pernicious anemia, polymyositis, psoriasis, psoriatic arthritis, rheumatoid arthritis, scleroderma, Sjögren's syndrome, systemic lupus erythematosus (SLE), vasculitis, and vitiligo. In an embodiment, the autoimmune disease that can be treated with a method of the present disclosure is T1D. In an embodiment, the autoimmune disease that can be treated with a method of the present disclosure is celiac disease. T1D and/or celiac disease also may be excluded from the autoimmune diseases subject to treatment with a method of the present disclosure.

A method of treatment or prophylaxis comprising administering to an individual with a deficiency in Th17 cells (e.g., individuals unable to sufficiently respond to bacterial and/or fungal infections in the gut) an effective amount of a masked TGF-β construct or complex and/or one or more nucleic acids (e.g., recombinant expression vectors) encoding the masked TGF-β construct or complex. In one instance, the masked TGF-β construct or complex comprises one or more (e.g., one, two or three) independently selected IL-6 or variant IL-6 MOD polypeptide sequences. A method of treatment or prophylaxis may comprise administering to an individual unable to sufficiently respond to bacterial and/or fungal infections in the gut an effective amount of a masked TGF-β construct or complex comprising one or more independently selected IL-6 and/or variant IL-6 polypeptides, or one or more nucleic acids (e.g., recombinant expression vectors) encoding the masked TGF-β construct or complex comprising one or more independently selected IL-6 and/or variant IL-6 polypeptides.

A method of treatment or prophylaxis comprising administering to an individual with a deficiency in Th9 cells (e.g., individuals unable to sufficiently respond to helminth infections) an effective amount of a masked TGF-β construct or complex and/or one or more nucleic acids (e.g., recombinant expression vectors) encoding the masked TGF-β construct or complex sufficient to respond to helminth infection. In one instance, the masked TGF-β construct or complex comprise one or more (e.g., one, two or three) independently selected IL-4 or variant IL-4 MOD polypeptide sequences. A method of treatment or prophylaxis may comprise administering to an individual unable to sufficiently respond to sufficiently respond to helminth infections an effective amount of a masked TGF-β construct or complex comprising one or more independently selected IL-4 and/or variant IL-4 polypeptides, or one or more nucleic acids (e.g., recombinant expression vectors) encoding the masked TGF-β construct or complex comprising one or more independently selected IL-4 and/or variant IL-4 polypeptides.

A method of treatment or prophylaxis comprising administering to an individual with a deficiency in Tfh cells (e.g., individuals unable to produce high affinity antibodies or sufficient amounts of high affinity antibodies) an effective amount of a masked TGF-β construct or complex and/or one or more nucleic acids (e.g., recombinant expression vectors) encoding the masked TGF-β construct or complex sufficient to increase the production of high affinity antibodies. In one instance, the masked TGF-β construct or complex comprises one or more (e.g., one, two or three) independently selected IL-21, IL-23, variant IL-21 or variant IL-23 MOD polypeptide sequences. A method of treatment or prophylaxis may comprise administering to an individual unable to produce high affinity antibodies or insufficient amounts of high affinity antibodies an effective amount of a masked TGF-β construct or complex comprising one or more independently selected IL-21, IL-23, variant IL-21 or variant IL-23 MOD polypeptide sequences, or one or more nucleic acids (e.g., recombinant expression vectors) encoding the masked TGF-β construct or complex comprising one or more independently selected IL-21, IL-23, variant IL-21 or variant IL-23 MOD polypeptide sequences.

A method of treatment or prophylaxis comprising administering to an individual having excess Th1 cell activity relative to a control group (e.g., and individual with elevated levels of activated macrophages and/or elevated levels of interferon gamma "IFN-γ" in a target tissue or circulating) an effective amount of a masked TGF-β construct or complex and/or one or more nucleic acids (e.g., recombinant expression vectors) encoding the masked TGF-β construct or complex. A method of treatment or prophylaxis may comprise administering to an individual with elevated levels of activated macrophages and/or elevated levels of interferon gamma "IFN-γ" (e.g., circulating or in a target tissue) an effective amount of a masked TGF-β construct or complex, or one or more nucleic acids (e.g., recombinant expression vectors) encoding the masked TGF-β construct or complex.

A method of treatment or prophylaxis comprising administering to an individual having excess Th2 cell activity relative to a control group (e.g., an individual with elevated levels of activated MAST cells and/or with elevated levels of IgE that circulating or tissue localize) an effective amount of a masked TGF-β construct or complex and/or one or more nucleic acids (e.g., recombinant expression vectors) encoding the masked TGF-β construct or complex. A method of treatment or prophylaxis may comprise administering to an individual with elevated levels of activated MAST cells and/or with elevated levels of IgE (circulating or tissue localize) an effective amount of a masked TGF-β construct or complex, or one or more nucleic acids (e.g., recombinant expression vectors) encoding the masked TGF-β construct or complex.

A method of treatment or prophylaxis comprising administering to an individual having T-cell receptor-driven activation of autoreactive T cells (or high affinity T-cells) an effective amount of a masked TGF-β construct or complex (e.g., PSM-4033-4039) and/or one or more nucleic acids (e.g., recombinant expression vectors) encoding the masked TGF-β construct or complex. A method of treatment or prophylaxis may comprise administering to an individual with autoreactive T-cells an effective amount of a masked TGF-β construct or complex (e.g., PSM-4033-4039), or one or more nucleic acids (e.g., recombinant expression vectors) encoding the masked TGF-β construct or complex.

A method of treatment or prophylaxis comprising administering to an individual in which it is desirable to promote IL-7-dependent survival of low-affinity CD4+ and/or CD8+ T cells (e.g., by control of thymocyte IL-7Ra expression) an effective amount of a masked TGF-β construct or complex and/or one or more nucleic acids (e.g., recombinant expression vectors) encoding the masked TGF-β construct or complex. In one instance, the masked TGF-β construct or complex comprise one or more (e.g., one, two or three) independently selected IL-7 or variant IL-7 MOD polypeptide sequences. A method of treatment or prophylaxis may comprise administering to an individual unable to sufficiently maintain levels of low-affinity CD4+ and/or CD8+ T cells an effective amount of a masked TGF-β construct or complex comprising one or more independently selected IL-7 and/or variant IL-7 polypeptides, or one or more nucleic acids (e.g., recombinant expression vectors) encoding the masked TGF-β construct or complex comprising one or more independently selected IL-7 and/or variant IL-7 polypeptides.

A method of treatment or prophylaxis comprising administering to an individual in which it is desirable to promote apoptosis of specific cells (e.g., cancer cells or cancer cells bearing a specific marker such as cancer antigens 15-3, 27-29, 125, carcinoembryonic antigen, Alpha-fetoprotein and/or Beta 2-microglobulin) an effective amount of a masked TGF-β construct or complex and/or one or more nucleic acids (e.g., recombinant expression vectors) encoding the masked TGF-β construct or complex (e.g., PSM-4033-4039). In one instance, the masked TGF-β construct or complex comprise one or more (e.g., one, two or three) independently selected wt. Fas ligand or variant Fas ligand MOD polypeptide sequences.

A method of treatment or prophylaxis comprising administering to an individual in which it is desirable to induce iTreg (CD4+ FoxP3+) cells (e.g., individuals in which it is desirable to induce peripheral tolerance to actively suppress effector T (T eff) cells and/or inhibit immune-mediated tissue damage) an effective amount of a masked TGF-β construct or complex (e.g., PSM-4033-4039) and/or one or more nucleic acids (e.g., recombinant expression vectors) encoding the masked TGF-β construct or complex. In one instance, the masked TGF-β construct or complex comprise one or more (e.g., one, two or three) independently selected wt. or variant PD-L1 MOD polypeptide sequences. In another instance, the masked TGF-β construct or complex comprise one or more (e.g., one, two or three) independently selected wt. and/or variant PD-L1 MOD polypeptide sequences and one or more wt. and/or variant IL-2 MOD polypeptide sequences. In an embodiment the masked TGF-β construct or complex comprise (i) one independently selected wt. or variant PD-L1 MOD polypeptide sequence and (ii) one wt. or variant IL-2 MOD sequence. See, e.g., Francisco et al., *J. Exp. Med.,* 206(13): 3015-3029 (2009).

A method of treatment or prophylaxis comprising administering to an individual in which it is desirable to inhibit type II innate lymphoid cells (ILC2 cells) (e.g., to suppress asthma, allergic reaction, and/or allergic inflammation) an effective amount of a masked TGF-β construct or complex (e.g., PSM-4033-4039) and/or one or more nucleic acids (e.g., recombinant expression vectors) encoding the masked TGF-β construct or complex. In one instance, the masked TGF-β construct or complex comprise one or more (e.g., one, two or three) independently selected IL-10 or variant IL-10 MOD polypeptide sequences. The masked TGF-β construct or complex and/or one or more nucleic acids (e.g., recombinant expression vectors) encoding the masked TGF-β construct or complex, with or without an IL-10 or variant IL-10 MOD, may be administered before, during (concurrent or combined administration) or after administration of a glucocorticoid (e.g., dexamethasone, prednisone, etc.), antihistamine (e.g., diphenhydramine, chlorpheniramine, etc.), and/or epinephrine.

A method of treatment or prophylaxis comprising administering to an individual having an allergy, allergic inflammation, and/or elevated levels of IgE (circulating or tissue localized) an effective amount of a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex. A method of treatment or prophylaxis may comprise administering to an individual with elevated levels of IgE (circulating or tissue localize) an effective amount a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex. The masked TGF-β construct or complex and/or one or more nucleic acids (e.g., recombinant expression vectors) encoding the masked TGF-β construct or complex, with or without an IL-10 or variant IL-10 MOD, may be administered before, during (concurrent or combined administration) or after administration of a glucocorticoid (e.g., dexamethasone, prednisone, etc.), antihistamine (e.g., diphenhydramine, chlorpheniramine, etc.), and/or epinephrine. The TGF-β and IL-10 act to suppress expression of the high-affinity IgE receptor (Fc1RI) that activates MAST cells and IL-10 additionally acts to prevent excessive MAST cell activation and the development of chronic inflammation. See e.g., Kennedy et al. *Journal of Immunology,* 180(5) 2848-2854 (2008).

A method of or prophylaxis comprising administering to an individual diagnosed with or having multiple sclerosis, an effective amount of a masked TGF-β construct or complex (e.g., PSM-4033-4039) and/or one or more nucleic acids (e.g., recombinant expression vectors) encoding the masked TGF-β construct or complex. In one instance, the masked TGF-β construct or complex comprise one or more (e.g., one, two or three) independently selected IL-10 or variant IL-10 MOD polypeptide sequences.

A method of treatment an individual having at least one cutaneous or mucosal burn, the method comprising administering the individual an effective amount of a masked TGF-β construct or complex (e.g., PSM-4033-4039) and/or one or more nucleic acids (e.g., recombinant expression vectors) encoding the masked TGF-β construct or complex. In an instance the method may comprise administering an effective amount of a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex. The burns may be first, second, or third-degree burns.

A method of treatment an individual having at least one cutaneous or mucosal wound (an abrasion, avulsion, incision, laceration, or puncture of the epidermis or mucosa), the method comprising administering the individual an effective amount of a masked TGF-β construct or complex (e.g., PSM-4033-4039) and/or one or more nucleic acids (e.g., recombinant expression vectors) encoding the masked TGF-β construct or complex to speed wound closure (reduce time until closure), reduce healing time, or to reduce scar formation relative to an untreated wound. In an instance, the method may comprise administering an effective amount of a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex. When the masked TGF-β construct or complex, either with or without an IL-10 MOD polypeptide, comprises TGF-β1 polypeptide, the method may further comprise one or more of: the recruitment of inflammatory cells into the injury site; expression of extracellular matrix proteins such as fibronectin, collagen (e.g., types I and/or III), and/or VEGF; stimulation fibroblasts contraction to enable wound closure; wound site expression of integrins, such as β1, α5, αv, and β5; and keratinocyte migration. When the masked TGF-β construct or complex, either with or without an IL-10 MOD polypeptide, comprises TGF-β2 polypeptide, the method may further comprise one or more of: the recruitment of both fibroblasts and immune cells from circulation and the wound edges into the wounded area; expression of collagen (e.g., types I and/or III); and expression of fibronectin. See, e.g., Pakyari et al *Adv Wound Care,* 2(5): 215-224 (2013). In such methods the masked TGF-β construct or complex may be applied directly to or injected into the wound.

A method of treatment an individual having at least one cutaneous or mucosal wound (an abrasion, avulsion, incision, laceration, or puncture of the epidermis or mucosa), the method comprising administering to the individual an effective amount of a masked TGF-β (e.g., TGF-β3) construct or complex (e.g., PSM-4033-4039) and/or one or more nucleic acids (e.g., recombinant expression vectors) encoding the masked TGF-β3 construct or complex to reduce scar formation relative to an untreated wound. In an instance, the method may comprise administering an effective amount of a masked TGF-β (e.g., TGF-β3) construct or complex comprising at least one (e.g., one, two or three) independently selected IL-10 or variant IL-10 MOD polypeptides and/or one or more nucleic acids (e.g., recombinant expression vectors) encoding the masked TGF-β (e.g., TGF-β3) construct or complex. In such methods the masked TGF-β (e.g., TGF-β3) construct or complex may be applied directly to or injected into the wound. Without being bound by theory, it may be understood that TGF-β3 reduces type/collagen deposition while promoting collagen degradation by MMP-9, leading to decreased scar formation. See. e.g., Pakyari et al *Adv Wound Care,* 2(5): 215-224 (2013).

A method of facilitating organ transplant in an individual, the method comprising administering the individual an effective amount of a masked TGF-β construct or complex (e.g., PSM-4033-4039) and/or one or more nucleic acids (e.g., recombinant expression vectors) encoding the masked TGF-β construct or complex to speed incision closure (reduce time until closure), reduce recovery time, or to reduce scar formation relative to the average time to closure, recovery time or scar formation in untreated individuals matched for the type of organ transplantation, age, sex, smoking habits, and/or body mass index. In an instance, the method may comprise administering an effective amount of a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex.

A method of treating an individual with graft vs. host disease (GVHD, including acute GVHD), the method comprising administering the individual an effective amount of a masked TGF-β construct or complex (e.g., PSM-4033-4039) and/or one or more nucleic acids (e.g., recombinant expression vectors) encoding the masked TGF-β construct or complex In any of the foregoing methods, unless specified otherwise, the TGF-β polypeptide of a masked TGF-β construct or complex can be a TGF-β1, TGF-β2, or TGF-β3 polypeptide or a variant thereof as discussed in the preceding section (e.g., a TGF-β3 C77S variant or a TGF-β1 or TGF-β2 variant with a corresponding mutation limiting TGF-β polypeptide dimerization). Similarly, the polypeptide masking the TGF-β polypeptide can be selected from those described above (e.g., antibodies or fragments thereof, single chain antibodies, or TβRI or TβRII ectodomain fragments that bind to TGF-β).

As noted above, in some cases, in carrying out a subject method of treatment or prophylaxis, a masked TGF-β construct or complex is administered to an individual in need thereof, as the polypeptide per se. In other instances, in carrying out a subject method of treatment or prophylaxis, one or more nucleic acids comprising nucleotide sequences encoding a masked TGF-β construct or complex is/are administering to an individual in need thereof. Thus, in other instances, one or more nucleic acids, e.g., one or more recombinant expression vectors, is/are administered to an individual in need thereof.

N. Dosages

A suitable dosage can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A masked TGF-β construct or complex may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute. A masked TGF-β construct or complex can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a masked TGF-β construct or complex is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a masked TGF-β construct or complex or a single-chain masked TGF-β construct or complex) is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific masked TGF-β construct or complex, the severity of the symptoms and the susceptibility of the subject to side effects. Preferred dosages for a given compound are readily determinable by those of skill in the art by a variety of means.

In some cases, multiple doses of a masked TGF-β construct or complex, a nucleic acid, or a recombinant expression vector are administered. The frequency of administration of a masked TGF-β construct or complex, a nucleic acid, or a recombinant expression vector can vary depending on any of a variety of factors, e.g., severity of the symptoms, etc. For example, in some cases, a masked TGF-β construct or complex, a nucleic acid, or a recombinant expression vectors administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a masked TGF-β construct or complex, a nucleic acid, or a recombinant expression vector, e.g., the period of time over which a masked TGF-β construct or complex, a nucleic acid, or a recombinant expression vector is administered, can vary, depending on any of a variety of factors, e.g., patient response, etc. For example, a masked TGF-β construct or complex, a nucleic acid, or a recombinant expression vector can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

O. Routes of Administration

An active agent (a masked TGF-β construct or complex, a nucleic acid, or a recombinant expression vector) is administered to an individual using any available method and route suitable for drug delivery, including in vivo and in vitro methods, as well as systemic and localized routes of administration.

Conventional and pharmaceutically acceptable routes of administration include intratumoral, peritumoral, intramuscular, intratracheal, intralymphatic, intracranial, cutaneous, subcutaneous, intradermal, topical application, intravenous, intraarterial, rectal, nasal, oral, and other enteral and parenteral routes of administration. Routes of administration may be combined, if desired, or adjusted depending upon the masked TGF-β construct or complex and/or the desired effect. A masked TGF-β construct or complex, or a nucleic acid or recombinant expression vector, can be administered in a single dose or in multiple doses.

In some cases, a masked TGF-β construct or complex, a nucleic acid, or a recombinant expression vector is administered intravenously. In some cases, a masked TGF-β construct or complex, a nucleic acid, or a recombinant expression vector is administered intramuscularly. In some cases, a masked TGF-β construct or complex, a nucleic acid, or a recombinant expression vector is administered intralymphatically. In some cases, a masked TGF-β construct or complex, a nucleic acid, or a recombinant expression vector is administered locally. In some cases, a masked TGF-β construct or complex, a nucleic acid, or a recombinant expression vector is administered intratumorally. In some cases, a masked TGF-β construct or complex, a nucleic acid, or a recombinant expression vector is administered peritumorally. In some cases, a masked TGF-β construct or complex, a nucleic acid, or a recombinant expression vector is administered intracranially. In some cases, a masked TGF-β construct or complex, a nucleic acid, or a recombinant expression vector is administered cutaneously. In some cases, a masked TGF-β construct or complex, a nucleic acid, or a recombinant expression vector is administered subcutaneously. In some cases, a masked TGF-β construct or complex, a nucleic acid, or a recombinant expression vector is administered to a wound (e.g., a dermal or mucosal wound). In some cases, a masked TGF-β construct or complex, a nucleic acid, or a recombinant expression vector is administered to burned tissue (e.g., a dermal burns).

In some cases, a masked TGF-β construct or complex is administered intravenously. In some cases, a masked TGF-β construct or complex is administered intramuscularly. In some cases, a masked TGF-β construct or complex is administered locally. In some cases, a masked TGF-β construct or complex is administered intratumorally. In some cases, a masked TGF-β construct or complex is administered peritumorally. In some cases, a masked TGF-β construct or complex is administered intracranially. In some cases, a masked TGF-β construct or complex is administered cutaneously. In some cases, a masked TGF-β construct or complex is administered subcutaneously. In some cases, a masked TGF-β construct or complex is administered intralymphatically. In some cases, a masked TGF-β construct or complex is administered to a wound (e.g., a dermal or mucosal wound). In some cases, a masked TGF-β construct or complex is administered to burned tissue (e.g., a dermal burns).

A masked TGF-β construct or complex, a nucleic acid, or a recombinant expression vector can be administered to a host using any available conventional methods and routes suitable for delivery of conventional drugs, including systemic or localized routes. In general, routes of administration contemplated for use in a method include, but are not necessarily limited to, enteral, parenteral, cutaneous, and inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, intralymphatic, peritumoral, and intravenous routes, i.e., any route of administration other than through the alimentary canal. Parenteral administration can be carried to effect systemic or local delivery of a masked TGF-β construct or complex, a nucleic acid, or a recombinant expression vector. Where systemic delivery is desired, administration typically involves invasive or systemically absorbed topical or mucosal administration of pharmaceutical preparations.

P. Subjects Suitable for Treatment

Subjects suitable for treatment with a masked TGF-β construct or complex e.g., PSM-4033-4039), such as by a method described herein, include individuals (e.g., humans) with an autoimmune disease, allergic reaction(s), wounds (e.g., dermal and/or mucosal wounds), and/or burns. Subjects additionally include individuals undergoing organ transplantation. In addition to humans, subjects include non-human mammals including, but not limited to, bovine canine, caprine, cercopithecine, feline, lapine, lapine, murine, ovine, porcine, or simian subjects or patients in need of treatment.

Subjects (individuals) who have an autoimmune disease or conditions and are suitable for treatment with a masked TGF-β construct or complex (e.g., PSM-4033-4039), including individuals those who have been diagnosed as having an autoimmune disease or condition, and individuals who have been treated for an autoimmune disease or condition but who failed to respond to the treatment. Autoimmune diseases and conditions that can be treated with a method of the present disclosure include, but are not limited to, Addison's disease, alopecia areata, ankylosing spondylitis, autoimmune encephalomyelitis, autoimmune colitis, autoimmune gastritis, autoimmune hemolytic anemia, autoimmune hepatitis, autoimmune-associated infertility, autoimmune pancreatitis, autoimmune retinopathy, autoimmune thrombocytopenic purpura, autoimmune urticaria, bullous pemphigoid, celiac disease, Crohn's disease, Goodpasture's syndrome, glomerulonephritis (e.g., crescentic glomerulonephritis, proliferative glomerulonephritis), graft vs. host disease (GVHD, including acute GVHD), Grave's disease, Hashimoto's thyroiditis, inflammatory bowel disease, mixed connective tissue disease, multiple sclerosis, myasthenia gravis (MG), pemphigus (e.g., pemphigus vulgaris), pernicious anemia, polymyositis, psoriasis, psoriatic arthritis, rheumatoid arthritis, scleroderma, Sjögren's syndrome, systemic lupus erythematosus (SLE), transplant rejection, type-1 diabetes (T1D) vasculitis, and vitiligo. In an embodiment, the autoimmune disease is T1D. In an embodiment, the autoimmune disease is celiac disease. Individuals with T1D and/or celiac disease may be excluded from the subjects suitable for treatment. Similarly, T1D and/or celiac disease may be excluded from the autoimmune disease subject to treatment.

In an embodiment, the autoimmune diseases and conditions that can be treated with a method of the present disclosure include, but are not limited to, rheumatoid arthritis (RA), psoriasis/psoriatic arthritis, multiple sclerosis, inflammatory bowel disease, Addison's disease, Graves' disease, Sjögren's syndrome, Hashimoto's thyroiditis, myasthenia gravis, autoimmune vasculitis, and pernicious anemia.

Subjects that have allergic reactions cannot easily categorized by the allergens because allergens are too numerous to recite. By way of example, however, subjects (e.g., individuals previously treated for their allergies or who have never been treated) who have an allergic reaction(s) include those with reactions to: peanuts and tree nuts, plant pollens, latex, and the like. For example, subjects with allergic reactions to peanut allergens include those with reactions to Ara h 1 to 13 proteins that come from seven protein families, include those in Ara h 1 (e.g., PGQFEDFF (SEQ ID NO:161), YLQGFSRN (SEQ ID NO:162), FNAEFNEIRR (SEQ ID NO:163), QEERGQRR (SEQ ID NO:164), DITNPINLRE (SEQ ID NO:165), NNFGKLFEVK (SEQ ID NO:166), GNLELV (SEQ ID NO:167), RRYTARLKEG (SEQ ID NO:168), ELHLLGFGIN (SEQ ID NO:169), HRIFLAGDKD (SEQ ID NO:170), IDQIEKQAKD (SEQ ID NO:171), KDLAFPGSGE (SEQ ID NO:172), KESHFVSARP (SEQ ID NO:173), NEGVIVKVSKEHVEELTKHAKSVSK (SEQ ID NO:174), Ara h 2 (e.g., HASARQQWEL (SEQ ID NO:175), QWELQGDRRC (SEQ ID NO:176), DRRCQSQLER (SEQ ID NO:177), LRPCEQHLMQ (SEQ ID NO:178), KIQRDEDSYE (SEQ ID NO:179), YERDPYSPSQ (SEQ ID NO:180), SQDPYSPSPY (SEQ ID NO:181), DRLQGRQQEQ (SEQ ID NO:182), KRELRNLPQQ (SEQ ID NO:183), QRCDLDVESG (SEQ ID NO:184), and Ara h 3 (e.g., IETWNPNNQEFECAG (SEQ ID NO:185), GNIFSGFTPEFLAQA (SEQ ID NO:186), VTVRGGLRILSPDRK (SEQ ID NO:187), DEDEYEYDEEDRRRG (SEQ ID NO:188). See, e.g., Zhou et al, (2013) Intl. J. of Food Sci. 2013: 8 pages article ID 909140. Subjects with allergic reactions also include those with reactions to hymenoptera proteins (e.g., allergens in bee and wasp venoms such as phospholipase A2, melittin, "antigen 5" found in wasp venom, and hyaluronidases).

Subjects that have wounds include individuals with abrasion, avulsion, incision, laceration, and puncture of skin or mucosa. It may be understood that subjects that have organ transplantation, will, by their nature have one or more of those wound types.

V. CERTAIN ASPECTS

Certain aspects including aspects of the subject matter directed to the TGF-β constructs or complexes described above, may be beneficial alone or in combination, with one or more other aspects, such as those recited below directed to TGF-β constructs and complexes, their method of manufacture, and their methods of use (e.g., as therapeutics).

1. A construct comprising as a first polypeptide:
   i) a scaffold polypeptide sequence;
   ii) a TGF-β polypeptide sequence;
   iii) a masking polypeptide sequence (e.g., a TGF-β receptor polypeptide sequence or anti-TGF-β polypeptide sequence);
   iv) optionally, one or more (e.g., one, two or more) independently selected MOD polypeptide sequences; and
   v) optionally one or more independently selected linker polypeptide sequences (e.g., between any of the foregoing polypeptide sequences);
   a construct comprising these elements being collectively referred to as a "masked TGF-β construct," wherein the masking polypeptide sequence (e.g., TGF-β receptor polypeptide sequence or anti-TGF-β polypeptide sequence) and the TGF-β polypeptide sequence bind to each other (interact with each other to mask the TGF-β polypeptide sequence). See e.g., FIG. 1, structure A.

2. The masked TGF-β construct of aspect 1, wherein the first polypeptide comprises, in order from N-terminus to C-terminus:
   i) the scaffold polypeptide sequence, the masking polypeptide sequence (e.g., TGF-β receptor polypeptide sequence), and the TGF-β polypeptide sequence; or
   ii) a first MOD polypeptide sequence, the scaffold polypeptide sequence, the masking polypeptide sequence (e.g., TGF-β receptor polypeptide sequence), and the TGF-β polypeptide sequence; or
   iii) a first independently selected MOD polypeptide sequence, a second independently selected MOD polypeptide sequence (MODs in tandem), the scaffold polypeptide sequence, the masking polypeptide sequence (e.g., TGF-β receptor polypeptide sequence), and the TGF-β polypeptide sequence;
   wherein masked TGF-β construct optionally comprise one or more independently selected linker polypeptide sequences (e.g. between any of the foregoing polypeptide sequences).

3. The masked TGF-β construct of aspect 1 or aspect 2, wherein the scaffold polypeptide comprises a dimerization (or multimerization) sequence.

4. The masked TGF-β construct of aspect 3, in the form of a masked TGF-β complex homodimer wherein the scaffold polypeptide sequences optionally have one or more (e.g., one, two or more) covalent attachments (e.g., disulfide bonds) to each other (e.g., wherein a first molecule of the masked TGF-β construct as the first polypeptide is dimerized with a second molecule of the masked TGF-β construct as a second polypeptide through covalent or non-covalent interactions of their scaffold polypeptide sequences to form a homodimer), optionally wherein, the scaffolds comprise Ig Fc polypeptides that include mutations (e.g., the LALA mutations) that substantially reduce or eliminate the ability of the Ig polypeptide to induce cell lysis, e.g., though complement-dependent cytotoxicity (CDC) and/or antibody-dependent cellular cytotoxicity (ADCC). See e.g., FIG. 1, structure B.

5. The masked TGF-β construct of any of aspects 1-3, wherein the scaffold polypeptide comprises an interspecific dimerization sequence (e.g., a dimerization sequence that preferentially dimerizes with its counterpart interspecific binding sequence as opposed to homodimerizing). See e.g., FIG. 1, structures C and F.

6. The masked TGF-β construct of aspect 5, further comprising a second polypeptide dimerized with the first polypeptide to form a masked TGF-β complex heterodimer; wherein the second polypeptide comprises a scaffold polypeptide sequence that comprises a counterpart interspecific dimerization sequence to the interspecific binding sequence of the first polypeptide; and wherein the interspecific binding sequence and the counterpart interspecific binding sequence interact with each other in the heterodimer.

7. The masked TGF-β complex of aspect 6, wherein the second polypeptide comprises:
   (i) a scaffold polypeptide sequence comprising the counterpart interspecific dimerization sequence;
   (ii) one or two (or more) independently selected MOD sequences (e.g., in tandem) and a scaffold polypeptide sequence comprising the counterpart interspecific dimerization sequence;
   (iii) a scaffold polypeptide sequence comprising the counterpart interspecific dimerization sequence, and an independently selected MOD sequence; or
   (iv) one or two (or more) independently selected MOD sequences (e.g., in tandem) and a scaffold polypeptide sequence comprising the counterpart interspecific dimerization sequence;
   wherein the first and or second polypeptides optionally comprise one or more independently selected linker polypeptide sequences (e.g. between any of the foregoing polypeptide sequences). See e.g., FIG. 1, structure F.

8. The masked TGF-β complex of aspect 6 or 7, wherein the second polypeptide comprises, from N-terminus to C-terminus:
   i) a scaffold polypeptide sequence comprising the counterpart interspecific dimerization sequence;
   (ii) one or two (or more) independently selected MOD sequences (e.g., in tandem) and a scaffold polypeptide sequence comprising the counterpart interspecific dimerization sequence;
   (iii) a scaffold polypeptide sequence comprising the counterpart interspecific dimerization sequence, and one or two (or more) independently selected MOD sequences; or
   (iv) one or two (or more) independently selected MOD sequences (e.g., in tandem) and a scaffold polypeptide sequence comprising the counterpart interspecific dimerization sequence
   wherein first and/or second polypeptides optionally comprises one or more independently selected linker polypeptide sequences (e.g., between any of the foregoing polypeptide sequences). See e.g., FIG. 1, structure F.

9. The masked TGF-β complex of aspect 6, wherein the second polypeptide comprises:
   i) optionally, one or more (e.g., one, two or more) independently selected MOD polypeptide sequences;
   ii) a scaffold polypeptide sequence comprising the counterpart interspecific dimerization sequence;
   iii) a TGF-β polypeptide sequence;
   iv) a masking polypeptide sequence (e.g., a TGF-β receptor polypeptide sequence or anti-TGF-β polypeptide sequence); and
   v) optionally one or more independently selected linker polypeptide sequences (e.g., between any of the foregoing polypeptide sequences of the second polypeptide);
   wherein the masking polypeptide sequence (e.g., TGF-β receptor polypeptide sequence or anti-TGF-β polypeptide sequence) and the TGF-β polypeptide sequence bind to each other (interact with each other to mask the TGF-β polypeptide sequence). See e.g., FIG. 1, structure C.

10. The masked TGF-β complex heterodimer of aspect 9, wherein the second polypeptide comprises in order from N-terminus to C-terminus:
   i) the scaffold polypeptide sequence comprising the counterpart interspecific dimerization sequence, the masking polypeptide sequence (e.g., TGF-β receptor polypeptide sequence), and the TGF-β polypeptide sequence;
   ii) a first MOD polypeptide sequence, the scaffold polypeptide sequence comprising the counterpart interspecific dimerization sequence, the masking polypeptide sequence (e.g., TGF-β receptor polypeptide sequence), and the TGF-β polypeptide sequence; or
   iii) a first independently selected MOD polypeptide sequence, a second independently selected MOD polypeptide sequence, the scaffold polypeptide sequence comprising the counterpart interspecific dimerization sequence, the masking polypeptide sequence (e.g., TGF-β receptor polypeptide sequence), and the TGF-β polypeptide sequence. See e.g., FIG. 1, structure C.

11. A complex comprising a first polypeptide and a second polypeptide as a heterodimer (or multimer), wherein:
   (i) the first polypeptide comprises
      a) a scaffold polypeptide sequence comprising an interspecific dimerization sequence,
      b) a masking polypeptide sequence (e.g., a TGF-β receptor polypeptide sequence or anti-TGF-β polypeptide sequence),
      c) optionally, one or more (e.g., one, two or more) independently selected MOD polypeptide sequences, and
      d) optionally one or more independently selected linker polypeptide sequences (e.g., between any of the foregoing polypeptide sequences of the first polypeptide);
   (ii) the second polypeptide comprises
      a) a scaffold polypeptide sequence comprising a counterpart interspecific dimerization sequence to the interspecific dimerization sequence in the first polypeptide,
      b) a TGF-β polypeptide sequence,
      c) optionally, one or more (e.g., one, two or more) independently selected MOD polypeptide sequences, and
      d) optionally one or more independently selected linker polypeptide sequences (e.g., between any of the foregoing polypeptide sequences of the second polypeptide);
a complex comprising these elements being collectively referred to as a "masked TGF-β complex," wherein the masking polypeptide sequence (e.g., TGF-β receptor polypeptide sequence or anti-TGF-β polypeptide sequence) and the TGF-β polypeptide sequence bind to each other (interact with each other to mask the TGF-β polypeptide sequence); wherein the interspecific binding sequence and the counterpart interspecific binding sequence interact with each other (e.g., bind non-covalently) in the heterodimer; and wherein masked TGF-β first polypeptide and/or the second polypeptide optionally comprise one or more independently selected linker polypeptide sequences (e.g., between any of their polypeptide sequences). See e.g., FIG. 1, structures D and E.

12. The masked TGF-β complex heterodimer of aspect 11, wherein the first polypeptide comprises, from N-terminus to C-terminus:
   a) one or two (or more) independently a) one or two (or more) independently selected MOD sequences, a scaffold polypeptide sequence comprising an interspecific dimerization sequence, and the masking polypeptide sequence (e.g., TGF-β receptor polypeptide sequence), or
   b) a scaffold polypeptide sequence comprising an interspecific dimerization sequence, and the masking polypeptide sequence (e.g., TGF-β receptor polypeptide sequence); and
the second polypeptide comprises, from N-terminus to C-terminus one or two (or more) independently selected MOD sequences, a scaffold polypeptide sequence comprising the counterpart interspecific dimerization sequence, and the TGF-β polypeptide sequence.

13. The masked TGF-β construct or complex of any of aspects 1-12, wherein the scaffold polypeptide sequence(s) are selected from the group consisting of Ig Fc polypeptide sequences (e.g., CH2-CH3 region sequences); Ig heavy chain region 1 (CH1) domains; light chain constant regions ("CL") (e.g. an Ig κ chain (kappa chain) constant region or an Ig λ chain (lambda chain)); leucine zipper polypeptide sequences; Fos or Jun binding pair sequences; collectin polypeptides (e.g., ACRP30 or ACRP30-like proteins); coiled-coil domains; and variants of any of the foregoing (e.g., knob-in-hole and other interspecific sequences in Table 1).

14. The masked TGF-β construct or complex of any of aspects 1-13, wherein the scaffold polypeptide sequence is selected from the group consisting of Ig Fc polypeptide sequences (immunoglobulin sequences); Ig heavy chain sequences (e.g., CH2-CH3 region sequences); Ig heavy chain region 1 (CH1) domains; light chain constant regions ("CL") (e.g. an Ig κ chain (kappa chain) and variants of any of the foregoing. In one embodiment, the scaffold polypeptide are selected from an Ig CH1 domain bearing MD13 substitutions or Ig κ chain sequence bearing MD13 substitutions.

15. The masked TGF-β construct or complex of aspect 14, where the immunoglobulin sequences comprise a sequence having at least about 70%, at least about 80%, at least about 90%, at least about 95%, at least about 98%, at least about 99%, or 100% aa sequence identity to any of SEQ ID NOs: 68 to 83 or 85-87. See, e.g., FIGS. 2A-2H, and 2J-2K (Immunoglobulin sequence can form dimers and in the case of IgM sequence, such as in FIG. 2H, multimers).

16. The masked TGF-β construct or complex of 15, where the immunoglobulin sequences comprise an immunoglobulin heavy chain sequence having at least about 70%, at least about 80%, at least about 90%, at least about 95%, at least about 98%, at least about 99%, or 100% aa sequence identity to any of SEQ ID NOs: 68 to 83. See, e.g., FIGS. 2A-2H (Immunoglobulin sequence can form dimers and in the case of IgM sequence, such as in FIG. 2H, multimers).

17. The masked TGF-β construct or complex of any one of aspects 4 and 6-16, wherein the scaffold polypeptide sequences have one or more (e.g., one, two or more) covalent attachments to each other.

18. The masked TGF-β construct or complex of aspect 17, where at least one (e.g., one, two or more) of the one or more covalent attachments is a disulfide bond between the scaffold polypeptide sequence of the first polypeptide and the scaffold polypeptide sequence of the second polypeptide.

19. The masked TGF-β construct or complex of any of aspects 14-18, wherein the scaffold sequences are immunoglobulin heavy chain constant region (Ig Fc) polypeptide sequences comprising CH2-CH3 immunoglobulin regions that are optionally covalently linked by one or more (e.g., one, two or more) disulfide bonds.

20. The masked TGF-β construct of aspects 5, wherein the scaffold polypeptide comprises an interspecific dimerization sequence selected from the group consisting of: i) an interspecific immunoglobulin (Ig) heavy chain sequence; ii) an Ig CH1 domain; iii) an Ig light chain constant region ("CL") (e.g. an Ig κ chain (kappa chain) or an Ig λ chain (lambda chain) constant region); and (iv) a polypeptide of a Fos/Jun binding pair. In one embodiment the scaffold polypeptide comprises an interspecific dimerization sequence selected from an Ig CH1 domain bearing MD13 substitutions or an Ig κ chain sequence bearing MD13 substitutions.

21. The masked TGF-β construct of aspect 20, wherein the interspecific binding sequence comprises a sequence having at least about 70%, at least about 80%, at least about 90%, at least about 95%, at least about 98%, at least about 99%, or 100% aa sequence identity to any of SEQ ID NOs: 68 to 82 or 85-87. See, e.g., FIGS. 2A-2G, and 2J-2K.

22. The masked TGF-β complex of any of aspects 4 and 6-12, wherein the scaffold polypeptide of the first polypeptide and the second polypeptide comprise an interspecific dimerization sequence and a counterpart interspecific dimerization sequence pair selected from the group consisting of: (i) interspecific immunoglobulin (Ig) heavy chain sequences (e.g., heavy chain CH1-CH2 regions); (ii) an Ig CH1 domain and one of its counterpart interspecific light chain constant region ("CL") (e.g. an Ig chain (kappa chain) constant region or an Ig λ chain (lambda chain) constant region); (iii) Fos/Jun binding pairs; and (iv) Ig heavy chain region 1 (CH1) and light chain constant region ("CL") sequences (CH1/CL pairs such as a CH1 sequence paired with a κ or λ Ig light chain constant region sequence). In one embodiment, the scaffold polypeptide of the first polypeptide and the second polypeptide comprise an interspecific dimerization sequence and a counterpart interspecific dimerization sequence pair that comprise an Ig CH1 domain bearing MD13 substitutions and an Ig κ chain sequence bearing MD13 substitutions.

23. The masked TGF-β complex of aspect 22, wherein the scaffold polypeptide sequences have one or more (e.g., one, two or more) covalent attachments to each other.

24. The masked TGF-β complex of aspect 22, where at least one (e.g., one, two or more) of the one or more covalent attachments is a disulfide bond between the scaffold sequence of the first polypeptide and the scaffold sequence of the second polypeptide.

25. The masked TGF-β complex of any of aspects 22-24, wherein the scaffold sequences are immunoglobulin heavy chain constant region (Ig Fc) polypeptide sequences comprising CH2-CH3 immunoglobulin regions that are optionally covalently linked by one or more (e.g., one, two or more) disulfide bonds (between the first and second polypeptides).

26. The masked TGF-β complex of any of aspects 22-25, wherein the interspecific binding sequence and/or the counterpart interspecific binding sequence comprise a sequence having at least about 70%, at least about 80%, at least about 90%, at least about 95%, at least about 98%, at least about 99%, or 100% aa sequence identity to any of SEQ ID NOs: 68 to 82 or 85-87. See, e.g., FIGS. 2A-2G, and 2J-2K.

27. The masked TGF-β complex of 26, where the immunoglobulin sequences comprise an immunoglobulin heavy chain sequence having at least about 70%, at least about 80%, at least about 90%, at least about 95%, at least about 98%, at least about 99%, or 100% aa sequence identity to any of SEQ ID NOs: 68 to 83. See, e.g., FIGS. 2A-2H (Immunoglobulin sequence can form dimers and in the case of IgM sequence, such as in FIG. 2H, multimers).

27. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 150 contiguous aas (at least 175, at least 200, at least 225, at least 250, at least 275, at least 300, at least 325, or at least 350 contiguous aas), or all aas, of the IgA Fc sequence depicted in FIG. 2A (SEQ ID NO:68).

28. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 150 contiguous aas (at least 175, at least 200, at least 225, at least 250, at least 275, at least 300, at least 325, or at least 350 contiguous aas), or all aas, of the IgD Fc sequence depicted in FIG. 2B (SEQ ID NO:69).

29. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to least 125 contiguous aas (at least 150, at least 175, or at least 200 contiguous aas), or all aas, of the IgE Fc sequence depicted in FIG. 2C (SEQ ID NO:70).

30. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to least 125 contiguous aas (at least 150, at least 175, or at least 200 contiguous aas), or all aas, of the wt. IgG Fc polypeptide sequence, such as the IgG1 Fc sequence depicted in FIG. 2D (SEQ ID NOs: 71-78).

31. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 125 contiguous aas (at least 150, at least 175, at least 200, at least 225, at least 250, at least 275, or at least 300), or all aas, of the IgG2 Fc polypeptide sequence depicted in FIG. 2E (SEQ ID NO:79).

32. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 125 contiguous aas (at least 150, at least 175, at least 200, or at least 225), or all aas, of the IgG3 Fc sequence depicted in FIG. 2F (SEQ ID NO:80).

33. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 125 contiguous aas (at least 150, at least 175, at least 200, at least 225, or at least 250), or all aas, of the IgG4 Fc sequence depicted in FIG. 2G (SEQ ID NO:81 or 82).

34. The masked TGF-β complex of any of aspects 27-33, comprising one or two interchain disulfide bonds between the first and second polypeptides (e.g., between cysteines adjacent to their hinge regions of the IgA, IgD, IgE, IgG1, IgG2, IgG3 or IgG4 sequences).

35. The masked TGF-β construct or complex of any of aspects 1-34, wherein one or more scaffold polypeptides comprise an immunoglobulin (Ig) polypeptide sequence bearing one or more substitutions that limits (e.g., reduces) binding of the polypeptide to complement component 1q (C1q) and/or Fc lambda receptor (FcλR) and/or that substantially reduces or eliminates the ability of the Ig polypeptide to induce cell lysis though complement-dependent cytotoxicity (CDC) and/or antibody-dependent cellular cytotoxicity (ADCC).

36. The masked TGF-β construct or complex of aspect 35, wherein each scaffold polypeptide comprises an immunoglobulin (Ig) polypeptide sequence comprising a polypeptide having at least about 70% (e.g., at least about 80%, at least about 85%, at least about 90%, at least about 95%, at least about 98%, at least about 99%, or 100%) aa sequence identity to least 125 contiguous aas (at least 150, at least 175, at least 200, or at least 220 contiguous aas) of wt. IgG1 Fc Sequence (SEQ ID NO:71).

37. The masked TGF-β construct or complex of aspect 36, wherein the immunoglobulin polypeptide sequence comprises a substitution of any one, two, or more of aas 234, 235, 236, 237, 238, and 239 (234-LLGGPS-239).

38. The masked TGF-β construct or complex of aspect 36 or 37, wherein the immunoglobulin polypeptide sequence comprises a substitution at any one, two or more of N297, P331, D270, K322, and/or P329.

39. The masked TGF-β construct or complex of any of aspects 36-38 wherein the immunoglobulin polypeptide sequence comprises an N297 substitution (N77 of SEQ ID NO:71) with an aa other than asparagine (e.g., alanine to give a N297A such as in SEQ ID NO:74).

40. The masked TGF-β construct or complex of any of aspects 36-38 wherein the immunoglobulin polypeptide sequence comprises an L234 and/or L235 (L14 and L15 in SEQ ID NO:71) substitution with an aa other than leucine (e.g., alanine, L234A and/or L235A).

41. The masked TGF-β construct or complex of 39, wherein the immunoglobulin polypeptide sequence comprises an L234A and/or L235A substitutions (see e.g., SEQ ID NO:75).

42. The masked TGF-β construct or complex of any of aspects 36-41 wherein the immunoglobulin polypeptide sequence comprises P331 (P111 of SEQ ID NO:71)) substituted with an aa other than proline (e.g., serine for a P331S substitution).

43. The masked TGF-β construct or complex of any of aspects 36-38, wherein the immunoglobulin polypeptide sequence comprises substitutions at L234 and/or L235, and a substitution of P331.

44. The masked TGF-β construct or complex of aspect 43 wherein the immunoglobulin polypeptide sequence comprises (i) L234F, L235E, and P331S or (ii) L234A, L235A, and P331S substitutions.

45. The masked TGF-β construct or complex of any of aspects 20-44, comprising an interspecific dimerization sequence of an interspecific dimerization pair selected from the group consisting of KiH, KiHs-s, HA-TF, ZW-1, 7.8.60, DD-KK, EW-RVT, EW-RVTs-s, and A107 sequences (see, e.g., Table 1).

46. The masked TGF-β complex of any of aspects 4 and 22-44, wherein interspecific dimerization sequence and a counterpart interspecific dimerization sequence are a pair of sequences is selected from the group consisting of KiH, KiHs-s, HA-TF, ZW-1, 7.8.60, DD-KK, EW-RVT, EW-RVTs-s, and A107 sequence pairs (see, e.g., Table 1).

47. The masked TGF-β complex of aspect 46, wherein one of the first polypeptide and the second polypeptides comprise an interspecific IgG1 polypeptide sequence (e.g., a sequence of SEQ ID NO:71) comprising a T366Y substitution and the other a Y407T substitution, or corresponding substitutions in other interspecific immunoglobulin heavy chain sequences (e.g., interspecific sequences comprising IgA, IgD, IgE, IgG2, IgG3 or IgG4 heavy chain sequences).

48. The masked TGF-β complex of aspect 46, wherein one of the first polypeptide and the second polypeptides comprise an interspecific IgG1 polypeptide sequence (e.g., a sequence of SEQ ID NO:71) comprising a T366W substitution and the other T366S, L368A and Y407V substitutions, or corresponding substitutions in other interspecific immunoglobulin heavy chain sequences (e.g., interspecific sequences comprising IgA, IgD, IgE, IgG2, IgG3 or IgG4 heavy chain sequences).

49. The masked TGF-β complex of aspect 46, wherein one of the first polypeptide and the second polypeptides comprise an interspecific IgG1 polypeptide sequence (e.g., a sequence of SEQ ID NO:71) comprising Y349C, T366S, L368A, and Y407V substitutions and the other S354C, and T366W substitutions, or corresponding substitutions in other interspecific immunoglobulin heavy chain sequences (e.g., interspecific sequences comprising IgA, IgD, IgE, IgG2, IgG3 or IgG4 heavy chain sequences).

50. The masked TGF-β complex of aspect 46, wherein the first polypeptide comprises an IgG1 scaffold having a T146W KiH sequence substitution, and the second polypeptide comprises an IgG1 scaffold having T146W, L148A, and Y187V KiH sequence substitutions, where the scaffolds comprises a sequence having at least 80%, 90%. 95%, 98%, 99%, or 100% sequence identity to at least 170 (e.g., at least 180, at least 190, at least 200, at least 210, at least 220, or all 227) contiguous aas of the IgG1 of SEQ ID NO:71, and optionally comprises substitutions at one of more of: L14 and L15 (e.g., L14A/L15A "LALA" or L14F/L15E); N77 (e.g., N77A); P111 (e.g. P111S); L131 (e.g., L131K); T146 (e.g., T146S); P175 (e.g., P175V); F185 (e.g., F185R); Y187 (e.g., Y187A); and K189 (e.g., K189Y) as numbered in SEQ ID NO:71.

51. The masked TGF-β complex of aspect 46, wherein the first polypeptide comprises an IgG1 scaffold having a T146W KiH sequence substitution, and the second polypeptide comprises an IgG1 scaffold having T146S, L148A, and Y187V KiH sequence substitutions, where the scaffolds comprises a sequence having at least 80%, 90%. 95%, 98%, 99%, or 100% sequence identity to at least 170 (e.g., at least 180, at least 190, at least 200, at least 210, at least 220, or all 227) contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering). See e.g., FIG. 2D SEQ ID NOs: 77 and 78, 52. The masked TGF-β complex of aspect 46, wherein the first polypeptide comprises an IgG1 scaffold having T146W and S134C KiHs-s substitutions, and the second polypeptide comprises an IgG1 scaffold having T146S, L148A, Y187V and Y129C KiHs-s substitutions, where the scaffolds comprise a sequence having at least 80%, 90%. 95%, 98%, 99%, or 100% sequence identity to at least 170 (e.g., at least 180, at least 190, at least 200, at least 210, at least 220, or all 227) contiguous aas of the IgG1 of SEQ ID NO:71; with none, one, or both of the scaffold aa sequences of the first and second polypeptide comprising L14 and L15 substitutions (e.g., L234A and L235A "LALA" in Kabat numbering), and/or N77 (N297 in Kabat numbering) substitution to remove effector function by blocking interactions with Fcγ receptors (e.g., N297A or N297G substitutions in Kabat numbering).

53. The masked TGF-β complex of aspect 46, wherein the first and second polypeptide are selected from:
 a first polypeptide comprising an IgG1 scaffold having S144H and F185A substitutions, and a second polypeptide comprising an IgG1 scaffold having Y129T and T174F substitutions;
 a first polypeptide comprising an IgG1 scaffold having T130V, L131Y, F185A, and Y187V substitutions, and a second polypeptide comprising an IgG1 scaffold having 130V, T146L, K172L, and T174W substitutions;
 a first polypeptide comprising an IgG1 scaffold having K140D, D179M, and Y187A substitutions, and a second polypeptide comprising an IgG1 scaffold having E125R, Q127R, T146V, and K189V substitutions;
 a first polypeptide comprising an IgG1 scaffold having K189D, and K172D substitutions, and a second polypeptide comprising an IgG1 scaffold having D179K and E β6K substitutions;
 a first polypeptide comprising an IgG1 scaffold having K140E and K189W substitutions, and a second polypeptide comprising an IgG1 scaffold having Q127R, D179V, and F185T substitutions;
 a first polypeptide comprising an IgG1 scaffold having K140E, K189W, and Y129C substitutions, and a second polypeptide comprising an IgG1 scaffold having Q127R, D179V, F185T, and S134C substitutions; and
 a first polypeptide comprising an IgG1 scaffold having K150E and K189W substitutions, and a second polypeptide comprising an IgG1 scaffold having E137N, D179V, and F185T substitutions;
wherein the scaffolds comprise a sequence having at least 80%, 90%. 95%, 98%, 99%, or 100% sequence identity to at least 170 (e.g., at least 180, at least 190, at least 200, at least 210, at least 220, or all 227) contiguous aas of the IgG1 of SEQ ID NO:71; and
wherein none, one, or both of the scaffold aa sequences of the first and second polypeptide comprising L14 and L15 substitutions (e.g., L234A and L235A "LALA" in Kabat numbering), and/or N77 (N297 in Kabat numbering) substitution to remove effector function by blocking interactions with Fcγ receptors (e.g., N297A or N297G substitutions in Kabat numbering).

54. The masked TGF-β construct of aspects 20, wherein the wherein the scaffold polypeptide comprises an interspecific dimerization sequence selected from the group consisting of:
 (i) an Ig heavy chain CH1 domain (e.g., the polypeptide of SEQ ID NO:85);
 (ii) an Ig κ chain constant region sequence (e.g., SEQ ID NO:86); and
 (iii) an Ig λ chain constant region sequence (e.g., SEQ ID NO:87);
where the scaffold comprises a sequence having at least 80% (85%, 90%. 95%, 98%, 99%, or 100%) sequence identity to at least 70, at least 80, at least 90, or at least 100 contiguous aas of SEQ ID NOs: 85, 86, or 87 respectively. See FIGS. 2J and 2K. The Ig CH1 domain and/or the Ig κ chain sequence optionally comprise their respective MD13 substitutions.

55. The masked TGF-β complex of aspect 22, wherein the scaffold polypeptide of one of the first and second polypeptides comprises an Ig heavy chain CH1 domain (e.g., the polypeptide of SEQ ID NO:85); and the other of the first and second polypeptides comprise either an Ig κ chain constant region sequence (e.g., SEQ ID NO:86 optionally comprising MD13 substitutions) or an Ig), chain constant region sequence (e.g., SEQ ID NO:87);
wherein the scaffolds comprise a sequence having at least 80% (85%, 90%. 95%, 98%, 99%, or 100%) sequence identity to at least 70, at least 80, at least 90, or at least 100) contiguous aas of SEQ ID NOs: 85, 86, or 87 respectively). See FIGS. 2J and 2K.

56. The masked TGF-β construct or complex of any of aspects 1-56, wherein the masked TGF-β construct or complex comprises at least one (e.g., at least two, or at least three) independently selected linker polypeptide sequences.

57. The masked TGF-β construct or complex of aspect 56, wherein the independently selected linkers have a length from about 1 aa to about 25 aa, (e.g., 1, 2, 3, 4, 5, 6, 7, 8, 9, 10, 11, 12, 13, 14, 15, 16, 17, 18, 19, 20, 21, 22, 23, 24, or 25 aa in length).

58. The masked TGF-β construct or complex of aspect 56, wherein the independently selected linkers have a length from about 25 to about 35 aa in length (e.g., 25, 26, 27, 28, 29, 30, 31, 32, 33, 34, or 35 aa in length).

59. The masked TGF-β construct or complex of aspect 56, wherein the independently selected linkers have a length from about 35 to about 50 aa in length (e.g., 35, 36, 37, 38, 39, 40, 41, 42, 43, 44, or 45, 46, 47, 48, 49, or 50, aa in length).

60. The masked TGF-β construct or complex of any of aspects 56 to 59, wherein at least one (e.g., at least two, or at least three) of the independently selected linkers comprises a
 (i) glycine or a polyglycine containing sequence having from about 2 to about 50 contiguous glycine residues;
 (ii) glycine-serine polymer (e.g., (GS)n, (GSGGS)n (SEQ ID NO:126), (GGGGS)n SEQ ID NO:β6, and (GGGS)n (SEQ ID NO:127), where n is an integer of at least one (e.g., 1-10, 10-20, or 20-30); or
 (iii) glycine-alanine polymer or alanine-serine polymer (e.g., having a length of 1-10, 10-20, or 20-30 aa).

61. The masked TGF-β construct or complex of any of aspects 56 to 59, wherein at least one (e.g., at least two, or at least three) of the independently selected linkers comprises an aa sequence selected from the group consisting of: GGSG (SEQ ID NO:128), GGSGG (SEQ ID NO:129), GSGSG (SEQ ID NO:130), GSGGG (SEQ ID NO:131), GGGSG (SEQ ID NO:132), GSSSG (SEQ ID NO:133), GSGS (SEQ ID NO:134), GSSSSS (SEQ ID NO:135), GGGGS SEQ ID NO:β6, and the like.

62. The masked TGF-β construct or complex of any of aspects 56 to 59, wherein at least one of the independently selected linkers comprises a cysteine residue (e.g., a G C GASGGGGSGGGGS linker aa sequence SEQ ID NO:137) that can or does form a disulfide bond with a cysteine residue present in a second polypeptide (e.g., in a linker of the second polypeptide) of the masked TGF-β construct or complex.

63. The masked TGF-β construct or complex of any of aspects 1 to 62, wherein the one or more (e.g., one, two or more) independently selected MOD polypeptide sequences are selected from the group consisting of: PD-L1, FAS-L, IL-1, IL-2, IL-4, IL-6, IL-7, IL-10, IL-15, IL-21, IL-23 MOD polypeptide sequences, and variants of any thereof (e.g., variants having reduced affinity for their receptor relative to the corresponding wt. MOD polypeptide sequence).

64. The masked TGF-β construct or complex of any of aspects 1 to 62, wherein the one or more (e.g., one, two or more) independently selected MOD polypeptide sequences are selected from the group consisting of: PD-L1, FAS-L, IL-2, IL-4, IL-6, IL-7, IL-10, IL-21, IL-23 MOD polypeptide sequences, and variants of any thereof (e.g., variants having reduced affinity for their receptor relative to the corresponding wt. MOD polypeptide sequence).

65. The masked TGF-β construct or complex of any of aspects 1 to 62, wherein the one or more (e.g., one, two or more) independently selected MOD polypeptide sequences are selected from the group consisting of: PD-L1, FAS-L, IL-2, IL-10 MOD polypeptide sequences, and variants of any thereof (e.g., variants having reduced affinity for their receptor relative to the corresponding wt. MOD polypeptide sequence).

66. The masked TGF-β construct or complex of any of aspects 1 to 62, wherein at least one (e.g., at least two) of the MOD polypeptide sequences is an IL-2 MOD polypeptide sequence or variant IL-2 MOD polypeptide sequence:

- (i) having at least 80% (e.g., at least 85%, at least 90%, at least 95%, at least 98%, or at least 99%) aa sequence identity to at least 80 (e.g., 90, 100, 110, 120, 130 or 133) contiguous aas of SEQ ID NO:9; or
- (ii) having at least 80% (e.g., at least 85%, at least 90%, at least 95%, at least 98%, or at least 99%) aa sequence identity to at least 80 (e.g., 90, 100, 110, 120, 130 or 133) contiguous aas of SEQ ID NO:13-27.

67. The masked TGF-β construct or complex of any of aspects 1 to 62, wherein the one or more (e.g., one, two or more) independently selected MOD polypeptide sequences comprise:

- (i) at least one (e.g., at least two) IL-2 MOD polypeptide sequence or variant IL-2 MOD polypeptide sequence (e.g., variant IL-2 MOD polypeptide sequence of aspect 66); and
- (ii) at least one (e.g., at least two) MOD polypeptide sequence selected from the group consisting of PD-L1, FAS-L, IL-1, IL-4, IL-6, IL-7, IL-10, IL-15, IL-21, IL-23 MOD polypeptide sequences, and variants of any thereof (e.g., variants having reduced affinity for their receptor relative to the corresponding wt. MOD polypeptide sequence).

68. The masked TGF-β construct or complex of any of aspects 1 to 62, wherein the one or more (e.g., one, two or more) independently selected MOD polypeptide sequences comprise:

- (i) at least one (e.g., at least two) wt. IL-2 MOD polypeptide sequence or variant IL-2 MOD polypeptide sequence (e.g., variant IL-2 MOD polypeptide sequence of aspect 66); and
- (ii) at least one (e.g., at least two) PD-L1 or PD-L2 MOD polypeptide sequence or variant PD-L1 or PD-L2 MOD polypeptide sequence (e.g., with reduced affinity for the PD1 receptor relative to the corresponding wt. sequence).

69. The masked TGF-β construct or complex of any of aspects 1 to 62, wherein the one or more (e.g., one, two or more) independently selected MOD polypeptide sequences comprise:

- (i) at least one (e.g., at least two) wt. IL-2 MOD polypeptide sequence or variant IL-2 MOD polypeptide sequence (e.g., variant IL-2 MOD polypeptide sequence of aspect 66); and
- (ii) at least one (e.g., at least two) FAS-L MOD polypeptide sequence or variant FAS-L MOD polypeptide sequence (e.g., with reduced affinity for the Fas receptor relative to the corresponding wt. sequence).

70. The masked TGF-β construct or complex of any of aspects 1 to 62, wherein the one or more (e.g., one, two or more) independently selected MOD polypeptide sequences comprise:

- (i) at least one (e.g., at least two) wt. IL-2 MOD polypeptide sequence or variant IL-2 MOD polypeptide sequence (e.g., variant IL-2 MOD polypeptide sequence of aspect 66); and
- (ii) at least one (e.g., at least two) IL-1 MOD polypeptide sequence or variant IL-1 MOD polypeptide sequence (e.g., with reduced affinity for the IL-1 receptor relative to the corresponding wt. sequence).

71. The masked TGF-β construct or complex of any of aspects 1 to 62, wherein the one or more (e.g., one, two or more) independently selected MOD polypeptide sequences comprise:

- (i) at least one (e.g., at least two) IL-2 MOD polypeptide sequence or variant IL-2 MOD polypeptide sequence (e.g., variant IL-2 MOD polypeptide sequence of aspect 66); and
- (ii) at least one (e.g., at least two), IL-4 MOD polypeptide sequence or variant, IL-4 MOD polypeptide sequence (e.g., with reduced affinity for the IL-4 receptor relative to the corresponding wt. sequence).

72. The masked TGF-β construct or complex of any of aspects 1 to 62, wherein the one or more (e.g., one, two or more) independently selected MOD polypeptide sequences comprise:

- (i) at least one (e.g., at least two) IL-2 MOD polypeptide sequence or variant IL-2 MOD polypeptide sequence (e.g., variant IL-2 MOD polypeptide sequence of aspect 66); and
- (ii) at least one (e.g., at least two) IL-6 MOD polypeptide sequence or variant IL-6 MOD polypeptide sequence (e.g., with reduced affinity for the IL-6 receptor relative to the corresponding wt. sequence).

73. The masked TGF-β construct or complex of any of aspects 1 to 62, wherein the one or more (e.g., one, two or more) independently selected MOD polypeptide sequences comprise:

(i) at least one (e.g., at least two) IL-2 MOD polypeptide sequence or variant IL-2 MOD polypeptide sequence (e.g., variant IL-2 MOD polypeptide sequence of aspect 66); and (ii) at least one (e.g., at least two) IL-7 MOD polypeptide sequence or variant IL-7 MOD polypeptide sequence (e.g., with reduced affinity for the IL-7 receptor relative to the corresponding wt. sequence).

74. The masked TGF-β construct or complex of any of aspects 1 to 62, wherein the one or more (e.g., one, two or more) independently selected MOD polypeptide sequences comprise:

(i) at least one (e.g., at least two) IL-2 MOD polypeptide sequence or variant IL-2 MOD polypeptide sequence (e.g., variant IL-2 MOD polypeptide sequence of aspect 66); and (ii) at least one (e.g., at least two) IL-10 MOD polypeptide sequence or variant IL-10 MOD polypeptide sequence (e.g., with reduced affinity for the IL-10 receptor relative to the corresponding wt. sequence).

75. The masked TGF-β construct or complex of any of aspects 1 to 62, wherein the one or more (e.g., one, two or more) independently selected MOD polypeptide sequences comprise:

(i) at least one (e.g., at least two) IL-2 MOD polypeptide sequence or variant IL-2 MOD polypeptide sequence (e.g., variant IL-2 MOD polypeptide sequence of aspect 66); and (ii) at least one (e.g., at least two) IL-15 MOD polypeptide sequence or variant IL-15 MOD polypeptide sequence (e.g., with reduced affinity for the IL-15 receptor relative to the corresponding wt. sequence).

76. The masked TGF-β construct or complex of any of aspects 1 to 62, wherein the one or more (e.g., one, two or more) independently selected MOD polypeptide sequences comprise:

(i) at least one (e.g., at least two) IL-2 MOD polypeptide sequence or variant IL-2 MOD polypeptide sequence (e.g., variant IL-2 MOD polypeptide sequence of aspect 66); and (ii) at least one (e.g., at least two) IL-21 MOD polypeptide sequence (e.g., a sequence of SEQ ID NO:58 or 60) or variant IL-21 (e.g., with reduced affinity for the IL-21 receptor relative to the corresponding wt. sequence) MOD polypeptide sequence.

77. The masked TGF-β construct or complex of any of aspects 1 to 62, wherein the one or more (e.g., one, two or more) independently selected MOD polypeptide sequences comprise:

(i) at least one (e.g., at least two) wt. IL-2 MOD polypeptide sequence (e.g., comprising the sequence of SEQ ID NO:9) or variant IL-2 MOD polypeptide sequence (e.g., variant IL-2 MOD polypeptide sequence of aspect 66); and (ii) at least one (e.g., at least two) IL-23 MOD polypeptide sequence (e.g., of SEQ ID NO:63 or 65) or variant IL-23 (e.g., with reduced affinity for the IL-23 receptor relative to the corresponding wt. sequence) MOD polypeptide sequence.

78. The masked TGF-β construct or complex of any of aspects 63 to 77, wherein when the TGF-β polypeptide/polypeptide complex comprises a variant IL-2 MOD polypeptide sequence, the variant IL-MOD polypeptide (e.g., a variant of SEQ ID NO:9) comprises a substitution at any one of, two of, or all of N88, F42 and/or H16.

79. The masked TGF-β construct or complex of aspect 78, wherein at least one variant IL-2 MOD polypeptide sequence comprises an F42A, F42T, H16A, or H16T substitution.

80. The masked TGF-β construct or complex of aspect 78, wherein at least one variant IL-2 MOD polypeptide sequence comprises: (i) F42A and H16A; (ii) F42T and H16A; (iii) F42A and H16T; or (iv) F42T and H16T substitutions.

81. The masked TGF-β construct or complex of aspect 78, wherein at least one variant IL-2 MOD polypeptide sequence comprises: (i) N88R, F42A, and H16A; (ii) N88R, F42T, and H16A; (iii) N88R, F42A, and H16T; or (iv) N88R, F42T, and H16T substitutions.

82. The masked TGF-β construct or complex of any of aspects 1 to 81, wherein the masking polypeptide sequence is a TGF-β receptor ("TβR") polypeptide sequence that comprises an ectodomain fragment of a type I (TβRI), type II (TβRII) or type III (TβRIII) TβR.

83. The masked TGF-β construct or complex of aspect 82, wherein the TβRII ectodomain sequence comprises an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 150, or 154) contiguous aas of the TβRII isoform A ectodomain set forth in SEQ ID NO:117.

84. The masked TGF-β construct or complex of aspect 82, wherein the TβRII ectodomain sequence comprises an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, or 143) contiguous aas of the TβRII isoform B ectodomain set forth in SEQ ID NO:119.

85. The masked TGF-β construct or complex of aspect 82, wherein the TβRII ectodomain sequence comprises an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, or 143) contiguous aas of the TβRII isoform B ectodomain set forth in SEQ ID NO:120.

86. The masked TGF-β construct or complex of aspect 82, wherein the TβRII ectodomain sequence comprises an amino acid sequence selected from a TβRII isoform B polypeptide sequence that comprises: the ectodomain fragment of SEQ ID NO:120; the TβRII ectodomain N-terminal Δ14 (delta 14) aa deletion sequence in SEQ ID NO:121; the N-terminal Δ25(delta 25) aa deletion sequence set forth in SEQ ID NO:122; or a sequence having at least 60% (e.g., at least 70%, at least 80%, at least 90%, at least 95%, at least 98%, at least 99%, or 100%) aa sequence identity to at least 70, at least 80, at least 90, at least 100, at least 110, or 118) contiguous aas of any of those TβRII isoform B polypeptide sequence.

87. The masked TGF-β construct or complex of any of aspects 83-86, wherein the TβRII ectodomain sequence comprises a substitution of any one, two, three, four, or all five of F30, D32, S52, E55, and/or D118 (e.g., with alanine or arginine).

88. The masked TGF-β construct or complex of any of aspects 83-87, comprising:

a D118A or D118 R substitution (see e.g., SEQ ID NO:123 for the TβRII ectodomain with an N-terminal Δ25 deletion and a D118 substitution); or a D118A or D118R substitution and one, two, three, or all four of a F30A, D32N, S52L and/or E55A substitutions.

89. The masked TGF-β construct or complex of aspect 87, wherein the TβRII ectodomain sequence comprises an N-terminal deletion up to 14 aas (a Δ14 aa deletion) of SEQ ID NO:119 or SEQ ID NO:120 (see, e.g., sequence in SEQ ID NO:121) and an D118 substitution (e.g., D118A or D118R); or a sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or 118) contiguous aas of any of those TβRII polypeptide sequences.

90. The masked TGF-β construct or complex of aspect 89, further comprising one, two, three, or all four of a F30A, D32N, S52L and/or E55A substitution.

91. The masked TGF-β construct or complex of aspect 87, wherein the TβRII ectodomain sequence comprises an N-terminal deletion up 25 aas (a Δ25 aa deletion) of SEQ ID NO:119 or SEQ ID NO:120 and D118 substitution (e.g., D118A or D118R, see SEQ ID NO:123); or a sequence having at least 60% (e.g., at least 70%, at least 80%, at least 90%, at least 95%, at least 98%, at least 99%, or 100%) aa sequence identity to at least 70 (e.g., at least 80, at least 90, or at least 100) contiguous aas of any of those TβRII polypeptide sequences.

92. The masked TGF-β construct or complex of aspect 91, further comprising one, two, three, or all four of a F30A, D32N, S52L and/or E55A substitution.

93. The masked TGF-β construct or complex of aspect 82, wherein the TβR polypeptide sequence comprises a TβRI ectodomain sequence.

94. The masked TGF-β construct or complex of aspect 93, wherein the TβRI ectodomain sequence comprises an amino acid sequence having at least 60% (e.g., at least 70%, at least 80%, at least 90%, at least 95%, at least 98%, at least 99%, or 100%) aa sequence identity to at least 70 (e.g., at least 80, at least 90, or 93) contiguous aas of SEQ ID NO:115.

95. The masked TGF-β construct or complex of aspect 82, wherein the TβR polypeptide sequence comprises a TβRIII ectodomain sequence.

96. The masked TGF-β construct or complex of aspect 95, wherein the TβRIII ectodomain sequence comprises an amino acid sequence having at least 60% (e.g., at least 70%, at least 80%, at least 90%, at least 95%, at least 98%, at least 99%, or 100%) aa sequence identity to at least 70 (e.g., at least 80, 90, 100, 150, 200, 250, 300, 400, 500 or 600) contiguous aas of (aas 27-787 of the A isoform SEQ ID NO:124 or aas 27-786 of the B isoform SEQ ID NO:125).

97. The masked TGF-β construct or complex of any of aspects 1 to 96, wherein the TGF-β polypeptide sequence comprises an amino acid sequence having at least 60% (e.g., at least 70%, at least 80%, at least 80%, at least 85%, at least 90%, at least 95%, at least 98%, at least 99%, or 100%) aa sequence identity to polypeptide comprising at least 70 (e.g., at least 80, at least 90, at least 100, or at least 110) contiguous aas the mature form of a human TGF-β1 polypeptide, a human TGF-β2 polypeptide, or a human TGF-β3 polypeptide.

98. The masked TGF-β construct or complex of any of aspects 1 to 96, wherein the TGF-β polypeptide sequence is a TGF-β1 polypeptide comprising an amino acid sequence having at least 60% (at least 70%, at least 80%, at least 90%, at least 95%, at least 98%, at least 99%, or 100%) aa sequence identity to at least 70 (e.g., at least 80, at least 90, at least 100, at least 110, or 112) contiguous aas of SEQ ID NO:105 (e.g., aas 279-390 of SEQ ID NO:106).

99. The masked TGF-β construct or complex of any of aspects 1 to 96, wherein the TGF-β polypeptide sequence is a TGF-β1 polypeptide bearing a C77S substitution comprising an amino acid sequence having at least 60% (at least 70%, at least 80%, at least 90%, at least 95%, at least 98%, at least 99%, or 100%) contiguous aa sequence identity to at least 70 (e.g., at least 80, at least 90, at least 100, at least 110, or 112) aas of SEQ ID NO:107.

100. The masked TGF-β construct or complex of any of aspects 1 to 96, wherein the TGF-β polypeptide sequence is a TGF-β2 polypeptide comprising an amino acid sequence having at least 60% (at least 70%, at least 80%, at least 90%, at least 95%, at least 98%, at least 99%, or 100%) aa sequence identity to at least 70 (e.g., at least 80, at least 90, at least 100, at least 110, or 112) contiguous aas of (SEQ ID NO:108) (e.g. aas 302-413 of SEQ ID NO:109).

101. The masked TGF-β construct or complex of any of aspects 1 to 96, wherein the TGF-β polypeptide sequence is a TGF-β2 polypeptide bearing a C77S substitution comprising an amino acid sequence having at least 60% (at least 70%, at least 80%, at least 90%, at least 95%, at least 98%, at least 99%, or 100%) contiguous aas sequence identity to at least 70 (e.g., at least 80, at least 90, at least 100, at least 110, or 112) aas of SEQ ID NO:110.

102. The masked TGF-β construct or complex of any of aspects 1 to 96, wherein the TGF-β polypeptide sequence is a TGF-β3 polypeptide comprising an amino acid sequence having at least 60% (at least 70%, at least 80%, at least 90%, at least 95%, at least 98%, at least 99%, or 100%) aa sequence identity to at least 70 (e.g., at least 80, at least 90, at least 100, at least 110, or 112) contiguous aas of SEQ ID NO:111 (e.g. aas 301-412 of SEQ ID NO:112).

103. The masked TGF-β construct or complex of any of aspects 1 to 96, wherein the TGF-β polypeptide sequence is a TGF-β3 polypeptide bearing a C77S substitution comprising an amino acid sequence having at least 60% (at least 70%, at least 80%, at least 90%, at least 95%, at least 98%, at least 99%, or 100%) aa sequence identity to at least 70 (e.g., at least 80, at least 90, at least 100, at least 110, or 112) contiguous aas of SEQ ID NO:113.

104. The masked TGF-β construct or complex of any of aspects 97-103, where in the TGF-β polypeptide sequence comprises a substitution at one or more of positions 25, 92 and/or 94 of the mature TGF-β polypeptide sequence (see e.g., SEQ ID NO:112 in FIG. 3 and FIG. 4).

105. The masked TGF-β construct or complex of any of aspects 100-101, where in the TGF-β polypeptide sequence comprises a substitution at one or more of positions 25, 92 and/or 94 of the mature TGF-β polypeptide sequence (see e.g., SEQ ID NO:112 in FIG. 3 and FIG. 4).

106. The masked TGF-β construct or complex of any of aspects 97-105 where in the TGF-β polypeptide sequence comprises:

(i) an aa other than Lys or Arg at position 25

(ii) an aa other than Ile or Val at position 92; and/or (iii) an aa other than Lys or Arg at position 94 (e.g., based on SEQ ID NO:108 or SEQ ID NO:110).

107. The masked TGF-β construct or complex of any of aspects 1-106, wherein the masked TGF-β construct or complex has the form of any one of structures A-F in FIG. 1.

108. The masked TGF-β construct or complex of aspect 107, wherein the masked TGF-β construct or complex is a masked TGF-β polypeptide having the form of structure A in FIG. 1.

109. The masked TGF-β polypeptide of aspect 108, comprising at least one (e.g., one, two or more) wt. or variant IL-2 MOD polypeptide sequence.

110. The masked TGF-β construct or complex of aspect 107, wherein the masked TGF-β construct or complex is a masked TGF-β complex having the form of structure B in FIG. 1.

111. The masked TGF-β polypeptide of aspect 110, comprising at least one (e.g., one, two or more) wt. or mutant IL-2 MOD polypeptide sequence.

112. The masked TGF-β construct or complex of aspect 107, wherein the masked TGF-β construct or complex is an interspecific masked TGF-β complex having the form of structure C in FIG. 1.

113. The masked TGF-β polypeptide of aspect 112, comprising at least one (e.g., one, two or more) wt. or mutant IL-2 MOD polypeptide sequence.

114. The masked TGF-β construct or complex of aspect 107, wherein the masked TGF-β construct or complex is an interspecific masked TGF-β complex having the form of structure D or E in FIG. 1.

115. The masked TGF-β polypeptide of aspect 114, comprising at least one (e.g., one, two or more) wt. or mutant IL-2 MOD polypeptide sequence.

116. The masked TGF-β construct or complex of aspect 107, wherein the masked TGF-β construct or complex is an interspecific masked TGF-β complex having the form of structure F in FIG. 1.

117. The masked TGF-β polypeptide of aspect 116, comprising at least one (e.g., one, two or more) wt. or mutant IL-2 MOD polypeptide sequence.

118. The masked TGF-β construct or complex of any of aspects 107-117, wherein:

the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;

the masking polypeptide sequence is a TβRII polypeptide sequence that comprises a wt. TβRII polypeptide sequence (e.g., comprising the sequence of SEQ ID NO:117) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 150, or 154) contiguous aas of the TβRII isoform A ectodomain set forth in SEQ ID NO:117; and wherein the masked TGF-β construct or complex comprises a wt. IL-2 MOD polypeptide sequence (e.g., comprising the sequence of SEQ ID NO:9).

119. The masked TGF-β construct or complex of any of aspects 107-117, wherein:

the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;

the masking polypeptide sequence is a TβRII polypeptide sequence that comprises a wt. TβRII polypeptide sequence (e.g., comprising the sequence of SEQ ID NO:119) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 143) contiguous aas of the TβRII isoform B ectodomain set forth in SEQ ID NO:119; and wherein the masked TGF-β construct or complex comprises a wt. IL-2 MOD polypeptide sequence (e.g., comprising the sequence of SEQ ID NO:9).

120. The masked TGF-β construct or complex of any of aspects 107-117, wherein:

the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;

the masking polypeptide sequence is a TβRII polypeptide sequence that comprises a wt. TβRII polypeptide sequence (e.g., comprising the sequence of SEQ ID NO:120) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, or at least 129) contiguous aas of the TβRII isoform B ectodomain set forth in SEQ ID NO:120; and wherein the masked TGF-β construct or complex comprises a wt. IL-2 MOD polypeptide sequence (e.g., comprising the sequence of SEQ ID NO:9).

121. The masked TGF-β construct or complex of any of aspects 107-117, wherein:

the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;

the masking polypeptide sequence is a TβRII polypeptide sequence that comprises a wt. TβRII polypeptide sequence (e.g., comprising the sequence of SEQ ID NO:117) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 150, or 154) contiguous aas of the TβRII isoform A ectodomain set forth in SEQ ID NO:117; and wherein the masked TGF-β construct or complex comprises a variant IL-2 MOD polypeptide sequence comprising an aa sequence having at least 80% (at least 85%, at least 90%, at least 95%, at least 98%, at least 99%, or 100%) aa sequence identity to at least 80 (e.g., 90, 100, 110, 120, 130 or 133) contiguous aas of SEQ ID NO:9.

122. The masked TGF-β construct or complex of any of aspects 107-117, wherein:
the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;
the masking polypeptide sequence is a TβRII polypeptide sequence that comprises a wt. TβRII polypeptide sequence (e.g., comprising the sequence of SEQ ID NO:119) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 143) contiguous aas of the TβRII isoform B ectodomain set forth in SEQ ID NO:119; and
wherein the masked TGF-β construct or complex comprises a variant IL-2 MOD polypeptide sequence comprising an aa sequence having at least 80% (at least 85%, at least 90%, at least 95%, at least 98%, at least 99%, or 100%) aa sequence identity to at least 80 (e.g., 90, 100, 110, 120, 130 or 133) contiguous aas of SEQ ID NO:9.

123. The masked TGF-β construct or complex of any of aspects 107-117, wherein:
the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;
the masking polypeptide sequence is a TβRII polypeptide sequence that comprises a wt. TβRII polypeptide sequence (e.g., comprising the sequence of SEQ ID NO:120) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, or at least 129) contiguous aas of the TβRII isoform B ectodomain set forth in SEQ ID NO:120; and
wherein the masked TGF-β construct or complex comprises a variant IL-2 MOD polypeptide sequence comprising an aa sequence having at least 80% (e.g., at least 85%, at least 90%, at least 95%, at least 98%, at least 99%, or 100%) aa sequence identity to at least 80 (e.g., 90, 100, 110, 120, 130 or 133) contiguous aas of SEQ ID NO:9.

124. The masked TGF-β construct or complex of any of aspects 121-123, wherein the TGF-β3 polypeptide sequence comprises a C77S substitution.

125. The masked TGF-β construct or complex of any of aspects 121-124, wherein the TβRII polypeptide sequence comprises a N-terminal Δ14 and either a D118A or a D118R sequence modifications, or a N-terminal Δ25 and either a D118A or a D118R sequence modifications.

126. The masked TGF-β construct or complex of any of aspects 121-125, wherein the IL-2 MOD polypeptide sequence comprises an aa substitution at H16 or an aa substitution at F42.

127. The masked TGF-β construct or complex of any of aspects 121-125, wherein the IL-2 MOD polypeptide sequence comprises an aa substitution at H16 and F42.

128. The masked TGF-β construct or complex of any of aspects 125-127, wherein the substitutions at H16 and F42 are selected from the group consisting of: H16A, H16T, F42A, and F42T (e.g., H16A and F42A or H16T and F42A).

129. The masked TGF-β construct or complex of any of aspects 121-128, wherein the IL-2 MOD polypeptide sequence further comprises an N88R aa substitution.

130a. The masked TGF-β construct or complex of any of aspects 121-129a wherein:
the TGF-β3 polypeptide sequence comprises a C77S substitution;
the TβRII polypeptide sequence comprises either N-terminal Δ14 and D118A or D118R sequence modifications or N-terminal Δ25 and D118A or D118R sequence modifications; and
the IL-2 MOD polypeptide sequence comprises an aa substitution at H16 and F42.

130b. The masked TGF-β construct or complex of aspect 130a, wherein the substitutions at H16 and F42 are either an H16A and F42A substitution or an H16T and F42A substitutions.

131. The masked TGF-β construct or complex of any of aspects 1-130b further comprising a wild type or variant MOD polypeptide sequence selected from the group consisting of: PD-L1, FAS-L, IL-1, IL-2, IL-4, IL-6, IL-7, IL-10, IL-15, IL-21 and IL-23.

132. The masked TGF-β construct or complex of any of aspects 1-130b comprising a wild type or variant MOD polypeptide sequence selected from the group consisting of: PD-L1, FAS-L, IL-10.

133. The masked TGF-β construct or complex of any of aspects 1-132, wherein the TGF-β polypeptide/complexes comprises a variant TGF-β polypeptide with reduced affinity for the masking polypeptide (e.g., TGF-β receptor polypeptide) sequence at least 10% less (e.g., at least 20% less, at least 30% less, at least 40% less, at least 50% less, at least 60% less, at least 70% less, at least 80% less, at least 90% less, at least 95% less, or more than 95% less) relative to an otherwise identical wt. TGF-β polypeptide without the sequence variations.

134. The masked TGF-β construct or complex of any of aspects 1-133, wherein the TGF-β polypeptide/complex comprises a TβR polypeptide sequence with one or more sequence variations (e.g., one or more aa deletions, insertions or substitutions) with reduced affinity for the TGF-β polypeptide (at least 10% less, at least 20% less, at least 30% less, at least 40% less, at least 50% less, at least 60% less, at least 70% less, at least 80% less, at least 90% less, at least 95% less, or more than 95% less) relative to the corresponding wt. TβR polypeptide sequence without the sequence variations.

135. The masked TGF-β complex PSM-4033-4039.

136. One or more nucleic acids (e.g., expression vector(s)) encoding a masked TGF-β construct or complex of any of aspects 1-135 or encoding a masked TGF-β complex of any of aspects 4 and 6-135.

137. A method of inducing Treg cells in a mammalian (e.g., a human) subject or a cell, tissue, or bodily fluid thereof, the method comprising administering to a subject one or more masked TGF-β constructs or complexes according to any of aspects 1-135.

138. The method of aspect 137, where at least one of the one or more masked TGF-β constructs or complexes comprises a wt. or variant IL-2 MOD polypeptide sequence.

139. The method of aspect 137, where at least one of the one or more masked TGF-β constructs or complexes comprises (i) a wt. or variant IL-2 MOD polypeptide sequence, and (ii) a wt. or variant PL-L1 polypeptide sequence.

140. The method of any of aspects 137-139, wherein the one or more masked TGF-β constructs or complexes is administered before, during (concurrent or combined administration) or after administration of any one or more of vitamin D (e.g., 1a, 25-dihydroxy vitamin D3 or a vitamin D analog (e.g., vitamin D3), an mTOR inhibitor (e.g., rapamycin), and/or a retinoic acid (e.g., all trans retinoic acid).

141. The method of any of aspects 137-140, wherein the administration leads to an increase in the number of FoxP3+ Treg cells (e.g., any one or more of induced regulatory T cells (iTregs); thymus-derived Treg cells (tTreg), and/or peripheral Treg cells (pTreg)) in a volume of tissue or bodily fluid (e.g., blood or lymph) fluid from a subject relative to the number of those cells either:
(i) before or absent administration of the one or more masked TGF-β constructs or complexes; or
(ii) relative to the amount of the Treg cells in the tissue or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

142. The method of aspect 141, wherein the number of Treg cells (e.g., FoxP3+ cells, iTregs, tTregs, and/or pTregs) increases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of Tregs in a volume of the tissue or the bodily fluid prior to administration of the one or more masked TGF-β constructs or complexes, or relative to the average value of the matched control group that did not receive the one or more masked TGF-β constructs or complexes.

143. A method of inducing Th9 cells a mammalian (e.g., a human) subject or a tissue or bodily fluid thereof, the method comprising administering to the subject one or more masked TGF-β constructs or complexes according to any of aspects 1-134.

144. The method of aspect 143, where at least one of the one or more masked TGF-β constructs or complexes comprises a wt. or variant IL-4 MOD polypeptide sequence.

145. The method of any of aspects 143-144, wherein the administration leads to an increase in the number of Th9 cells in a volume of tissue or bodily fluid (e.g., blood or lymph) fluid from a subject relative to the number of those cells either:
  (i) before or absent administration of the one or more masked TGF-β constructs or complexes; or
  (ii) relative to the amount of Th9 cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

146. The method of aspect 145, wherein the number of Th9 cells increases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of Th9 cells in a volume of the tissue or the bodily fluid prior to administration of the one or more masked TGF-β constructs or complexes, or relative to the average value of the matched control group that did not receive the one or more masked TGF-β constructs or complexes.

147. A method of inducing Th17 cells a mammalian (e.g., a human) subject or a tissue or bodily fluid thereof, the method comprising administering to the subject one or more masked TGF-β constructs or complexes according to any of aspects 1-134.

148. The method of aspect 147, where at least one of the one or more masked TGF-β constructs or complexes comprises a wt. or variant IL-6 MOD polypeptide sequence.

149. The method of any of aspects 147-148, wherein the administration leads to an increase in the number of Th17 cells in a volume of tissue or bodily fluid (e.g., blood or lymph) fluid from a subject relative to the number of those cells either:
(i) before or absent administration of the one or more masked TGF-β constructs or complexes; or
(ii) relative to the amount of Th17 cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

150. The method of aspect 149, wherein the number of Th17 cells increases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of Th17 cells in a volume of the tissue or the bodily fluid prior to administration of the one or more masked TGF-β constructs or complexes, or relative to the average value of the matched control group that did not receive the one or more masked TGF-β constructs or complexes.

151. A method of inducing Thf cells in a mammalian (e.g., a human) subject or a tissue or bodily fluid thereof, the method comprising administering to the subject one or more masked TGF-β constructs or complexes according to any of aspects 1-134.

152. The method of aspect 151, where at least one of the one or more masked TGF-β constructs or complexes comprises at least one wt. or variant IL-21 and/or IL-23 MOD polypeptide sequence.

153. The method of aspect 152, where at least one of the one or more masked TGF-β constructs or complexes comprises at least one wt. or variant IL-21 and at least one wt. or variant IL-23 MOD polypeptide sequence.

154. The method of any of aspects 151-153, wherein the administration leads to an increase in the number of Thf cells in a volume of tissue or bodily fluid (e.g., blood or lymph) fluid from a subject relative to the number of those cells either:
(i) before or absent administration of the one or more masked TGF-β constructs or complexes; or
(ii) relative to the number of Thf in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

155. The method of aspect 154, wherein the number of Thf cells increases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of Thf cells in a volume of the tissue or the bodily fluid prior to administration of the one or more masked TGF-β constructs or complexes, or relative to the average value of the matched control group that did not receive the one or more masked TGF-β constructs or complexes.

156. A method of inhibiting the action of Th1 cells in a mammalian subject (or a tissue or bodily fluid thereof), the method comprising administering to the subject one or more masked TGF-β constructs or complexes according to any of aspects 1-134.

157. The method of aspect 156, where at least one of the one or more masked TGF-β constructs or complexes comprises a wt. or variant IL-4 MOD polypeptide sequence.

158. The method of any of aspects 156-157, wherein the administration leads to an inhibition of Th1 mediated release of interferon γ and/or TNF into (or resulting concentration in) a volume of tissue or bodily fluid (e.g., blood or lymph) fluid from a subject relative to amount:
(i) before or absent administration of the one or more masked TGF-β constructs or complexes; or (ii) relative to the amount of interferon γ and/or TNF in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

159. The method of aspect 149, wherein the amount of interferon γ and/or TNF in a volume of tissue or bodily fluid is decreased by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the amount of interferon γ and/or TNF in a volume of the tissue or the bodily fluid prior to administration of the one or more masked TGF-β constructs or complexes, or relative to the average value of the matched control group that did not receive the one or more masked TGF-β constructs or complexes.

160. A method of inhibiting the action and/or proliferation of Th2 cells in a mammalian (e.g., a human) subject or a tissue or bodily fluid thereof, the method comprising administering to the subject one or more masked TGF-β constructs or complexes according to any of aspects 1-134.

161. The method of aspect 160, wherein the administration leads to an inhibition of Th2 mediated release of IL-4, IL-5, and/or IL-13 into (or resulting concentration in) a volume of tissue or bodily fluid (e.g., blood or lymph) fluid from a subject relative to amount:

(i) before or absent administration of the one or more masked TGF-β constructs or complexes; or (ii) relative to the amount in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

162. The method of aspect 161, wherein the amount of IL-4, IL-5, and/or IL-13 in a volume of tissue or bodily fluid is decreased by at least 5% (e.g., at least 10%, at least 15%, at least 20%, at least 25%, at least 30%, at least 40%, at least 50%, at least 60%, at least 70%, at least 80%, or at least 90%) relative to the amount of IL-4, IL-5, and/or IL-13 in a volume of the tissue or the bodily fluid prior to administration of the one or more masked TGF-β constructs or complexes, or relative to the average value of IL-4, IL-5, and/or IL-13 in the tissue, or the bodily fluid from the matched control group that did not receive the one or more masked TGF-β constructs or complexes.

163. A method of inhibiting the action of type II innate lymphoid cells (ILC2 cells) in a mammalian (e.g., a human) subject or a tissue or bodily fluid thereof, the method comprising administering to the subject one or more masked TGF-β constructs or complexes according to any of aspects 1-134, wherein at least one of the one or more masked TGF-β constructs or complexes optionally comprise one or more independently selected wt. or variant IL-10 polypeptide sequences (e.g., a monomeric form such as IL-10M1).

164. The method of aspect 160, wherein the administration leads to an inhibition of ILC2 cells mediated release of IL-5, and/or IL-13 into (or resulting concentration in) a volume of tissue or bodily fluid (e.g., blood or lymph) fluid from a subject relative to amount:

(i) before or absent administration of the treatment with the one or more masked TGF-β constructs or complexes; or (ii) relative to the amount in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

165. The method of aspect 164, wherein the amount of IL-5, and/or IL-13 in a volume of tissue or bodily fluid is decreased by at least 5% (e.g., at least 10%, at least 15%, at least 20%, at least 25%, at least 30%, at least 40%, at least 50%, at least 60%, at least 70%, at least 80%, or at least 90%) relative to the amount of IL-5 and/or IL-13 in a volume of tissue, or the bodily fluid prior to administration of the one or more masked TGF-β constructs or complexes, or relative to the average value of IL-5 and/or IL-13 in the volume of tissue or the bodily fluid from the matched control group that did not receive the one or more masked TGF-β constructs or complexes.

166. The method of aspect 164, wherein the amount of IL-5, and/or IL-13 in a volume of tissue or bodily fluid is decreased by at least 25%, relative to the amount of IL-5 and/or IL-13 in a volume of tissue, or the bodily fluid prior to administration of the one or more masked TGF-β constructs or complexes, or relative to the average value of IL-5 and/or IL-13 in the volume of tissue or the bodily fluid from the matched control group that did not receive the one or more masked TGF-β constructs or complexes.

167. A method of supporting the development and/or survival of invariant natural killer T (iNKT) cells in a mammalian (e.g., a human) subject, or a tissue or bodily fluid thereof, the method comprising administering to the subject one or more masked TGF-β constructs or complexes according to any of aspects 1-134.

168. The method of aspect 167, where at least one of the one or more masked TGF-β constructs or complexes comprises at least one wt. or variant MOD polypeptide sequence.

169. The method of any of aspects 167-168, wherein the administration leads to an increase in the number of iNKT cells in a volume of tissue or bodily fluid (e.g., blood or lymph) fluid from a subject relative to the number of those cells either:

(i) before or absent administration of the one or more masked TGF-β constructs or complexes; or (ii) relative to the number of iNKT cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

170. The method of aspect 169, wherein the number of iNKT cells increases in a volume of tissue or bodily fluid by at least 5% (e.g., at least 10%, at least 15%, at least 20%, at least 25%, at least 30%, at least 40%, at least 50%, at least 60%, at least 70%, at least 80%, or at least 90%) relative to the number of iNKT cells in a volume of the tissue or the bodily fluid prior to administration of the one or more masked TGF-β constructs or complexes, or relative to the average value of the matched control group that did not receive the one or more masked TGF-β constructs or complexes.

171. The method of aspect 169, wherein the number of iNKT cells increases in a volume of tissue or bodily fluid by at least 25 relative to the number of iNKT cells in a volume of the tissue or the bodily fluid prior to administration of the one or more masked TGF-β constructs or complexes, or relative to the average value of the matched control group that did not receive the one or more masked TGF-β constructs or complexes.

172. A method of blocking an increase in the number of CD4+ T cells or reducing the number of CD4+ T cells in a mammalian (e.g., a human) subject or a tissue or bodily fluid thereof, the method comprising administering to the subject one or more masked TGF-β constructs or complexes according to any of aspects 1-134.

173. The method of aspect 172, where at least one of the one or more masked TGF-β constructs or complexes comprises at least one wt. or variant MOD polypeptide sequence in addition to the TGF-β polypeptide sequence.

174. The method of any of aspects 172-173, wherein the administration leads to a decrease in the number of CD4+ T cells in a volume of tissue or bodily fluid (e.g., blood or lymph) fluid from a subject relative to the number of those cells either:

(i) before or absent administration of the one or more masked TGF-β constructs or complexes; or (ii) relative to the number of CD4+ T cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

175. The method of aspect 174, wherein the number of CD4+ cells decreases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of CD4+ cells in a volume of the tissue or the bodily fluid prior to administration of the one or more masked TGF-β constructs or complexes, or relative to the average value of the matched control group that did not receive the one or more masked TGF-β constructs or complexes.

176. The method of aspect 174, wherein the number of CD4+ cells decreases in a volume of tissue or bodily fluid by at least 25% relative to the number of CD4+ cells in a volume of the tissue or the bodily fluid prior to administration of the one or more masked TGF-β constructs or complexes, or relative to the average value of the matched control group that did not receive the one or more masked TGF-β constructs or complexes.

177. A method of blocking an increase in the number of CD8+ T cells or reducing the number of CD4+ T cells in a mammalian (e.g., a human) subject or a tissue or bodily fluid thereof, the method comprising administering to the subject one or more masked TGF-β constructs or complexes according to any of aspects 1-134.

178. The method of aspect 172, where at least one of the one or more masked TGF-β constructs or complexes comprises at least one wt. or variant MOD polypeptide sequence in addition to the TGF-β polypeptide sequence.

179. The method of any of aspects 172-173, wherein the administration leads to a decrease in the number of CD8+ T cells in a volume of tissue or bodily fluid (e.g., blood or lymph) fluid from a subject relative to the number of those cells either:

(i) before or absent administration of the one or more masked TGF-β constructs or complexes; or (ii) relative to the number of CD8+ T cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

180. The method of aspect 174, wherein the number of CD8+ cells decreases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of CD8+ cells in a volume of the tissue or the bodily fluid prior to administration of the one or more masked TGF-β constructs or complexes, or relative to the average value of the matched control group that did not receive the one or more masked TGF-β constructs or complexes.

181. A method of providing treatment or prophylaxis of a wound, an allergic reaction, a disease or disorder, the method comprising administering to a subject (e.g., a human) in need thereof either (i) one or more independently selected masked TGF-β constructs or complexes according to any of aspects 1-134, and/or (ii) one more nucleic acids encoding the one or more independently selected masked TGF-β constructs or complexes according to any of aspects 1-134.

182. The method of aspect 181, wherein at least one of the one or more masked TGF-β constructs or complexes comprises at least one (e.g., at least two, or at least three) independently selected wt. or variant IL-2 MOD polypeptide sequences.

183. The method of aspect 182, wherein the independently selected wt. or variant IL-2 MOD polypeptide comprises the IL-2 polypeptide of SEQ ID NO:9 or a variant thereof.

184. The method of aspect 183, wherein the independently selected variant IL-2 MOD polypeptide sequence comprises a sequence having:

(i) at least 80% (e.g., at least 85%, at least 90%, at least 95%, at least 98%, or at least 99%, aa sequence identity to at least 80 (e.g., at least 90, 100, 110, 120, 130 or 133) contiguous aas of SEQ ID NO:9; or (ii) at least 80% (e.g., at least 85%, at least 90%, at least 95%, at least 98%, or at least 99%) aa sequence identity to at least 80 (e.g., at least 90, 100, 110, 120, 130 or 133) contiguous aas of any of SEQ ID NOs: 15-27.

185. The method of any one of aspects 182-184, wherein the independently selected variant IL-2 MOD polypeptide sequence comprises a substitution at any one, two, or all three of N88, F42 and/or H16.

186. The method of any one of aspects 182-185, wherein the independently selected variant IL-2 MOD polypeptide sequence comprises a substitution or pair of substitutions selected from the group consisting of: (i) F42A; (ii) F42T; (iii) H16A; (iv) H16T; (v) F42A and H16A; (vi) F42T and H16A; (vii) F42A and H16T; or (viii) F42T and H16T substitutions.

187. The method of any one of aspects 181-186, wherein the masked TGF-β constructs or complexes comprise at least one (e.g., at least two) independently selected wt. or variant PD-L1 polypeptide sequences.

188. The method of aspect 187, wherein the independently selected variant PD-L1 polypeptide sequence comprises a polypeptide sequences having at least 80% (e.g., at least 85%, at least 90%, at least 95%, at least 98%, or at least 99%) aa sequence identity to at least 170 contiguous aa (e.g., at least 180, 190 or 200 contiguous aa) of SEQ ID NO:2.

189. The method of any one of aspects 181-188, wherein at least one of the one or more masked TGF-β polypeptides comprise an independently selected wt. or variant IL-10 polypeptide sequence (e.g., a monomeric isomer such as IL-10M1).

190. The method of aspect 189, wherein the independently selected wt. or variant IL-10 polypeptide sequence comprise a polypeptide sequence with at least 80% (at least 85%, at least 90%, at least 95%, at least 98%, or at least 99%) aa sequence identity to at least 50 contiguous aa (e.g., at least 60, at least 70, at least 80, at least 90, at least 100, at least 110, at least 120, at least 130, at least 140, at least 150, or at least 160) contiguous aa of SEQ ID NOs: 50 or 51 (e.g. which have at least one aa substitution, deletion or insertion when the sequence is a variant IL-10 sequence); and wherein variant IL-10 polypeptide sequence optionally comprises a 5-7 aa insertion between N49 and K50 of SEQ ID NO:51, or at the equivalent location in SEQ ID NOs:49 or 50 (e.g., IL-10M1 GGGSGG inserted into SEQ ID NO:51 between aa 49 and aa 50).

191. The method of any one of aspects 181-190, wherein at least one of the independently selected masked TGF-β constructs or complexes comprise an independently selected wt. or variant FasL polypeptide sequence.

192. The method of aspect 191, wherein the independently selected wt. or variant FasL polypeptide sequence comprise a polypeptide sequence with at least 80% (e.g., at least 85%, at least 90%, at least 95%, at least 98%, or at least 99%) aa sequence identity to at least 50 contiguous aa (e.g., at least 60, at least 70, at least 80, at least 90, at least 100, at least 110, at least 120, at least 140, at least 160, or at least 180 contiguous aa) of SEQ ID NO:144 (e.g., which have at least one aa substitution, deletion or insertion).

193. The method of any one of aspects 181-192, wherein the one or more masked TGF-β constructs or complexes is administered before, concurrently, combined with, or following administration of any one, two or all three of vitamin D (e.g., 1 α,25-dihydroxy vitamin D3), retinoic acid (e.g., all trans retinoic acid), and/or rapamycin.

194. The method of any one of aspects 181-193, wherein the autoimmune disease is selected from the group consisting of: Addison's disease, alopecia areata, ankylosing spondylitis, autoimmune encephalomyelitis, autoimmune hemolytic anemia, autoimmune hepatitis, autoimmune-associated infertility, autoimmune thrombocytopenic purpura, bullous pemphigoid, celiac disease, Crohn's disease, Goodpasture's syndrome, glomerulonephritis (e.g., crescentic glomerulonephritis, proliferative glomerulonephritis), Grave's disease, Hashimoto's thyroiditis, mixed connective tissue disease, multiple sclerosis, myasthenia gravis (MG), pemphigus (e.g., pemphigus vulgaris), pernicious anemia, polymyositis, psoriasis, psoriatic arthritis, rheumatoid arthritis, scleroderma, Sjögren's syndrome, systemic lupus erythematosus (SLE), type 1 diabetes (T1D), vasculitis, and vitiligo.

195. The method of any of aspects 181-193, wherein the autoimmune disease is T1D or celiac disease.

196. The method of any of aspects 181-193, wherein the autoimmune disease is other than T1D or celiac disease.

197. The method of any one of aspects 181-193, wherein the method is a method of treatment or prophylaxis of an allergic reaction.

198. The method of aspect 197 where the allergic reaction is a reaction to a peanut, tree nut, plant pollens, latex, bee venom or wasp venom allergen.

199. The method of any one of aspects 181-190, wherein the method is a method of providing treatment or prophylaxis for a burn or a wound 200. The method of aspect 199, wherein the wound is an abrasion, avulsion, incision, laceration, or puncture of the epidermis or mucosa.

201. The method of aspect 200, wherein the i) one or more independently selected masked TGF-β constructs or complexes according to any of aspects 1-134, and/or (ii) one more nucleic acids encoding the one or more independently selected masked TGF-β constructs or complexes according to any of aspects 1-134, is administered before, during and/or after formation of the wound.

202. The method of any of aspects 199-201, wherein the burn and/or wound occurs during, or is the result of, a surgical or other medical procedure.

203. The method of any of aspects 199-202, wherein one or more independently selected masked TGF-β constructs or complexes is administered to the site of the wound or burn.

204. The method of any of aspects 199-203, wherein administration of a masked TGF-β construct or complex (an effective amount) and/or one or more nucleic acids (e.g., recombinant expression vectors) encoding the masked TGF-β construct or complex speeds wound closure (reduce time until closure), reduce healing time, or to reduce scar formation relative to an untreated subject or wound.

205. The method of aspect 181, wherein at least one of the masked TGF-β constructs or complexes comprises at least one (e.g., at least two, or at least three) independently selected wt. (e.g., SEQ ID NO:29 or SEQ ID NO:31) or variant IL-4 polypeptide sequences.

206. The method of aspect 205, wherein the variant IL-4 polypeptide sequences comprise a polypeptide sequences having at least 80%, at least 85%, at least 90%, at least 95%, at least 98%, or at least 99% aa sequence identity to at least 80 contiguous aa (e.g., at least 100, or 110 contiguous aa) of SEQ ID NO:29 or SEQ ID NO:31 (e.g., which have at least one aa substitution, deletion or insertion).

207. The method of any of aspects 205-206, wherein the disease or disorder is a helminth infection.

208. The method of aspect 181, wherein at least one of the masked TGF-β constructs or complexes comprises at least one (e.g., at least two, or at least three) independently selected wt. (e.g., the polypeptide of SEQ ID NO:35) or variant IL-6 polypeptide sequences.

209. The method of aspect 208, wherein the variant IL-6 polypeptide sequences comprise a polypeptide sequences having at least 80%, at least 85%, at least 90%, at least 95%, at least 98%, or at least 99% aa sequence identity to at least 80 contiguous aa (e.g., at least 100, or 110 contiguous aa) of SEQ ID NO:35 (e.g., which has at least one aa substitution, deletion or insertion).

210. The method of any of aspects 204-209, wherein the disease or disorder is a bacterial and/or fungal infection (e.g., in the gut).

211. The method of aspect 181, wherein at least one of the masked TGF-β constructs or complexes comprises at least one (e.g., at least two, or at least three) independently selected wt. or variant IL-21 and/or IL-23 polypeptide sequences.

212. The method of aspect 209, wherein the at least one (e.g., at least two) IL-21 MOD polypeptide sequence comprises (i) a polypeptide of sequence of SEQ ID NO:58 or 60) or (ii) a polypeptide sequence having at least 80% (e.g., at least 85%, at least 90%, at least 95%, at least 98%, or at least 99%) aa sequence identity to at least 50 (e.g., at least 60, at least 70, at least 80, at least 90, at least 100, or at least 110) contiguous aa of SEQ ID NO:58 or 60, and which have at least one aa substitution, deletion or insertion.

213. The method of aspect 211 or 212, wherein the at least one (e.g., at least two) IL-23 MOD polypeptide sequence comprises (i) a polypeptide of sequence of SEQ ID NO:63 or 65) or (ii) a polypeptide sequence having at least 80% (e.g., at least 85%, at least 90%, at least 95%, at least 98%, or at least 99%) aa sequence identity to at least 50 (e.g., at least 60, at least 70, at least 80, at least 90, at least 100, at least 110, at least 120, at least 140, at least 160, at least 180, at least 200, at least 220, at least 240, at least 260, at least 280, at least 300, at least 320, or at least 340) contiguous aas of SEQ ID NO:63 and/or 65, and which have at least one aa substitution, deletion or insertion.

214. The method of any of aspects 211-213, wherein the disease or disorder is an inability to produce high affinity antibodies or sufficient amounts of high affinity antibodies.

215. A method of inducing tolerance a mammalian subject, the method comprising administering to the subject:
(i) one or more masked TGF-β constructs or complexes, or one or more nucleic acids (e.g., expression vector(s)) encoding a masked TGF-β construct or complex according to any of aspects 1-β6,
(ii) one or more masked TGF-β constructs or complexes, or one or more nucleic acids (e.g., expression vector(s)) encoding a masked TGF-β construct or complex according to any of aspects 1-β6, wherein at least one of the one or more masked TGF-β constructs or complexes comprises an wt. or variant IL-2 polypeptide sequence;
(iii) one or more masked TGF-β constructs or complexes, or one or more nucleic acids (e.g., expression vector(s)) encoding a masked TGF-β construct or complex according to any of aspects 1-β6, wherein at least one of the one or more masked TGF-β constructs or complexes comprises an wt. or variant FasL polypeptide sequence; or
(iv) one or more masked TGF-β constructs or complexes, or one or more nucleic acids (e.g., expression vector(s)) encoding a masked TGF-β construct or complex according to any of aspects 1-β6, wherein at least one of the one or more masked TGF-β constructs or complexes comprises an wt. or variant IL-2 polypeptide sequence, and wherein at least one of the one or more masked TGF-β constructs or complexes comprises an wt. or variant FasL polypeptide sequence or a wt. or variant IL-1β polypeptide sequence.

216. The method of any of aspects 137-215, further comprising administering a non-steroidal anti-inflammatory drug (NSAID) (e.g., Cox-1 and/or Cox-2 inhibitors such as Celecoxib, Diclofenac, Diflunisal, Etodolac, Ibuprofen, Indomethacin, Ketoprofen, and Naproxen) before, during (concurrent or combined administration) or after administering the one or more masked TGF-β constructs or complexes.

217. The method of any of aspects 137-216, further comprising administering a Corticosteroid (e.g., Cortisone, Dexamethasone, Hydrocortisone, Ethamethasoneb, Fludrocortisone, Methylprednisolone, Prednisone, Prednisolone and Triamcinolone) before, during (concurrent or combined administration) or after administering the one or more masked TGF-β constructs or complexes.

218. The method of any of aspects 137-217, further comprising administering an agent that blocks one or more actions of tumor necrosis factor alpha (e.g., an anti-TNF alpha such as golimumab, infliximab, certolizumab, adalimumab or a TNF alpha decoy receptor such as etanercept) before, during (concurrent or combined administration) or after administering the one or more masked TGF-β constructs or complexes.

219. The method of any of aspects 137-218, further comprising administering an agent that binds to the IL-1 receptor competitively with IL-1 (e g, anakinra) before, during (concurrent or combined administration) or after administering the one or more masked TGF-β constructs or complexes. This aspect can be subject to the proviso that an agent that binds to the IL-1 receptor competitively with IL-1 is not administered if any of the one or more masked TGF-β constructs or complexes administered to the subject comprises an IL-1 polypeptide.

220. The method of any of aspects 137-219, further comprising administering an agent that binds to the IL-6 receptor and inhibits IL-6 from signaling through the receptor (e.g., tocilizumab) before, during (concurrent or combined administration) or after administering the one or more masked TGF-β constructs or complexes. This aspect can be subject to the proviso that an agent that binds to the IL-6 receptor is not administered if any of the one or more masked TGF-β constructs or complexes administered to the subject comprises an IL-6 polypeptide.

221. The method of any of aspects 137-220, further comprising administering an agent that binds to CD80 or CD86 receptors and inhibits T cell proliferation and/or B cell immune response (e.g., abatacept) before, during (concurrent or combined administration) or after administering the one or more masked TGF-β constructs or complexes.

222. The method of any of aspects 137-221, further comprising administering an agent that binds to CD20 resulting in B-Cell death (e.g., rituximab) before, during (concurrent or combined administration) or after administering the one or more masked TGF-β constructs or complexes.

223. The method of any of aspects 137-222, wherein the mammalian subject is selected from: human, bovine canine, feline, rodent, murine, caprine, simian, ovine, equine, lappine, porcine, etc. subjects.

224. The method of any of aspects 137-223, wherein the subject is a human (e.g., a human patient or a human subject in need of treatment or prophylaxis).

225. A method of delivering a TGF-β polypeptide or a TGF-β polypeptide and an immunomodulatory polypeptide (MOD) to a cell, comprising contacting the cell with (i) a one or more masked TGF-β constructs or complexes of any one of aspects 1-134, (ii) one or more masked TGF-β constructs or complexes comprising one or more independently selected wt. or variant MOD sequences of any one of aspects 1-134, or (iii) one or more nucleic acids encoding one or more masked TGF-β constructs or complexes of any one of aspects 135-β6 optionally encoding one or more independently selected wt. or variant MODs.

226. A method of producing cells expressing a masked TGF-β construct or complex, the method comprising introducing one or more nucleic acids (e.g., expression vector(s)) encoding a masked TGF-β construct or complex of any of aspects 1-134 into the cells (e.g., a mammalian cell in vitro), and optionally selecting for cells comprising all or part of the one or more nucleic acids unintegrated and/or integrated into at least one cellular chromosome (e.g., antibiotic selection followed by analysis to determine if any of the one or more nucleic acids had integrated into a cell chromosome).

227. The method of aspect 224, wherein the cell is a cell of a mammalian cell line selected from the HeLa cells, CHO cells, 293 cells, Vero cells, NIH 3T3 cells, Huh-7 cells, BHK cells, PC12, COS cells, COS-7 cells, RAT1 cells, mouse L cells, human embryonic kidney (HEK) cells, and HLHepG2 cells.

228. A cell transiently or stably expressing a masked TGF-β construct or complex prepared by the method of aspect 226 or 227.

229. The cell of aspect 228, wherein cells express from about 25 to about 350 mg/liter or more (e.g., from about 25 to about 100, from about 100 to about 200, from about 200 to about 300, from about 300 to about 350 mg/liter, or greater than 350 mg/liter) of masked TGF-β construct or complex without substantial reduction (less than a 5%, 10%, or 15% reduction) in viability relative to otherwise identical cells not expressing the masked TGF-β construct or complex.

230. The method of any of aspects β8-142, wherein the administering of the masked TGF-β constructs or complexes comprising a wt. or variant IL-2 MOD polypeptide sequence results in modulation of one or more T cells (e.g., inflammatory T cell such as Th1, Th2, Th17 and/or Th22 cells) in the subject, cell, tissue, or bodily fluid.

231. The method of aspect 230, wherein the one or more T cells are Th1 cells and modulation is assessed by a reduction in the number of Th1 cells, a reduction in the expression or secretion of interferon γ by the Th1 cells, or the level of interferon γ in the subject, cell, tissue, or bodily fluid:
(i) before or absent administration of the one or more masked TGF-β constructs or complexes; or
(ii) relative to the amount of interferon γ in the subject, cell, tissue, or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

232. The method of aspect 230, wherein the one or more T cells are Th2 cells, and modulation is assessed by a reduction in the number of Th2 cells, a reduction in the expression or secretion of IL-4, IL-5, and/or IL-13 by the Th2 cells, or the level of L-4, IL-5, and/or IL-13 in the subject, cell, tissue, or bodily fluid:

(i) before or absent administration of the one or more masked TGF-β constructs or complexes; or (ii) relative to the amount of L-4, IL-5, and/or IL-13 in the subject, cell, tissue, or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

233. The method of aspect 230, wherein the one or more T cells are Th17, cell and modulation is assessed by a reduction in the number of Th17 cells, a reduction in the expression or secretion of IL-17 and/or IL-22 by the Th17 cells, or the level of IL-17 and/or IL-22 in the subject, cell, tissue, or bodily fluid:

(i) before or absent administration of the one or more masked TGF-β constructs or complexes; or (ii) relative to the amount of IL-17 and/or IL-22 in the subject, cell, tissue, or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

234. The method of aspect 230, wherein the one or more T cells are Th22, cell and modulation is assessed by a reduction in the number of Th22 cells, a reduction in the expression or secretion of at least two or IL-22, IL-13 and/or TNF-alpha by the Th22 cells, or the level of IL-22, IL-13 and/or TNF-alpha in the subject, cell, tissue, or bodily fluid:

(i) before or absent administration of the one or more masked TGF-β constructs or complexes; or (ii) relative to the amount of IL-22, IL-13, and TNF-alpha in the subject, cell, tissue, or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

235. The method of aspect 234, wherein the method further comprises assessing the expression, secretion of one or more of IL-4, IL-17 and/or interferon γ, or the levels one or more of IL-4, IL-17 and/or interferon γ in the subject, cell, tissue, or bodily fluid.

236. The method of any of aspects 230-235, wherein the T cells are bystander T cells.

237. The method of any of aspects 230-236, wherein the one or more masked TGF-β constructs or complexes is administered before, during (concurrent or combined administration) or after administration of any one or more of vitamin D (e.g., 1α, 25-dihydroxy vitamin D3 or a vitamin D analog (e.g., vitamin D3), an mTOR inhibitor (e.g., rapamycin), and/or a retinoic acid (e.g., all trans retinoic acid).

238. The method of any of aspects 230-237 wherein the masked-TGF-β constructs or complexes comprising a wt. or variant IL-2 MOD has a structure set forth in FIG. 1 structures A to F.

239. The method of aspect 238, wherein the Fc region lacks immunoglobulin effector sequences (reduced complement component 1q ("C1q") binding compared to the wt. protein, and accordingly a reduction in the ability to participate in complement-dependent cytotoxicity).

VI. EXAMPLES

The following examples are put forth so as to provide those of ordinary skill in the art with a more complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); μl, microliter(s); pl, picolitre(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); wt., wild type; and the like.

A. Example 1

1 Single Polypeptide Chain Masked TGF-β Constructs

Figure 7G:
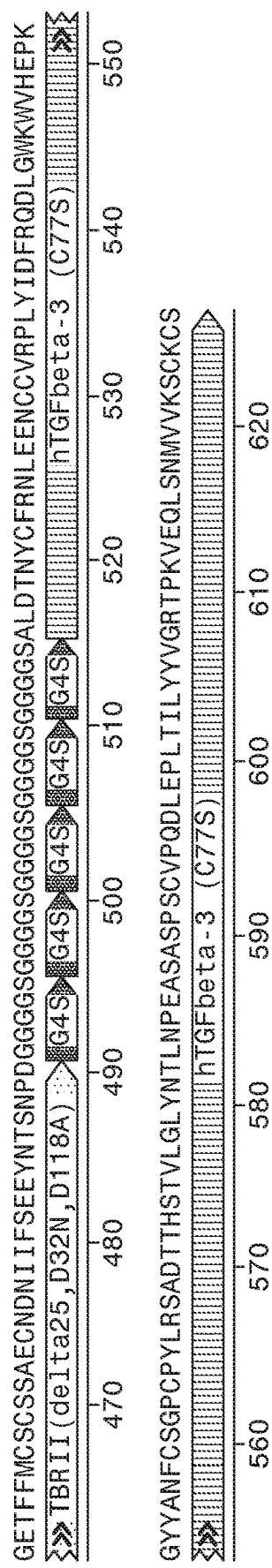
Figure 7H:
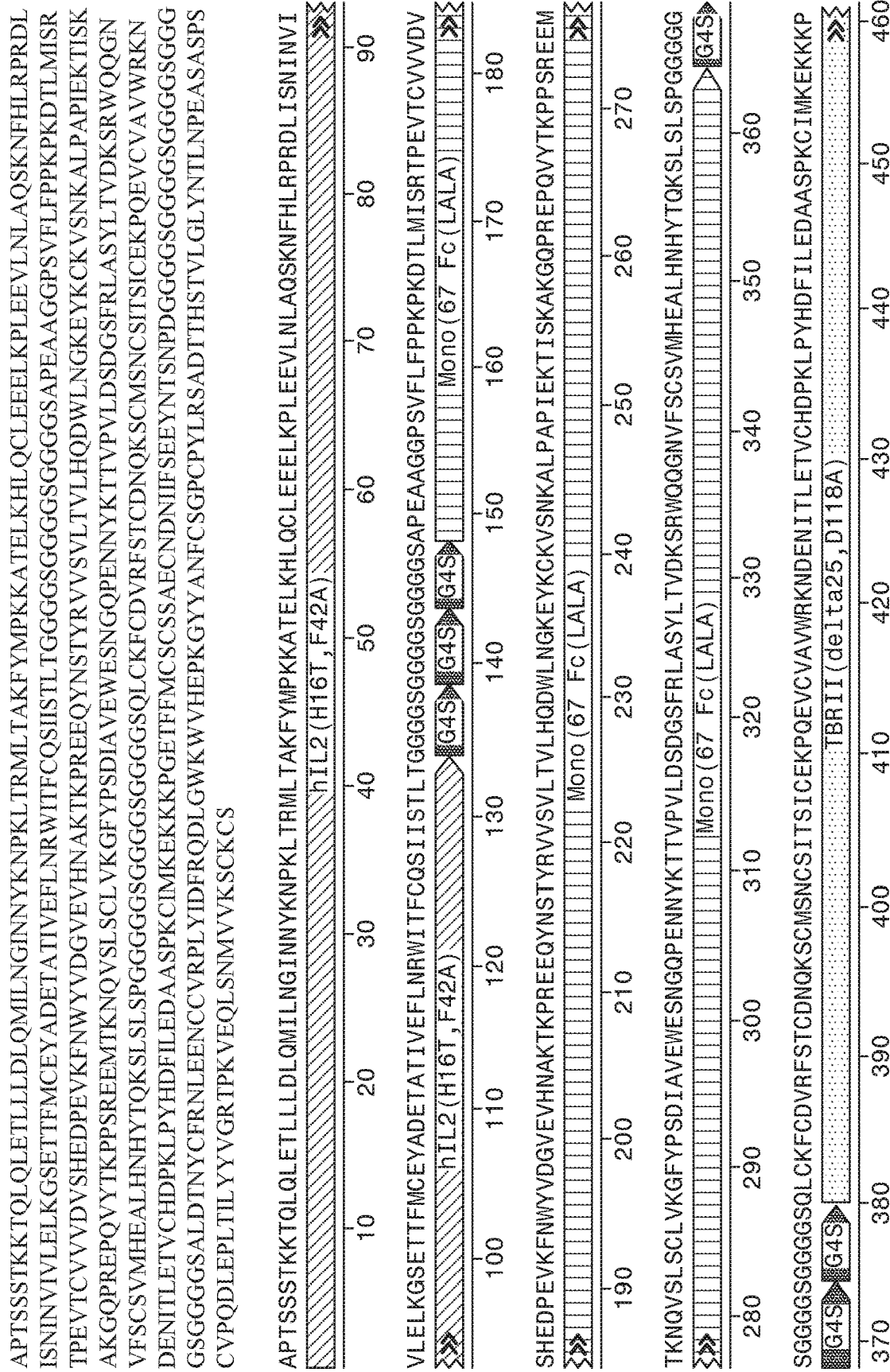
Figure 7H:
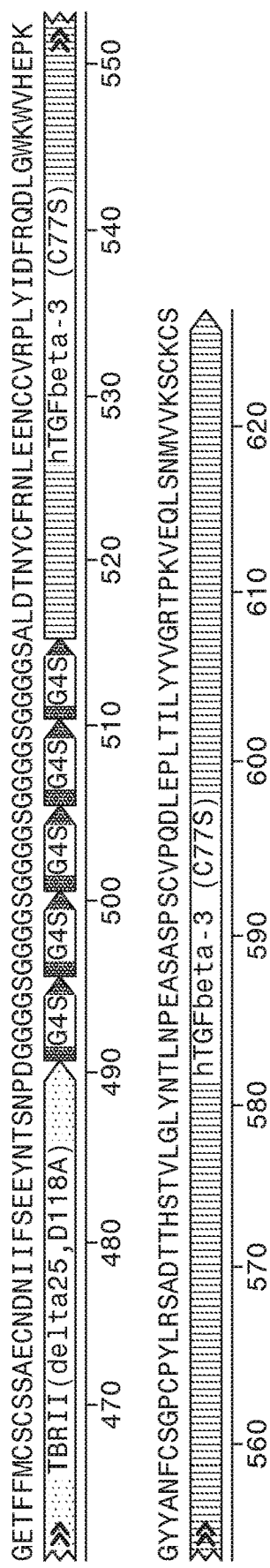
Figure 7I:
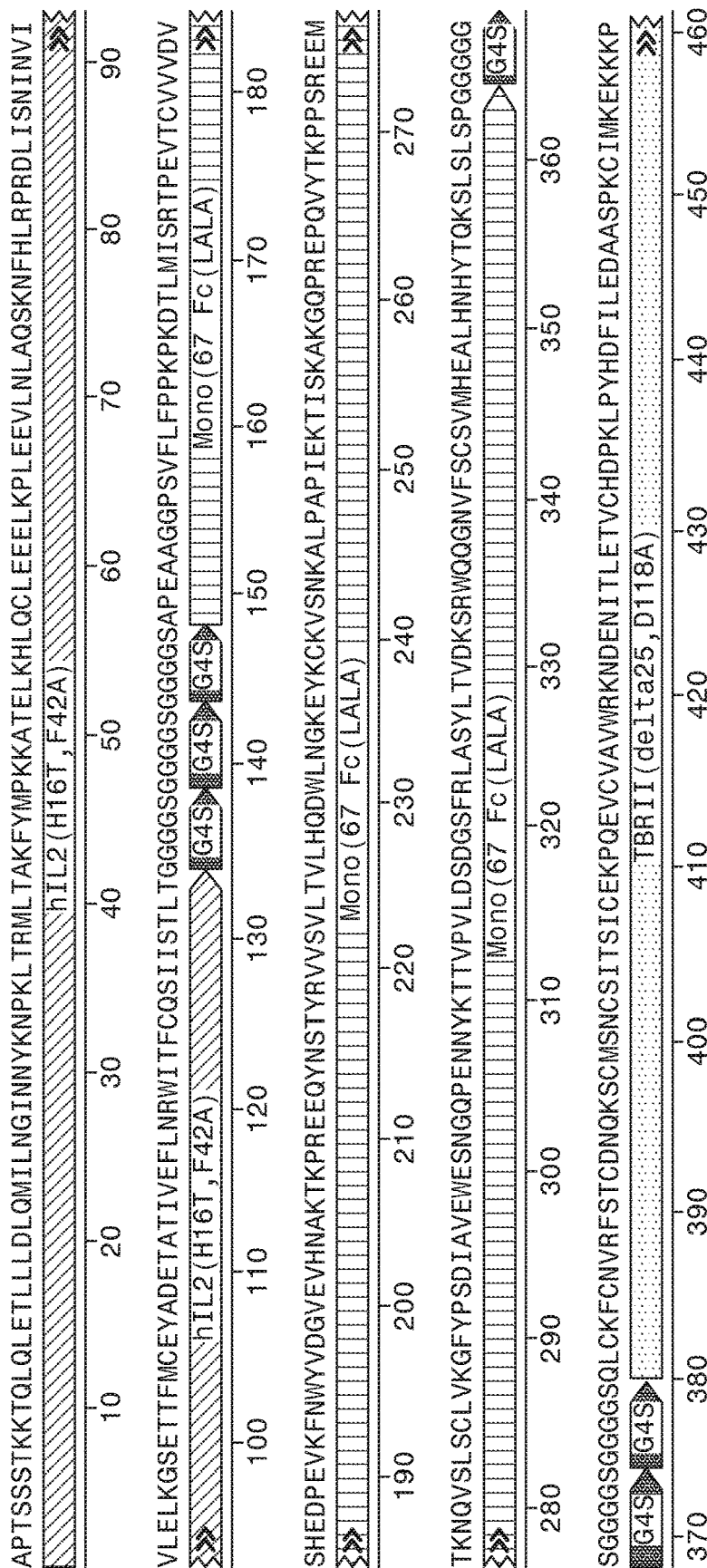
Figure 7I:
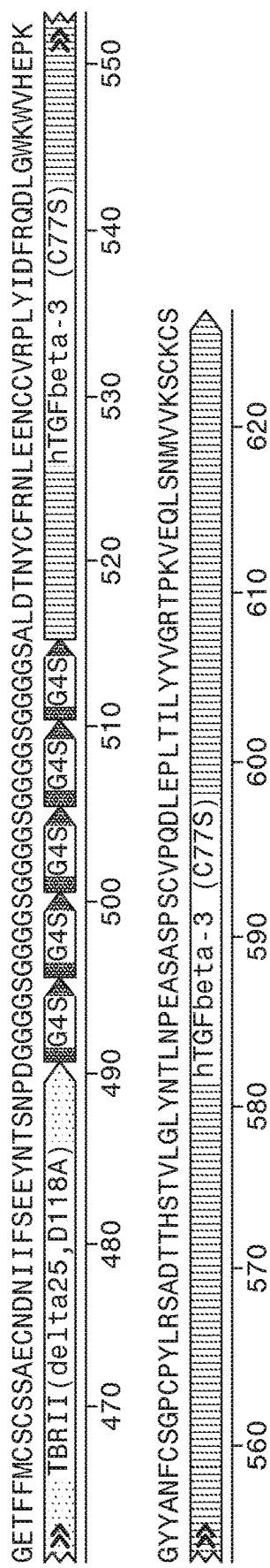

The stable expression of an intact single polypeptide chain presenting a masked TGF-β protein was demonstrated by preparing a nucleic acid encoding the desired components, and driving expression using an expression vector for a mammalian cell. The nucleic acids encode polypeptides comprising, from N- to C-terminus: a MOD polypeptide sequence (e.g., a wt. IL-2 polypeptide sequence, such as SEQ ID NO:20, or a variant of that IL-2 polypeptide bearing substitutions at H16 and/or F42; an IgG1 Fc scaffold polypeptide sequence bearing L234A and L235A substitutions along with substitutions that prevent Fc dimerization, a type II TGF-β receptor (e.g., a TGF-βRII B isoform polypeptide sequence with D32N and/or D118A sequence variations), and a TGF-β polypeptide sequence (e.g. wt. TGF-β3 or a C77S sequence variant). A schematic having the overall structure of the expressed proteins is shown in FIG. 1 as structure A, one example of which is shown in FIG. 7A as construct 3470 (SEQ ID NO:146), another example of such a polypeptide's aa sequence is construct No. 3472 aligned with the elements labeled is shown in FIG. 7G as SEQ ID NO:157. After constructing the nucleic acid in a plasmid suitable for mammalian protein expression (e.g., in Chinese Hamster Ovary or CHO cells) the proteins were expressed and purified using protein A and size separation chromatography.

In addition to the construction and isolation of constructs 3470 and 3472 two additional single polypeptide chain masked TGF-β constructs, 3466 and 3468 were prepared. Construct 3470, along with constructs 3472, 3466, and 3468 (numbered as (i) to (iii) below) demonstrate the feasibility of preparing single chain masked TGF-β proteins, that do not substantially dimerize, particularly through classical Fc association. The polypeptides comprise, from N- to C-terminus the following polypeptide sequences:
  (i) wt. IL-2-IgG Fc-TβRII$_{A25}$(D32N, D118A) substitutions-TGF-β3 (C77S) (FIG. 7G, Construct No. 3472) SEQ ID NO:157;
  (ii) IL-2 (H16T, F42A)-IgG Fc-TβRII A25(D118)-TGF-β3 (C77S) (FIG. 7H, Construct No. 3466) SEQ ID NO:158; and
  (iii) IL-2 (H16T, F42A)-IgG Fc-TβRII$_{A25}$(D32N, D118)-TGF-β3 (C77S) (FIG. 7I, Construct No. 3468) SEQ ID NO:159.

As indicated above, single polypeptide chain masked TGF-β constructs may comprise substitutions that prevent the dimerization of the Fc region, for example at L131 (e.g., L131K), T146 (e.g., T146S), P175 (e.g., P175V), F185 (e.g., F185R), Y187 (e.g., Y187A), and K189 (e.g., K189Y) numbered as in the IgG1 sequence of SEQ ID NO:71. Above-mentioned constructs in (i) to (iii) comprise L131K, T146S, P175V, F185R, Y187A, and K189Y as numbered in the IgG1 sequence of SEQ ID NO:71.

2 Heterodimeric Polypeptide Chain

The stable expression of a masked TGF-β complex comprised of two polypeptides was demonstrated masked TGF-β constructs by preparing a nucleic acid encoding a first polypeptide comprising a TGF-β polypeptide sequence, and a second nucleic acid encoding a TGF-β receptor polypeptide sequence, and expressing the polypeptides using mammalian expression vectors (e.g., plasmid expression systems in CHO cells). The first polypeptide comprising, for example, a MOD polypeptide sequence (e.g., a wt. or variant IL-2 polypeptide sequence), an IgG Fc scaffold polypeptide sequence (e.g., a KiH Fc), and a TGF-β polypeptide sequence (e.g. wt. or sequence variant bearing TGF-β1 or wt. TGF-β3) (see e.g., FIG. 7J construct 3618). The second polypeptide comprising, for example, a MOD polypeptide sequence (e.g., a wt. or variant IL-2 polypeptide sequence), an IgG Fc scaffold polypeptide sequence (e.g., the counter part of the KiH sequence of the first polypeptide), and a type II TGF-β receptor (TGF-β RII) polypeptide sequence (wt. or with sequence variations) (see e.g., FIG. 7J construct 3621). A schematic structure of the expressed protein is shown in FIG. 1 as structure D. Expression and purification (protein A and size separation by chromatography) of one such pair of polypeptides, (iv.a) and (iv.b), comprising, from N- to C-terminus the following polypeptide sequences:
  (iv.a) IL-2 (wt. MOD)-knob-in-hole Fc (e.g., knob Fc)-TGF-β3 (wt.) see FIG. 7J construct 3618 (SEQ ID NO:148); and
  (iv.b) IL-2 (wt. MOD)-knob-in-hole Fc (e.g., hole Fc)-TβRII (D32N) see FIG. 7J construct 3621 (SEQ ID) NO:160.

In construct (iv.a) or (iv.b), the IL-2 polypeptide may comprise substitutions at H16 and/or H42, such as H16T and F42A substitutions or H16A and F42A substitutions.

3 Activity of Masked TGF-β Constructs

Various concentrations of the purified masked TGF-β polypeptides complexes and constructs (e.g., constructs (i) to (iii) and the complex of polypeptides (vi.a) and (vi.b) prepared in parts 1 and 2 of this example) were tested for their ability to induce naïve CD4 cells to produce FoxP3. For the assays $10^5$ naïve CD4 cells were plated in wells containing 5 µg/ml bound anti-CD3 with 1 µg/ml of anti-CD28 and the masked TGF-β polypeptides complexes or constructs as indicated. After five days in culture the number of FoxP3 CD4+ double positive cells were assessed using fluorescently labeled anti-CD4 and anti-FoxP3 by flow cytometry. Controls providing stimulation by either TGF-β3 or TGF-β3 and recombinant human IL-2 100 U/ml were also run in parallel.

Figure 6B:
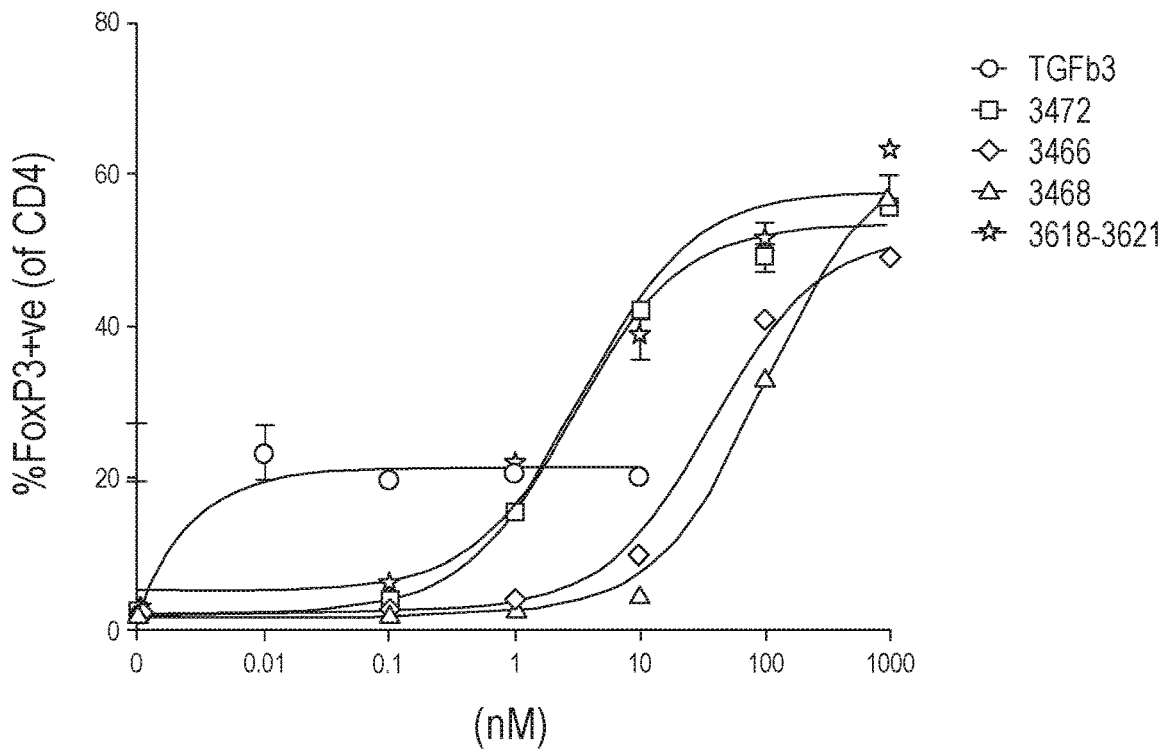
Figure 6C:
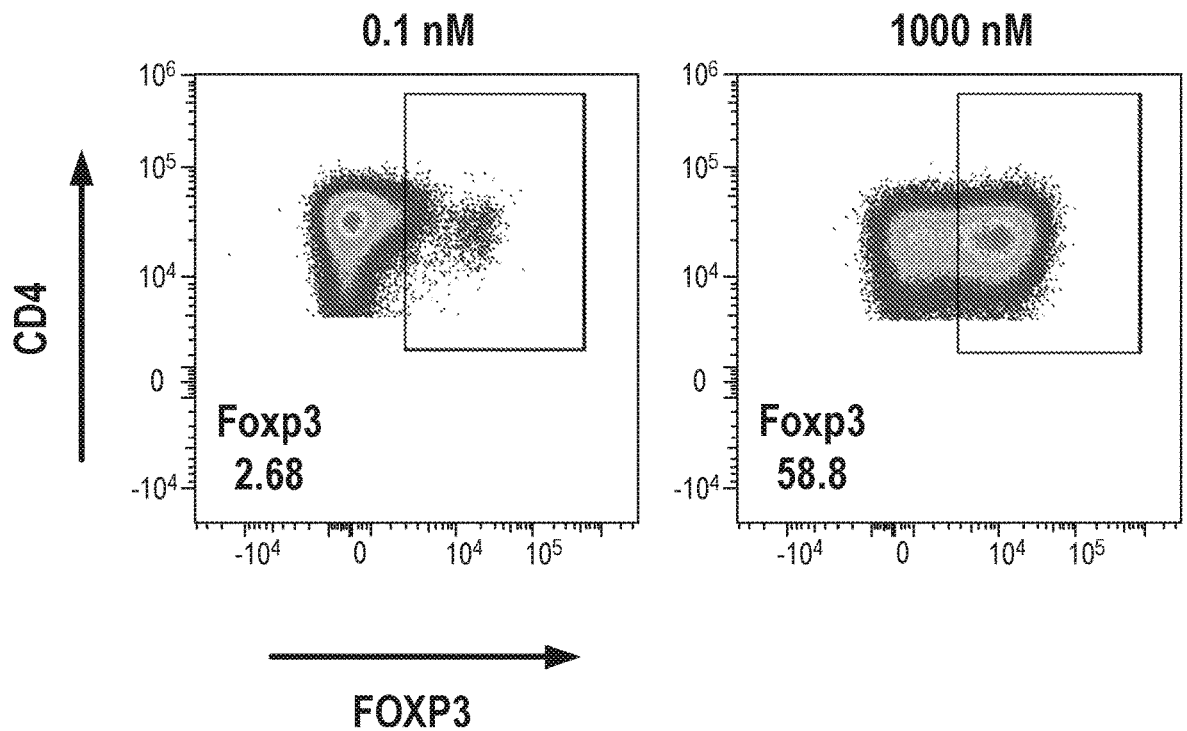

In FIG. 6 at A a comparison of a masked TGF-β construct having the overall structure shown in FIG. 1 at A comprising wt. IL-2-IgG Fc (mFc)-TβRII with a D32N substitution—TGF-β3 was tested for FoxP3 expression in comparison to the effect of wt. TGF-β3 in the presence or absence of IL-2. The results show in FIG. 6 at A indicate that wt. TGF-β3 does not effectively stimulate FoxP3 under the test conditions, but that wt. IL-2 supplementation can lead to FoxP3 expression.

In FIG. 6 at B a comparison of a masked TGF-β construct (i), (ii) and (iii) from parts 1 and 2 of this example, and masked TGF-β complex comprising polypeptides (iv.a) and (iv.b) were tested for FoxP3 expression in comparison to the effect of wt. TGF-β3 in the presence of IL-2. The results show in FIG. 6 at B indicate that masked TGF-β constructs and complexes with wt. IL-2 are more potent than those with the IL-2 substitution H16T and F42A. The substitutions at H16T and F42A shift the potency of the masked complexes by an order of magnitude from about 5 nanomolar to about 50 nanomolar without substantive change in the maximal efficacy based on the number of cells expressing FoxP3. As with the results shown in FIG. 6 at A, the and masked TGF-β constructs and complexes were more effective at inducing T cells to produce FoxP3 than IL-2 and TGF-β3.

An example of the gating and separation of cells based on CD4+ and FoxP3 is shown in FIG. 6 at C. The results demonstrate an induction of FoxP3 in cells exposed to a masked TGF-β construct at 1,000 nM show an increase of approximately 30-fold in FoxP3 expression over cells exposed to 0.1 nM of the same construct.

B. Example 2

1 Scaffolds that are Non-Interspecific

This section describes masked TGF beta sequences that do not employ interspecific scaffolds, and accordingly are either monomeric, or if they dimerize, they do not preferentially form heterodimers with a counterpart sequence.

a. Single Polypeptide Chain Masked TGF-β Constructs

A nucleic acids encoding a polypeptide comprising, from N- to C-terminus, a MOD polypeptide sequence: a wt. IL-2 polypeptide sequence (SEQ ID NO:20), an IgG1 Fc scaffold polypeptide sequence wt. IgG1 aas 11-215 (Δ10) bearing a L234A and L235A ("LALA"), L351K, T366S, P395V, F405R, Y407A, and K409Y substitutions, a TGF-β RII isoform B polypeptide sequence from aa 26 to β6 aas of the mature protein with a D118A substitution (*D119A see the note in FIG. 5B), and a human TGF-β type 3 isoform 1 polypeptide sequence with a C77S substitution. A schematic structure of the expressed protein is shown in FIG. 1 as structure A (SEQ ID NO:146). The protein was purified by protein A and size chromatography.

b. Homodimeric Polypeptide Complex

A nucleic acids encoding a polypeptide comprising, from N- to C-terminus, a MOD polypeptide sequence (IL-2 SEQ ID NO:20 with H16T and F42A substitutions), an IgG1 Fc scaffold polypeptide sequence (e.g., wt. IgG1 bearing a L234A and L235A ("LALA") substitutions), a TGF-β RII isoform B polypeptide sequence from aa 26 to β6 aas of the mature protein with a D118A substitution (*D119A see the note in FIG. 5B), and a human TGF-β type 3 isoform 1 polypeptide sequence with a C77S substitution. A schematic structure of the expressed protein is shown in FIG. 1 as structure B. The corresponding aa acid sequence aligned with the elements labeled is shown in FIG. 7B (SEQ ID NO:147). The protein was purified by protein A and size chromatograph.

2 Heterodimeric Masked TGF-β Complexes with Interspecific Scaffolds Polypeptides a. Heterodimeric Masked TGF-β Complexes Having Interspecific Scaffolds Each Bearing IL-2 MOD Polypeptides The stable expression of a masked TGF-β complex comprised of two polypeptides was demonstrated masked TGF-β constructs by preparing a nucleic acid encoding a first polypeptide comprising a TGF-β polypeptide sequence, and a second nucleic acid encoding a TGF-β receptor polypeptide sequence, and expressing the polypeptides using mammalian expression vectors (e.g., plasmid expression systems in CHO cells).

The first polypeptide comprising, a wt. IL-2 polypeptide (SEQ ID NO:20), an IgG1 Fc scaffold polypeptide sequence (e.g., wt. IgG1 residues 1-225 bearing L234A and L235A ("LALA") substitutions), and a T366W KiH "knob" substitution, and a human TGF-β type 3 isoform 1 polypeptide sequence with a C77S substitution.

The second polypeptide comprising a wt. IL-2 polypeptide (SEQ ID NO:20), an IgG1 Fc scaffold polypeptide sequence (e.g., wt. IgG1 residues 1-225 bearing L234A and L235A ("LALA") substitutions), and T366S, L368A and Y407V KiH "hole" substitutions, and a TGF-β RII isoform B polypeptide sequence from aa 26 to β6 aas of the mature protein with a D118A substitution. A schematic structure of the expressed protein is shown in FIG. 1 as structure D. The corresponding aa acid sequences are aligned with the elements labeled is shown in FIG. 7C. Expression and purification (protein A followed by size exclusion chromatography) provides the heterodimer complex.

b. Heterodimeric Masked TGF-β Complexes Having Interspecific Scaffolds with a Single Chain Bearing an MOD Polypeptides The stable expression of a masked TGF-β complex comprised of two polypeptides was demonstrated masked TGF-β constructs by preparing a nucleic acid encoding a first polypeptide comprising a TGF-β polypeptide sequence, and a second nucleic acid encoding a TGF-β receptor polypeptide sequence, and expressing the polypeptides using mammalian expression vectors (e.g., plasmid expression systems in CHO cells).

The first polypeptide comprising, a wt. IL-2 polypeptide (SEQ ID NO:20), an IgG1 Fc scaffold polypeptide sequence (e.g., wt. IgG1 residues 1-225 bearing L234A and L235A ("LALA") substitutions), and a T366W (knob) substitution, and a human TGF-β type 3 isoform 1 polypeptide sequence with a C77S substitution.

The second polypeptide comprising an IgG1 Fc scaffold polypeptide sequence (e.g., wt. IgG1 residues 1-225 bearing L234A and L235A ("LALA") substitutions), and T366S, L368A and Y407V "hole" substitutions, and a TGF-β RII isoform B polypeptide sequence from aa 26 to β6 aas of the mature protein with a D118A substitution.

A schematic structure of the expressed protein is shown in FIG. 1 as structure E. The corresponding aa acid sequence aligned with the elements labeled is shown in FIG. 7 D Expression and purification (protein A followed by size exclusion chromatography) provides the heterodimer complex.

c. Heterodimeric Masked TGF-β Complexes Having Interspecific Scaffold Polypeptide Stabilization, with a Single Chain Bearing MOD Polypeptides The stable expression of a masked TGF-β complex comprised of two polypeptides was demonstrated masked TGF-β constructs by preparing a nucleic acid encoding a first polypeptide comprising a TGF-β polypeptide sequence, and a second nucleic acid encoding a TGF-β receptor polypeptide sequence, and expressing the polypeptides using mammalian expression vectors (e.g., plasmid expression systems in CHO cells).

The first polypeptide comprising an IL-2 polypeptide sequence (SEQ ID NO 20 with H16T and F42A substitutions), an IgG1 Fc scaffold polypeptide sequence (e.g., wt. IgG1 residues 1-225 bearing L234A and L235A ("LALA") substitutions), and a T366W (knob) substitution, a TGF-β RII isoform B polypeptide sequence from aa 26 to β6 aas of the mature protein with a D118A substitution, and a human TGF-β type 3 isoform 1 polypeptide sequence with a C77S substitution.

The second polypeptide comprising an IgG1 Fc scaffold polypeptide sequence (e.g., wt. IgG1 residues 1-225 bearing L234A and L235A ("LALA") substitutions), and T366S, L368A and Y407V "hole" substitutions.

A schematic structure of the expressed protein is shown a variation of the structure in FIG. 1 as structure F, but lacking any immunomodulatory polypeptide sequences on the second polypeptide. The corresponding aa acid sequence aligned with the elements labeled is shown in FIG. 7E.

Expression and purification (protein A followed by size exclusion chromatography) provides the heterodimer complex.

C. Example 3 Expression and Purification

Figure 8:
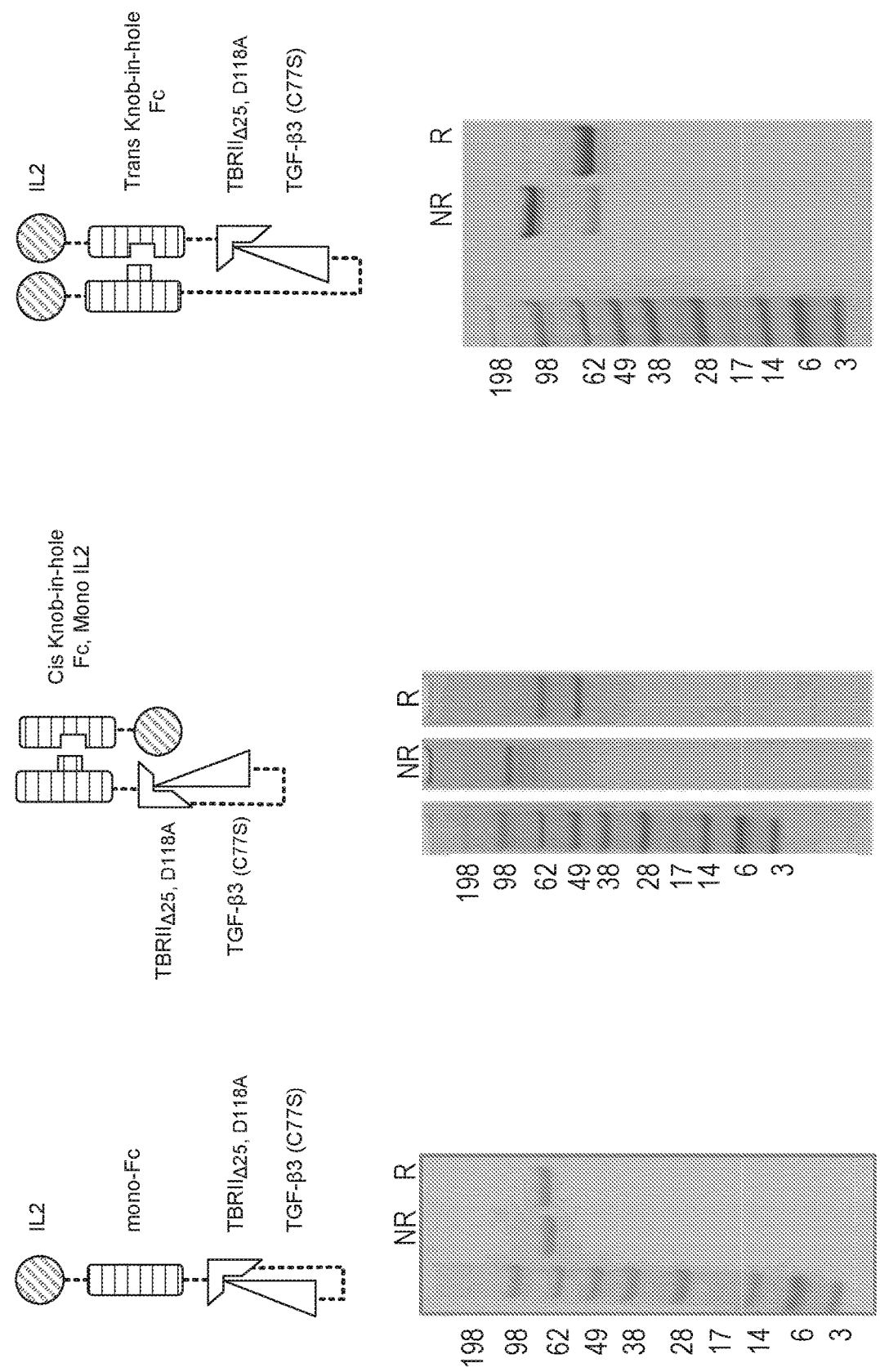

Nucleic acids encoding a masked TGF-β construct nucleic acids encoding two masked TGF-β complexes were prepared (see FIG. 8). Samples of the complexes were prepared by transfecting ExpiCHO cells with the nucleic acid constructs and permitting the cells to expressing the polypeptides. The polypeptides were purified by protein A chromatography followed by size exclusion chromatography. The purified proteins were subjected to SDS-PAGE and the resulting gels were stained with Coomassie blue. NR=not reducing or unreduced samples, and R=reduced samples (reduction with a disulfide reducing agent).

D. Example 4 Biological Activity and Affinity Between the Masking Polypeptide and TGF-β

A series of masked TGF-β constructs were prepared to demonstrate the biological availability of TGF-β, and that its ability to interact with TβRII is inversely proportional to the affinity of the masking polypeptide for the TGF-β polypeptide sequence. The constructs were of the form structure A in FIG. 1, and, from N-terminus to C-terminus, the MOD is an IL-2 polypeptide; the scaffold is an IgG polypeptide; the masking receptor is a TβRII polypeptide of SEQ ID NO. 119 with N-terminal aas 1-25 (Δ25) deleted and a D118A substitution (and that comprise the additional substitution E55A, D32N, or S52L as indicated), and a TGF-β3 polypeptide sequence.

Interaction of the masked TGF-β constructs with TβRII was assessed using a capture assay in which a TβRII-Ig Fc fusion was captured in the wells of a microtiter plate and various concentrations of the four constructs were applied to the wells. After rinsing off unbound constructs, the bound construct was detected and measured using biotin labeled anti IL-2 followed by streptavidin-horse radish peroxidase and colorimetric detection (3,3',5,5'-tetramethylbenzidine) at 450 nm. The results, which are shown in FIG. 9, indicate that the Δ25-D118A construct had a dissociation constant of 2.69 μM for the TβRII (TβRII-Ig fusion). Addition of an E55A, D32N or S52L, with have increasingly larger impacts of the dissociation constant for TGF-β3-TβRII complexes, provides complexes with increasing affinity for exogenous TβRII (the TβRII-Ig fusion in this case).

Figure 10A:
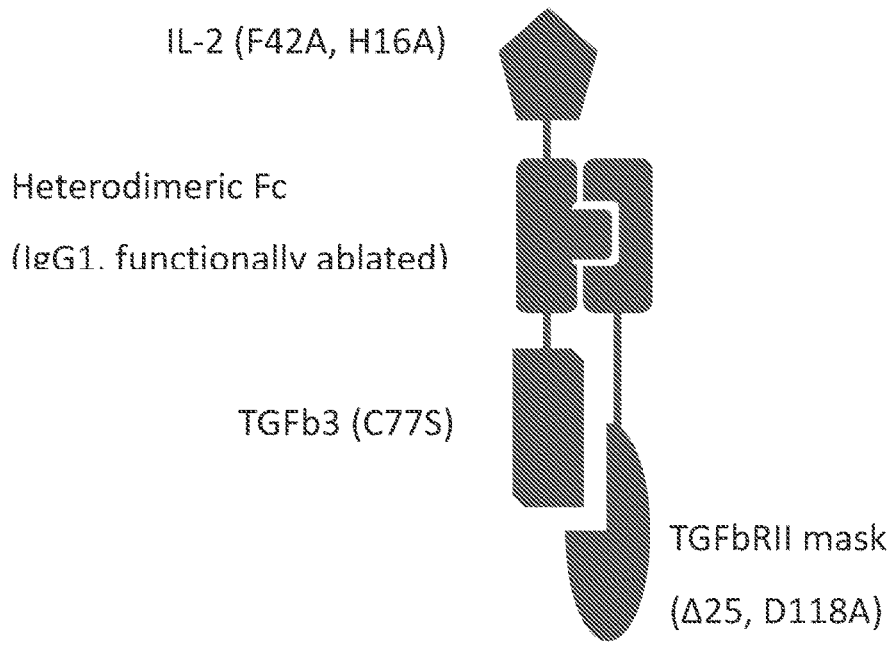
FIG. 10 shows the structure and amino acid sequences of the polypeptides that form the masked TGF-β3 complex PSM-4033-4039.

E. Example 5 Biological Activity of Heterodimeric Masked TGF-β Complex (PSM-4033-4039) Having Interspecific Scaffold Polypeptide Stabilization, with a Single Chain Bearing a Variant IL-2 MOD Polypeptide A masked TGF-β complex, PSM-4033-4039, as shown in FIG. 10A was prepared. The complex comprises first and second polypeptides 4033 and 4039 shown in FIGS. 10B and 10C, respectively. A series of experiments then was performed with PSM-4033-4039.

Experiment 1: Induction of Foxp3$^+$ iTregs from Human Peripheral Naïve CD4$^+$ T Cells Naïve CD4+ T cells were sorted from human blood and plated with anti-human CD3 (5 ug/mL), anti-human CD28 (1 ug/mL), and an increasing dose of PSM-4033-4039 or a single dose of recombinant TGFb3 and IL-2 as a positive control. After 5 days in culture, cells were assessed by flow cytometry for expression of the transcription factor Foxp3. n=2, stdev. The results, provided in FIG. 11 show a significant induction of FoxP3 in cells exposed to PSM-4033-4039 at concentrations up to 1,000 nM. These results are similar to those shown in FIG. 6B with other masked TGF-β constructs and complexes, further demonstrating that masked TGF-β3 constructs and complexes disclosed herein can effect a significant induction of FoxP3, which is a master regulator of gene expression in Tregs, including both natural and induced Tregs, and central to Treg identity and function.

Figure 12:
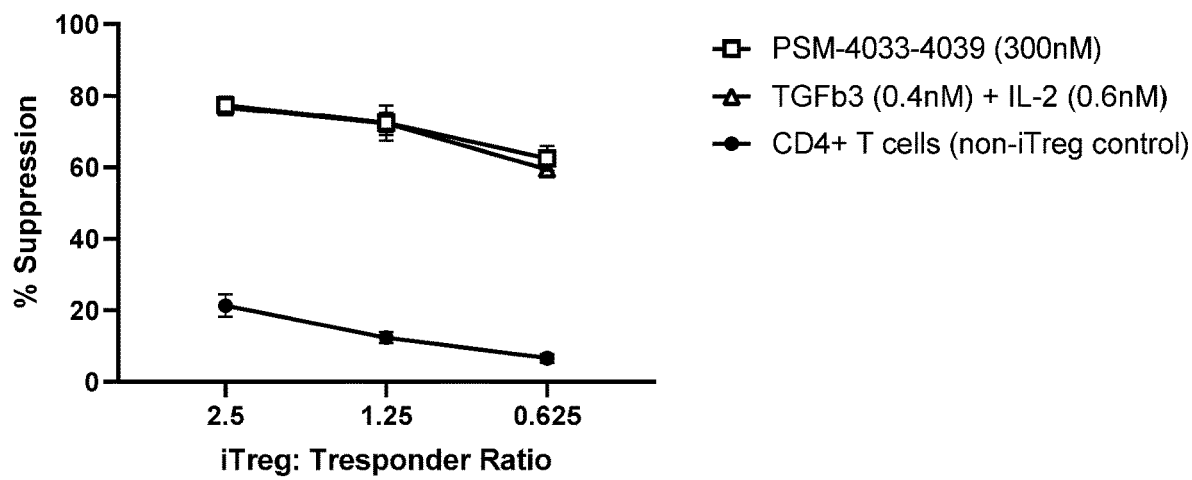
FIG. 12 shows the results of an experiment in which Foxp3+ iTregs induced by PSM-4033-4039 are used to suppress T cell proliferation. See Example 4.

Experiment 2: Suppression of T Cell Proliferation by PSM-4033-4039 Induced Foxp3$^+$ iTregs PSM-4033-4039 induced Foxp3+T regulatory cells (iTreg) were cultured at different ratios to conventional T cells (T responder) and stimulated with anti-human CD3 (1 ug/mL) and mitomycin C treated peripheral blood mononuclear cells (PBMCs). Proliferation was assessed by flow cytometry after four days by the dilution of cell trace violet (CTV) dye in T responder cells. The data, shown in FIG. 12, represents an average of three donors, each plated in duplicate. TGF-β3 and IL-2 induced T regulatory cells or total peripheral CD4+ T cells were used in place of iTregs, as controls. Suppression is defined as % less CTV dilution compared to no added iTreg controls (avg. 78% CTV diluted). The results of this experiment demonstrate that Foxp3+T regulatory cells induced by the masked TGF-β3 constructs and complexes disclosed herein, e.g., PSM-4033-4039, can suppress the proliferation of T cells activated by CD3 cross-linking and co-stimulation, provided by antigen presenting cells in PBMCs.

A defining characteristic of Tregs beyond their expression of the transcription factor, Foxp3, is their ability to suppress the activation and function of other leukocytes. This experiment demonstrates that iTregs induced by masked TGF-β3 constructs and complexes disclosed herein can indeed suppress the proliferation of T cells activated by CD3 cross-linking and co-stimulation, provided by antigen presenting cells in PBMCs.

Experiment 3: Induction of Foxp3$^+$ Expression from Human Peripheral CD4$^+$ T Cells by PSM-4033-4039

Figure 13A:
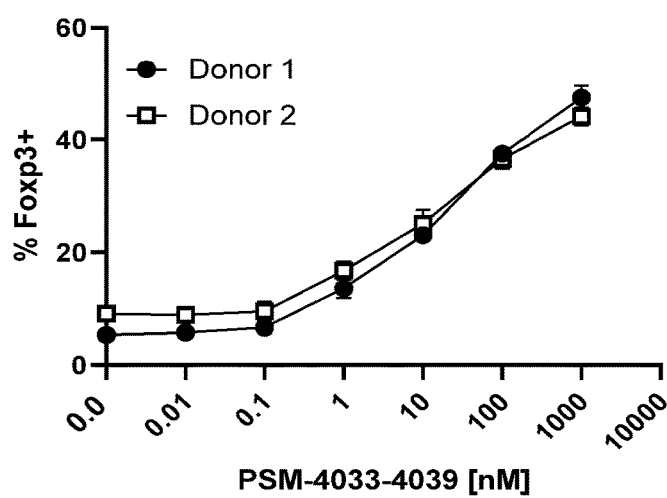
FIG. 13 shows the results of an experiment in which PSM-4033-4039 is used to induce expression of Foxp3+ iTregs from human peripheral CD4+ T cells, including naïve and memory CD4+ T cells. See Example 4.

Total CD4+ T cells were sorted from human blood and plated with anti-human CD3 (5 ug/mL), anti-human CD28 (1 ug/mL), and an increasing dose of PSM-4033-4039. After 5 days in culture, cells were assessed by flow cytometry for expression of the transcription factor Foxp3. n=2. The data is illustrated in FIG. 13A.

Figure 13B:
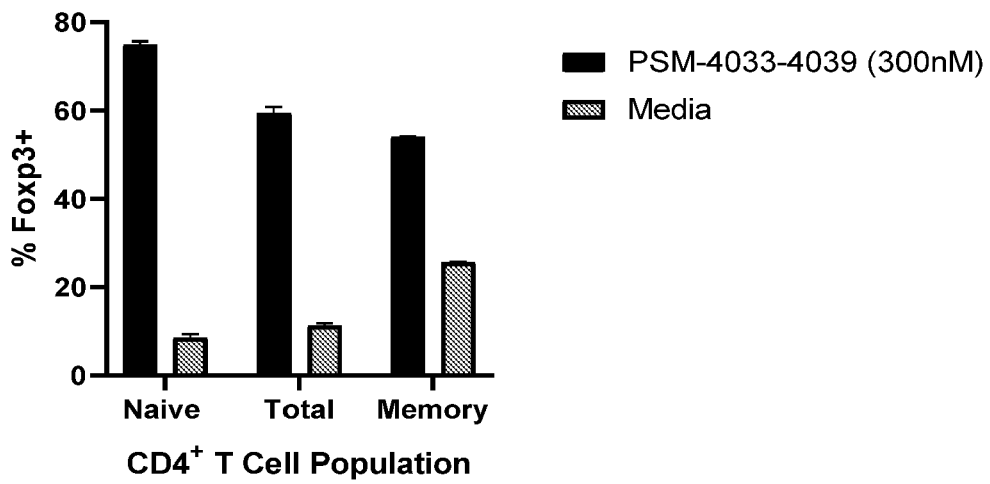

To determine which cell type in a mixture of CD4+ T cell types could differentiate into Foxp3 expressing cells, different populations were sorted and treated with PSM-4033-4039 individually. Accordingly, naïve, total, and memory CD4+ T cells for a different donor than the donors of FIG. 13A were sorted and cultured in the same way as above, with or without PSM-4033-4039 (300 nM), and Foxp3 was assessed by flow cytometry at day 5. The data is illustrated in FIG. 13B.

Total CD4+ T cells, which were differentiated into Foxp3 expressing cells in this experiment, represent both naïve and memory peripheral T cells, a mixture of cell types that masked TGF-β3 constructs and complexes disclosed herein, e.g., PSM-4033-4039, would encounter when administered in vivo. This data shows that even in a mixed T cell population, masked TGF-β3 constructs and complexes disclosed herein, e.g., PSM-4033-4039, can increase the frequency of cells that express Foxp3, a master regulator of a gene expression defining T regulatory cells. The results shown in FIG. 13B show that PSM-4033-4039 can induce memory CD4+ T cells to differentiate into Foxp3+ cells, even if at a lower frequency than naïve CD4+ T cells.

Experiment 4: Induction of Foxp3$^+$ iTregs by PSM-4033-4039 from CD4+ T Cells Activated by an Allogeneic Lymphocyte Reaction Total peripheral CD4+ T cells were sorted from human blood and plated with allogeneic monocyte-derived DCs (moDCs) to induce T cell proliferation. T cells were mixed with autologous moDCs as a control, and both allogeneic or autologous donor combinations were treated with soluble anti-CD3 (1 ug/mL) as an additional control. T cells were labeled with cell trace violet (CTV) dye to track cells which responded to allogeneic activation. Proliferation and expression of Foxp3 were analyzed by flow cytometry on day 5, and the frequency of proliferated cells that express Foxp3 are plotted in FIGS. 14A and B. Two donor combinations are shown. n=2, stdev. Among other things, the results demonstrate to potential use of the masked TGF-β3 constructs and complexes disclosed herein, e.g., PSM-4033-4039, for the treatment of graft vs. host disease occurring in bone marrow or stem cell transplantation patients.

Experiment 5: PK Experiment in Mice Using PSM-4033-4039

PSM-4033-4039 was administered intravenously as single doses to Balb/c mice at 0.1, 1, or 10 mg/kg. Peripheral serum samples were then collected 5 minutes, 2, 8, 24, and 72 hours post-dose. Serum concentrations of PSM-4033-4039 were then determined using a ligand binding assay that captured the molecule using an anti-IL2 antibody, and detected the molecule using an anti-TGFB3 antibody. The results provided in FIG. 15 show that the masked TGF-β3 constructs and complexes disclosed herein, e.g., PSM-4033-4039, can remain present in the serum at biologically relevant concentrations for more than 72 hours after administration. The sequence of construct 4033 is provided in FIG. 10B (SEQ ID NO:191), and the sequence of construct 4039 is provided in FIG. 10C (SEQ ID NO:192).

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

The invention claimed is:

1. A heterodimer comprising a first polypeptide and a second polypeptide, wherein:
   (i) the first polypeptide comprises, in the N-terminal to C-terminal direction,
      a) a scaffold polypeptide sequence comprising an interspecific dimerization sequence and having at least 95% sequence identity to at least 175 contiguous amino acids of an IgG1 sequence selected from SEQ ID NOs:71 to 76,
      b) a masking polypeptide sequence comprising a TGF-β receptor polypeptide sequence having at least 95% sequence identity to SEQ ID NO:122, and
         optionally, an independently selected linker polypeptide sequence comprising from 1 to 25 amino acids interposed between the scaffold polypeptide sequence and the masking polypeptide sequence of the first polypeptide; and
   (ii) the second polypeptide comprises, in the N-terminal to C-terminal direction,
      a) an IL-2 immunomodulatory polypeptide sequence having at least 95% sequence identity to 120 contiguous amino acids of SEQ ID NO:9,
      b) a scaffold polypeptide sequence comprising a counterpart interspecific dimerization sequence to the interspecific dimerization sequence in the first polypeptide and having at least 95% sequence identity to at least 175 contiguous amino acids of an IgG1 sequence selected from SEQ ID NOs:71 to 76,
      c) a TGF-β3 polypeptide sequence having at least 95% sequence identity to at least 100 contiguous amino acids of SEQ ID NO:111, and
         optionally independently selected linker polypeptide sequences comprising from 1 to 25 amino acids interposed
         (A) between the IL-2 immunomodulatory polypeptide sequence and the scaffold polypeptide sequence of the second polypeptide, and/or
         (B) between the scaffold polypeptide sequence and the TGF-β3 polypeptide sequence of the second polypeptide;
      wherein the TGF-β receptor polypeptide sequence and the TGF-β3 polypeptide sequence interact with each other to reversibly mask the TGF-β3 polypeptide sequence; and
      wherein the interspecific dimerization sequence and the counterpart interspecific dimerization sequence interact with each other to form the heterodimer.

2. The heterodimer of claim 1, wherein each scaffold polypeptide comprises a substitution that reduces or eliminates the ability of the IgG1 sequence to induce cell lysis through complement-dependent cytotoxicity (CDC) and/or antibody-dependent cellular cytotoxicity (ADCC).

3. The heterodimer of claim 1, wherein each scaffold polypeptide comprises an IgG1 sequence having at least 95% amino acid sequence identity to SEQ ID NO:71.

4. The heterodimer of claim 3, wherein the Ig polypeptide sequence comprises a substitution of L14 and/or L15 of SEQ ID NO:71 with an amino acid other than leucine.

5. The heterodimer of claim 3, wherein the IL-2 immunomodulatory polypeptide sequence of SEQ ID NO:9 comprises a substitution at any one, any two, or all of amino acids N88, F42, and H16.

6. The heterodimer of claim 3, wherein the IL-2 immunomodulatory polypeptide sequence comprises an F42A, F42T, H16A, or H16T substitution.

7. The heterodimer of claim 3, wherein the TGF-β receptor polypeptide sequence comprises a substitution of any one, any two, any three, any four, or all five of amino acids F30, D32, S52, E55, and D118.

8. The heterodimer of claim 6, wherein the TGF-β receptor polypeptide sequence comprises a substitution of any one, any two, any three, any four, or all five of amino acids F30, D32, S52, E55, and D118.

9. The heterodimer of claim 6, wherein the TGF-β receptor polypeptide sequence comprises a D118A substitution.

10. The heterodimer of claim 3, wherein the TGF-β3 polypeptide sequence comprises a C77S substitution.

11. The heterodimer of claim 9, wherein the TGF-β3 polypeptide sequence comprises a C77S substitution.

12. A pharmaceutical composition comprising the heterodimer of claim 1.

13. A heterodimer comprising a first polypeptide comprising the amino acid sequence of polypeptide 4033 (SEQ ID NO:191), and a second polypeptide comprising the amino acid sequence of polypeptide 4039 (SEQ ID NO:192),
   wherein the first polypeptide and the second polypeptide are linked together by disulfide bonds formed between cysteine residues in an IgG1 Fc interspecific polypeptide sequence in the first polypeptide and cysteine residues in an IgG1 Fc counterpart interspecific polypeptide sequence in the second polypeptide.

14. A heterodimer consisting essentially of a first polypeptide comprising the amino acid sequence of polypeptide 4033 (SEQ ID NO:191), and a second polypeptide comprising the amino acid sequence of polypeptide 4039 (SEQ ID NO:192),
   wherein the first polypeptide and the second polypeptide are linked together by disulfide bonds formed between cysteine residues in an IgG1 Fc interspecific polypeptide sequence in the first polypeptide and cysteine residues in an IgG1 Fc counterpart interspecific polypeptide sequence in the second polypeptide.

15. A heterodimer consisting of a first polypeptide comprising the amino acid sequence of polypeptide 4033 (SEQ ID NO:191), and a second polypeptide comprising the amino acid sequence of polypeptide 4039 (SEQ ID NO:192),
wherein the first polypeptide and the second polypeptide are linked together by disulfide bonds formed between cysteine residues in an IgG1 Fc interspecific polypeptide sequence in the first polypeptide and cysteine residues in an IgG1 Fc counterpart interspecific polypeptide sequence in the second polypeptide.

16. A pharmaceutical composition comprising the heterodimer of claim 13.

17. A pharmaceutical composition comprising the heterodimer of claim 14.

18. A pharmaceutical composition comprising the heterodimer of claim 15.

19. The heterodimer of claim 1, wherein the second polypeptide comprises first and second IL-2 immunomodulatory polypeptide sequences, each having at least 95% sequence identity to 120 contiguous amino acids of SEQ ID NO:9, and wherein
the first and second IL-2 immunomodulatory sequences are positioned N-terminal to the scaffold polypeptide of the second polypeptide, and
optionally a linker polypeptide sequence comprising from 1 to 25 amino acids is interposed between the first and second IL-2 immunomodulatory polypeptide sequences.

20. The heterodimer of claim 1, wherein the second polypeptide comprises first, second and third IL-2 immunomodulatory polypeptide sequences, each having at least 95% sequence identity to 120 contiguous amino acids of SEQ ID NO:9, and wherein
the first, second and third IL-2 immunomodulatory sequences are positioned N-terminal to the scaffold polypeptide of the second polypeptide, and
optionally a linker polypeptide sequence comprising from 1 to 25 amino acids is interposed between one or both of (i) the first and second IL-2 immunomodulatory polypeptide sequences, and (ii) the second and third IL-2 immunomodulatory polypeptide sequences.

21. The heterodimer of claim 1, wherein the first polypeptide further comprises an IL-2 immunomodulatory polypeptide sequence having at least 95% sequence identity to 120 contiguous amino acids of SEQ ID NO:9, and wherein
the IL-2 immunomodulatory sequence is positioned N-terminal to the scaffold polypeptide of the first polypeptide, and
optionally a linker polypeptide sequence comprising from 1 to 25 amino acids is interposed between the IL-2 immunomodulatory polypeptide-sequence and the scaffold polypeptide sequence of the first polypeptide.

22. The heterodimer of claim 1, wherein the first polypeptide comprises first and second IL-2 immunomodulatory polypeptide sequences, each having at least 95% sequence identity to 120 contiguous amino acids of SEQ ID NO:9, and wherein
the two IL-2 immunomodulatory sequences are positioned N-terminal to the scaffold polypeptide of the first polypeptide, and
optionally a linker polypeptide sequence comprising from 1 to 25 amino acids is interposed between one or both of (i) the first IL-2 immunomodulatory polypeptide-sequence and the scaffold polypeptide sequence of the first polypeptide, and (ii) the first and second IL-2 immunomodulatory polypeptide sequences of the first polypeptide.

23. The heterodimer of claim 1, wherein the first polypeptide comprises first, second and third IL-2 immunomodulatory polypeptide sequences, each having at least 95% sequence identity to 120 contiguous amino acids of SEQ ID NO:9, and wherein
the three IL-2 immunomodulatory sequences are positioned N-terminal to the scaffold polypeptide of the first polypeptide, and
optionally a linker polypeptide sequence comprising from 1 to 25 amino acids is interposed between one, two or all three of (i) the first IL-2 immunomodulatory polypeptide sequence and the scaffold polypeptide sequence of the first polypeptide, (ii) the first and second IL-2 immunomodulatory polypeptide sequences of the first polypeptide, and (iii) the second and third IL-2 immunomodulatory polypeptide sequences of the first polypeptide.

* * * * *

SEQUENCE LISTING

```
<160> NUMBER OF SEQ ID NOS: 192

<210> SEQ ID NO 1
<211> LENGTH: 245
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175
```

```
Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Gly Asn Ile Leu Asn Val Ser Ile Lys Ile Cys Leu Thr
225                 230                 235                 240

Leu Ser Pro Ser Thr
                245

<210> SEQ ID NO 2
<211> LENGTH: 219
<212> TYPE: PRT
<213> ORGANISM: Homo sapiens

<400> SEQUENCE: 2

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Gly Asn Ile Leu Asn Val Ser Ile Lys Ile
    210                 215

<210> SEQ ID NO 3
<211> LENGTH: 268
<212> TYPE: PRT
<213> ORGANISM: Homo sapiens

<400> SEQUENCE: 3

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30
```

Thr Cys Ser Phe Ser Asn Thr Ser Glu Ser Phe Val Leu Asn Trp Tyr
         35                  40                  45

Arg Met Ser Pro Ser Asn Gln Thr Asp Lys Leu Ala Ala Phe Pro Glu
 50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Arg Ala Arg Asn
                 85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
 130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
                180                 185                 190

Pro Ser Ala Val Pro Val Phe Ser Val Asp Tyr Gly Glu Leu Asp Phe
                195                 200                 205

Gln Trp Arg Glu Lys Thr Pro Glu Pro Pro Val Pro Cys Val Pro Glu
 210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
                260                 265

<210> SEQ ID NO 4
<211> LENGTH: 271
<212> TYPE: PRT
<213> ORGANISM: Homo sapiens

<400> SEQUENCE: 4

Met Ala Lys Val Pro Asp Met Phe Glu Asp Leu Lys Asn Cys Tyr Ser
 1                5                  10                  15

Glu Asn Glu Glu Asp Ser Ser Ser Ile Asp His Leu Ser Leu Asn Gln
                 20                  25                  30

Lys Ser Phe Tyr His Val Ser Tyr Gly Pro Leu His Glu Gly Cys Met
             35                  40                  45

Asp Gln Ser Val Ser Leu Ser Ile Ser Glu Thr Ser Lys Thr Ser Lys
 50                  55                  60

Leu Thr Phe Lys Glu Ser Met Val Val Ala Thr Asn Gly Lys Val
 65                  70                  75                  80

Leu Lys Lys Arg Arg Leu Ser Leu Ser Gln Ser Ile Thr Asp Asp Asp
                 85                  90                  95

Leu Glu Ala Ile Ala Asn Asp Ser Glu Glu Ile Ile Lys Pro Arg
                100                 105                 110

Ser Ala Pro Phe Ser Phe Leu Ser Asn Val Lys Tyr Asn Phe Met Arg
                115                 120                 125

Ile Ile Lys Tyr Glu Phe Ile Leu Asn Asp Ala Leu Asn Gln Ser Ile

```
                130             135             140
Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205

Glu Ile Pro Lys Thr Ile Thr Gly Ser Glu Thr Asn Leu Leu Phe Phe
    210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 5
<211> LENGTH: 161
<212> TYPE: PRT
<213> ORGANISM: Homo sapiens

<400> SEQUENCE: 5

Pro Arg Ser Ala Pro Phe Ser Phe Leu Ser Asn Val Lys Tyr Asn Phe
1               5                   10                  15

Met Arg Ile Ile Lys Tyr Glu Phe Ile Leu Asn Asp Ala Leu Asn Gln
            20                  25                  30

Ser Ile Ile Arg Ala Asn Asp Gln Tyr Leu Thr Ala Ala Leu His
        35                  40                  45

Asn Leu Asp Glu Ala Val Lys Phe Asp Met Gly Ala Tyr Lys Ser Ser
50                  55                  60

Lys Asp Asp Ala Lys Ile Thr Val Ile Leu Arg Ile Ser Lys Thr Gln
65                  70                  75                  80

Leu Tyr Val Thr Ala Gln Asp Glu Asp Gln Pro Val Leu Leu Lys Glu
                85                  90                  95

Met Pro Glu Ile Pro Lys Thr Ile Thr Gly Ser Glu Thr Asn Leu Leu
            100                 105                 110

Phe Phe Trp Glu Thr His Gly Thr Lys Asn Tyr Phe Thr Ser Val Ala
        115                 120                 125

His Pro Asn Leu Phe Ile Ala Thr Lys Gln Asp Tyr Trp Val Cys Leu
    130                 135                 140

Ala Gly Gly Pro Pro Ser Ile Thr Asp Phe Gln Ile Leu Glu Asn Gln
145                 150                 155                 160

Ala

<210> SEQ ID NO 6
<211> LENGTH: 269
<212> TYPE: PRT
<213> ORGANISM: Homo sapiens

<400> SEQUENCE: 6

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30
```

```
Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
 50                  55                  60

Ala Ser Val Val Val Ala Met Asp Lys Leu Arg Lys Met Leu Val Pro
 65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
            210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265

<210> SEQ ID NO 7
<211> LENGTH: 153
<212> TYPE: PRT
<213> ORGANISM: Homo sapiens

<400> SEQUENCE: 7

Ala Pro Val Arg Ser Leu Asn Cys Thr Leu Arg Asp Ser Gln Gln Lys
 1               5                  10                  15

Ser Leu Val Met Ser Gly Pro Tyr Glu Leu Lys Ala Leu His Leu Gln
                20                  25                  30

Gly Gln Asp Met Glu Gln Gln Val Val Phe Ser Met Ser Phe Val Gln
            35                  40                  45

Gly Glu Glu Ser Asn Asp Lys Ile Pro Val Ala Leu Gly Leu Lys Glu
 50                  55                  60

Lys Asn Leu Tyr Leu Ser Cys Val Leu Lys Asp Asp Lys Pro Thr Leu
 65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
                100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
```

```
            130                 135                 140
Asp Phe Thr Met Gln Phe Val Ser Ser
145                 150
```

<210> SEQ ID NO 8
<211> LENGTH: 569
<212> TYPE: PRT
<213> ORGANISM: Homo sapiens

<400> SEQUENCE: 8

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350
```

```
Val Phe Ile Tyr Lys Ile Phe Lys Ile Asp Ile Val Leu Trp Tyr Arg
            355                 360                 365

Asp Ser Cys Tyr Asp Phe Leu Pro Ile Lys Ala Ser Asp Gly Lys Thr
370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
            405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
            435                 440                 445

Arg Leu Ile Ile Ile Leu Val Arg Glu Thr Ser Gly Phe Ser Trp Leu
            450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
            485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
            515                 520                 525

Arg Phe Trp Lys Asn Val Arg Tyr His Met Pro Val Gln Arg Arg Ser
            530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 9
<211> LENGTH: 133
<212> TYPE: PRT
<213> ORGANISM: Homo sapiens

<400> SEQUENCE: 9

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 10
```

```
<211> LENGTH: 251
<212> TYPE: PRT
<213> ORGANISM: Homo sapiens

<400> SEQUENCE: 10

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250

<210> SEQ ID NO 11
<211> LENGTH: 524
<212> TYPE: PRT
<213> ORGANISM: Homo sapiens

<400> SEQUENCE: 11

Val Asn Gly Thr Ser Gln Phe Thr Cys Phe Tyr Asn Ser Arg Ala Asn
1               5                   10                  15

Ile Ser Cys Val Trp Ser Gln Asp Gly Ala Leu Gln Asp Thr Ser Cys
            20                  25                  30

Gln Val His Ala Trp Pro Asp Arg Arg Arg Trp Asn Gln Thr Cys Glu
        35                  40                  45

Leu Leu Pro Val Ser Gln Ala Ser Trp Ala Cys Asn Leu Ile Leu Gly
    50                  55                  60

Ala Pro Asp Ser Gln Lys Leu Thr Thr Val Asp Ile Val Thr Leu Arg
65                  70                  75                  80

Val Leu Cys Arg Glu Gly Val Arg Trp Arg Val Met Ala Ile Gln Asp
                85                  90                  95
```

```
Phe Lys Pro Phe Glu Asn Leu Arg Leu Met Ala Pro Ile Ser Leu Gln
            100                 105                 110

Val Val His Val Glu Thr His Arg Cys Asn Ile Ser Trp Glu Ile Ser
            115                 120                 125

Gln Ala Ser His Tyr Phe Glu Arg His Leu Glu Phe Glu Ala Arg Thr
            130                 135                 140

Leu Ser Pro Gly His Thr Trp Glu Glu Ala Pro Leu Leu Thr Leu Lys
145                 150                 155                 160

Gln Lys Gln Glu Trp Ile Cys Leu Glu Thr Leu Thr Pro Asp Thr Gln
                165                 170                 175

Tyr Glu Phe Gln Val Arg Val Lys Pro Leu Gln Gly Glu Phe Thr Thr
            180                 185                 190

Trp Ser Pro Trp Ser Gln Pro Leu Ala Phe Arg Thr Lys Pro Ala Ala
            195                 200                 205

Leu Gly Lys Asp Thr Ile Pro Trp Leu Gly His Leu Leu Val Gly Leu
            210                 215                 220

Ser Gly Ala Phe Gly Phe Ile Ile Leu Val Tyr Leu Leu Ile Asn Cys
225                 230                 235                 240

Arg Asn Thr Gly Pro Trp Leu Lys Lys Val Leu Lys Cys Asn Thr Pro
                245                 250                 255

Asp Pro Ser Lys Phe Phe Ser Gln Leu Ser Ser Glu His Gly Gly Asp
            260                 265                 270

Val Gln Lys Trp Leu Ser Ser Pro Phe Pro Ser Ser Ser Phe Ser Pro
            275                 280                 285

Gly Gly Leu Ala Pro Glu Ile Ser Pro Leu Glu Val Leu Glu Arg Asp
            290                 295                 300

Lys Val Thr Gln Leu Leu Leu Gln Gln Asp Lys Val Pro Glu Pro Ala
305                 310                 315                 320

Ser Leu Ser Ser Asn His Ser Leu Thr Ser Cys Phe Thr Asn Gln Gly
                325                 330                 335

Tyr Phe Phe Phe His Leu Pro Asp Ala Leu Glu Ile Glu Ala Cys Gln
            340                 345                 350

Val Tyr Phe Thr Tyr Asp Pro Tyr Ser Glu Glu Asp Pro Asp Glu Gly
            355                 360                 365

Val Ala Gly Ala Pro Thr Gly Ser Ser Pro Gln Pro Leu Gln Pro Leu
            370                 375                 380

Ser Gly Glu Asp Asp Ala Tyr Cys Thr Phe Pro Ser Arg Asp Asp Leu
385                 390                 395                 400

Leu Leu Phe Ser Pro Ser Leu Leu Gly Gly Pro Ser Pro Pro Ser Thr
                405                 410                 415

Ala Pro Gly Gly Ser Gly Ala Gly Glu Glu Arg Met Pro Pro Ser Leu
            420                 425                 430

Gln Glu Arg Val Pro Arg Asp Trp Asp Pro Gln Pro Leu Gly Pro Pro
            435                 440                 445

Thr Pro Gly Val Pro Asp Leu Val Asp Phe Gln Pro Pro Pro Glu Leu
            450                 455                 460

Val Leu Arg Glu Ala Gly Glu Glu Val Pro Asp Ala Gly Pro Arg Glu
465                 470                 475                 480

Gly Val Ser Phe Pro Trp Ser Arg Pro Pro Gly Gln Gly Glu Phe Arg
                485                 490                 495

Ala Leu Asn Ala Arg Leu Pro Leu Asn Thr Asp Ala Tyr Leu Ser Leu
            500                 505                 510
```

Gln Glu Leu Gln Gly Gln Asp Pro Thr His Leu Val
        515                 520

<210> SEQ ID NO 12
<211> LENGTH: 347
<212> TYPE: PRT
<213> ORGANISM: Homo sapiens

<400> SEQUENCE: 12

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
210                 215                 220

Gly Ser Asn Thr Ser Lys Glu Asn Pro Phe Leu Phe Ala Leu Glu Ala
225                 230                 235                 240

Val Val Ile Ser Val Gly Ser Met Gly Leu Ile Ile Ser Leu Leu Cys
                245                 250                 255

Val Tyr Phe Trp Leu Glu Arg Thr Met Pro Arg Ile Pro Thr Leu Lys
            260                 265                 270

Asn Leu Glu Asp Leu Val Thr Glu Tyr His Gly Asn Phe Ser Ala Trp
        275                 280                 285

Ser Gly Val Ser Lys Gly Leu Ala Glu Ser Leu Gln Pro Asp Tyr Ser
290                 295                 300

Glu Arg Leu Cys Leu Val Ser Glu Ile Pro Pro Lys Gly Gly Ala Leu
305                 310                 315                 320

Gly Glu Gly Pro Gly Ala Ser Pro Cys Asn Gln His Ser Pro Tyr Trp
                325                 330                 335

Ala Pro Pro Cys Tyr Thr Leu Lys Pro Glu Thr
            340                 345

<210> SEQ ID NO 13

```
<211> LENGTH: 133
<212> TYPE: PRT
<213> ORGANISM: Homo sapiens
<220> FEATURE:
<221> NAME/KEY: VARIANT
<222> LOCATION: (15)..(15)
<223> OTHER INFORMATION: X is any amino acid other than Glu, or X is
      Ala.

<400> SEQUENCE: 13
```

Ala Pro Thr Ser Ser Ser Thr Lys Lys Thr Gln Leu Gln Leu Xaa His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
            130

```
<210> SEQ ID NO 14
<211> LENGTH: 133
<212> TYPE: PRT
<213> ORGANISM: Homo sapiens
<220> FEATURE:
<221> NAME/KEY: VARIANT
<222> LOCATION: (20)..(20)
<223> OTHER INFORMATION: X is any amino acid other than Asp, or X is
      Ala.

<400> SEQUENCE: 14
```

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
            130

```
<210> SEQ ID NO 15
<211> LENGTH: 133
<212> TYPE: PRT
<213> ORGANISM: Homo sapiens
<220> FEATURE:
<221> NAME/KEY: VARIANT
<222> LOCATION: (16)..(16)
<223> OTHER INFORMATION: X is any amino acid other than His, or X is
      Ala, Arg, Asn, Asp, Cys, Glu, Gln, Gly, Ile, Lys, Leu, Met, Phe,
      Pro, Ser, Thr, Tyr, Trp, or Val.

<400> SEQUENCE: 15

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 16
<211> LENGTH: 133
<212> TYPE: PRT
<213> ORGANISM: Homo sapiens
<220> FEATURE:
<221> NAME/KEY: UNSURE
<222> LOCATION: (42)..(42)
<223> OTHER INFORMATION: X is any amino acid other than Phe, or X is Ala
      or Thr.

<400> SEQUENCE: 16

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

```
<210> SEQ ID NO 17
<211> LENGTH: 133
<212> TYPE: PRT
<213> ORGANISM: Homo sapiens
<220> FEATURE:
<221> NAME/KEY: VARIANT
<222> LOCATION: (45)..(45)
<223> OTHER INFORMATION: X is any amino acid other than Tyr, or X is
      Ala.

<400> SEQUENCE: 17
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Xaa Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

```
<210> SEQ ID NO 18
<211> LENGTH: 133
<212> TYPE: PRT
<213> ORGANISM: Homo sapiens
<220> FEATURE:
<221> NAME/KEY: VARIANT
<222> LOCATION: (88)..(88)
<223> OTHER INFORMATION: X is any amino acid other than Asn, or X is Ala
      or Arg.

<400> SEQUENCE: 18
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Xaa Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr

<210> SEQ ID NO 19
<211> LENGTH: 133
<212> TYPE: PRT
<213> ORGANISM: Homo sapiens
<220> FEATURE:
<221> NAME/KEY: VARIANT
<222> LOCATION: (126)..(126)
<223> OTHER INFORMATION: X is any amino acid other than Gln, or X is Ala.

<400> SEQUENCE: 19

Ala Pro Thr Ser Ser Ser Thr Lys Lys Thr Gln Leu Gln Leu Glu His
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
    130

<210> SEQ ID NO 20
<211> LENGTH: 133
<212> TYPE: PRT
<213> ORGANISM: Homo sapiens
<220> FEATURE:
<221> NAME/KEY: VARIANT
<222> LOCATION: (16)..(16)
<223> OTHER INFORMATION: X is any amino acid other than His, or X is Ala or Thr.
<220> FEATURE:
<221> NAME/KEY: VARIANT
<222> LOCATION: (42)..(42)
<223> OTHER INFORMATION: X is any amino acid other than Phe, or X is Ala or Thr.

<400> SEQUENCE: 20

Ala Pro Thr Ser Ser Ser Thr Lys Lys Thr Gln Leu Gln Leu Glu Xaa
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala

```
                  100                 105                 110
Thr Ile Val Glu Phe Leu Asn Arg Trp Ile Thr Phe Cys Gln Ser Ile
            115                 120                 125

Ile Ser Thr Leu Thr
        130
```

<210> SEQ ID NO 21
<211> LENGTH: 133
<212> TYPE: PRT
<213> ORGANISM: Homo sapiens
<220> FEATURE:
<221> NAME/KEY: VARIANT
<222> LOCATION: (16)..(16)
<223> OTHER INFORMATION: X is any amino acid other than His, or X is Ala
      or Thr.
<220> FEATURE:
<221> NAME/KEY: VARIANT
<222> LOCATION: (42)..(42)
<223> OTHER INFORMATION: X is any amino acid other than Phe, or X is Ala
      or Thr.

<400> SEQUENCE: 21

```
Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130
```

<210> SEQ ID NO 22
<211> LENGTH: 133
<212> TYPE: PRT
<213> ORGANISM: Homo sapiens
<220> FEATURE:
<221> NAME/KEY: VARIANT
<222> LOCATION: (20)..(20)
<223> OTHER INFORMATION: X is any amino acid other than Asp, or X is
      Ala.
<220> FEATURE:
<221> NAME/KEY: VARIANT
<222> LOCATION: (42)..(42)
<223> OTHER INFORMATION: X is any amino acid other than Phe, or X is
      Ala.

<400> SEQUENCE: 22

```
Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45
```

```
Lys Ala Thr Glu Leu Lys His Leu Gln Cys Leu Glu Glu Glu Leu Lys
 50                  55                  60
Pro Leu Glu Glu Val Leu Asn Leu Ala Gln Ser Lys Asn Phe His Leu
 65                      70                  75                  80
Arg Pro Arg Asp Leu Ile Ser Asn Ile Asn Val Ile Val Leu Glu Leu
                     85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
            115                 120                 125
Ile Ser Thr Leu Thr
            130

<210> SEQ ID NO 23
<211> LENGTH: 133
<212> TYPE: PRT
<213> ORGANISM: Homo sapiens
<220> FEATURE:
<221> NAME/KEY: VARIANT
<222> LOCATION: (15)..(15)
<223> OTHER INFORMATION: X is any amino acid other than Glu, or X is
      Ala.
<220> FEATURE:
<221> NAME/KEY: VARIANT
<222> LOCATION: (20)..(20)
<223> OTHER INFORMATION: X is any amino acid other than Asp, or X is
      Ala.
<220> FEATURE:
<221> NAME/KEY: VARIANT
<222> LOCATION: (42)..(42)
<223> OTHER INFORMATION: X is any amino acid other than Phe, or X is
      Ala.

<400> SEQUENCE: 23

Ala Pro Thr Ser Ser Ser Thr Lys Lys Thr Gln Leu Gln Leu Xaa His
 1               5                  10                  15
Leu Leu Leu Xaa Leu Gln Met Ile Leu Asn Gly Ile Asn Asn Tyr Lys
                 20                  25                  30
Asn Pro Lys Leu Thr Arg Met Leu Thr Xaa Lys Phe Tyr Met Pro Lys
             35                  40                  45
Lys Ala Thr Glu Leu Lys His Leu Gln Cys Leu Glu Glu Glu Leu Lys
 50                  55                  60
Pro Leu Glu Glu Val Leu Asn Leu Ala Gln Ser Lys Asn Phe His Leu
 65                      70                  75                  80
Arg Pro Arg Asp Leu Ile Ser Asn Ile Asn Val Ile Val Leu Glu Leu
                     85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
            115                 120                 125
Ile Ser Thr Leu Thr
            130

<210> SEQ ID NO 24
<211> LENGTH: 133
<212> TYPE: PRT
<213> ORGANISM: Homo sapiens
<220> FEATURE:
<221> NAME/KEY: VARIANT
<222> LOCATION: (16)..(16)
<223> OTHER INFORMATION: X is any amino acid other than His, or X is
      Ala.
```

```
<220> FEATURE:
<221> NAME/KEY: VARIANT
<222> LOCATION: (20)..(20)
<223> OTHER INFORMATION: X is any amino acid other than Asp, or X is
      Ala.
<220> FEATURE:
<221> NAME/KEY: VARIANT
<222> LOCATION: (42)..(42)
<223> OTHER INFORMATION: X is any amino acid other than Phe, or X is
      Ala.

<400> SEQUENCE: 24

Ala Pro Thr Ser Ser Ser Thr Lys Lys Thr Gln Leu Gln Leu Glu Xaa
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 25
<211> LENGTH: 133
<212> TYPE: PRT
<213> ORGANISM: Homo sapiens
<220> FEATURE:
<221> NAME/KEY: VARIANT
<222> LOCATION: (20)..(20)
<223> OTHER INFORMATION: X is any amino acid other than Asp, or X is
      Ala.
<220> FEATURE:
<221> NAME/KEY: VARIANT
<222> LOCATION: (42)..(42)
<223> OTHER INFORMATION: X is any amino acid other than Phe, or X is
      Ala.
<220> FEATURE:
<221> NAME/KEY: VARIANT
<222> LOCATION: (126)..(126)
<223> OTHER INFORMATION: X is any amino acid other than Gln, or X is
      Ala.

<400> SEQUENCE: 25

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
```

85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
        130

<210> SEQ ID NO 26
<211> LENGTH: 133
<212> TYPE: PRT
<213> ORGANISM: Homo sapiens
<220> FEATURE:
<221> NAME/KEY: VARIANT
<222> LOCATION: (20)..(20)
<223> OTHER INFORMATION: X is any amino acid other than Asp, or X is
      Ala.
<220> FEATURE:
<221> NAME/KEY: VARIANT
<222> LOCATION: (42)..(42)
<223> OTHER INFORMATION: X is any amino acid other than Phe, or X is
      Ala.
<220> FEATURE:
<221> NAME/KEY: VARIANT
<222> LOCATION: (45)..(45)
<223> OTHER INFORMATION: X is any amino acid other than Tyr, or X is
      Ala.

<400> SEQUENCE: 26

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Xaa Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 27
<211> LENGTH: 133
<212> TYPE: PRT
<213> ORGANISM: Homo sapiens
<220> FEATURE:
<221> NAME/KEY: VARIANT
<222> LOCATION: (16)..(16)
<223> OTHER INFORMATION: X is any amino acid other than His, or X is
      Ala.
<220> FEATURE:
<221> NAME/KEY: VARIANT
<222> LOCATION: (20)..(20)
<223> OTHER INFORMATION: X is any amino acid other than Asp, or X is
      Ala.
<220> FEATURE:
<221> NAME/KEY: VARIANT
<222> LOCATION: (42)..(42)

```
<223> OTHER INFORMATION: X is any amino acid other than Phe, or X is
      Ala.
<220> FEATURE:
<221> NAME/KEY: VARIANT
<222> LOCATION: (45)..(45)
<223> OTHER INFORMATION: X is any amino acid other than Tyr, or X is
      Ala.

<400> SEQUENCE: 27

Ala Pro Thr Ser Ser Ser Thr Lys Lys Thr Gln Leu Gln Leu Glu Xaa
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Xaa Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 28
<211> LENGTH: 153
<212> TYPE: PRT
<213> ORGANISM: Homo sapiens

<400> SEQUENCE: 28

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 29
<211> LENGTH: 128
<212> TYPE: PRT
```

<213> ORGANISM: Homo sapiens

<400> SEQUENCE: 29

Lys Cys Asp Ile Thr Leu Gln Glu Ile Ile Lys Thr Leu Asn Ser Leu
1               5                   10                  15
Thr Glu Gln Lys Thr Leu Cys Thr Glu Leu Thr Val Thr Asp Ile Phe
            20                  25                  30
Ala Ala Ser Lys Asn Thr Thr Glu Lys Glu Thr Phe Cys Arg Ala Ala
        35                  40                  45
Thr Val Leu Arg Gln Phe Tyr Ser His His Glu Lys Asp Thr Arg Cys
50                  55                  60
Leu Gly Ala Thr Ala Gln Gln Phe His Arg His Lys Gln Leu Ile Arg
65                  70                  75                  80
Phe Leu Lys Arg Leu Asp Arg Asn Leu Trp Gly Leu Ala Gly Leu Asn
                85                  90                  95
Ser Cys Pro Val Lys Glu Ala Asn Gln Ser Thr Leu Glu Asn Phe Leu
            100                 105                 110
Glu Arg Leu Lys Thr Ile Met Arg Glu Lys Tyr Ser Lys Cys Ser Ser
        115                 120                 125

<210> SEQ ID NO 30
<211> LENGTH: 137
<212> TYPE: PRT
<213> ORGANISM: Homo sapiens

<400> SEQUENCE: 30

Met Gly Leu Thr Ser Gln Leu Leu Pro Pro Leu Phe Phe Leu Leu Ala
1               5                   10                  15
Cys Ala Gly Asn Phe Val His Gly His Lys Cys Asp Ile Thr Leu Gln
            20                  25                  30
Glu Ile Ile Lys Thr Leu Asn Ser Leu Thr Glu Gln Lys Asn Thr Thr
        35                  40                  45
Glu Lys Glu Thr Phe Cys Arg Ala Ala Thr Val Leu Arg Gln Phe Tyr
50                  55                  60
Ser His His Glu Lys Asp Thr Arg Cys Leu Gly Ala Thr Ala Gln Gln
65                  70                  75                  80
Phe His Arg His Lys Gln Leu Ile Arg Phe Leu Lys Arg Leu Asp Arg
                85                  90                  95
Asn Leu Trp Gly Leu Ala Gly Leu Asn Ser Cys Pro Val Lys Glu Ala
            100                 105                 110
Asn Gln Ser Thr Leu Glu Asn Phe Leu Glu Arg Leu Lys Thr Ile Met
        115                 120                 125
Arg Glu Lys Tyr Ser Lys Cys Ser Ser
    130                 135

<210> SEQ ID NO 31
<211> LENGTH: 112
<212> TYPE: PRT
<213> ORGANISM: Homo sapiens

<400> SEQUENCE: 31

Lys Cys Asp Ile Thr Leu Gln Glu Ile Ile Lys Thr Leu Asn Ser Leu
1               5                   10                  15
Thr Glu Gln Lys Asn Thr Thr Glu Lys Glu Thr Phe Cys Arg Ala Ala
            20                  25                  30
Thr Val Leu Arg Gln Phe Tyr Ser His His Glu Lys Asp Thr Arg Cys
        35                  40                  45

```
Leu Gly Ala Thr Ala Gln Gln Phe His Arg His Lys Gln Leu Ile Arg
        50                  55                  60

Phe Leu Lys Arg Leu Asp Arg Asn Leu Trp Gly Leu Ala Gly Leu Asn
 65                  70                  75                  80

Ser Cys Pro Val Lys Glu Ala Asn Gln Ser Thr Leu Glu Asn Phe Leu
                85                  90                  95

Glu Arg Leu Lys Thr Ile Met Arg Glu Lys Tyr Ser Lys Cys Ser Ser
                100                 105                 110
```

<210> SEQ ID NO 32
<211> LENGTH: 825
<212> TYPE: PRT
<213> ORGANISM: Homo sapiens

<400> SEQUENCE: 32

```
Met Gly Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
                20                  25                  30

Thr Cys Val Ser Asp Tyr Met Ser Ile Ser Thr Cys Glu Trp Lys Met
                35                  40                  45

Asn Gly Pro Thr Asn Cys Ser Thr Glu Leu Arg Leu Leu Tyr Gln Leu
        50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
                100                 105                 110

Gly Ser Phe Lys Pro Ser Glu His Val Lys Pro Arg Ala Pro Gly Asn
                115                 120                 125

Leu Thr Val His Thr Asn Val Ser Asp Thr Leu Leu Leu Thr Trp Ser
        130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
                180                 185                 190

Ser Gly Ile Ser Tyr Arg Ala Arg Val Arg Ala Trp Ala Gln Cys Tyr
                195                 200                 205

Asn Thr Thr Trp Ser Glu Trp Ser Pro Ser Thr Lys Trp His Asn Ser
        210                 215                 220

Tyr Arg Glu Pro Phe Glu Gln His Leu Leu Leu Gly Val Ser Val Ser
225                 230                 235                 240

Cys Ile Val Ile Leu Ala Val Cys Leu Leu Cys Tyr Val Ser Ile Thr
                245                 250                 255

Lys Ile Lys Lys Glu Trp Trp Asp Gln Ile Pro Asn Pro Ala Arg Ser
                260                 265                 270

Arg Leu Val Ala Ile Ile Ile Gln Asp Ala Gln Gly Ser Gln Trp Glu
                275                 280                 285

Lys Arg Ser Arg Gly Gln Glu Pro Ala Lys Cys Pro His Trp Lys Asn
        290                 295                 300

Cys Leu Thr Lys Leu Leu Pro Cys Phe Leu Glu His Asn Met Lys Arg
```

```
            305                 310                 315                 320
        Asp Glu Asp Pro His Lys Ala Ala Lys Glu Met Pro Phe Gln Gly Ser
                        325                 330                 335
        Gly Lys Ser Ala Trp Cys Pro Val Glu Ile Ser Lys Thr Val Leu Trp
                        340                 345                 350
        Pro Glu Ser Ile Ser Val Val Arg Cys Val Glu Leu Phe Glu Ala Pro
                        355                 360                 365
        Val Glu Cys Glu Glu Glu Glu Val Glu Glu Lys Gly Ser Phe
            370                 375                 380
        Cys Ala Ser Pro Glu Ser Ser Arg Asp Asp Phe Gln Glu Gly Arg Glu
        385                 390                 395                 400
        Gly Ile Val Ala Arg Leu Thr Glu Ser Leu Phe Leu Asp Leu Leu Gly
                        405                 410                 415
        Glu Glu Asn Gly Gly Phe Cys Gln Gln Asp Met Gly Glu Ser Cys Leu
                        420                 425                 430
        Leu Pro Pro Ser Gly Ser Thr Ser Ala His Met Pro Trp Asp Glu Phe
                        435                 440                 445
        Pro Ser Ala Gly Pro Lys Glu Ala Pro Pro Trp Gly Lys Glu Gln Pro
                        450                 455                 460
        Leu His Leu Glu Pro Ser Pro Pro Ala Ser Pro Thr Gln Ser Pro Asp
        465                 470                 475                 480
        Asn Leu Thr Cys Thr Glu Thr Pro Leu Val Ile Ala Gly Asn Pro Ala
                        485                 490                 495
        Tyr Arg Ser Phe Ser Asn Ser Leu Ser Gln Ser Pro Cys Pro Arg Glu
                        500                 505                 510
        Leu Gly Pro Asp Pro Leu Leu Ala Arg His Leu Glu Glu Val Glu Pro
                        515                 520                 525
        Glu Met Pro Cys Val Pro Gln Leu Ser Glu Pro Thr Thr Val Pro Gln
                        530                 535                 540
        Pro Glu Pro Glu Thr Trp Glu Gln Ile Leu Arg Arg Asn Val Leu Gln
        545                 550                 555                 560
        His Gly Ala Ala Ala Pro Val Ser Ala Pro Thr Ser Gly Tyr Gln
                        565                 570                 575
        Glu Phe Val His Ala Val Glu Gln Gly Gly Thr Gln Ala Ser Ala Val
                        580                 585                 590
        Val Gly Leu Gly Pro Pro Gly Glu Ala Gly Tyr Lys Ala Phe Ser Ser
                        595                 600                 605
        Leu Leu Ala Ser Ser Ala Val Ser Pro Glu Lys Cys Gly Phe Gly Ala
                        610                 615                 620
        Ser Ser Gly Glu Glu Gly Tyr Lys Pro Phe Gln Asp Leu Ile Pro Gly
        625                 630                 635                 640
        Cys Pro Gly Asp Pro Ala Pro Val Pro Val Pro Leu Phe Thr Gly Phe
                        645                 650                 655
        Leu Asp Arg Glu Pro Pro Arg Ser Pro Gln Ser Ser His Leu Pro Ser
                        660                 665                 670
        Ser Ser Pro Glu His Leu Gly Leu Glu Pro Gly Glu Lys Val Glu Asp
                        675                 680                 685
        Met Pro Lys Pro Pro Leu Pro Gln Glu Gln Ala Thr Asp Pro Leu Val
                        690                 695                 700
        Asp Ser Leu Gly Ser Gly Ile Val Tyr Ser Ala Leu Thr Cys His Leu
        705                 710                 715                 720
        Cys Gly His Leu Lys Gln Cys His Gly Gln Glu Asp Gly Gly Gln Thr
                        725                 730                 735
```

```
Pro Val Met Ala Ser Pro Cys Cys Gly Cys Cys Gly Asp Arg Ser
            740             745             750

Ser Pro Pro Thr Thr Pro Leu Arg Ala Pro Asp Pro Ser Pro Gly Gly
        755             760             765

Val Pro Leu Glu Ala Ser Leu Cys Pro Ala Ser Leu Ala Pro Ser Gly
770             775             780

Ile Ser Glu Lys Ser Lys Ser Ser Ser Phe His Pro Ala Pro Gly
785             790             795             800

Asn Ala Gln Ser Ser Ser Gln Thr Pro Lys Ile Val Asn Phe Val Ser
            805             810             815

Val Gly Pro Thr Tyr Met Arg Val Ser
            820             825

<210> SEQ ID NO 33
<211> LENGTH: 227
<212> TYPE: PRT
<213> ORGANISM: Homo sapiens

<400> SEQUENCE: 33

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
    210                 215                 220

Asn Ile Cys
225

<210> SEQ ID NO 34
<211> LENGTH: 212
<212> TYPE: PRT
<213> ORGANISM: Homo sapiens

<400> SEQUENCE: 34
```

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 35
<211> LENGTH: 183
<212> TYPE: PRT
<213> ORGANISM: Homo sapiens

<400> SEQUENCE: 35

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
130                 135                 140

Ser Leu Leu Thr Lys Leu Gln Ala Gln Asn Gln Trp Leu Gln Asp Met
```

```
                145                 150                 155                 160
Thr Thr His Leu Ile Leu Arg Ser Phe Lys Glu Phe Leu Gln Ser Ser
            165                 170                 175

Leu Arg Ala Leu Arg Gln Met
            180

<210> SEQ ID NO 36
<211> LENGTH: 468
<212> TYPE: PRT
<213> ORGANISM: Homo sapiens

<400> SEQUENCE: 36

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
            130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
            210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
            290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335
```

```
Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
            405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
450                 455                 460

Phe Phe Pro Arg
465

<210> SEQ ID NO 37
<211> LENGTH: 918
<212> TYPE: PRT
<213> ORGANISM: Homo sapiens

<400> SEQUENCE: 37

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Gly Phe Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240
```

```
Lys Leu Thr Trp Thr Asn Pro Ser Ile Lys Ser Val Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
                275                 280                 285

Leu Lys Pro Phe Thr Glu Tyr Val Phe Arg Ile Arg Cys Met Lys Glu
        290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
                355                 360                 365

Thr Leu Thr Arg Trp Lys Ser His Leu Gln Asn Tyr Thr Val Asn Ala
        370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
                500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Thr Phe
                595                 600                 605

Thr Thr Pro Lys Phe Ala Gln Gly Glu Ile Glu Ala Ile Val Val Pro
        610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655
```

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
            675                 680                 685

Thr Asp Val Ser Val Val Glu Ile Glu Ala Asn Asp Lys Lys Pro Phe
            690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
            725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
            770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
            805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
            885                 890                 895

Thr Asp Glu Gly Met Pro Lys Ser Tyr Leu Pro Gln Thr Val Arg Gln
            900                 905                 910

Gly Gly Tyr Met Pro Gln
            915

<210> SEQ ID NO 38
<211> LENGTH: 468
<212> TYPE: PRT
<213> ORGANISM: Homo sapiens

<400> SEQUENCE: 38

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65              70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

```
Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
                195                 200                 205

Gln Gly Cys Gly Ile Leu Gln Pro Asp Pro Pro Ala Asn Ile Thr Val
                210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
                275                 280                 285

Val Val Gln Leu Arg Ala Gln Glu Glu Phe Gly Gln Gly Glu Trp Ser
                290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ser Ser Val Pro Leu Pro Thr Phe Leu
                355                 360                 365

Val Ala Gly Gly Ser Leu Ala Phe Gly Thr Leu Leu Cys Ile Ala Ile
                370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
                435                 440                 445

Asp Ala Arg Asp Pro Arg Ser Pro Tyr Asp Ile Ser Asn Thr Asp Tyr
450                 455                 460

Phe Phe Pro Arg
465

<210> SEQ ID NO 39
<211> LENGTH: 177
<212> TYPE: PRT
<213> ORGANISM: Homo sapiens

<400> SEQUENCE: 39

Met Phe His Val Ser Phe Arg Tyr Ile Phe Gly Leu Pro Pro Leu Ile
```

```
1               5                   10                  15
Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
        50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 40
<211> LENGTH: 152
<212> TYPE: PRT
<213> ORGANISM: Homo sapiens

<400> SEQUENCE: 40

```
                    5                   10                  15
Asp Cys Asp Ile Glu Gly Lys Asp Gly Lys Gln Tyr Glu Ser Val Leu
1                   5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 41
<211> LENGTH: 133
<212> TYPE: PRT
<213> ORGANISM: Homo sapiens

<400> SEQUENCE: 41

-continued

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
        50                  55                  60

Asn Phe Phe Lys Arg His Ile Cys Asp Ala Asn Lys Val Lys Gly Arg
65                  70                  75                  80

Lys Pro Ala Ala Leu Gly Glu Ala Gln Pro Thr Lys Ser Leu Glu Glu
                85                  90                  95

Asn Lys Ser Leu Lys Glu Gln Lys Lys Leu Asn Asp Leu Cys Phe Leu
            100                 105                 110

Lys Arg Leu Leu Gln Glu Ile Lys Thr Cys Trp Asn Lys Ile Leu Met
        115                 120                 125

Gly Thr Lys Glu His
    130

<210> SEQ ID NO 42
<211> LENGTH: 109
<212> TYPE: PRT
<213> ORGANISM: Homo sapiens

<400> SEQUENCE: 42

Ser Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
                20                  25                  30

Ser Asn Cys Leu Asn Asn Glu Phe Asn Phe Phe Lys Arg His Ile Cys
            35                  40                  45

Asp Ala Asn Lys Val Lys Gly Arg Lys Pro Ala Ala Leu Gly Glu Ala
        50                  55                  60

Gln Pro Thr Lys Ser Leu Glu Glu Asn Lys Ser Leu Lys Glu Gln Lys
65                  70                  75                  80

Lys Leu Asn Asp Leu Cys Phe Leu Lys Arg Leu Leu Gln Glu Ile Lys
                85                  90                  95

Thr Cys Trp Asn Lys Ile Leu Met Gly Thr Lys Glu His
            100                 105

<210> SEQ ID NO 43
<211> LENGTH: 159
<212> TYPE: PRT
<213> ORGANISM: Homo sapiens

<400> SEQUENCE: 43

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
        50                  55                  60

Asn Phe Phe Lys Arg His Ile Cys Asp Ala Asn Lys Glu Gly Met Phe
65                  70                  75                  80
```

```
Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Glu Glu Asn Lys Ser Leu Lys Glu
        115                 120                 125

Gln Lys Lys Leu Asn Asp Leu Cys Phe Leu Lys Arg Leu Leu Gln Glu
130                 135                 140

Ile Lys Thr Cys Trp Asn Lys Ile Leu Met Gly Thr Lys Glu His
145                 150                 155

<210> SEQ ID NO 44
<211> LENGTH: 133
<212> TYPE: PRT
<213> ORGANISM: Homo sapiens

<400> SEQUENCE: 44

Cys Asp Ile Glu Gly Lys Asp Gly Lys Gln Tyr Glu Ser Val Leu Met
1               5                   10                  15

Val Ser Ile Asp Gln Leu Leu Asp Ser Met Lys Glu Ile Gly Ser Asn
            20                  25                  30

Cys Leu Asn Asn Glu Phe Asn Phe Phe Lys Arg His Ile Cys Asp Ala
        35                  40                  45

Asn Lys Glu Gly Met Phe Leu Phe Arg Ala Ala Arg Lys Leu Arg Gln
    50                  55                  60

Phe Leu Lys Met Asn Ser Thr Gly Asp Phe Asp Leu His Leu Leu Lys
65                  70                  75                  80

Val Ser Glu Gly Thr Thr Ile Leu Leu Asn Cys Thr Gly Gln Glu Glu
                85                  90                  95

Asn Lys Ser Leu Lys Glu Gln Lys Lys Leu Asn Asp Leu Cys Phe Leu
            100                 105                 110

Lys Arg Leu Leu Gln Glu Ile Lys Thr Cys Trp Asn Lys Ile Leu Met
        115                 120                 125

Gly Thr Lys Glu His
    130

<210> SEQ ID NO 45
<211> LENGTH: 115
<212> TYPE: PRT
<213> ORGANISM: Homo sapiens

<400> SEQUENCE: 45

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Lys
65                  70                  75                  80

Ser Leu Lys Glu Gln Lys Lys Leu Asn Asp Leu Cys Phe Leu Lys Arg
                85                  90                  95

Leu Leu Gln Glu Ile Lys Thr Cys Trp Asn Lys Ile Leu Met Gly Thr
            100                 105                 110
```

```
Lys Glu His
        115

<210> SEQ ID NO 46
<211> LENGTH: 91
<212> TYPE: PRT
<213> ORGANISM: Homo sapiens

<400> SEQUENCE: 46

Ser Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Glu Asn Lys Ser Leu Lys Glu Gln Lys Lys Leu
    50                  55                  60

Asn Asp Leu Cys Phe Leu Lys Arg Leu Leu Gln Glu Ile Lys Thr Cys
65                  70                  75                  80

Trp Asn Lys Ile Leu Met Gly Thr Lys Glu His
                85                  90

<210> SEQ ID NO 47
<211> LENGTH: 459
<212> TYPE: PRT
<213> ORGANISM: Homo sapiens

<400> SEQUENCE: 47

Met Thr Ile Leu Gly Thr Thr Gly Phe Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Val Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220
```

```
Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
                260                 265                 270

Trp Pro Ser Leu Pro Asp His Lys Lys Thr Leu Glu His Leu Cys Lys
            275                 280                 285

Lys Pro Arg Lys Asn Leu Asn Val Ser Phe Asn Pro Glu Ser Phe Leu
        290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
                340                 345                 350

Asp Val Val Ile Thr Pro Glu Ser Phe Gly Arg Asp Ser Ser Leu Thr
            355                 360                 365

Cys Leu Ala Gly Asn Val Ser Ala Cys Asp Ala Pro Ile Leu Ser Ser
            370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
            435                 440                 445

Tyr Val Thr Met Ser Ser Phe Tyr Gln Asn Gln
    450                 455

<210> SEQ ID NO 48
<211> LENGTH: 369
<212> TYPE: PRT
<213> ORGANISM: Homo sapiens

<400> SEQUENCE: 48

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
            35                  40                  45

Ser Leu Ser Val Ser Thr Leu Pro Leu Pro Glu Val Gln Cys Phe Val
50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
            115                 120                 125

Val Val Gln Leu Gln Asp Pro Arg Glu Pro Arg Arg Gln Ala Thr Gln
```

```
             130                 135                 140
Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
                    180                 185                 190

Trp Asp His Ser Trp Thr Glu Gln Ser Val Asp Tyr Arg His Lys Phe
                195                 200                 205

Ser Leu Pro Ser Val Asp Gly Gln Lys Arg Tyr Thr Phe Arg Val Arg
210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                    245                 250                 255

Leu Phe Ala Leu Glu Ala Val Val Ile Ser Val Gly Ser Met Gly Leu
                260                 265                 270

Ile Ile Ser Leu Leu Cys Val Tyr Phe Trp Leu Glu Arg Thr Met Pro
275                 280                 285

Arg Ile Pro Thr Leu Lys Asn Leu Glu Asp Leu Val Thr Glu Tyr His
        290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
                340                 345                 350

Gln His Ser Pro Tyr Trp Ala Pro Pro Cys Tyr Thr Leu Lys Pro Glu
                355                 360                 365

Thr

<210> SEQ ID NO 49
<211> LENGTH: 178
<212> TYPE: PRT
<213> ORGANISM: Homo sapiens

<400> SEQUENCE: 49

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
```

```
            130                 135                 140
Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 50
<211> LENGTH: 160
<212> TYPE: PRT
<213> ORGANISM: Homo sapiens

<400> SEQUENCE: 50

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
        50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 51
<211> LENGTH: 74
<212> TYPE: PRT
<213> ORGANISM: Homo sapiens

<400> SEQUENCE: 51

Met Ile Gln Phe Tyr Leu Glu Glu Val Met Pro Gln Ala Glu Asn Gln
1               5                   10                  15

Asp Pro Asp Ile Lys Ala His Val Asn Ser Leu Gly Glu Asn Leu Lys
                20                  25                  30

Thr Leu Arg Leu Arg Leu Arg Arg Cys His Arg Phe Leu Pro Cys Glu
            35                  40                  45

Asn Lys Ser Lys Ala Val Glu Gln Val Lys Asn Ala Phe Asn Lys Leu
        50                  55                  60

Gln Glu Lys Gly Ile Tyr Lys Ala Met Ser
65                  70

<210> SEQ ID NO 52
<211> LENGTH: 578
<212> TYPE: PRT
<213> ORGANISM: Homo sapiens

<400> SEQUENCE: 52
```

```
Met Leu Pro Cys Leu Val Val Leu Ala Leu Leu Ser Leu Arg
1               5                   10                  15

Leu Gly Ser Asp Ala His Gly Thr Glu Leu Pro Ser Pro Ser Val
            20              25              30

Trp Phe Glu Ala Glu Phe Phe His His Ile Leu His Trp Thr Pro Ile
                35              40              45

Pro Asn Gln Ser Glu Ser Thr Cys Tyr Glu Val Ala Leu Leu Arg Tyr
        50              55              60

Gly Ile Glu Ser Trp Asn Ser Ile Ser Asn Cys Ser Gln Thr Leu Ser
65                  70              75                      80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100             105             110

Val Thr Asn Thr Arg Phe Ser Val Asp Glu Val Thr Leu Thr Val Gly
            115             120             125

Ser Val Asn Leu Glu Ile His Asn Gly Phe Ile Leu Gly Lys Ile Gln
    130             135             140

Leu Pro Arg Pro Lys Met Ala Pro Ala Asn Asp Thr Tyr Glu Ser Ile
145             150             155             160

Phe Ser His Phe Arg Glu Tyr Glu Ile Ala Ile Arg Lys Val Pro Gly
                165             170             175

Asn Phe Thr Phe Thr His Lys Lys Val Lys His Glu Asn Phe Ser Leu
            180             185             190

Leu Thr Ser Gly Glu Val Gly Glu Phe Cys Val Gln Val Lys Pro Ser
            195             200             205

Val Ala Ser Arg Ser Asn Lys Gly Met Trp Ser Lys Glu Glu Cys Ile
            210             215             220

Ser Leu Thr Arg Gln Tyr Phe Thr Val Thr Asn Val Ile Ile Phe Phe
225             230             235             240

Ala Phe Val Leu Leu Leu Ser Gly Ala Leu Ala Tyr Cys Leu Ala Leu
                245             250             255

Gln Leu Tyr Val Arg Arg Arg Lys Lys Leu Pro Ser Val Leu Leu Phe
                260             265             270

Lys Lys Pro Ser Pro Phe Ile Phe Ile Ser Gln Arg Pro Ser Pro Glu
            275             280             285

Thr Gln Asp Thr Ile His Pro Leu Asp Glu Glu Ala Phe Leu Lys Val
            290             295             300

Ser Pro Glu Leu Lys Asn Leu Asp Leu His Gly Ser Thr Asp Ser Gly
305             310             315             320

Phe Gly Ser Thr Lys Pro Ser Leu Gln Thr Glu Glu Pro Gln Phe Leu
                325             330             335

Leu Pro Asp Pro His Pro Gln Ala Asp Arg Thr Leu Gly Asn Arg Glu
            340             345             350

Pro Pro Val Leu Gly Asp Ser Cys Ser Ser Gly Ser Ser Asn Ser Thr
            355             360             365

Asp Ser Gly Ile Cys Leu Gln Glu Pro Ser Leu Ser Pro Ser Thr Gly
    370             375             380

Pro Thr Trp Glu Gln Val Gly Ser Asn Ser Arg Gly Gln Asp Asp
385             390             395             400

Ser Gly Ile Asp Leu Val Gln Asn Ser Glu Gly Arg Ala Gly Asp Thr
            405             410             415

Gln Gly Gly Ser Ala Leu Gly His His Ser Pro Pro Glu Pro Glu Val
```

```
                420             425             430
Pro Gly Glu Glu Asp Pro Ala Ala Val Ala Phe Gln Gly Tyr Leu Arg
            435             440             445
Gln Thr Arg Cys Ala Glu Lys Ala Thr Lys Thr Gly Cys Leu Glu
450             455             460
Glu Glu Ser Pro Leu Thr Asp Gly Leu Gly Pro Lys Phe Gly Arg Cys
465             470             475             480
Leu Val Asp Glu Ala Gly Leu His Pro Pro Ala Leu Ala Lys Gly Tyr
                485             490             495
Leu Lys Gln Asp Pro Leu Glu Met Thr Leu Ala Ser Ser Gly Ala Pro
                500             505             510
Thr Gly Gln Trp Asn Gln Pro Thr Glu Glu Trp Ser Leu Leu Ala Leu
                515             520             525
Ser Ser Cys Ser Asp Leu Gly Ile Ser Asp Trp Ser Phe Ala His Asp
                530             535             540
Leu Ala Pro Leu Gly Cys Val Ala Ala Pro Gly Gly Leu Leu Gly Ser
545             550             555             560
Phe Asn Ser Asp Leu Val Thr Leu Pro Leu Ile Ser Ser Leu Gln Ser
                565             570             575
Ser Glu

<210> SEQ ID NO 53
<211> LENGTH: 325
<212> TYPE: PRT
<213> ORGANISM: Homo sapiens

<400> SEQUENCE: 53

Met Ala Trp Ser Leu Gly Ser Trp Leu Gly Gly Cys Leu Leu Val Ser
1               5                   10                  15
Ala Leu Gly Met Val Pro Pro Glu Asn Val Arg Met Asn Ser Val
                20                  25                  30
Asn Phe Lys Asn Ile Leu Gln Trp Glu Ser Pro Ala Phe Ala Lys Gly
                35                  40                  45
Asn Leu Thr Phe Thr Ala Gln Tyr Leu Ser Tyr Arg Ile Phe Gln Asp
                50                  55                  60
Lys Cys Met Asn Thr Thr Leu Thr Glu Cys Asp Phe Ser Ser Leu Ser
65              70                  75                  80
Lys Tyr Gly Asp His Thr Leu Arg Val Arg Ala Glu Phe Ala Asp Glu
                85                  90                  95
His Ser Asp Trp Val Asn Ile Thr Phe Cys Pro Val Asp Asp Thr Ile
                100                 105                 110
Ile Gly Pro Pro Gly Met Gln Val Glu Val Leu Ala Asp Ser Leu His
            115                 120                 125
Met Arg Phe Leu Ala Pro Lys Ile Glu Asn Glu Tyr Glu Thr Trp Thr
            130                 135                 140
Met Lys Asn Val Tyr Asn Ser Trp Thr Tyr Asn Val Gln Tyr Trp Lys
145                 150                 155                 160
Asn Gly Thr Asp Glu Lys Phe Gln Ile Thr Pro Gln Tyr Asp Phe Glu
                165                 170                 175
Val Leu Arg Asn Leu Glu Pro Trp Thr Thr Tyr Cys Val Gln Val Arg
                180                 185                 190
Gly Phe Leu Pro Asp Arg Asn Lys Ala Gly Glu Trp Ser Glu Pro Val
            195                 200                 205
Cys Glu Gln Thr Thr His Asp Glu Thr Val Pro Ser Trp Met Val Ala
```

```
                    210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
                260                 265                 270

Pro His His Asn Thr Leu Leu Phe Phe Ser Phe Pro Leu Ser Asp Glu
            275                 280                 285

Asn Asp Val Phe Asp Lys Leu Ser Val Ile Ala Glu Asp Ser Glu Ser
        290                 295                 300

Gly Lys Gln Asn Pro Gly Asp Ser Cys Ser Leu Gly Thr Pro Pro Gly
305                 310                 315                 320

Gln Gly Pro Gln Ser
                325

<210> SEQ ID NO 54
<211> LENGTH: 162
<212> TYPE: PRT
<213> ORGANISM: Homo sapiens

<400> SEQUENCE: 54

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 55
<211> LENGTH: 114
<212> TYPE: PRT
<213> ORGANISM: Homo sapiens

<400> SEQUENCE: 55

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45
```

```
Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 56
<211> LENGTH: 267
<212> TYPE: PRT
<213> ORGANISM: Homo sapiens

<400> SEQUENCE: 56

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
                 20                  25                  30

Cys Pro Pro Pro Met Ser Val Glu His Ala Asp Ile Trp Val Lys Ser
                 35                  40                  45

Tyr Ser Leu Tyr Ser Arg Glu Arg Tyr Ile Cys Asn Ser Gly Phe Lys
 50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Arg Asp
                 85                  90                  95

Pro Ala Leu Val His Gln Arg Pro Ala Pro Pro Ser Thr Val Thr Thr
                100                 105                 110

Ala Gly Val Thr Pro Gln Pro Glu Ser Leu Ser Pro Ser Gly Lys Glu
                115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
                180                 185                 190

Pro Pro Gly Val Tyr Pro Gln Gly His Ser Asp Thr Thr Val Ala Ile
                195                 200                 205

Ser Thr Ser Thr Val Leu Leu Cys Gly Leu Ser Ala Val Ser Leu Leu
210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
                260                 265

<210> SEQ ID NO 57
<211> LENGTH: 162
<212> TYPE: PRT
<213> ORGANISM: Homo sapiens
```

<400> SEQUENCE: 57

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
        50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
                100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
        130                 135                 140

Gln Lys Met Ile His Gln His Leu Ser Ser Arg Thr His Gly Ser Glu
145                 150                 155                 160

Asp Ser

<210> SEQ ID NO 58
<211> LENGTH: 133
<212> TYPE: PRT
<213> ORGANISM: Homo sapiens

<400> SEQUENCE: 58

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
        130

<210> SEQ ID NO 59
<211> LENGTH: 162
<212> TYPE: PRT
<213> ORGANISM: Homo sapiens

<400> SEQUENCE: 59

Met Arg Ser Ser Pro Gly Asn Met Glu Arg Ile Val Ile Cys Leu Met

```
            1               5                  10                 15
Val Ile Phe Leu Gly Thr Leu Val His Lys Ser Ser Gln Gly Gln
            20                 25                 30

Asp Arg His Met Ile Arg Met Arg Gln Leu Ile Asp Ile Val Asp Gln
            35                 40                 45

Leu Lys Asn Tyr Val Asn Asp Leu Val Pro Glu Phe Leu Pro Ala Pro
            50                 55                 60

Glu Asp Val Glu Thr Asn Cys Glu Trp Ser Ala Phe Ser Cys Phe Gln
65                    70                 75                 80

Lys Ala Gln Leu Lys Ser Ala Asn Thr Gly Asn Asn Glu Arg Ile Ile
                85                 90                 95

Asn Val Ser Ile Lys Lys Leu Lys Arg Lys Pro Pro Ser Thr Asn Ala
                100                105                110

Gly Arg Arg Gln Lys His Arg Leu Thr Cys Pro Ser Cys Asp Ser Tyr
                115                120                125

Glu Lys Lys Pro Pro Lys Glu Phe Leu Glu Arg Phe Lys Ser Leu Leu
                130                135                140

Gln Lys Met Ile His Gln His Leu Ser Ser Arg Thr His Gly Ser Glu
145                  150                155                160

Asp Ser

<210> SEQ ID NO 60
<211> LENGTH: 153
<212> TYPE: PRT
<213> ORGANISM: Homo sapiens

<400> SEQUENCE: 60

Met Arg Ser Ser Pro Gly Asn Met Glu Arg Ile Val Ile Cys Leu Met
1               5                  10                 15

Val Ile Phe Leu Gly Thr Leu Val His Lys Ser Ser Gln Gly Gln
            20                 25                 30

Asp Arg His Met Ile Arg Met Arg Gln Leu Ile Asp Ile Val Asp Gln
            35                 40                 45

Leu Lys Asn Tyr Val Asn Asp Leu Val Pro Glu Phe Leu Pro Ala Pro
            50                 55                 60

Glu Asp Val Glu Thr Asn Cys Glu Trp Ser Ala Phe Ser Cys Phe Gln
65                    70                 75                 80

Lys Ala Gln Leu Lys Ser Ala Asn Thr Gly Asn Asn Glu Arg Ile Ile
                85                 90                 95

Asn Val Ser Ile Lys Lys Leu Lys Arg Lys Pro Pro Ser Thr Asn Ala
                100                105                110

Gly Arg Arg Gln Lys His Arg Leu Thr Cys Pro Ser Cys Asp Ser Tyr
                115                120                125

Glu Lys Lys Pro Pro Lys Glu Phe Leu Glu Arg Phe Lys Ser Leu Leu
                130                135                140

Gln Lys Val Ser Thr Leu Ser Phe Ile
145                  150

<210> SEQ ID NO 61
<211> LENGTH: 538
<212> TYPE: PRT
<213> ORGANISM: Homo sapiens

<400> SEQUENCE: 61

Met Pro Arg Gly Trp Ala Ala Pro Leu Leu Leu Leu Leu Leu Gln Gly
1               5                  10                 15
```

```
Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
         50                  55                  60

Cys Ser Leu His Arg Ser Ala His Asn Ala Thr His Ala Thr Tyr Thr
 65                  70                  75                  80

Cys His Met Asp Val Phe His Phe Met Ala Asp Asp Ile Phe Ser Val
                 85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285

Lys Lys Trp Val Gly Ala Pro Phe Thr Gly Ser Ser Leu Glu Leu Gly
290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430
```

```
Ala Gly Ser Pro Gly Leu Gly Pro Leu Gly Ser Leu Leu Asp Arg
            435                 440                 445

Leu Lys Pro Pro Leu Ala Asp Gly Glu Asp Trp Ala Gly Gly Leu Pro
    450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
                500                 505                 510

Glu Gly Pro Pro Arg Ser Tyr Leu Arg Gln Trp Val Val Ile Pro Pro
            515                 520                 525

Pro Leu Ser Ser Pro Gly Pro Gln Ala Ser
    530                 535

<210> SEQ ID NO 62
<211> LENGTH: 189
<212> TYPE: PRT
<213> ORGANISM: Homo sapiens

<400> SEQUENCE: 62

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 63
<211> LENGTH: 170
<212> TYPE: PRT
<213> ORGANISM: Homo sapiens

<400> SEQUENCE: 63

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30
```

```
Gly His Met Asp Leu Arg Glu Glu Gly Asp Glu Thr Asn Asp
         35                  40                  45

Val Pro His Ile Gln Cys Gly Asp Gly Cys Pro Gln Gly Leu Arg
 50                  55                  60

Asp Asn Ser Gln Phe Cys Leu Gln Arg Ile His Gln Gly Leu Ile Phe
 65                  70                  75                  80

Tyr Glu Lys Leu Leu Gly Ser Asp Ile Phe Thr Gly Glu Pro Ser Leu
                 85                  90                  95

Leu Pro Asp Ser Pro Val Gly Gln Leu His Ala Ser Leu Leu Gly Leu
             100                 105                 110

Ser Gln Leu Leu Gln Pro Glu Gly His His Trp Glu Thr Gln Gln Ile
         115                 120                 125

Pro Ser Leu Ser Pro Ser Gln Pro Trp Gln Arg Leu Leu Leu Arg Phe
130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                 165                 170

<210> SEQ ID NO 64
<211> LENGTH: 328
<212> TYPE: PRT
<213> ORGANISM: Homo sapiens

<400> SEQUENCE: 64

Met Cys His Gln Gln Leu Val Ile Ser Trp Phe Ser Leu Val Phe Leu
 1               5                  10                  15

Ala Ser Pro Leu Val Ala Ile Trp Glu Leu Lys Lys Asp Val Tyr Val
                 20                  25                  30

Val Glu Leu Asp Trp Tyr Pro Asp Ala Pro Gly Glu Met Val Val Leu
                 35                  40                  45

Thr Cys Asp Thr Pro Glu Glu Asp Gly Ile Thr Trp Thr Leu Asp Gln
 50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
             100                 105                 110

Ser Thr Asp Ile Leu Lys Asp Gln Lys Glu Pro Lys Asn Lys Thr Phe
         115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                 165                 170                 175

Ala Glu Arg Val Arg Gly Asp Asn Lys Glu Tyr Glu Tyr Ser Val Glu
                 180                 185                 190

Cys Gln Glu Asp Ser Ala Cys Pro Ala Ala Glu Glu Ser Leu Pro Ile
             195                 200                 205

Glu Val Met Val Asp Ala Val His Lys Leu Lys Tyr Glu Asn Tyr Thr
         210                 215                 220

Ser Ser Phe Phe Ile Arg Asp Ile Ile Lys Pro Asp Pro Pro Lys Asn
225                 230                 235                 240
```

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
        260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 65
<211> LENGTH: 306
<212> TYPE: PRT
<213> ORGANISM: Homo sapiens

<400> SEQUENCE: 65

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala

```
            275                 280                 285
Gln Asp Arg Tyr Tyr Ser Ser Trp Ser Glu Trp Ala Ser Val Pro
        290                 295                 300

Cys Ser
305

<210> SEQ ID NO 66
<211> LENGTH: 629
<212> TYPE: PRT
<213> ORGANISM: Homo sapiens

<400> SEQUENCE: 66

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Glu Gln Tyr Leu Thr Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335
```

-continued

Thr Val Ala Ser Ile Ser Thr Gly His Leu Thr Asp Asn Arg Gly
            340                 345                 350

Asp Ile Gly Leu Leu Leu Gly Met Ile Val Phe Ala Val Met Leu Ser
        355                 360                 365

Ile Leu Ser Leu Ile Gly Ile Phe Asn Arg Ser Phe Arg Thr Gly Ile
    370                 375                 380

Lys Arg Arg Ile Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
                405                 410                 415

Glu Leu Met Asn Asn Asn Ser Ser Glu Gln Val Leu Tyr Val Asp Pro
            420                 425                 430

Met Ile Thr Glu Ile Lys Glu Ile Phe Ile Pro Glu His Lys Pro Thr
        435                 440                 445

Asp Tyr Lys Lys Glu Asn Thr Gly Pro Leu Glu Thr Arg Asp Tyr Pro
    450                 455                 460

Gln Asn Ser Leu Phe Asp Asn Thr Thr Val Val Tyr Ile Pro Asp Leu
465                 470                 475                 480

Asn Thr Gly Tyr Lys Pro Gln Ile Ser Asn Phe Leu Pro Glu Gly Ser
                485                 490                 495

His Leu Ser Asn Asn Asn Glu Ile Thr Ser Leu Thr Leu Lys Pro Pro
            500                 505                 510

Val Asp Ser Leu Asp Ser Gly Asn Asn Pro Arg Leu Gln Lys His Pro
        515                 520                 525

Asn Phe Ala Phe Ser Val Ser Ser Val Asn Ser Leu Ser Asn Thr Ile
    530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Thr Thr Met Leu Leu Glu
                565                 570                 575

Asn Asp Ser Pro Ser Glu Thr Ile Pro Glu Gln Thr Leu Leu Pro Asp
            580                 585                 590

Glu Phe Val Ser Cys Leu Gly Ile Val Asn Glu Glu Leu Pro Ser Ile
        595                 600                 605

Asn Thr Tyr Phe Pro Gln Asn Ile Leu Glu Ser His Phe Asn Arg Ile
    610                 615                 620

Ser Leu Leu Glu Lys
625

<210> SEQ ID NO 67
<211> LENGTH: 662
<212> TYPE: PRT
<213> ORGANISM: Homo sapiens

<400> SEQUENCE: 67

Met Glu Pro Leu Val Thr Trp Val Val Pro Leu Leu Phe Leu Phe Leu
1                   5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

```
Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
    210                 215                 220

Trp Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
        355                 360                 365

Ile Glu Trp Gln Pro Val Gly Gln Asp Gly Gly Leu Ala Thr Cys Ser
    370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
            420                 425                 430

Val Leu Ser Thr Tyr His Phe Gly Gly Asn Ala Ser Ala Ala Gly Thr
        435                 440                 445

Pro His His Val Ser Val Lys Asn His Ser Leu Asp Ser Val Ser Val
    450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495
```

```
Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser
        530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
                580                 585                 590

Pro Gly Gly Lys Glu Thr Trp Gln Trp Ile Asn Pro Val Asp Phe Gln
            595                 600                 605

Glu Glu Ala Ser Leu Gln Glu Ala Leu Val Val Glu Met Ser Trp Asp
            610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Lys Ala Lys Met
                660

<210> SEQ ID NO 68
<211> LENGTH: 353
<212> TYPE: PRT
<213> ORGANISM: Homo sapiens

<400> SEQUENCE: 68

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205
```

-continued

```
Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 69
<211> LENGTH: 383
<212> TYPE: PRT
<213> ORGANISM: Homo sapiens

<400> SEQUENCE: 69

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
        35                  40                  45

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Lys Lys Lys Glu
    130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220
```

```
Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
            245                 250                 255

Pro Gln Arg Leu Met Ala Leu Arg Glu Pro Ala Ala Gln Ala Pro Val
        260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
        290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Val Thr Asp His Gly Pro Met Lys
    370                 375                 380

<210> SEQ ID NO 70
<211> LENGTH: 222
<212> TYPE: PRT
<213> ORGANISM: Homo sapiens

<400> SEQUENCE: 70

Ala Asp Pro Cys Asp Ser Asn Pro Arg Gly Val Ser Ala Tyr Leu Ser
1               5                   10                  15

Arg Pro Ser Pro Phe Asp Leu Phe Ile Arg Lys Ser Pro Thr Ile Thr
            20                  25                  30

Cys Leu Val Val Asp Leu Ala Pro Ser Lys Gly Thr Val Asn Leu Thr
        35                  40                  45

Trp Ser Arg Ala Ser Gly Lys Pro Val Asn His Ser Thr Arg Lys Glu
50                  55                  60

Glu Lys Gln Arg Asn Gly Thr Leu Thr Val Thr Ser Thr Leu Pro Val
65                  70                  75                  80

Gly Thr Arg Asp Trp Ile Glu Gly Glu Thr Tyr Gln Cys Arg Val Thr
            85                  90                  95

His Pro His Leu Pro Arg Ala Leu Met Arg Ser Thr Thr Lys Thr Ser
        100                 105                 110

Gly Pro Arg Ala Ala Pro Glu Val Tyr Ala Phe Ala Thr Pro Glu Trp
        115                 120                 125

Pro Gly Ser Arg Asp Lys Arg Thr Leu Ala Cys Leu Ile Gln Asn Phe
    130                 135                 140

Met Pro Glu Asp Ile Ser Val Gln Trp Leu His Asn Glu Val Gln Leu
145                 150                 155                 160

Pro Asp Ala Arg His Ser Thr Thr Gln Pro Arg Lys Thr Lys Gly Ser
            165                 170                 175

Gly Phe Phe Val Phe Ser Arg Leu Glu Val Thr Arg Ala Glu Trp Glu
        180                 185                 190

Gln Lys Asp Glu Phe Ile Cys Arg Ala Val His Glu Ala Ala Ser Pro
        195                 200                 205

Ser Gln Thr Val Gln Arg Ala Val Ser Val Asn Pro Gly Lys
```

<210> SEQ ID NO 71
<211> LENGTH: 227
<212> TYPE: PRT
<213> ORGANISM: Homo sapiens

<400> SEQUENCE: 71

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 72
<211> LENGTH: 227
<212> TYPE: PRT
<213> ORGANISM: Homo sapiens

<400> SEQUENCE: 72

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly

```
                    85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 73
<211> LENGTH: 227
<212> TYPE: PRT
<213> ORGANISM: Homo sapiens

<400> SEQUENCE: 73

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220
```

-continued

```
Pro Gly Lys
225

<210> SEQ ID NO 74
<211> LENGTH: 227
<212> TYPE: PRT
<213> ORGANISM: Homo sapiens

<400> SEQUENCE: 74

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 75
<211> LENGTH: 227
<212> TYPE: PRT
<213> ORGANISM: Homo sapiens

<400> SEQUENCE: 75

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 76
<211> LENGTH: 215
<212> TYPE: PRT
<213> ORGANISM: Homo sapiens

<400> SEQUENCE: 76

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Lys Pro Pro Ser Arg Glu Glu Met
        115                 120                 125

Thr Lys Asn Gln Val Ser Leu Ser Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Val Pro Val Leu Asp Ser Asp Gly Ser Phe Arg Leu
                165                 170                 175

Ala Ser Tyr Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro
    210                 215
```

```
<210> SEQ ID NO 77
<211> LENGTH: 225
<212> TYPE: PRT
<213> ORGANISM: Homo sapiens

<400> SEQUENCE: 77
```

| | | | | | | | | | | | | | | |
|---|---|---|---|---|---|---|---|---|---|---|---|---|---|---|
| Asp | Lys | Thr | His | Thr | Cys | Pro | Pro | Cys | Pro | Ala | Pro | Glu | Ala | Ala | Gly
| 1 | | | | 5 | | | | | 10 | | | | | 15 |

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

```
<210> SEQ ID NO 78
<211> LENGTH: 225
<212> TYPE: PRT
<213> ORGANISM: Homo sapiens

<400> SEQUENCE: 78
```

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 79
<211> LENGTH: 325
<212> TYPE: PRT
<213> ORGANISM: Homo sapiens

<400> SEQUENCE: 79

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
```

```
                225                 230                 235                 240
Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
                325

<210> SEQ ID NO 80
<211> LENGTH: 246
<212> TYPE: PRT
<213> ORGANISM: Homo sapiens

<400> SEQUENCE: 80

His Lys Pro Ser Asn Thr Lys Val Asp Lys Arg Val Glu Leu Lys Thr
1               5                   10                  15

Pro Leu Gly Asp Thr Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 81
<211> LENGTH: 327
```

```
<212> TYPE: PRT
<213> ORGANISM: Homo sapiens

<400> SEQUENCE: 81

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 82
<211> LENGTH: 223
<212> TYPE: PRT
<213> ORGANISM: Homo sapiens

<400> SEQUENCE: 82

Pro Pro Cys Pro Ser Cys Pro Ala Pro Glu Phe Leu Gly Gly Pro Ser
1               5                   10                  15
```

```
Val Phe Leu Phe Pro Pro Lys Pro Lys Asp Thr Leu Met Ile Ser Arg
            20                  25                  30

Thr Pro Glu Val Thr Cys Val Val Asp Val Ser Gln Glu Asp Pro
        35                  40                  45

Glu Val Gln Phe Asn Trp Tyr Val Asp Gly Val Glu Val His Asn Ala
 50                      55                  60

Lys Thr Lys Pro Arg Glu Glu Gln Phe Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Gly Leu Pro Ser Ser Ile Glu Lys Thr
             100                 105                 110

Ile Ser Lys Ala Lys Gly Gln Pro Arg Glu Pro Gln Val Tyr Thr Leu
         115                 120                 125

Pro Pro Ser Gln Glu Glu Met Thr Lys Asn Gln Val Ser Leu Thr Cys
     130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                 165                 170                 175

Ser Asp Gly Ser Phe Phe Leu Tyr Ser Arg Leu Thr Val Asp Lys Ser
             180                 185                 190

Arg Trp Gln Glu Gly Asn Val Phe Ser Cys Ser Val Met His Glu Ala
         195                 200                 205

Leu His Asn His Tyr Thr Gln Lys Ser Leu Ser Leu Ser Pro Gly
     210                 215                 220

<210> SEQ ID NO 83
<211> LENGTH: 276
<212> TYPE: PRT
<213> ORGANISM: Homo sapiens

<400> SEQUENCE: 83

Val Thr Ser Thr Leu Thr Ile Lys Glx Ser Asp Trp Leu Gly Glu Ser
1               5                   10                  15

Met Phe Thr Cys Arg Val Asp His Arg Gly Leu Thr Phe Gln Gln Asn
            20                  25                  30

Ala Ser Ser Met Cys Val Pro Asp Gln Asp Thr Ala Ile Arg Val Phe
        35                  40                  45

Ala Ile Pro Pro Ser Phe Ala Ser Ile Phe Leu Thr Lys Ser Thr Lys
 50                      55                  60

Leu Thr Cys Leu Val Thr Asp Leu Thr Thr Tyr Asx Ser Val Thr Ile
65                  70                  75                  80

Ser Trp Thr Arg Glu Glu Asn Gly Ala Val Lys Thr His Thr Asn Ile
                 85                  90                  95

Ser Glu Ser His Pro Asn Ala Thr Phe Ser Ala Val Gly Glu Ala Ser
             100                 105                 110

Ile Cys Glu Asp Asx Asp Trp Ser Gly Glu Arg Phe Thr Cys Thr Val
         115                 120                 125

Thr His Thr Asp Leu Pro Ser Pro Leu Lys Gln Thr Ile Ser Arg Pro
     130                 135                 140

Lys Gly Val Ala Leu His Arg Pro Asx Val Tyr Leu Leu Pro Pro Ala
145                 150                 155                 160

Arg Glx Glx Leu Asn Leu Arg Glu Ser Ala Thr Ile Thr Cys Leu Val
                 165                 170                 175
```

```
Thr Gly Phe Ser Pro Ala Asp Val Phe Val Glu Trp Met Gln Arg Gly
            180                 185                 190

Glu Pro Leu Ser Pro Gln Lys Tyr Val Thr Ser Ala Pro Met Pro Glu
            195                 200                 205

Pro Gln Ala Pro Gly Arg Tyr Phe Ala His Ser Ile Leu Thr Val Ser
    210                 215                 220

Glu Glu Glu Trp Asn Thr Gly Gly Thr Tyr Thr Cys Val Val Ala His
225                 230                 235                 240

Glu Ala Leu Pro Asn Arg Val Thr Glu Arg Thr Val Asp Lys Ser Thr
                245                 250                 255

Gly Lys Pro Thr Leu Tyr Asn Val Ser Leu Val Met Ser Asp Thr Ala
                260                 265                 270

Gly Thr Cys Tyr
            275

<210> SEQ ID NO 84
<211> LENGTH: 159
<212> TYPE: PRT
<213> ORGANISM: Homo sapiens

<400> SEQUENCE: 84

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
    115                 120                 125

Asn Lys Cys Tyr Thr Ala Val Val Pro Leu Val Tyr Gly Gly Glu Thr
130                 135                 140

Lys Met Val Glu Thr Ala Leu Thr Pro Asp Ala Cys Tyr Pro Asp
145                 150                 155

<210> SEQ ID NO 85
<211> LENGTH: 112
<212> TYPE: PRT
<213> ORGANISM: Homo sapiens

<400> SEQUENCE: 85

Phe Thr Val Arg Glu Thr Ala Ser Thr Lys Gly Pro Ser Val Phe Pro
1               5                   10                  15

Leu Ala Pro Ser Ser Lys Ser Thr Ser Gly Gly Thr Ala Ala Leu Gly
                20                  25                  30

Cys Leu Val Lys Asp Tyr Phe Pro Glu Pro Val Thr Val Ser Trp Asn
            35                  40                  45

Ser Gly Ala Leu Thr Ser Gly Val His Thr Phe Pro Ala Val Leu Gln
    50                  55                  60
```

```
Ser Ser Gly Leu Tyr Ser Leu Ser Ser Val Val Thr Val Pro Ser Ser
 65                  70                  75                  80

Ser Leu Gly Thr Gln Thr Tyr Ile Cys Asn Val Asn His Lys Pro Ser
                 85                  90                  95

Asn Thr Lys Val Asp Lys Lys Val Glu Pro Lys Ser Cys Asp Lys Thr
            100                 105                 110
```

<210> SEQ ID NO 86
<211> LENGTH: 106
<212> TYPE: PRT
<213> ORGANISM: Homo sapiens

<400> SEQUENCE: 86

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

<210> SEQ ID NO 87
<211> LENGTH: 106
<212> TYPE: PRT
<213> ORGANISM: Homo sapiens

<400> SEQUENCE: 87

```
Gly Gln Pro Lys Ala Asn Pro Thr Val Thr Leu Phe Pro Pro Ser Ser
 1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Gly Ser Pro
         35                  40                  45

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 88
<211> LENGTH: 33
<212> TYPE: PRT
<213> ORGANISM: Homo sapiens

<400> SEQUENCE: 88

```
Arg Met Lys Gln Ile Glu Asp Lys Ile Glu Glu Ile Leu Ser Lys Ile
 1               5                  10                  15
```

Tyr His Ile Glu Asn Glu Ile Ala Arg Ile Lys Lys Leu Ile Gly Glu
            20                  25                  30

Arg

<210> SEQ ID NO 89
<211> LENGTH: 32
<212> TYPE: PRT
<213> ORGANISM: Homo sapiens

<400> SEQUENCE: 89

Leu Ser Ser Ile Glu Lys Lys Gln Glu Gln Thr Ser Trp Leu Ile
1               5                   10                  15

Trp Ile Ser Asn Glu Leu Thr Leu Ile Arg Asn Glu Leu Ala Gln Ser
            20                  25                  30

<210> SEQ ID NO 90
<211> LENGTH: 31
<212> TYPE: PRT
<213> ORGANISM: Homo sapiens

<400> SEQUENCE: 90

Leu Ser Ser Ile Glu Lys Lys Leu Glu Glu Ile Thr Ser Gln Leu Ile
1               5                   10                  15

Gln Ile Ser Asn Glu Leu Thr Leu Ile Arg Asn Glu Leu Ala Gln
            20                  25                  30

<210> SEQ ID NO 91
<211> LENGTH: 31
<212> TYPE: PRT
<213> ORGANISM: Homo sapiens

<400> SEQUENCE: 91

Leu Ser Ser Ile Glu Lys Lys Leu Glu Glu Ile Thr Ser Gln Leu Ile
1               5                   10                  15

Gln Ile Arg Asn Glu Leu Thr Leu Ile Arg Asn Glu Leu Ala Gln
            20                  25                  30

<210> SEQ ID NO 92
<211> LENGTH: 31
<212> TYPE: PRT
<213> ORGANISM: Homo sapiens

<400> SEQUENCE: 92

Leu Ser Ser Ile Glu Lys Lys Leu Glu Glu Ile Thr Ser Gln Leu Gln
1               5                   10                  15

Gln Ile Arg Asn Glu Leu Thr Leu Ile Arg Asn Glu Leu Ala Gln
            20                  25                  30

<210> SEQ ID NO 93
<211> LENGTH: 31
<212> TYPE: PRT
<213> ORGANISM: Homo sapiens

<400> SEQUENCE: 93

Leu Ser Ser Leu Glu Lys Lys Leu Glu Glu Leu Thr Ser Gln Leu Ile
1               5                   10                  15

Gln Leu Arg Asn Glu Leu Thr Leu Leu Arg Asn Glu Leu Ala Gln
            20                  25                  30

<210> SEQ ID NO 94
<211> LENGTH: 31
<212> TYPE: PRT

<213> ORGANISM: Homo sapiens

<400> SEQUENCE: 94

Ile Ser Ser Leu Glu Lys Lys Ile Glu Glu Leu Thr Ser Gln Ile Gln
1               5                   10                  15

Gln Leu Arg Asn Glu Ile Thr Leu Leu Arg Asn Glu Ile Ala Gln
            20                  25                  30

<210> SEQ ID NO 95
<211> LENGTH: 47
<212> TYPE: PRT
<213> ORGANISM: Homo sapiens

<400> SEQUENCE: 95

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
            20                  25                  30

Val Ser Gln Tyr Arg Thr Arg Tyr Gly Pro Leu Gly Gly Gly Lys
        35                  40                  45

<210> SEQ ID NO 96
<211> LENGTH: 31
<212> TYPE: PRT
<213> ORGANISM: Homo sapiens

<400> SEQUENCE: 96

Leu Lys Ser Val Glu Asn Arg Leu Ala Val Val Glu Asn Gln Leu Lys
1               5                   10                  15

Thr Val Ile Glu Glu Leu Lys Thr Val Lys Asp Leu Leu Ser Asn
            20                  25                  30

<210> SEQ ID NO 97
<211> LENGTH: 31
<212> TYPE: PRT
<213> ORGANISM: Homo sapiens

<400> SEQUENCE: 97

Leu Ala Arg Ile Glu Glu Lys Leu Lys Thr Ile Lys Ala Gln Leu Ser
1               5                   10                  15

Glu Ile Ala Ser Thr Leu Asn Met Ile Arg Glu Gln Leu Ala Gln
            20                  25                  30

<210> SEQ ID NO 98
<211> LENGTH: 31
<212> TYPE: PRT
<213> ORGANISM: Homo sapiens

<400> SEQUENCE: 98

Val Ser Arg Leu Glu Glu Lys Val Lys Thr Leu Lys Ser Gln Val Thr
1               5                   10                  15

Glu Leu Ala Ser Thr Val Ser Leu Leu Arg Gly Gln Val Ala Gln
            20                  25                  30

<210> SEQ ID NO 99
<211> LENGTH: 30
<212> TYPE: PRT
<213> ORGANISM: Homo sapiens

<400> SEQUENCE: 99

Ile Gln Ser Glu Lys Lys Ile Glu Asp Ile Ser Ser Leu Ile Gly Gln
1               5                   10                  15

-continued

Ile Gln Ser Glu Ile Thr Leu Ile Arg Asn Glu Ile Ala Gln
            20                  25                  30

<210> SEQ ID NO 100
<211> LENGTH: 31
<212> TYPE: PRT
<213> ORGANISM: Homo sapiens

<400> SEQUENCE: 100

Leu Met Ser Leu Glu Lys Lys Leu Glu Glu Leu Thr Gln Thr Leu Met
1               5                   10                  15

Gln Leu Gln Asn Glu Leu Ser Met Leu Lys Asn Glu Leu Ala Gln
            20                  25                  30

<210> SEQ ID NO 101
<211> LENGTH: 18
<212> TYPE: PRT
<213> ORGANISM: Homo sapiens

<400> SEQUENCE: 101

Val Asp Leu Glu Gly Ser Thr Ser Asn Gly Arg Gln Cys Ala Gly Ile
1               5                   10                  15

Arg Leu

<210> SEQ ID NO 102
<211> LENGTH: 27
<212> TYPE: PRT
<213> ORGANISM: Homo sapiens

<400> SEQUENCE: 102

Glu Asp Asp Val Thr Thr Thr Glu Glu Leu Ala Pro Ala Leu Val Pro
1               5                   10                  15

Pro Pro Lys Gly Thr Cys Ala Gly Trp Met Ala
            20                  25

<210> SEQ ID NO 103
<211> LENGTH: 27
<212> TYPE: PRT
<213> ORGANISM: Homo sapiens

<400> SEQUENCE: 103

Gly His Asp Gln Glu Thr Thr Thr Gln Gly Pro Gly Val Leu Leu Pro
1               5                   10                  15

Leu Pro Lys Gly Ala Cys Thr Gly Gln Met Ala
            20                  25

<210> SEQ ID NO 104
<211> LENGTH: 64
<212> TYPE: PRT
<213> ORGANISM: Homo sapiens

<400> SEQUENCE: 104

Val Thr Ala Phe Ser Asn Met Asp Asp Met Leu Gln Lys Ala His Leu
1               5                   10                  15

Val Ile Glu Gly Thr Phe Ile Tyr Leu Arg Asp Ser Thr Glu Phe Phe
            20                  25                  30

Ile Arg Val Arg Asp Gly Trp Lys Lys Leu Gln Leu Gly Glu Leu Ile
                35                  40                  45

Pro Ile Pro Ala Asp Ser Pro Pro Pro Ala Leu Ser Ser Asn Pro
        50                  55                  60

<210> SEQ ID NO 105
<211> LENGTH: 112
<212> TYPE: PRT
<213> ORGANISM: Homo sapiens

<400> SEQUENCE: 105

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 106
<211> LENGTH: 390
<212> TYPE: PRT
<213> ORGANISM: Homo sapiens

<400> SEQUENCE: 106

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
        260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
        340                 345                 350

Ala Pro Cys Cys Val Pro Gln Ala Leu Glu Pro Leu Pro Ile Val Tyr
    355                 360                 365

Tyr Val Gly Arg Lys Pro Lys Val Glu Gln Leu Ser Asn Met Ile Val
370                 375                 380

Arg Ser Cys Lys Cys Ser
385                 390

<210> SEQ ID NO 107
<211> LENGTH: 112
<212> TYPE: PRT
<213> ORGANISM: Homo sapiens

<400> SEQUENCE: 107

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 108
<211> LENGTH: 112
<212> TYPE: PRT
<213> ORGANISM: Homo sapiens

<400> SEQUENCE: 108

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

```
Pro Tyr Leu Trp Ser Ser Asp Thr Gln His Ser Arg Val Leu Ser Leu
    50                  55                  60
Tyr Asn Thr Ile Asn Pro Glu Ala Ser Ala Ser Pro Cys Cys Val Ser
 65                  70                  75                  80
Gln Asp Leu Glu Pro Leu Thr Ile Leu Tyr Tyr Ile Gly Lys Thr Pro
                 85                  90                  95
Lys Ile Glu Gln Leu Ser Asn Met Ile Val Lys Ser Cys Lys Cys Ser
                100                 105                 110

<210> SEQ ID NO 109
<211> LENGTH: 413
<212> TYPE: PRT
<213> ORGANISM: Homo sapiens

<400> SEQUENCE: 109

Met His Tyr Cys Val Leu Ser Ala Phe Leu Ile Leu His Leu Val Thr
 1               5                  10                  15
Val Ala Leu Ser Leu Ser Thr Cys Ser Thr Leu Asp Met Asp Gln Phe
                 20                  25                  30
Met Arg Lys Arg Ile Glu Ala Ile Arg Gly Gln Ile Leu Ser Lys Leu
             35                  40                  45
Lys Leu Thr Ser Pro Pro Glu Asp Tyr Pro Glu Pro Glu Glu Val Pro
 50                  55                  60
Pro Glu Val Ile Ser Ile Tyr Asn Ser Thr Arg Asp Leu Leu Gln Glu
 65                  70                  75                  80
Lys Ala Ser Arg Arg Ala Ala Ala Cys Glu Arg Glu Arg Ser Asp Glu
                 85                  90                  95
Glu Tyr Tyr Ala Lys Glu Val Tyr Lys Ile Asp Met Pro Pro Phe Phe
                100                 105                 110
Pro Ser Glu Ala Ile Pro Pro Thr Phe Tyr Arg Pro Tyr Phe Arg Ile
                115                 120                 125
Val Arg Phe Asp Val Ser Ala Met Glu Lys Asn Ala Ser Asn Leu Val
            130                 135                 140
Lys Ala Glu Phe Arg Val Phe Arg Leu Gln Asn Pro Lys Ala Arg Val
145                 150                 155                 160
Pro Glu Gln Arg Ile Glu Leu Tyr Gln Ile Leu Lys Ser Lys Asp Leu
                165                 170                 175
Thr Ser Pro Thr Gln Arg Tyr Ile Asp Ser Lys Val Val Lys Thr Arg
            180                 185                 190
Ala Glu Gly Glu Trp Leu Ser Phe Asp Val Thr Asp Ala Val His Glu
            195                 200                 205
Trp Leu His His Lys Asp Arg Asn Leu Gly Phe Lys Ile Ser Leu His
210                 215                 220
Cys Pro Cys Cys Thr Phe Val Pro Ser Asn Asn Tyr Ile Ile Pro Asn
225                 230                 235                 240
Lys Ser Glu Glu Leu Glu Ala Arg Phe Ala Gly Ile Asp Gly Thr Ser
                245                 250                 255
Thr Tyr Thr Ser Gly Asp Gln Lys Thr Ile Lys Ser Thr Arg Lys Lys
            260                 265                 270
Asn Ser Gly Lys Thr Pro His Leu Leu Leu Met Leu Leu Pro Ser Tyr
        275                 280                 285
Arg Leu Glu Ser Gln Gln Thr Asn Arg Arg Lys Lys Arg Ala Leu Asp
    290                 295                 300
Ala Ala Tyr Cys Phe Arg Asn Val Gln Asp Asn Cys Cys Leu Arg Pro
305                 310                 315                 320
```

```
Leu Tyr Ile Asp Phe Lys Arg Asp Leu Gly Trp Lys Trp Ile His Glu
            325                 330                 335

Pro Lys Gly Tyr Asn Ala Asn Phe Cys Ala Gly Ala Cys Pro Tyr Leu
        340                 345                 350

Trp Ser Ser Asp Thr Gln His Ser Arg Val Leu Ser Leu Tyr Asn Thr
    355                 360                 365

Ile Asn Pro Glu Ala Ser Ala Ser Pro Cys Cys Val Ser Gln Asp Leu
370                 375                 380

Glu Pro Leu Thr Ile Leu Tyr Tyr Ile Gly Lys Thr Pro Lys Ile Glu
385                 390                 395                 400

Gln Leu Ser Asn Met Ile Val Lys Ser Cys Lys Cys Ser
            405                 410

<210> SEQ ID NO 110
<211> LENGTH: 112
<212> TYPE: PRT
<213> ORGANISM: Homo sapiens

<400> SEQUENCE: 110

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Ser Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 111
<211> LENGTH: 112
<212> TYPE: PRT
<213> ORGANISM: Homo sapiens

<400> SEQUENCE: 111

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 112
```

```
<211> LENGTH: 412
<212> TYPE: PRT
<213> ORGANISM: Homo sapiens

<400> SEQUENCE: 112

Met Lys Met His Leu Gln Arg Ala Leu Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
50                      55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
370                 375                 380

Pro Leu Thr Ile Leu Tyr Tyr Val Gly Arg Thr Pro Lys Val Glu Gln
```

```
              385                 390                 395                 400
Leu Ser Asn Met Val Val Lys Ser Cys Lys Cys Ser
                405                 410

<210> SEQ ID NO 113
<211> LENGTH: 112
<212> TYPE: PRT
<213> ORGANISM: Homo sapiens

<400> SEQUENCE: 113

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
                20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
        50                  55                  60

Tyr Asn Thr Leu Asn Pro Glu Ala Ser Ala Ser Pro Ser Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 114
<211> LENGTH: 503
<212> TYPE: PRT
<213> ORGANISM: Homo sapiens

<400> SEQUENCE: 114

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
```

```
              195                 200                 205
Glu Ser Ile Gly Lys Gly Arg Phe Gly Glu Val Trp Arg Gly Lys Trp
210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
        355                 360                 365

Pro Asn His Arg Val Gly Thr Lys Arg Tyr Met Ala Pro Glu Val Leu
370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500

<210> SEQ ID NO 115
<211> LENGTH: 93
<212> TYPE: PRT
<213> ORGANISM: Homo sapiens

<400> SEQUENCE: 115

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
            20                  25                  30

Ile His Asn Ser Met Cys Ile Ala Glu Ile Asp Leu Ile Pro Arg Asp
        35                  40                  45

Arg Pro Phe Val Cys Ala Pro Ser Ser Lys Thr Gly Ser Val Thr Thr
50                  55                  60
```

```
Thr Tyr Cys Cys Asn Gln Asp His Cys Asn Lys Ile Glu Leu Pro Thr
 65                  70                  75                  80

Thr Val Lys Ser Ser Pro Gly Leu Gly Pro Val Glu Leu
                 85                  90

<210> SEQ ID NO 116
<211> LENGTH: 592
<212> TYPE: PRT
<213> ORGANISM: Homo sapiens

<400> SEQUENCE: 116

Met Gly Arg Gly Leu Leu Arg Gly Leu Trp Pro Leu His Ile Val Leu
  1               5                  10                  15

Trp Thr Arg Ile Ala Ser Thr Ile Pro Pro His Val Gln Lys Ser Asp
             20                  25                  30

Val Glu Met Glu Ala Gln Lys Asp Glu Ile Ile Cys Pro Ser Cys Asn
         35                  40                  45

Arg Thr Ala His Pro Leu Arg His Ile Asn Asn Asp Met Ile Val Thr
     50                  55                  60

Asp Asn Asn Gly Ala Val Lys Phe Pro Gln Leu Cys Lys Phe Cys Asp
 65                  70                  75                  80

Val Arg Phe Ser Thr Cys Asp Asn Gln Lys Ser Cys Met Ser Asn Cys
                 85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350
```

His Ala Lys Gly Asn Leu Gln Glu Tyr Leu Thr Arg His Val Ile Ser
            355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
            435                 440                 445

Tyr Met Ala Pro Glu Val Leu Glu Ser Arg Met Asn Leu Glu Asn Val
        450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
            515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 117
<211> LENGTH: 154
<212> TYPE: PRT
<213> ORGANISM: Homo sapiens

<400> SEQUENCE: 117

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu

```
            130                 135                 140
Cys Asn Asp Asn Ile Ile Phe Ser Glu Glu
145                 150

<210> SEQ ID NO 118
<211> LENGTH: 567
<212> TYPE: PRT
<213> ORGANISM: Homo sapiens

<400> SEQUENCE: 118

Met Gly Arg Gly Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys
                115                 120                 125

Pro Gly Glu Thr Phe Phe Met Cys Ser Cys Ser Ser Asp Glu Cys Asn
        130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
                180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
                260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
        290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
                340                 345                 350
```

```
Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
        370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 119
<211> LENGTH: 143
<212> TYPE: PRT
<213> ORGANISM: Homo sapiens

<400> SEQUENCE: 119

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Leu Leu Leu Val Ile Phe Gln
    130                 135                 140

<210> SEQ ID NO 120
```

```
<211> LENGTH: 129
<212> TYPE: PRT
<213> ORGANISM: Homo sapiens

<400> SEQUENCE: 120

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu

<210> SEQ ID NO 121
<211> LENGTH: 114
<212> TYPE: PRT
<213> ORGANISM: Homo sapiens

<400> SEQUENCE: 121

Thr Asp Asn Asn Gly Ala Val Lys Phe Pro Gln Leu Cys Lys Phe Cys
1               5                   10                  15

Asp Val Arg Phe Ser Thr Cys Asp Asn Gln Lys Ser Cys Met Ser Asn
                20                  25                  30

Cys Ser Ile Thr Ser Ile Cys Glu Lys Pro Gln Glu Val Cys Val Ala
            35                  40                  45

Val Trp Arg Lys Asn Asp Glu Asn Ile Thr Leu Glu Thr Val Cys His
        50                  55                  60

Asp Pro Lys Leu Pro Tyr His Asp Phe Ile Leu Glu Asp Ala Ala Ser
65                  70                  75                  80

Pro Lys Cys Ile Met Lys Glu Lys Lys Pro Gly Glu Thr Phe Phe
                85                  90                  95

Met Cys Ser Cys Ser Ser Asp Glu Cys Asn Asp Asn Ile Ile Phe Ser
            100                 105                 110

Glu Glu

<210> SEQ ID NO 122
<211> LENGTH: 104
<212> TYPE: PRT
<213> ORGANISM: Homo sapiens

<400> SEQUENCE: 122

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
                20                  25                  30

Gln Glu Val Cys Val Ala Val Trp Arg Lys Asn Asp Glu Asn Ile Thr
            35                  40                  45
```

Leu Glu Thr Val Cys His Asp Pro Lys Leu Pro Tyr His Asp Phe Ile
 50                  55                  60

Leu Glu Asp Ala Ala Ser Pro Lys Cys Ile Met Lys Glu Lys Lys
 65                  70                  75                  80

Pro Gly Glu Thr Phe Phe Met Cys Ser Cys Ser Ser Asp Glu Cys Asn
                 85                  90                  95

Asp Asn Ile Ile Phe Ser Glu Glu
            100

<210> SEQ ID NO 123
<211> LENGTH: 111
<212> TYPE: PRT
<213> ORGANISM: Homo sapiens

<400> SEQUENCE: 123

Gln Leu Cys Lys Phe Cys Asp Val Arg Phe Ser Thr Cys Asp Asn Gln
 1               5                  10                  15

Lys Ser Cys Met Ser Asn Cys Ser Ile Thr Ser Ile Cys Glu Lys Pro
                 20                  25                  30

Gln Glu Val Cys Val Ala Val Trp Arg Lys Asn Asp Glu Asn Ile Thr
             35                  40                  45

Leu Glu Thr Val Cys His Asp Pro Lys Leu Pro Tyr His Asp Phe Ile
 50                  55                  60

Leu Glu Asp Ala Ala Ser Pro Lys Cys Ile Met Lys Glu Lys Lys
 65                  70                  75                  80

Pro Gly Glu Thr Phe Phe Met Cys Ser Cys Ser Ser Ala Glu Cys Asn
                 85                  90                  95

Asp Asn Ile Ile Phe Ser Glu Glu Tyr Asn Thr Ser Asn Pro Asp
            100                 105                 110

<210> SEQ ID NO 124
<211> LENGTH: 851
<212> TYPE: PRT
<213> ORGANISM: Homo sapiens

<400> SEQUENCE: 124

Met Thr Ser His Tyr Val Ile Ala Ile Phe Ala Leu Met Ser Ser Cys
 1               5                  10                  15

Leu Ala Thr Ala Gly Pro Glu Pro Gly Ala Leu Cys Glu Leu Ser Pro
             20                  25                  30

Val Ser Ala Ser His Pro Val Gln Ala Leu Met Glu Ser Phe Thr Val
             35                  40                  45

Leu Ser Gly Cys Ala Ser Arg Gly Thr Thr Gly Leu Pro Gln Glu Val
 50                  55                  60

His Val Leu Asn Leu Arg Thr Ala Gly Gln Pro Gly Gln Leu Gln
 65                  70                  75                  80

Arg Glu Val Thr Leu His Leu Asn Pro Ile Ser Ser Val His Ile His
                 85                  90                  95

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
            115                 120                 125

Val Ser Glu Gly Ser Val Val Gln Phe Ser Ser Ala Asn Phe Ser Leu
        130                 135                 140

Thr Ala Glu Thr Glu Glu Arg Asn Phe Pro His Gly Asn Glu His Leu
145                 150                 155                 160

-continued

```
Leu Asn Trp Ala Arg Lys Glu Tyr Gly Ala Val Thr Ser Phe Thr Glu
                165                 170                 175
Leu Lys Ile Ala Arg Asn Ile Tyr Ile Lys Val Gly Glu Asp Gln Val
            180                 185                 190
Phe Pro Pro Lys Cys Asn Ile Gly Lys Asn Phe Leu Ser Leu Asn Tyr
        195                 200                 205
Leu Ala Glu Tyr Leu Gln Pro Lys Ala Ala Glu Gly Cys Val Met Ser
    210                 215                 220
Ser Gln Pro Gln Asn Glu Val His Ile Ile Glu Leu Ile Thr Pro
225                 230                 235                 240
Asn Ser Asn Pro Tyr Ser Ala Phe Gln Val Asp Ile Thr Ile Asp Ile
                245                 250                 255
Arg Pro Ser Gln Glu Asp Leu Glu Val Val Lys Asn Leu Ile Leu Ile
            260                 265                 270
Leu Lys Cys Lys Lys Ser Val Asn Trp Val Ile Lys Ser Phe Asp Val
        275                 280                 285
Lys Gly Ser Leu Lys Ile Ile Ala Pro Asn Ser Ile Gly Phe Gly Lys
    290                 295                 300
Glu Ser Glu Arg Ser Met Thr Met Thr Lys Ser Ile Arg Asp Asp Ile
305                 310                 315                 320
Pro Ser Thr Gln Gly Asn Leu Val Lys Trp Ala Leu Asp Asn Gly Tyr
                325                 330                 335
Ser Pro Ile Thr Ser Tyr Thr Met Ala Pro Val Ala Asn Arg Phe His
            340                 345                 350
Leu Arg Leu Glu Asn Asn Ala Glu Glu Met Gly Asp Glu Val His
        355                 360                 365
Thr Ile Pro Pro Glu Leu Arg Ile Leu Leu Asp Pro Gly Ala Leu Pro
    370                 375                 380
Ala Leu Gln Asn Pro Pro Ile Arg Gly Gly Glu Gly Gln Asn Gly Gly
385                 390                 395                 400
Leu Pro Phe Pro Phe Pro Asp Ile Ser Arg Arg Val Trp Asn Glu Glu
                405                 410                 415
Gly Glu Asp Gly Leu Pro Arg Pro Lys Asp Pro Val Ile Pro Ser Ile
            420                 425                 430
Gln Leu Phe Pro Gly Leu Arg Glu Pro Glu Val Gln Gly Ser Val
        435                 440                 445
Asp Ile Ala Leu Ser Val Lys Cys Asp Asn Glu Lys Met Ile Val Ala
    450                 455                 460
Val Glu Lys Asp Ser Phe Gln Ala Ser Gly Tyr Ser Gly Met Asp Val
465                 470                 475                 480
Thr Leu Leu Asp Pro Thr Cys Lys Ala Lys Met Asn Gly Thr His Phe
                485                 490                 495
Val Leu Glu Ser Pro Leu Asn Gly Cys Gly Thr Arg Pro Arg Trp Ser
            500                 505                 510
Ala Leu Asp Gly Val Val Tyr Tyr Asn Ser Ile Val Ile Gln Val Pro
        515                 520                 525
Ala Leu Gly Asp Ser Ser Gly Trp Pro Asp Gly Tyr Glu Asp Leu Glu
    530                 535                 540
Ser Gly Asp Asn Gly Phe Pro Gly Asp Met Asp Glu Gly Asp Ala Ser
545                 550                 555                 560
Leu Phe Thr Arg Pro Glu Ile Val Val Phe Asn Cys Ser Leu Gln Gln
                565                 570                 575
```

```
Val Arg Asn Pro Ser Ser Phe Gln Glu Gln Pro His Gly Asn Ile Thr
            580                 585                 590

Phe Asn Met Glu Leu Tyr Asn Thr Asp Leu Phe Leu Val Pro Ser Gln
        595                 600                 605

Gly Val Phe Ser Val Pro Glu Asn Gly His Val Tyr Val Glu Val Ser
    610                 615                 620

Val Thr Lys Ala Glu Gln Leu Gly Phe Ala Ile Gln Thr Cys Phe
625                 630                 635                 640

Ile Ser Pro Tyr Ser Asn Pro Asp Arg Met Ser His Tyr Thr Ile Ile
            645                 650                 655

Glu Asn Ile Cys Pro Lys Asp Glu Ser Val Lys Phe Tyr Ser Pro Lys
        660                 665                 670

Arg Val His Phe Pro Ile Pro Gln Ala Asp Met Asp Lys Lys Arg Phe
    675                 680                 685

Ser Phe Val Phe Lys Pro Val Phe Asn Thr Ser Leu Leu Phe Leu Gln
    690                 695                 700

Cys Glu Leu Thr Leu Cys Thr Lys Met Glu Lys His Pro Gln Lys Leu
705                 710                 715                 720

Pro Lys Cys Val Pro Pro Asp Glu Ala Cys Thr Ser Leu Asp Ala Ser
            725                 730                 735

Ile Ile Trp Ala Met Met Gln Asn Lys Lys Thr Phe Thr Lys Pro Leu
        740                 745                 750

Ala Val Ile His His Glu Ala Ser Lys Glu Lys Gly Pro Ser Met
    755                 760                 765

Lys Glu Pro Asn Pro Ile Ser Pro Ile Phe His Gly Leu Asp Thr
770                 775                 780

Leu Thr Val Met Gly Ile Ala Phe Ala Ala Phe Val Ile Gly Ala Leu
785                 790                 795                 800

Leu Thr Gly Ala Leu Trp Tyr Ile Tyr Ser His Thr Gly Glu Thr Ala
            805                 810                 815

Gly Arg Gln Gln Val Pro Thr Ser Pro Pro Ala Ser Glu Asn Ser Ser
        820                 825                 830

Ala Ala His Ser Ile Gly Ser Thr Gln Ser Thr Pro Cys Ser Ser Ser
    835                 840                 845

Ser Thr Ala
    850

<210> SEQ ID NO 125
<211> LENGTH: 850
<212> TYPE: PRT
<213> ORGANISM: Homo sapiens

<400> SEQUENCE: 125

Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
        35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65                  70                  75                  80

Arg Glu Val Thr Leu His Leu Asn Pro Ile Ser Ser Val His Ile His
            85                  90                  95
```

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
        115                 120                 125

Val Ser Glu Gly Ser Val Val Gln Phe Ser Ser Ala Asn Phe Ser Leu
130                 135                 140

Thr Ala Glu Thr Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
            180                 185                 190

Phe Pro Pro Lys Cys Asn Ile Gly Lys Asn Phe Leu Ser Leu Asn Tyr
        195                 200                 205

Leu Ala Glu Tyr Leu Gln Pro Lys Ala Ala Glu Gly Cys Val Met Ser
210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
            260                 265                 270

Leu Lys Cys Lys Lys Ser Val Asn Trp Val Ile Lys Ser Phe Asp Val
        275                 280                 285

Lys Gly Ser Leu Lys Ile Ile Ala Pro Asn Ser Ile Gly Phe Gly Lys
290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His
            340                 345                 350

Leu Arg Leu Glu Asn Asn Glu Glu Met Gly Asp Glu Glu Val His Thr
        355                 360                 365

Ile Pro Pro Glu Leu Arg Ile Leu Leu Asp Pro Gly Ala Leu Pro Ala
370                 375                 380

Leu Gln Asn Pro Pro Ile Arg Gly Gly Glu Gly Gln Asn Gly Gly Leu
385                 390                 395                 400

Pro Phe Pro Phe Pro Asp Ile Ser Arg Arg Val Trp Asn Glu Glu Gly
                405                 410                 415

Glu Asp Gly Leu Pro Arg Pro Lys Asp Pro Val Ile Pro Ser Ile Gln
            420                 425                 430

Leu Phe Pro Gly Leu Arg Glu Pro Glu Glu Val Gln Gly Ser Val Asp
        435                 440                 445

Ile Ala Leu Ser Val Lys Cys Asp Asn Glu Lys Met Ile Val Ala Val
450                 455                 460

Glu Lys Asp Ser Phe Gln Ala Ser Gly Tyr Ser Gly Met Asp Val Thr
465                 470                 475                 480

Leu Leu Asp Pro Thr Cys Lys Ala Lys Met Asn Gly Thr His Phe Val
                485                 490                 495

Leu Glu Ser Pro Leu Asn Gly Cys Gly Thr Arg Pro Arg Trp Ser Ala
            500                 505                 510

```
Leu Asp Gly Val Val Tyr Tyr Asn Ser Ile Val Ile Gln Val Pro Ala
515                 520                 525

Leu Gly Asp Ser Ser Gly Trp Pro Asp Gly Tyr Glu Asp Leu Glu Ser
530                 535                 540

Gly Asp Asn Gly Phe Pro Gly Asp Met Asp Glu Gly Asp Ala Ser Leu
545                 550                 555                 560

Phe Thr Arg Pro Glu Ile Val Val Phe Asn Cys Ser Leu Gln Gln Val
                565                 570                 575

Arg Asn Pro Ser Ser Phe Gln Glu Gln Pro His Gly Asn Ile Thr Phe
            580                 585                 590

Asn Met Glu Leu Tyr Asn Thr Asp Leu Phe Leu Val Pro Ser Gln Gly
        595                 600                 605

Val Phe Ser Val Pro Glu Asn Gly His Val Tyr Val Glu Val Ser Val
610                 615                 620

Thr Lys Ala Glu Gln Glu Leu Gly Phe Ala Ile Gln Thr Cys Phe Ile
625                 630                 635                 640

Ser Pro Tyr Ser Asn Pro Asp Arg Met Ser His Tyr Thr Ile Ile Glu
                645                 650                 655

Asn Ile Cys Pro Lys Asp Glu Ser Val Lys Phe Tyr Ser Pro Lys Arg
            660                 665                 670

Val His Phe Pro Ile Pro Gln Ala Asp Met Asp Lys Lys Arg Phe Ser
        675                 680                 685

Phe Val Phe Lys Pro Val Phe Asn Thr Ser Leu Leu Phe Leu Gln Cys
    690                 695                 700

Glu Leu Thr Leu Cys Thr Lys Met Glu Lys His Pro Gln Lys Leu Pro
705                 710                 715                 720

Lys Cys Val Pro Pro Asp Glu Ala Cys Thr Ser Leu Asp Ala Ser Ile
                725                 730                 735

Ile Trp Ala Met Met Gln Asn Lys Lys Thr Phe Thr Lys Pro Leu Ala
            740                 745                 750

Val Ile His His Glu Ala Glu Ser Lys Glu Lys Gly Pro Ser Met Lys
        755                 760                 765

Glu Pro Asn Pro Ile Ser Pro Pro Ile Phe His Gly Leu Asp Thr Leu
    770                 775                 780

Thr Val Met Gly Ile Ala Phe Ala Ala Phe Val Ile Gly Ala Leu Leu
785                 790                 795                 800

Thr Gly Ala Leu Trp Tyr Ile Tyr Ser His Thr Gly Glu Thr Ala Gly
                805                 810                 815

Arg Gln Gln Val Pro Thr Ser Pro Pro Ala Ser Glu Asn Ser Ser Ala
            820                 825                 830

Ala His Ser Ile Gly Ser Thr Gln Ser Thr Pro Cys Ser Ser Ser Ser
        835                 840                 845

Thr Ala
850

<210> SEQ ID NO 126
<211> LENGTH: 5
<212> TYPE: PRT
<213> ORGANISM: Artificial Sequence
<220> FEATURE:
<223> OTHER INFORMATION: Linker

<400> SEQUENCE: 126

Gly Ser Gly Gly Ser
1               5
```

```
<210> SEQ ID NO 127
<211> LENGTH: 4
<212> TYPE: PRT
<213> ORGANISM: Artificial Sequence
<220> FEATURE:
<223> OTHER INFORMATION: Linker

<400> SEQUENCE: 127

Gly Gly Gly Ser
1

<210> SEQ ID NO 128
<211> LENGTH: 4
<212> TYPE: PRT
<213> ORGANISM: Artificial Sequence
<220> FEATURE:
<223> OTHER INFORMATION: Linker

<400> SEQUENCE: 128

Gly Gly Ser Gly
1

<210> SEQ ID NO 129
<211> LENGTH: 5
<212> TYPE: PRT
<213> ORGANISM: Artificial Sequence
<220> FEATURE:
<223> OTHER INFORMATION: Linker

<400> SEQUENCE: 129

Gly Gly Ser Gly Gly
1               5

<210> SEQ ID NO 130
<211> LENGTH: 5
<212> TYPE: PRT
<213> ORGANISM: Artificial Sequence
<220> FEATURE:
<223> OTHER INFORMATION: Linker

<400> SEQUENCE: 130

Gly Ser Gly Ser Gly
1               5

<210> SEQ ID NO 131
<211> LENGTH: 5
<212> TYPE: PRT
<213> ORGANISM: Artificial Sequence
<220> FEATURE:
<223> OTHER INFORMATION: Linker

<400> SEQUENCE: 131

Gly Ser Gly Gly Gly
1               5

<210> SEQ ID NO 132
<211> LENGTH: 5
<212> TYPE: PRT
<213> ORGANISM: Artificial Sequence
<220> FEATURE:
<223> OTHER INFORMATION: Linker

<400> SEQUENCE: 132

Gly Gly Gly Ser Gly
1               5
```

-continued

```
<210> SEQ ID NO 133
<211> LENGTH: 5
<212> TYPE: PRT
<213> ORGANISM: Artificial Sequence
<220> FEATURE:
<223> OTHER INFORMATION: Linker

<400> SEQUENCE: 133

Gly Ser Ser Ser Gly
1               5

<210> SEQ ID NO 134
<211> LENGTH: 4
<212> TYPE: PRT
<213> ORGANISM: Artificial Sequence
<220> FEATURE:
<223> OTHER INFORMATION: Linker

<400> SEQUENCE: 134

Gly Gly Ser Gly
1

<210> SEQ ID NO 135
<211> LENGTH: 5
<212> TYPE: PRT
<213> ORGANISM: Artificial Sequence
<220> FEATURE:
<223> OTHER INFORMATION: Linker

<400> SEQUENCE: 135

Gly Ser Ser Ser Ser
1               5

<210> SEQ ID NO 136
<211> LENGTH: 5
<212> TYPE: PRT
<213> ORGANISM: Artificial Sequence
<220> FEATURE:
<223> OTHER INFORMATION: Linker

<400> SEQUENCE: 136

Gly Gly Gly Gly Ser
1               5

<210> SEQ ID NO 137
<211> LENGTH: 15
<212> TYPE: PRT
<213> ORGANISM: Artificial Sequence
<220> FEATURE:
<223> OTHER INFORMATION: Linker

<400> SEQUENCE: 137

Gly Cys Gly Ala Ser Gly Gly Gly Ser Gly Gly Gly Ser
1               5                   10                  15

<210> SEQ ID NO 138
<211> LENGTH: 124
<212> TYPE: PRT
<213> ORGANISM: Homo sapiens

<400> SEQUENCE: 138

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
                20                  25                  30

Leu Ala Ala Leu Ile Val Tyr Trp Glu Met Glu Asp Lys Asn Ile Ile
```

```
                35                  40                  45
Gln Phe Val His Gly Glu Glu Asp Leu Lys Thr Gln His Ser Ser Tyr
     50                  55                  60

Arg Gln Arg Ala Arg Leu Leu Lys Asp Gln Leu Ser Leu Gly Asn Ala
 65                  70                  75                  80

Ala Leu Gln Ile Thr Asp Val Lys Leu Gln Asp Ala Gly Val Tyr Arg
                 85                  90                  95

Cys Met Ile Ser Tyr Gly Gly Ala Asp Tyr Lys Arg Ile Thr Val Lys
                100                 105                 110

Val Asn Ala Pro Tyr Ala Ala Ala Leu His Glu His
            115                 120

<210> SEQ ID NO 139
<211> LENGTH: 133
<212> TYPE: PRT
<213> ORGANISM: Homo sapiens
<220> FEATURE:
<221> NAME/KEY: VARIANT
<222> LOCATION: (20)..(20)
<223> OTHER INFORMATION: X is any amino acid other than Asp, or X is
      Ala.
<220> FEATURE:
<221> NAME/KEY: VARIANT
<222> LOCATION: (42)..(42)
<223> OTHER INFORMATION: X is any amino acid other than Phe, or X is
      Ala.
<220> FEATURE:
<221> NAME/KEY: VARIANT
<222> LOCATION: (45)..(45)
<223> OTHER INFORMATION: X is any amino acid other than Tyr, or X is
      Ala.
<220> FEATURE:
<221> NAME/KEY: VARIANT
<222> LOCATION: (126)..(126)
<223> OTHER INFORMATION: X is any amino acid other than Gln, or X is
      Ala.

<400> SEQUENCE: 139

Ala Pro Thr Ser Ser Thr Lys Lys Thr Gln Leu Gln Leu Glu His
  1               5                  10                  15

Leu Leu Leu Xaa Leu Gln Met Ile Leu Asn Gly Ile Asn Asn Tyr Lys
                 20                  25                  30

Asn Pro Lys Leu Thr Arg Met Leu Thr Xaa Lys Phe Xaa Met Pro Lys
             35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Xaa Ser Ile
            115                 120                 125

Ile Ser Thr Leu Thr
        130

<210> SEQ ID NO 140
<211> LENGTH: 133
<212> TYPE: PRT
<213> ORGANISM: Homo sapiens
<220> FEATURE:
<221> NAME/KEY: VARIANT
```

```
<222> LOCATION: (16)..(16)
<223> OTHER INFORMATION: X is any amino acid other than His, or X is
      Ala.
<220> FEATURE:
<221> NAME/KEY: VARIANT
<222> LOCATION: (20)..(20)
<223> OTHER INFORMATION: X is any amino acid other than Asp, or X is
      Ala.
<220> FEATURE:
<221> NAME/KEY: VARIANT
<222> LOCATION: (42)..(42)
<223> OTHER INFORMATION: X is any amino acid other than Phe, or X is
      Ala.
<220> FEATURE:
<221> NAME/KEY: VARIANT
<222> LOCATION: (45)..(45)
<223> OTHER INFORMATION: X is any amino acid other than Tyr, or X is
      Ala.
<220> FEATURE:
<221> NAME/KEY: VARIANT
<222> LOCATION: (126)..(126)
<223> OTHER INFORMATION: X is any amino acid other than Gln, or X is
      Ala.

<400> SEQUENCE: 140

Ala Pro Thr Ser Ser Ser Thr Lys Lys Thr Gln Leu Gln Leu Glu Xaa
1               5                   10                  15

Leu Leu Leu Xaa Leu Gln Met Ile Leu Asn Gly Ile Asn Asn Tyr Lys
                20                  25                  30

Asn Pro Lys Leu Thr Arg Met Leu Thr Xaa Lys Phe Xaa Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
        130

<210> SEQ ID NO 141
<211> LENGTH: 133
<212> TYPE: PRT
<213> ORGANISM: Homo sapiens
<220> FEATURE:
<221> NAME/KEY: VARIANT
<222> LOCATION: (16)..(16)
<223> OTHER INFORMATION: X is any amino acid other than His, or X is
      Ala.
<220> FEATURE:
<221> NAME/KEY: VARIANT
<222> LOCATION: (42)..(42)
<223> OTHER INFORMATION: X is any amino acid other than Phe, or X is
      Ala.
<220> FEATURE:
<221> NAME/KEY: VARIANT
<222> LOCATION: (126)..(126)
<223> OTHER INFORMATION: X is any amino acid other than Gln, or X is
      Ala.

<400> SEQUENCE: 141

Ala Pro Thr Ser Ser Ser Thr Lys Lys Thr Gln Leu Gln Leu Glu Xaa
1               5                   10                  15
```

```
Leu Leu Leu Asp Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
        130

<210> SEQ ID NO 142
<211> LENGTH: 8
<212> TYPE: PRT
<213> ORGANISM: Homo sapiens

<400> SEQUENCE: 142

Gly Gly Gly Gly Ser Gly Gly Gly
1               5

<210> SEQ ID NO 143
<211> LENGTH: 281
<212> TYPE: PRT
<213> ORGANISM: Homo sapiens

<400> SEQUENCE: 143

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
            85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190
```

```
Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
                275                 280

<210> SEQ ID NO 144
<211> LENGTH: 179
<212> TYPE: PRT
<213> ORGANISM: Homo sapiens

<400> SEQUENCE: 144

Gln Leu Phe His Leu Gln Lys Glu Leu Ala Glu Leu Arg Glu Ser Thr
1               5                   10                  15

Ser Gln Met His Thr Ala Ser Ser Leu Glu Lys Gln Ile Gly His Pro
                20                  25                  30

Ser Pro Pro Pro Glu Lys Lys Glu Leu Arg Lys Val Ala His Leu Thr
            35                  40                  45

Gly Lys Ser Asn Ser Arg Ser Met Pro Leu Glu Trp Glu Asp Thr Tyr
    50                  55                  60

Gly Ile Val Leu Leu Ser Gly Val Lys Tyr Lys Lys Gly Gly Leu Val
65                  70                  75                  80

Ile Asn Glu Thr Gly Leu Tyr Phe Val Tyr Ser Lys Val Tyr Phe Arg
                85                  90                  95

Gly Gln Ser Cys Asn Asn Leu Pro Leu Ser His Lys Val Tyr Met Arg
            100                 105                 110

Asn Ser Lys Tyr Pro Gln Asp Leu Val Met Met Glu Gly Lys Met Met
        115                 120                 125

Ser Tyr Cys Thr Thr Gly Gln Met Trp Ala Arg Ser Ser Tyr Leu Gly
    130                 135                 140

Ala Val Phe Asn Leu Thr Ser Ala Asp His Leu Tyr Val Asn Val Ser
145                 150                 155                 160

Glu Leu Ser Leu Val Asn Phe Glu Glu Ser Gln Thr Phe Phe Gly Leu
                165                 170                 175

Tyr Lys Leu

<210> SEQ ID NO 145
<211> LENGTH: 335
<212> TYPE: PRT
<213> ORGANISM: Homo sapiens

<400> SEQUENCE: 145

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
                20                  25                  30

Lys Gly Leu Glu Leu Arg Lys Thr Val Thr Thr Val Glu Thr Gln Asn
            35                  40                  45

Leu Glu Gly Leu His His Asp Gly Gln Phe Cys His Lys Pro Cys Pro
```

```
            50                  55                  60
Pro Gly Glu Arg Lys Ala Arg Asp Cys Thr Val Asn Gly Asp Glu Pro
 65                  70                  75                  80

Asp Cys Val Pro Cys Gln Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 146
<211> LENGTH: 627
<212> TYPE: PRT
<213> ORGANISM: Homo sapiens

<400> SEQUENCE: 146

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
            115                 120                 125
Ile Ser Thr Leu Thr Gly Gly Gly Ser Gly Gly Gly Ser Gly
130                 135                 140
Gly Gly Gly Ser Ala Pro Glu Ala Ala Gly Gly Pro Ser Val Phe Leu
145                 150                 155                 160
Phe Pro Pro Lys Pro Lys Asp Thr Leu Met Ile Ser Arg Thr Pro Glu
                165                 170                 175
Val Thr Cys Val Val Val Asp Val Ser His Glu Asp Pro Glu Val Lys
            180                 185                 190
Phe Asn Trp Tyr Val Asp Gly Val Glu Val His Asn Ala Lys Thr Lys
        195                 200                 205
Pro Arg Glu Glu Gln Tyr Asn Ser Thr Tyr Arg Val Val Ser Val Leu
    210                 215                 220
Thr Val Leu His Gln Asp Trp Leu Asn Gly Lys Glu Tyr Lys Cys Lys
225                 230                 235                 240
Val Ser Asn Lys Ala Leu Pro Ala Pro Ile Glu Lys Thr Ile Ser Lys
                245                 250                 255
Ala Lys Gly Gln Pro Arg Glu Pro Gln Val Tyr Thr Lys Pro Pro Ser
            260                 265                 270
Arg Glu Glu Met Thr Lys Asn Gln Val Ser Leu Ser Cys Leu Val Lys
        275                 280                 285
Gly Phe Tyr Pro Ser Asp Ile Ala Val Glu Trp Glu Ser Asn Gly Gln
    290                 295                 300
Pro Glu Asn Asn Tyr Lys Thr Thr Pro Pro Val Leu Asp Ser Asp Gly
305                 310                 315                 320
Ser Phe Arg Leu Ala Ser Tyr Leu Thr Val Asp Lys Ser Arg Trp Gln
                325                 330                 335
Gln Gly Asn Val Phe Ser Cys Ser Val Met His Glu Ala Leu His Asn
            340                 345                 350
His Tyr Thr Gln Lys Ser Leu Ser Leu Ser Pro Gly Gly Gly Gly Gly
        355                 360                 365
Ser Gly Gly Gly Gly Ser Gly Gly Gly Gly Ser Gln Leu Cys Lys Phe
    370                 375                 380
Cys Asp Val Arg Phe Ser Thr Cys Asp Asn Gln Lys Ser Cys Met Ser
385                 390                 395                 400
Asn Cys Ser Ile Thr Ser Ile Cys Glu Lys Pro Gln Glu Val Cys Val
                405                 410                 415
Ala Val Trp Arg Lys Asn Asp Glu Asn Ile Thr Leu Glu Thr Val Cys
            420                 425                 430
His Asp Pro Lys Leu Pro Tyr His Asp Phe Ile Leu Glu Asp Ala Ala
        435                 440                 445
Ser Pro Lys Cys Ile Met Lys Glu Lys Lys Pro Gly Glu Thr Phe
    450                 455                 460
Phe Met Cys Ser Cys Ser Ser Ala Glu Cys Asn Asp Asn Ile Ile Phe
465                 470                 475                 480
Ser Glu Glu Tyr Asn Thr Ser Asn Pro Asp Gly Gly Gly Gly Ser Gly
                485                 490                 495
Gly Gly Gly Ser Gly Gly Gly Ser Gly Gly Gly Ser Gly Gly
            500                 505                 510
Gly Gly Ser Ala Leu Asp Thr Asn Tyr Cys Phe Arg Asn Leu Glu Glu
```

```
                515                 520                 525
Asn Cys Cys Val Arg Pro Leu Tyr Ile Asp Phe Arg Gln Asp Leu Gly
        530                 535                 540

Trp Lys Trp Val His Glu Pro Lys Gly Tyr Tyr Ala Asn Phe Cys Ser
545                 550                 555                 560

Gly Pro Cys Pro Tyr Leu Arg Ser Ala Asp Thr Thr His Ser Thr Val
                565                 570                 575

Leu Gly Leu Tyr Asn Thr Leu Asn Pro Glu Ala Ser Ala Ser Pro Ser
            580                 585                 590

Cys Val Pro Gln Asp Leu Glu Pro Leu Thr Ile Leu Tyr Tyr Val Gly
                595                 600                 605

Arg Thr Pro Lys Val Glu Gln Leu Ser Asn Met Val Val Lys Ser Cys
        610                 615                 620

Lys Cys Ser
625

<210> SEQ ID NO 147
<211> LENGTH: 637
<212> TYPE: PRT
<213> ORGANISM: Homo sapiens

<400> SEQUENCE: 147

Ala Pro Thr Ser Ser Ser Thr Lys Lys Thr Gln Leu Gln Leu Glu Thr
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
    130                 135                 140

Gly Gly Gly Ser Asp Lys Thr His Thr Cys Pro Cys Pro Ala Pro
145                 150                 155                 160

Glu Ala Ala Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255
```

```
Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Gly Gly Gly Ser Gly Gly Gly Gly Ser
    370                 375                 380

Gly Gly Gly Ser Gln Leu Cys Lys Phe Cys Asp Val Arg Phe Ser
385                 390                 395                 400

Thr Cys Asp Asn Gln Lys Ser Cys Met Ser Asn Cys Ser Ile Thr Ser
                405                 410                 415

Ile Cys Glu Lys Pro Gln Glu Val Cys Val Ala Val Trp Arg Lys Asn
            420                 425                 430

Asp Glu Asn Ile Thr Leu Glu Thr Val Cys His Asp Pro Lys Leu Pro
        435                 440                 445

Tyr His Asp Phe Ile Leu Glu Asp Ala Ala Ser Pro Lys Cys Ile Met
    450                 455                 460

Lys Glu Lys Lys Lys Pro Gly Glu Thr Phe Phe Met Cys Ser Cys Ser
465                 470                 475                 480

Ser Ala Glu Cys Asn Asp Asn Ile Ile Phe Ser Glu Glu Tyr Asn Thr
                485                 490                 495

Ser Asn Pro Asp Gly Gly Gly Gly Ser Gly Gly Gly Gly Ser Gly Gly
            500                 505                 510

Gly Gly Ser Gly Gly Gly Gly Ser Gly Gly Gly Ser Ala Leu Asp
        515                 520                 525

Thr Asn Tyr Cys Phe Arg Asn Leu Glu Glu Asn Cys Cys Val Arg Pro
    530                 535                 540

Leu Tyr Ile Asp Phe Arg Gln Asp Leu Gly Trp Lys Trp Val His Glu
545                 550                 555                 560

Pro Lys Gly Tyr Tyr Ala Asn Phe Cys Ser Gly Pro Cys Pro Tyr Leu
                565                 570                 575

Arg Ser Ala Asp Thr Thr His Ser Thr Val Leu Gly Leu Tyr Asn Thr
            580                 585                 590

Leu Asn Pro Glu Ala Ser Ala Ser Pro Cys Cys Val Pro Gln Asp Leu
        595                 600                 605

Glu Pro Leu Thr Ile Leu Tyr Tyr Val Gly Arg Thr Pro Lys Val Glu
    610                 615                 620

Gln Leu Ser Asn Met Val Val Lys Ser Cys Lys Cys Ser
625                 630                 635
```

<210> SEQ ID NO 148
<211> LENGTH: 511
<212> TYPE: PRT
<213> ORGANISM: Homo sapiens

<400> SEQUENCE: 148

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Gly Ser Gly
130                 135                 140

Gly Gly Ser Asp Lys Thr His Thr Cys Pro Pro Cys Pro Ala Pro
145                 150                 155                 160

Glu Ala Ala Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Trp Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Gly Gly Gly Ser Gly Gly Gly Gly Ser
370                 375                 380

Gly Gly Gly Gly Ser Gly Gly Gly Ser Gly Gly Gly Gly Ser Ala
385                 390                 395                 400

Leu Asp Thr Asn Tyr Cys Phe Arg Asn Leu Glu Glu Asn Cys Cys Val
                405                 410                 415
```

```
Arg Pro Leu Tyr Ile Asp Phe Arg Gln Asp Leu Gly Trp Lys Trp Val
                420                 425                 430

His Glu Pro Lys Gly Tyr Tyr Ala Asn Phe Cys Ser Gly Pro Cys Pro
            435                 440                 445

Tyr Leu Arg Ser Ala Asp Thr Thr His Ser Thr Val Leu Gly Leu Tyr
        450                 455                 460

Asn Thr Leu Asn Pro Glu Ala Ser Ala Ser Pro Ser Cys Val Pro Gln
465                 470                 475                 480

Asp Leu Glu Pro Leu Thr Ile Leu Tyr Tyr Val Gly Arg Thr Pro Lys
                485                 490                 495

Val Glu Gln Leu Ser Asn Met Val Val Lys Ser Cys Lys Cys Ser
                500                 505                 510

<210> SEQ ID NO 149
<211> LENGTH: 500
<212> TYPE: PRT
<213> ORGANISM: Homo sapiens

<400> SEQUENCE: 149

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
130                 135                 140

Gly Gly Gly Ser Asp Lys Thr His Thr Cys Pro Pro Cys Pro Ala Pro
145                 150                 155                 160

Glu Ala Ala Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285
```

```
Asn Gln Val Ser Leu Ser Cys Ala Val Lys Gly Phe Tyr Pro Ser Asp
        290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Val Ser
                325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly Gly Gly Gly Ser Gly Gly Gly Gly Ser
        370                 375                 380

Gly Gly Gly Ser Gln Leu Cys Lys Phe Cys Asp Val Arg Phe Ser
385                 390                 395                 400

Thr Cys Asp Asn Gln Lys Ser Cys Met Ser Asn Cys Ser Ile Thr Ser
                405                 410                 415

Ile Cys Glu Lys Pro Gln Glu Val Cys Val Ala Val Trp Arg Lys Asn
                420                 425                 430

Asp Glu Asn Ile Thr Leu Glu Thr Val Cys His Asp Pro Lys Leu Pro
            435                 440                 445

Tyr His Asp Phe Ile Leu Glu Asp Ala Ala Ser Pro Lys Cys Ile Met
        450                 455                 460

Lys Glu Lys Lys Lys Pro Gly Glu Thr Phe Phe Met Cys Ser Cys Ser
465                 470                 475                 480

Ser Ala Glu Cys Asn Asp Asn Ile Ile Phe Ser Glu Glu Tyr Asn Thr
                485                 490                 495

Ser Asn Pro Asp
        500

<210> SEQ ID NO 150
<211> LENGTH: 511
<212> TYPE: PRT
<213> ORGANISM: Homo sapiens

<400> SEQUENCE: 150

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
130                 135                 140

Gly Gly Gly Ser Asp Lys Thr His Thr Cys Pro Pro Cys Pro Ala Pro
```

```
                145                 150                 155                 160
Glu Ala Ala Gly Gly Pro Ser Val Phe Leu Phe Pro Pro Lys Pro Lys
                    165                 170                 175
Asp Thr Leu Met Ile Ser Arg Thr Pro Glu Val Thr Cys Val Val Val
                180                 185                 190
Asp Val Ser His Glu Asp Pro Glu Val Lys Phe Asn Trp Tyr Val Asp
                195                 200                 205
Gly Val Glu Val His Asn Ala Lys Thr Lys Pro Arg Glu Glu Gln Tyr
210                 215                 220
Asn Ser Thr Tyr Arg Val Val Ser Val Leu Thr Val Leu His Gln Asp
225                 230                 235                 240
Trp Leu Asn Gly Lys Glu Tyr Lys Cys Lys Val Ser Asn Lys Ala Leu
                245                 250                 255
Pro Ala Pro Ile Glu Lys Thr Ile Ser Lys Ala Lys Gly Gln Pro Arg
                260                 265                 270
Glu Pro Gln Val Tyr Thr Leu Pro Pro Ser Arg Glu Glu Met Thr Lys
                275                 280                 285
Asn Gln Val Ser Leu Trp Cys Leu Val Lys Gly Phe Tyr Pro Ser Asp
290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Lys Leu Thr Val Asp Lys Ser Arg Trp Gln Gln Gly Asn Val Phe Ser
                340                 345                 350
Cys Ser Val Met His Glu Ala Leu His Asn His Tyr Thr Gln Lys Ser
                355                 360                 365
Leu Ser Leu Ser Pro Gly Gly Gly Gly Ser Gly Gly Gly Gly Ser
                370                 375                 380
Gly Gly Gly Gly Ser Gly Gly Gly Ser Gly Gly Gly Gly Ser Ala
385                 390                 395                 400
Leu Asp Thr Asn Tyr Cys Phe Arg Asn Leu Glu Glu Asn Cys Cys Val
                405                 410                 415
Arg Pro Leu Tyr Ile Asp Phe Arg Gln Asp Leu Gly Trp Lys Trp Val
                420                 425                 430
His Glu Pro Lys Gly Tyr Tyr Ala Asn Phe Cys Ser Gly Pro Cys Pro
                435                 440                 445
Tyr Leu Arg Ser Ala Asp Thr Thr His Ser Thr Val Leu Gly Leu Tyr
                450                 455                 460
Asn Thr Leu Asn Pro Glu Ala Ser Ala Ser Pro Ser Cys Val Pro Gln
465                 470                 475                 480
Asp Leu Glu Pro Leu Thr Ile Leu Tyr Tyr Val Gly Arg Thr Pro Lys
                485                 490                 495
Val Glu Gln Leu Ser Asn Met Val Val Lys Ser Cys Lys Cys Ser
                500                 505                 510

<210> SEQ ID NO 151
<211> LENGTH: 352
<212> TYPE: PRT
<213> ORGANISM: Homo sapiens

<400> SEQUENCE: 151

Asp Lys Thr His Thr Cys Pro Pro Cys Pro Ala Pro Glu Ala Ala Gly
1               5                   10                  15
```

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Gly Gly Gly Gly
225                 230                 235                 240

Ser Gln Leu Cys Lys Phe Cys Asp Val Arg Phe Ser Thr Cys Asp Asn
                245                 250                 255

Gln Lys Ser Cys Met Ser Asn Cys Ser Ile Thr Ser Ile Cys Glu Lys
            260                 265                 270

Pro Gln Glu Val Cys Val Ala Val Trp Arg Lys Asn Asp Glu Asn Ile
        275                 280                 285

Thr Leu Glu Thr Val Cys His Asp Pro Lys Leu Pro Tyr His Asp Phe
290                 295                 300

Ile Leu Glu Asp Ala Ala Ser Pro Lys Cys Ile Met Lys Glu Lys Lys
305                 310                 315                 320

Lys Pro Gly Glu Thr Phe Phe Met Cys Ser Cys Ser Ser Ala Glu Cys
                325                 330                 335

Asn Asp Asn Ile Ile Phe Ser Glu Glu Tyr Asn Thr Ser Asn Pro Asp
            340                 345                 350

<210> SEQ ID NO 152
<211> LENGTH: 637
<212> TYPE: PRT
<213> ORGANISM: Homo sapiens

<400> SEQUENCE: 152

Ala Pro Thr Ser Ser Ser Thr Lys Lys Thr Gln Leu Gln Leu Glu Thr
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

```
Lys Ala Thr Glu Leu Lys His Leu Gln Cys Leu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                     85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
             115                 120                 125

Ile Ser Thr Leu Thr Gly Gly Gly Ser Gly Gly Gly Gly Ser Gly
     130                 135                 140

Gly Gly Ser Asp Lys Thr His Thr Cys Pro Pro Cys Pro Ala Pro
145                 150                 155                 160

Glu Ala Ala Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
             180                 185                 190

Asp Val Ser His Glu Asp Pro Glu Val Lys Phe Asn Trp Tyr Val Asp
         195                 200                 205

Gly Val Glu Val His Asn Ala Lys Thr Lys Pro Arg Glu Glu Gln Tyr
 210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
             260                 265                 270

Glu Pro Gln Val Tyr Thr Leu Pro Pro Ser Arg Glu Glu Met Thr Lys
         275                 280                 285

Asn Gln Val Ser Leu Trp Cys Leu Val Lys Gly Phe Tyr Pro Ser Asp
 290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
             340                 345                 350

Cys Ser Val Met His Glu Ala Leu His Asn His Tyr Thr Gln Lys Ser
         355                 360                 365

Leu Ser Leu Ser Pro Gly Gly Gly Gly Ser Gly Gly Gly Gly Ser
 370                 375                 380

Gly Gly Gly Gly Ser Gln Leu Cys Lys Phe Cys Asp Val Arg Phe Ser
385                 390                 395                 400

Thr Cys Asp Asn Gln Lys Ser Cys Met Ser Asn Cys Ser Ile Thr Ser
                405                 410                 415

Ile Cys Glu Lys Pro Gln Glu Val Cys Val Ala Val Trp Arg Lys Asn
             420                 425                 430

Asp Glu Asn Ile Thr Leu Glu Thr Val Cys His Asp Pro Lys Leu Pro
         435                 440                 445

Tyr His Asp Phe Ile Leu Glu Asp Ala Ala Ser Pro Lys Cys Ile Met
 450                 455                 460
```

```
Lys Glu Lys Lys Lys Pro Gly Glu Thr Phe Phe Met Cys Ser Cys Ser
465                 470                 475                 480

Ser Ala Glu Cys Asn Asp Asn Ile Ile Phe Ser Glu Glu Tyr Asn Thr
            485                 490                 495

Ser Asn Pro Asp Gly Gly Gly Ser Gly Gly Gly Ser Gly Gly
            500                 505                 510

Gly Gly Ser Gly Gly Gly Ser Gly Gly Gly Ser Ala Leu Asp
        515                 520                 525

Thr Asn Tyr Cys Phe Arg Asn Leu Glu Glu Asn Cys Cys Val Arg Pro
            530                 535                 540

Leu Tyr Ile Asp Phe Arg Gln Asp Leu Gly Trp Lys Trp Val His Glu
545                 550                 555                 560

Pro Lys Gly Tyr Tyr Ala Asn Phe Cys Ser Gly Pro Cys Pro Tyr Leu
                565                 570                 575

Arg Ser Ala Asp Thr Thr His Ser Thr Val Leu Gly Leu Tyr Asn Thr
            580                 585                 590

Leu Asn Pro Glu Ala Ser Ala Ser Pro Ser Cys Val Pro Gln Asp Leu
        595                 600                 605

Glu Pro Leu Thr Ile Leu Tyr Tyr Val Gly Arg Thr Pro Lys Val Glu
610                 615                 620

Gln Leu Ser Asn Met Val Val Lys Ser Cys Lys Cys Ser
625                 630                 635

<210> SEQ ID NO 153
<211> LENGTH: 226
<212> TYPE: PRT
<213> ORGANISM: Homo sapiens

<400> SEQUENCE: 153

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220

Pro Gly
225

<210> SEQ ID NO 154
<211> LENGTH: 11
<212> TYPE: PRT
<213> ORGANISM: Homo sapiens

<400> SEQUENCE: 154

Cys Glu Gln Lys Leu Ile Ser Glu Glu Asp Leu
1               5                   10

<210> SEQ ID NO 155
<211> LENGTH: 374
<212> TYPE: PRT
<213> ORGANISM: Homo sapiens

<400> SEQUENCE: 155

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly
225                 230                 235                 240

Ser Ala Pro Thr Ser Ser Ser Thr Lys Lys Thr Gln Leu Gln Leu Glu
                245                 250                 255

His Leu Leu Leu Asp Leu Gln Met Ile Leu Asn Gly Ile Asn Asn Tyr
            260                 265                 270

Lys Asn Pro Lys Leu Thr Arg Met Leu Thr Phe Lys Phe Tyr Met Pro
        275                 280                 285
```

```
Lys Lys Ala Thr Glu Leu Lys His Leu Gln Cys Leu Glu Glu Glu Leu
            290                 295                 300

Lys Pro Leu Glu Glu Val Leu Asn Leu Ala Gln Ser Lys Asn Phe His
305                 310                 315                 320

Leu Arg Pro Arg Asp Leu Ile Ser Asn Ile Asn Val Ile Val Leu Glu
                    325                 330                 335

Leu Lys Gly Ser Glu Thr Thr Phe Met Cys Glu Tyr Ala Asp Glu Thr
                340                 345                 350

Ala Thr Ile Val Glu Phe Leu Asn Arg Trp Ile Thr Phe Cys Gln Ser
            355                 360                 365

Ile Ile Ser Thr Leu Thr
        370

<210> SEQ ID NO 156
<211> LENGTH: 489
<212> TYPE: PRT
<213> ORGANISM: Homo sapiens

<400> SEQUENCE: 156

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Gly Ser Gly Gly Gly Gly
225                 230                 235                 240

Ser Gln Leu Cys Lys Phe Cys Asn Val Arg Phe Ser Thr Cys Asp Asn
                245                 250                 255

Gln Lys Ser Cys Met Ser Asn Cys Ser Ile Thr Ser Ile Cys Glu Lys
            260                 265                 270

Pro Gln Glu Val Cys Val Ala Val Trp Arg Lys Asn Asp Glu Asn Ile
```

```
                  275                 280                 285
Thr Leu Glu Thr Val Cys His Asp Pro Lys Leu Pro Tyr His Asp Phe
            290                 295                 300

Ile Leu Glu Asp Ala Ala Ser Pro Lys Cys Ile Met Lys Glu Lys Lys
305                 310                 315                 320

Lys Pro Gly Glu Thr Phe Phe Met Cys Ser Cys Ser Ser Ala Glu Cys
                            325                 330                 335

Asn Asp Asn Ile Ile Phe Ser Glu Glu Tyr Asn Thr Ser Asn Pro Asp
                340                 345                 350

Gly Gly Gly Gly Ser Gly Gly Gly Ser Gly Gly Gly Gly Ser Gly
                355                 360                 365

Gly Gly Gly Ser Gly Gly Gly Ser Ala Leu Asp Thr Asn Tyr Cys
            370                 375                 380

Phe Arg Asn Leu Glu Glu Asn Cys Cys Val Arg Pro Leu Tyr Ile Asp
385                 390                 395                 400

Phe Arg Gln Asp Leu Gly Trp Lys Trp Val His Glu Pro Lys Gly Tyr
                            405                 410                 415

Tyr Ala Asn Phe Cys Ser Gly Pro Cys Pro Tyr Leu Arg Ser Ala Asp
                420                 425                 430

Thr Thr His Ser Thr Val Leu Gly Leu Tyr Asn Thr Leu Asn Pro Glu
            435                 440                 445

Ala Ser Ala Ser Pro Ser Cys Val Pro Gln Asp Leu Glu Pro Leu Thr
450                 455                 460

Ile Leu Tyr Tyr Val Gly Arg Thr Pro Lys Val Glu Gln Leu Ser Asn
465                 470                 475                 480

Met Val Val Lys Ser Cys Lys Cys Ser
                            485

<210> SEQ ID NO 157
<211> LENGTH: 627
<212> TYPE: PRT
<213> ORGANISM: Homo sapiens

<400> SEQUENCE: 157

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Gly Ser Gly
        130                 135                 140

Gly Gly Gly Ser Ala Pro Glu Ala Ala Gly Gly Pro Ser Val Phe Leu
145                 150                 155                 160
```

```
Phe Pro Pro Lys Pro Lys Asp Thr Leu Met Ile Ser Arg Thr Pro Glu
                165                 170                 175

Val Thr Cys Val Val Asp Val Ser His Glu Asp Pro Glu Val Lys
        180                 185                 190

Phe Asn Trp Tyr Val Asp Gly Val Glu Val His Asn Ala Lys Thr Lys
            195                 200                 205

Pro Arg Glu Glu Gln Tyr Asn Ser Thr Tyr Arg Val Val Ser Val Leu
        210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Lys Pro Pro Ser
            260                 265                 270

Arg Glu Glu Met Thr Lys Asn Gln Val Ser Leu Ser Cys Leu Val Lys
        275                 280                 285

Gly Phe Tyr Pro Ser Asp Ile Ala Val Glu Trp Glu Ser Asn Gly Gln
            290                 295                 300

Pro Glu Asn Asn Tyr Lys Thr Thr Val Pro Val Leu Asp Ser Asp Gly
305                 310                 315                 320

Ser Phe Arg Leu Ala Ser Tyr Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Gly Gly Gly Gly
        355                 360                 365

Ser Gly Gly Gly Gly Ser Gly Gly Gly Gly Ser Gln Leu Cys Lys Phe
    370                 375                 380

Cys Asn Val Arg Phe Ser Thr Cys Asp Asn Gln Lys Ser Cys Met Ser
385                 390                 395                 400

Asn Cys Ser Ile Thr Ser Ile Cys Glu Lys Pro Gln Glu Val Cys Val
                405                 410                 415

Ala Val Trp Arg Lys Asn Asp Glu Asn Ile Thr Leu Glu Thr Val Cys
            420                 425                 430

His Asp Pro Lys Leu Pro Tyr His Asp Phe Ile Leu Glu Asp Ala Ala
        435                 440                 445

Ser Pro Lys Cys Ile Met Lys Glu Lys Lys Pro Gly Glu Thr Phe
    450                 455                 460

Phe Met Cys Ser Cys Ser Ser Ala Glu Cys Asn Asp Asn Ile Ile Phe
465                 470                 475                 480

Ser Glu Glu Tyr Asn Thr Ser Asn Pro Asp Gly Gly Gly Gly Ser Gly
                485                 490                 495

Gly Gly Gly Ser Gly Gly Gly Gly Ser Gly Gly Gly Gly Ser Gly Gly
            500                 505                 510

Gly Gly Ser Ala Leu Asp Thr Asn Tyr Cys Phe Arg Asn Leu Glu Glu
        515                 520                 525

Asn Cys Cys Val Arg Pro Leu Tyr Ile Asp Phe Arg Gln Asp Leu Gly
    530                 535                 540

Trp Lys Trp Val His Glu Pro Lys Gly Tyr Tyr Ala Asn Phe Cys Ser
545                 550                 555                 560

Gly Pro Cys Pro Tyr Leu Arg Ser Ala Asp Thr Thr His Ser Thr Val
                565                 570                 575

Leu Gly Leu Tyr Asn Thr Leu Asn Pro Glu Ala Ser Ala Ser Pro Ser
```

-continued

```
                580                 585                 590
Cys Val Pro Gln Asp Leu Glu Pro Leu Thr Ile Leu Tyr Tyr Val Gly
                    595                 600                 605

Arg Thr Pro Lys Val Glu Gln Leu Ser Asn Met Val Val Lys Ser Cys
            610                 615                 620

Lys Cys Ser
625

<210> SEQ ID NO 158
<211> LENGTH: 627
<212> TYPE: PRT
<213> ORGANISM: Homo sapiens

<400> SEQUENCE: 158

Ala Pro Thr Ser Ser Thr Lys Lys Thr Gln Leu Gln Leu Glu Thr
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Gly Ser Gly Gly Gly Ser Gly
130                 135                 140

Gly Gly Gly Ser Ala Pro Glu Ala Ala Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Lys Pro Pro Ser
            260                 265                 270

Arg Glu Glu Met Thr Lys Asn Gln Val Ser Leu Ser Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Val Pro Val Leu Asp Ser Asp Gly
305                 310                 315                 320
```

```
Ser Phe Arg Leu Ala Ser Tyr Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Gly Gly Gly Gly
        355                 360                 365

Ser Gly Gly Gly Ser Gly Gly Gly Ser Gln Leu Cys Lys Phe
    370                 375             380

Cys Asp Val Arg Phe Ser Thr Cys Asp Asn Gln Lys Ser Cys Met Ser
385                 390                 395                 400

Asn Cys Ser Ile Thr Ser Ile Cys Glu Lys Pro Gln Glu Val Cys Val
                405                 410                 415

Ala Val Trp Arg Lys Asn Asp Glu Asn Ile Thr Leu Glu Thr Val Cys
            420                 425                 430

His Asp Pro Lys Leu Pro Tyr His Asp Phe Ile Leu Glu Asp Ala Ala
        435                 440                 445

Ser Pro Lys Cys Ile Met Lys Glu Lys Lys Pro Gly Glu Thr Phe
    450                 455                 460

Phe Met Cys Ser Cys Ser Ser Ala Glu Cys Asn Asp Asn Ile Ile Phe
465                 470                 475                 480

Ser Glu Glu Tyr Asn Thr Ser Asn Pro Asp Gly Gly Gly Ser Gly
                485                 490                 495

Gly Gly Gly Ser Gly Gly Gly Ser Gly Gly Gly Ser Gly Gly
            500                 505                 510

Gly Gly Ser Ala Leu Asp Thr Asn Tyr Cys Phe Arg Asn Leu Glu Glu
            515                 520                 525

Asn Cys Cys Val Arg Pro Leu Tyr Ile Asp Phe Arg Gln Asp Leu Gly
530                 535                 540

Trp Lys Trp Val His Glu Pro Lys Gly Tyr Tyr Ala Asn Phe Cys Ser
545                 550                 555                 560

Gly Pro Cys Pro Tyr Leu Arg Ser Ala Asp Thr Thr His Ser Thr Val
                565                 570                 575

Leu Gly Leu Tyr Asn Thr Leu Asn Pro Glu Ala Ser Ala Ser Pro Ser
            580                 585                 590

Cys Val Pro Gln Asp Leu Glu Pro Leu Thr Ile Leu Tyr Tyr Val Gly
        595                 600                 605

Arg Thr Pro Lys Val Glu Gln Leu Ser Asn Met Val Val Lys Ser Cys
        610                 615                 620

Lys Cys Ser
625

<210> SEQ ID NO 159
<211> LENGTH: 627
<212> TYPE: PRT
<213> ORGANISM: Homo sapiens

<400> SEQUENCE: 159

Ala Pro Thr Ser Ser Ser Thr Lys Lys Thr Gln Leu Gln Leu Glu Thr
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
130                 135                 140

Gly Gly Gly Ser Ala Pro Glu Ala Ala Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Lys Pro Pro Ser
            260                 265                 270

Arg Glu Glu Met Thr Lys Asn Gln Val Ser Leu Ser Cys Leu Val Lys
        275                 280                 285

Gly Phe Tyr Pro Ser Asp Ile Ala Val Glu Trp Glu Ser Asn Gly Gln
290                 295                 300

Pro Glu Asn Asn Tyr Lys Thr Thr Val Pro Val Leu Asp Ser Asp Gly
305                 310                 315                 320

Ser Phe Arg Leu Ala Ser Tyr Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Gly Gly Gly Gly
        355                 360                 365

Ser Gly Gly Gly Gly Ser Gly Gly Gly Gly Ser Gln Leu Cys Lys Phe
370                 375                 380

Cys Asn Val Arg Phe Ser Thr Cys Asp Asn Gln Lys Ser Cys Met Ser
385                 390                 395                 400

Asn Cys Ser Ile Thr Ser Ile Cys Glu Lys Pro Gln Glu Val Cys Val
                405                 410                 415

Ala Val Trp Arg Lys Asn Asp Glu Asn Ile Thr Leu Glu Thr Val Cys
            420                 425                 430

His Asp Pro Lys Leu Pro Tyr His Asp Phe Ile Leu Glu Asp Ala Ala
        435                 440                 445

Ser Pro Lys Cys Ile Met Lys Glu Lys Lys Pro Gly Glu Thr Phe
450                 455                 460

Phe Met Cys Ser Cys Ser Ser Ala Glu Cys Asn Asp Asn Ile Ile Phe
465                 470                 475                 480
```

Ser Glu Glu Tyr Asn Thr Ser Asn Pro Asp Gly Gly Gly Ser Gly
                485                 490                 495

Gly Gly Gly Ser Gly Gly Gly Ser Gly Gly Gly Ser Gly Gly
            500                 505                 510

Gly Gly Ser Ala Leu Asp Thr Asn Tyr Cys Phe Arg Asn Leu Glu Glu
            515                 520                 525

Asn Cys Cys Val Arg Pro Leu Tyr Ile Asp Phe Arg Gln Asp Leu Gly
530                 535                 540

Trp Lys Trp Val His Glu Pro Lys Gly Tyr Ala Asn Phe Cys Ser
545                 550                 555                 560

Gly Pro Cys Pro Tyr Leu Arg Ser Ala Asp Thr Thr His Ser Thr Val
                565                 570                 575

Leu Gly Leu Tyr Asn Thr Leu Asn Pro Glu Ala Ser Ala Ser Pro Ser
                580                 585                 590

Cys Val Pro Gln Asp Leu Glu Pro Leu Thr Ile Leu Tyr Tyr Val Gly
                595                 600                 605

Arg Thr Pro Lys Val Gln Leu Ser Asn Met Val Val Lys Ser Cys
                610                 615                 620

Lys Cys Ser
625

<210> SEQ ID NO 160
<211> LENGTH: 500
<212> TYPE: PRT
<213> ORGANISM: Homo sapiens

<400> SEQUENCE: 160

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
130                 135                 140

Gly Gly Gly Ser Asp Lys Thr His Thr Cys Pro Pro Cys Pro Ala Pro
145                 150                 155                 160

Glu Ala Ala Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Ser Val Leu Thr Val Leu His Gln Asp
225                 230                 235                 240

Trp Leu Asn Gly Lys Glu Tyr Lys Cys Lys Val Ser Asn Lys Ala Leu
            245                 250                 255

Pro Ala Pro Ile Glu Lys Thr Ile Ser Lys Ala Lys Gly Gln Pro Arg
        260                 265                 270

Glu Pro Gln Val Tyr Thr Leu Pro Pro Ser Arg Glu Glu Met Thr Lys
    275                 280                 285

Asn Gln Val Ser Leu Ser Cys Ala Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Val Ser
            325                 330                 335

Lys Leu Thr Val Asp Lys Ser Arg Trp Gln Gln Gly Asn Val Phe Ser
        340                 345                 350

Cys Ser Val Met His Glu Ala Leu His Asn His Tyr Thr Gln Lys Ser
    355                 360                 365

Leu Ser Leu Ser Pro Gly Gly Gly Gly Ser Gly Gly Gly Gly Ser
370                 375                 380

Gly Gly Gly Gly Ser Gln Leu Cys Lys Phe Cys Asn Val Arg Phe Ser
385                 390                 395                 400

Thr Cys Asp Asn Gln Lys Ser Cys Met Ser Asn Cys Ser Ile Thr Ser
            405                 410                 415

Ile Cys Glu Lys Pro Gln Glu Val Cys Val Ala Val Trp Arg Lys Asn
        420                 425                 430

Asp Glu Asn Ile Thr Leu Glu Thr Val Cys His Asp Pro Lys Leu Pro
    435                 440                 445

Tyr His Asp Phe Ile Leu Glu Asp Ala Ala Ser Pro Lys Cys Ile Met
450                 455                 460

Lys Glu Lys Lys Lys Pro Gly Glu Thr Phe Phe Met Cys Ser Cys Ser
465                 470                 475                 480

Ser Ala Glu Cys Asn Asp Asn Ile Ile Phe Ser Glu Gly Tyr Asn Thr
            485                 490                 495

Ser Asn Pro Asp
            500

<210> SEQ ID NO 161
<211> LENGTH: 8
<212> TYPE: PRT
<213> ORGANISM: Arachis hypogaea

<400> SEQUENCE: 161

Pro Gly Gln Phe Glu Asp Phe Phe
1               5

<210> SEQ ID NO 162
<211> LENGTH: 8
<212> TYPE: PRT
<213> ORGANISM: Arachis hypogaea

<400> SEQUENCE: 162

Tyr Leu Gln Gly Phe Ser Arg Asn
1               5

<210> SEQ ID NO 163

```
<211> LENGTH: 10
<212> TYPE: PRT
<213> ORGANISM: Arachis hypogaea

<400> SEQUENCE: 163

Phe Asn Ala Glu Phe Asn Glu Ile Arg Arg
1               5                   10

<210> SEQ ID NO 164
<211> LENGTH: 8
<212> TYPE: PRT
<213> ORGANISM: Arachis hypogaea

<400> SEQUENCE: 164

Gln Glu Glu Arg Gly Gln Arg Arg
1               5

<210> SEQ ID NO 165
<211> LENGTH: 10
<212> TYPE: PRT
<213> ORGANISM: Arachis hypogaea

<400> SEQUENCE: 165

Asp Ile Thr Asn Pro Ile Asn Leu Arg Glu
1               5                   10

<210> SEQ ID NO 166
<211> LENGTH: 10
<212> TYPE: PRT
<213> ORGANISM: Arachis hypogaea

<400> SEQUENCE: 166

Asn Asn Phe Gly Lys Leu Phe Glu Val Lys
1               5                   10

<210> SEQ ID NO 167
<211> LENGTH: 6
<212> TYPE: PRT
<213> ORGANISM: Arachis hypogaea

<400> SEQUENCE: 167

Gly Asn Leu Glu Leu Val
1               5

<210> SEQ ID NO 168
<211> LENGTH: 10
<212> TYPE: PRT
<213> ORGANISM: Arachis hypogaea

<400> SEQUENCE: 168

Arg Arg Tyr Thr Ala Arg Leu Lys Glu Gly
1               5                   10

<210> SEQ ID NO 169
<211> LENGTH: 10
<212> TYPE: PRT
<213> ORGANISM: Arachis hypogaea

<400> SEQUENCE: 169

Glu Leu His Leu Leu Gly Phe Gly Ile Asn
1               5                   10

<210> SEQ ID NO 170
<211> LENGTH: 10
<212> TYPE: PRT
```

<213> ORGANISM: Arachis hypogaea

<400> SEQUENCE: 170

His Arg Ile Phe Leu Ala Gly Asp Lys Asp
1               5                   10

<210> SEQ ID NO 171
<211> LENGTH: 10
<212> TYPE: PRT
<213> ORGANISM: Arachis hypogaea

<400> SEQUENCE: 171

Ile Asp Gln Ile Glu Lys Gln Ala Lys Asp
1               5                   10

<210> SEQ ID NO 172
<211> LENGTH: 10
<212> TYPE: PRT
<213> ORGANISM: Arachis hypogaea

<400> SEQUENCE: 172

Lys Asp Leu Ala Phe Pro Gly Ser Gly Glu
1               5                   10

<210> SEQ ID NO 173
<211> LENGTH: 10
<212> TYPE: PRT
<213> ORGANISM: Arachis hypogaea

<400> SEQUENCE: 173

Lys Glu Ser His Phe Val Ser Ala Arg Pro
1               5                   10

<210> SEQ ID NO 174
<211> LENGTH: 25
<212> TYPE: PRT
<213> ORGANISM: Arachis hypogaea

<400> SEQUENCE: 174

Asn Glu Gly Val Ile Val Lys Val Ser Lys Glu His Val Glu Glu Leu
1               5                   10                  15

Thr Lys His Ala Lys Ser Val Ser Lys
            20                  25

<210> SEQ ID NO 175
<211> LENGTH: 10
<212> TYPE: PRT
<213> ORGANISM: Arachis hypogaea

<400> SEQUENCE: 175

His Ala Ser Ala Arg Gln Gln Trp Glu Leu
1               5                   10

<210> SEQ ID NO 176
<211> LENGTH: 10
<212> TYPE: PRT
<213> ORGANISM: Arachis hypogaea

<400> SEQUENCE: 176

Gln Trp Glu Leu Gln Gly Asp Arg Arg Cys
1               5                   10

<210> SEQ ID NO 177
<211> LENGTH: 10

-continued

```
<212> TYPE: PRT
<213> ORGANISM: Arachis hypogaea

<400> SEQUENCE: 177

Asp Arg Arg Cys Gln Ser Gln Leu Glu Arg
1               5                   10

<210> SEQ ID NO 178
<211> LENGTH: 10
<212> TYPE: PRT
<213> ORGANISM: Arachis hypogaea

<400> SEQUENCE: 178

Leu Arg Pro Cys Glu Gln His Leu Met Gln
1               5                   10

<210> SEQ ID NO 179
<211> LENGTH: 10
<212> TYPE: PRT
<213> ORGANISM: Arachis hypogaea

<400> SEQUENCE: 179

Lys Ile Gln Arg Asp Glu Asp Ser Tyr Glu
1               5                   10

<210> SEQ ID NO 180
<211> LENGTH: 10
<212> TYPE: PRT
<213> ORGANISM: Arachis hypogaea

<400> SEQUENCE: 180

Tyr Glu Arg Asp Pro Tyr Ser Pro Ser Gln
1               5                   10

<210> SEQ ID NO 181
<211> LENGTH: 10
<212> TYPE: PRT
<213> ORGANISM: Arachis hypogaea

<400> SEQUENCE: 181

Ser Gln Asp Pro Tyr Ser Pro Ser Pro Tyr
1               5                   10

<210> SEQ ID NO 182
<211> LENGTH: 10
<212> TYPE: PRT
<213> ORGANISM: Arachis hypogaea

<400> SEQUENCE: 182

Asp Arg Leu Gln Gly Arg Gln Gln Glu Gln
1               5                   10

<210> SEQ ID NO 183
<211> LENGTH: 10
<212> TYPE: PRT
<213> ORGANISM: Arachis hypogaea

<400> SEQUENCE: 183

Lys Arg Glu Leu Arg Asn Leu Pro Gln Gln
1               5                   10

<210> SEQ ID NO 184
<211> LENGTH: 10
<212> TYPE: PRT
<213> ORGANISM: Arachis hypogaea
```

<400> SEQUENCE: 184

Gln Arg Cys Asp Leu Asp Val Glu Ser Gly
1               5                   10

<210> SEQ ID NO 185
<211> LENGTH: 15
<212> TYPE: PRT
<213> ORGANISM: Arachis hypogaea

<400> SEQUENCE: 185

Ile Glu Thr Trp Asn Pro Asn Gln Glu Phe Glu Cys Ala Gly
1               5                   10                  15

<210> SEQ ID NO 186
<211> LENGTH: 15
<212> TYPE: PRT
<213> ORGANISM: Arachis hypogaea

<400> SEQUENCE: 186

Gly Asn Ile Phe Ser Gly Phe Thr Pro Glu Phe Leu Ala Gln Ala
1               5                   10                  15

<210> SEQ ID NO 187
<211> LENGTH: 15
<212> TYPE: PRT
<213> ORGANISM: Arachis hypogaea

<400> SEQUENCE: 187

Val Thr Val Arg Gly Gly Leu Arg Ile Leu Ser Pro Asp Arg Lys
1               5                   10                  15

<210> SEQ ID NO 188
<211> LENGTH: 15
<212> TYPE: PRT
<213> ORGANISM: Arachis hypogaea

<400> SEQUENCE: 188

Asp Glu Asp Glu Tyr Glu Tyr Asp Glu Glu Asp Arg Arg Arg Gly
1               5                   10                  15

<210> SEQ ID NO 189
<211> LENGTH: 6
<212> TYPE: PRT
<213> ORGANISM: Homo sapiens

<400> SEQUENCE: 189

Gly Gly Gly Ser Gly Gly
1               5

<210> SEQ ID NO 190
<211> LENGTH: 390
<212> TYPE: PRT
<213> ORGANISM: Homo sapiens

<400> SEQUENCE: 190

Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser

```
                50                  55                  60
Gln Gly Glu Val Pro Pro Gly Pro Leu Pro Glu Ala Val Leu Ala Leu
 65                  70                  75                  80

Tyr Asn Ser Thr Arg Asp Arg Val Ala Gly Glu Ser Ala Glu Pro Glu
                 85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 191
<211> LENGTH: 511
<212> TYPE: PRT
<213> ORGANISM: Artificial Sequence
<220> FEATURE:
<223> OTHER INFORMATION: Protein construct

<400> SEQUENCE: 191

Ala Pro Thr Ser Ser Thr Lys Lys Thr Gln Leu Gln Leu Glu Ala
 1               5                  10                  15

Leu Leu Leu Asp Leu Gln Met Ile Leu Asn Gly Ile Asn Asn Tyr Lys
```

```
            20                  25                  30
Asn Pro Lys Leu Thr Arg Met Leu Thr Ala Lys Phe Tyr Met Pro Lys
            35                  40                  45
Lys Ala Thr Glu Leu Lys His Leu Gln Cys Leu Glu Glu Glu Leu Lys
            50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
            115                 120                 125
Ile Ser Thr Leu Thr Gly Gly Gly Gly Ser Gly Gly Gly Gly Ser Gly
            130                 135                 140
Gly Gly Gly Ser Asp Lys Thr His Thr Cys Pro Pro Cys Pro Ala Pro
145                 150                 155                 160
Glu Ala Ala Gly Gly Pro Ser Val Phe Leu Phe Pro Pro Lys Pro Lys
                    165                 170                 175
Asp Thr Leu Met Ile Ser Arg Thr Pro Glu Val Thr Cys Val Val Val
            180                 185                 190
Asp Val Ser His Glu Asp Pro Glu Val Lys Phe Asn Trp Tyr Val Asp
            195                 200                 205
Gly Val Glu Val His Asn Ala Lys Thr Lys Pro Arg Glu Glu Gln Tyr
            210                 215                 220
Asn Ser Thr Tyr Arg Val Val Ser Val Leu Thr Val Leu His Gln Asp
225                 230                 235                 240
Trp Leu Asn Gly Lys Glu Tyr Lys Cys Lys Val Ser Asn Lys Ala Leu
                    245                 250                 255
Pro Ala Pro Ile Glu Lys Thr Ile Ser Lys Ala Lys Gly Gln Pro Arg
            260                 265                 270
Glu Pro Gln Val Tyr Thr Leu Pro Pro Cys Arg Glu Glu Met Thr Lys
            275                 280                 285
Asn Gln Val Ser Leu Trp Cys Leu Val Lys Gly Phe Tyr Pro Ser Asp
            290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                    325                 330                 335
Lys Leu Thr Val Asp Lys Ser Arg Trp Gln Gln Gly Asn Val Phe Ser
            340                 345                 350
Cys Ser Val Met His Glu Ala Leu His Asn His Tyr Thr Gln Lys Ser
            355                 360                 365
Leu Ser Leu Ser Pro Gly Gly Gly Gly Ser Gly Gly Gly Gly Ser
            370                 375                 380
Gly Gly Gly Gly Ser Gly Gly Gly Ser Gly Gly Gly Ser Ala
385                 390                 395                 400
Leu Asp Thr Asn Tyr Cys Phe Arg Asn Leu Glu Glu Asn Cys Cys Val
                    405                 410                 415
Arg Pro Leu Tyr Ile Asp Phe Arg Gln Asp Leu Gly Trp Lys Trp Val
            420                 425                 430
His Glu Pro Lys Gly Tyr Tyr Ala Asn Phe Cys Ser Gly Pro Cys Pro
            435                 440                 445
```

Tyr Leu Arg Ser Ala Asp Thr Thr His Ser Thr Val Leu Gly Leu Tyr
            450                 455                 460

Asn Thr Leu Asn Pro Glu Ala Ser Ala Ser Pro Ser Cys Val Pro Gln
465                 470                 475                 480

Asp Leu Glu Pro Leu Thr Ile Leu Tyr Tyr Val Gly Arg Thr Pro Lys
                485                 490                 495

Val Glu Gln Leu Ser Asn Met Val Val Lys Ser Cys Lys Cys Ser
            500                 505                 510

<210> SEQ ID NO 192
<211> LENGTH: 352
<212> TYPE: PRT
<213> ORGANISM: Artificial Sequence
<220> FEATURE:
<223> OTHER INFORMATION: protein construct

<400> SEQUENCE: 192

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Gly Ser Gly Gly Gly Gly
225                 230                 235                 240

Ser Gln Leu Cys Lys Phe Cys Asp Val Arg Phe Ser Thr Cys Asp Asn
                245                 250                 255

Gln Lys Ser Cys Met Ser Asn Cys Ser Ile Thr Ser Ile Cys Glu Lys
            260                 265                 270

Pro Gln Glu Val Cys Val Ala Val Trp Arg Lys Asn Asp Glu Asn Ile
        275                 280                 285

Thr Leu Glu Thr Val Cys His Asp Pro Lys Leu Pro Tyr His Asp Phe
290                 295                 300

```
Ile Leu Glu Asp Ala Ala Ser Pro Lys Cys Ile Met Lys Glu Lys Lys
305                 310                 315                 320

Lys Pro Gly Glu Thr Phe Phe Met Cys Ser Cys Ser Ser Ala Glu Cys
                325                 330                 335

Asn Asp Asn Ile Ile Phe Ser Glu Glu Tyr Asn Thr Ser Asn Pro Asp
                340                 345                 350
```